US012534516B2

(12) United States Patent
Landais et al.

(10) Patent No.: US 12,534,516 B2
(45) Date of Patent: Jan. 27, 2026

(54) ANTI-HIV ANTIBODIES

(71) Applicant: INTERNATIONAL AIDS VACCINE INITIATIVE, New York, NY (US)

(72) Inventors: Elise Landais, La Jolla, CA (US); Devin Sok, San Diego, CA (US)

(73) Assignee: International AIDS Vaccine Initiative, New York, NY (US)

( * ) Notice: Subject to any disclaimer, the term of this patent is extended or adjusted under 35 U.S.C. 154(b) by 1016 days.

(21) Appl. No.: 17/287,188

(22) PCT Filed: Oct. 21, 2019

(86) PCT No.: PCT/US2019/057180
§ 371 (c)(1),
(2) Date: Apr. 21, 2021

(87) PCT Pub. No.: WO2020/086446
PCT Pub. Date: Apr. 30, 2020

(65) Prior Publication Data

US 2021/0355197 A1 Nov. 18, 2021

Related U.S. Application Data

(60) Provisional application No. 62/748,610, filed on Oct. 22, 2018.

(51) Int. Cl.
*C07K 16/10* (2006.01)
*G01N 33/569* (2006.01)

(52) U.S. Cl.
CPC ... *C07K 16/1063* (2013.01); *G01N 33/56988* (2013.01); *C07K 2317/21* (2013.01); *C07K 2317/76* (2013.01); *G01N 2333/162* (2013.01); *G01N 2800/26* (2013.01)

(58) Field of Classification Search
CPC ............ C07K 16/1063; C07K 2317/21; C07K 2317/76; G01N 33/56988; G01N 2333/162; G01N 2800/26
See application file for complete search history.

(56) References Cited

U.S. PATENT DOCUMENTS

| | | | | |
|---|---|---|---|---|
| 10,093,720 | B2 * | 10/2018 | Burton | C07K 16/1063 |
| RE49,037 | E * | 4/2022 | Burton | C07K 16/1063 |
| 11,332,541 | B2 * | 5/2022 | Hipp | A61P 35/00 |
| 11,760,789 | B2 * | 9/2023 | Sajadi | A61P 31/18 424/148.1 |
| 11,795,211 | B2 * | 10/2023 | Sok | C07K 14/162 |
| RE50,268 | E * | 1/2025 | Burton | C07K 16/1063 |
| 2002/0128450 | A1 * | 9/2002 | Nishida | C07K 16/244 530/388.23 |
| 2018/0194809 | A1 | 7/2018 | Schief et al. | |
| 2018/0298083 | A1 | 10/2018 | Connors et al. | |
| 2021/0292396 | A1 * | 9/2021 | Sok | A61K 39/42 |
| 2022/0090054 | A1 * | 3/2022 | Itzhaki | C12N 15/62 |
| 2023/0134571 | A1 * | 5/2023 | Sok | A61P 31/18 424/148.1 |
| 2023/0365661 | A1 * | 11/2023 | Scheid | A61P 31/18 |
| 2024/0109956 | A1 * | 4/2024 | Sok | A61K 39/12 |

FOREIGN PATENT DOCUMENTS

| | | | |
|---|---|---|---|
| CN | 104151426 | A * | 11/2014 |
| WO | 2011038290 | A2 | 3/2011 |
| WO | 2016196975 | A1 | 12/2018 |

OTHER PUBLICATIONS

Sun et al. 2014. CN 104151426 A. Machine Translation. (Year: 2014).*
Jeffrey Umotoy, "Rapid and Focused Maturation of a VRC01-Class HIV Broadly Neutralizing Antibody Lineage Involves Both Binding and Accommodation of the N276-Glycan", Immunity, vol. 51, No. 1, pp. 141-154, 2019.
International Search Report and the Written Opinion of the ISA for PCT/US2019/057180, mailed Feb. 27, 2020.
Havenar-Daughton, C. et al., "The Human Naive B Cell Repertoire Contains Distinct Subclasses for a Germline-Targeting IV-1 Vaccine Immunogen," Sci. Transl. Med., 10, eaat0381 (2018).
Landais, E. et. al., "Development of Broadly Neutralizing Antibodies in HIV-1 Infected Elie Neutralizers," Retrovirology, 15:61, (2018).
Nusbaum, C. et al., "Annotation of Phytophthora Infestans T30-4," NCBI Reference Sequence XP_002896469.1, Jul. 2010.
Unknown, Third Party Observation for International Application No. PCT/US2019/057180, submitted Feb. 22, 2021.
Cottrell, C.A., et al., "The 2017 Keystone Symposium on HIV Vaccines," Human Vaccines & Immunotherapeutics, vol. 13, Issue 10, pp. 2348-2351, Oct. 18, 2017.
Wu, X. et al., "Maturation and Diversity of the VRC01-Antibody Lineage Over 15 Years of Chronic HIV 1 Infection," Cell, vol. 161, Issue 3, pp. 470-485, Apr. 23, 2015.
Hwang, J. et al., "Sequence Intrinsic Somatic Mutation Mechanisms Contribute to Affinity Maturation of CRC01-class HIV-1 Broadly Neutralizing Antibodies," Proceedings of the National Academy Sciences of the United States of America, vol. 114, Issue 32, pp. 8614-8619, Aug. 8, 2017.
Klein, F et al., "Somatic Mutations of the Immunoglobulin Framework Are Generally Required for Broad and Potent HIV-1 Neutralization," Cell, vol. 153, pp. 126-138, Mar. 28, 2013.
Landais, E., "Broadly Neutralizing Antibodies Development: Lessons From the Protocol C Cohort," Keystone Symposia, Steamboat Springs; oral presentation; Mar. 2017; Best Available Copy.

* cited by examiner

*Primary Examiner* — Janet L Andres
*Assistant Examiner* — Carey Alexander Stuart
(74) *Attorney, Agent, or Firm* — Nixon & Vanderhye, PC

(57) ABSTRACT

Provided herein are anti-HIV Env antibodies and their use in the treatment or prevention of HIV/AIDS.

16 Claims, 41 Drawing Sheets

Specification includes a Sequence Listing.

C

D

A

```
                     FR1                CDR1          FR2        CDR2                    FR3
IGHV1-2*02  QVQLVQSGAEVKKPGASVKVSCKASGYTFTGYYMHWVRQAPGQGLEWMGWINPNSGGTNYAQKFQGRVTMTRDTSISTAYMELSRLRSDDTAVYY

min12A21    ..................R...........N.IL..W..............K.VF.AV...RQ..........IYREI.................
12A12       SQH....TQ.........RI..Q....S..D.VL..W..............K.VY.AR...RR....INFD..IYREI.F.D..G.......L.F
12A21       SQH....TQ.........R...Q.......N.IL..W............L.K.VF.AV...RQ....IQL...IYREI.FLD..G..........

minVRC01    ...............................CTLN................K.RF.AV...R...........VYSD..................
VRC01       ........GQM....E.MRI..R....E.IDCTLN.I.L...KRP.....LK.RG.AV...RPL.........VYSD..FL..RS.TV......F
                                          Motif 1                Motif 2  Motif 3

                     FR1                CDR1         FR2      CDR2             FR3                CDR3
IGKV1-33*01 DIQMTQSPSSLSASVGDRVTITCQASQDISNYLNWYQQKPGKAPKLLIYDASNLETGVPSRFSGSGSGTDFTFTISSLQPEDIATYYCQQYDN

min12A21    .........................G.G.GSS.........R........................FH.T..................AVFQW
12A12       .....................N...G.G.GSS.....K...R.....VHG....QR..........FH.T..L.......D.V...F.AVFQW
12A21       .....................N...G.G.GSS.....K...R.....VHG....QR..........FH.T..L.......D.V...F.AVFQW

IGKV3-11*01 EIVLTQSPATLSLSPGERATLSCRASQSVSSYLAWYQQKPGQAPRLLIYDASNRATGIPARFSGSGSGTDFTLTISSLEPEDFAVYYCQQRSN
minVRC01    ........................T..YG.--..................G..............RW.P.....................YEF
VRC01       ........G........T.II...T..YG.--......R.......V..SG.T..A.........RW.P.YN....N..SG..G......YEF
                                    Motif 4                Motif 5        Motif 6             Motif 7
```

Figure 2

C

| VC | mAb name | mpi | mAb name | CDRH3 sequence (15aa) | $V_H+J_H$ % SHM (nt) | $V_H+J_H$ % SHM (aa) | UCA-H % SHM (nt) | UCA-H % SHM (aa) | CDRL3 sequence (5aa) | $V_K+J_K$ % SHM (nt) | $V_K+J_K$ % SHM (aa) | UCA-K % SHM (nt) | UCA-K % SHM (aa) |
|---|---|---|---|---|---|---|---|---|---|---|---|---|---|
| | | | | Heavy Chain — Putative Gemline Genes: IGHV1-2*02 / IGHJ5*02 | | | | | Light Chain Chain — IGKV1-5*03 / IGKJ1*01 | | | | |
| 72 | P2D11#1a | 66 | 66Aa | | | | | | QVVQW | 12.04 | 15.63 | 14.56 | 17.76 |
| 72 | P2C3 | 66 | 66B | TRDSSRRDTNWWLDP | 9.59 | 18.42 | 11.38 | 20.33 | QVLET | 12.71 | 17.71 | 14.24 | 18.69 |
| 78 | P1B5#1a | 71 | 71Aa | | | | | | QVYES | 10.70 | 19.79 | 12.30 | 20.56 |
| 78 | P1C11 | 71 | 71B | TTHSSSRDFQWSLDP | 9.88 | 16.67 | 11.92 | 20.33 | QVYES | 11.04 | 16.67 | 12.94 | 17.76 |
| 78 | P2B10#2b | 71 | 71D2b | TRDSSRRDTNWWLDP | 10.47 | 21.05 | 12.20 | 22.76 | QVLET | 12.71 | 19.79 | 14.24 | 20.56 |
| 78 | P3F5 | 71 | 71C | TRDSSRRDTNWWLDP | 10.76 | 20.18 | 12.47 | 21.95 | QVLET | 12.37 | 18.75 | 13.92 | 19.63 |
| 78 | P3C6#1a | 71 | 71E1 | TRDSSRRDTNWWLDP | 10.76 | 20.18 | 12.47 | 21.95 | | | | | |
| 78 | P3D6 | 71 | 71F | TRDSSRQQRDWWLDP | 12.50 | 21.05 | 13.01 | 21.14 | QVYES | 11.04 | 18.75 | 12.62 | 19.63 |
| 78 | P2C6 | 71 | 71G | TRDASRDDRAWRLDP | 13.08 | 21.05 | 15.72 | 23.58 | QVVEW | 12.37 | 15.63 | 14.56 | 16.82 |
| 78 | P1D5 | 71 | 71H | ARDSSREETNWWLDP | 13.08 | 21.93 | 14.36 | 23.58 | QVLET | 13.04 | 20.83 | 14.24 | 21.50 |
| 78 | P1D7#1a | 71 | 71I1a | TRDASRDDRAWRLDP | 13.66 | 21.05 | 16.26 | 23.58 | QVFEW | 13.04 | 17.71 | 14.56 | 18.69 |
| 78 | P1G8#2a | 71 | 71J2a | TRDASRDDRAWRLDP | 10.76 | 20.18 | 12.47 | 21.95 | QVLET | 12.71 | 18.75 | 14.24 | 19.63 |
| 78 | P1B9 | 71 | 71K | TRDSSRDETNWWLDP | 14.24 | 23.68 | 15.45 | 25.20 | QVLET | 13.04 | 18.75 | 14.56 | 19.63 |
| 78 | P3B9 | 71 | 71L | TRDSSRDETNWWLDP | 14.24 | 24.56 | 15.45 | 26.02 | QVLET | 13.04 | 18.75 | 14.56 | 19.63 |
| 78 | P2F8#1a | 71 | 71M1a | ARDSSRDETNWWLDP | 14.53 | 21.05 | 15.72 | 22.76 | QVLET | 12.37 | 18.75 | 13.92 | 19.63 |
| 78 | P2E4#1a | 71 | 71N1a | TRDSSRGNTEWRLDP | 14.53 | 21.05 | 15.72 | 22.76 | QVYQT | 12.71 | 18.75 | 14.89 | 20.56 |
| 78 | P1C4 | 71 | 71O | TRDSSRDNLEWRLDP | 15.99 | 23.68 | 17.07 | 23.58 | QVFEW | 12.71 | 15.63 | 14.56 | 16.82 |
| 78 | P3F6 | 71 | 71P | TRDSSRGDTEWRLDP | 15.99 | 23.68 | 17.89 | 24.39 | QVFEW | 13.04 | 16.67 | 14.89 | 17.76 |
| 84 | P3C7 | 77 | 77A | TTHSSRRDFQWSLDP | 10.47 | 17.54 | 12.20 | 20.33 | | | | | |
| 84 | P2B6#1b | 77 | 77B1b | TRDSSRDETNWWLDP | 11.34 | 23.68 | 13.82 | 25.20 | QVLET | 12.71 | 19.79 | 14.24 | 20.56 |
| 84 | P1C8 | 77 | 77C | TRDSSRRDLEWRLDP | 11.92 | 21.05 | 12.74 | 21.14 | QVLET | 13.71 | 19.79 | 15.53 | 20.56 |
| 84 | P3B6 | 77 | 77D | ARDSSRDETNWWLDP | 13.08 | 20.18 | 14.36 | 21.95 | QAYES | 12.37 | 19.79 | 14.24 | 20.56 |
| 84 | P3C9#1a | 77 | 77E1 | TRDSSRDETNWWLDP | 13.95 | 23.68 | 15.18 | 25.20 | | | | | |
| 84 | P2B9#1a | 77 | 77F1 | TRDSSRDETNWWLDP | 14.53 | 23.68 | 15.72 | 25.20 | | | | | |

Figure 6 (cont.)

A

| | SHM ($V_H$+$J_H$) | 9.59 | 9.86 | 10.76 | 10.76 | 12.50 | 13.08 | 13.08 | 13.66 | 13.37 | 14.24 | 14.24 | 14.53 | 14.53 | 15.99 | 15.99 | 11.34 | 11.92 | 13.08 | | 7.22 | 21.31 | 3.44 | 12.37 |
|---|---|---|---|---|---|---|---|---|---|---|---|---|---|---|---|---|---|---|---|---|---|---|---|---|
| | SHM ($V_K$+$J_K$) | 12.71 | 11.04 | 12.37 | 12.71 | 11.04 | 12.37 | 13.04 | 13.04 | 12.71 | 13.04 | 13.04 | 12.37 | 12.37 | 12.71 | 13.04 | 13.04 | 13.71 | 12.37 | | 6.48 | 29.32 | 8.33 | 21.91 |
| | Time point | PCIN | PCIN | PCIN | PCIN | PCIN | PCIN | PCIN | PCIN | PCIN | PCIN | PCIN | PCIN | PCIN | PCIN | PCIN | PCIN | PCIN | PCIN | PC63 M33 | VRC01 | VRC01 | 12A21 | 12A21 |
| | Ab name | 65B | 71B | 71C | 71D2b | 71F | 71G | 71H | 71I1a | 71J2a | 71K | 71L | 71M1a | 71N1a | 71O | 71P | 77B1b | 77C | 77D | Serum | min | MAT | min | MAT |
| Ctrl | MLV | >100 | >100 | >100 | >100 | >100 | >100 | >100 | >100 | >100 | >100 | >100 | >100 | >100 | >100 | >100 | >100 | >100 | >100 | 6 | >100 | >100 | >100 | >100 |
| | VSV | >100 | >100 | >100 | >100 | >100 | >100 | >100 | >100 | >100 | >100 | >100 | >100 | >100 | >100 | >100 | >100 | >100 | >100 | | >100 | >100 | >100 | >100 |
| | 92RW020 | 0.79 | >100 | 0.67 | 0.59 | >100 | 0.86 | 0.26 | 0.39 | 1.1 | 0.20 | 0.096 | 0.20 | >100 | 0.58 | 2.2 | 9.5 | 0.94 | 2.4 | 491 | 0.11 | 0.50 | 0.09 | 0.06 |
| | 94UG103 | >100 | >100 | >100 | >100 | >100 | 4.3 | 10 | 3.1 | >100 | 7.1 | 5.7 | 2.4 | >100 | 7.0 | 18 | >100 | >100 | >100 | 1 | 0.20 | 0.35 | >100 | 0.46 |
| A | BG505 | 1.3 | >100 | 5.2 | >100 | >100 | 1.4 | 1.1 | 0.49 | 0.76 | 0.72 | >100 | 139 | >100 | 0.75 | 1.5 | 15 | 1.1 | 29 | 564 | 0.12 | 0.09 | 0.12 | 0.09 |
| | KNH1144 | 1.2 | >100 | 0.98 | 1.5 | >100 | 5.1 | 0.45 | 1.3 | 1.1 | 0.32 | 0.42 | 0.66 | >100 | 1.9 | 23 | 37 | 4.3 | 46 | 248 | 1.56 | 0.37 | 0.59 | 0.54 |
| | KNH1207 | 0.38 | >100 | 0.23 | 0.47 | >100 | 1.2 | 0.33 | 0.36 | 0.25 | 0.29 | 0.29 | 0.62 | >100 | 0.57 | 3.0 | 68 | 1.3 | >100 | n.d. | 63 | 0.88 | 0.68 | 0.32 |
| AE | 92TH021 | 0.36 | >100 | 0.12 | 9.1 | >100 | 0.60 | 0.11 | 0.13 | 0.23 | 0.12 | 0.33 | 6.6 | >100 | 0.30 | 0.36 | 0.94 | 0.24 | >100 | 456 | 0.28 | 0.24 | 0.09 | 0.06 |
| | 89.6 | >100 | >100 | 3.0 | 1.8 | >100 | 0.24 | >100 | 0.22 | 2.3 | 14 | >100 | >100 | >100 | 1.4 | 0.60 | >100 | >100 | >100 | 1 | 0.78 | 0.63 | >100 | 1.96 |
| | 6535 | 0.62 | >100 | 0.18 | 0.22 | >100 | 1.9 | 2.0 | 0.19 | 0.16 | 0.42 | 0.16 | 0.13 | >100 | 0.74 | 0.54 | >100 | 62 | >100 | 263 | 0.29 | 0.32 | >100 | 0.15 |
| | 92BR020 | 0.26 | >100 | 0.15 | 0.25 | >100 | 0.64 | 0.20 | 0.23 | 0.32 | 0.14 | 0.13 | 0.18 | >100 | 0.58 | 0.58 | 10 | 0.69 | >100 | 834 | 0.81 | 0.04 | 0.11 | 0.08 |
| | ADA | 45 | >100 | 2.1 | 5.1 | >100 | 2.3 | 2.6 | 1.5 | 3.2 | 1.3 | 0.54 | 0.88 | >100 | 5.6 | 16 | 50 | >100 | >100 | 192 | 0.32 | 0.48 | >100 | 0.62 |
| | BaL | 0.11 | 0.041 | 0.025 | 0.044 | 0.71 | 0.093 | 44 | 0.017 | 0.068 | 1.9 | 1.0 | 21 | >100 | 0.25 | 0.085 | 0.0074 | >100 | 2.8 | 1790 | 0.01 | 0.02 | >100 | 0.12 |
| | CAAN | 2.2 | >100 | 0.93 | 0.49 | >100 | 0.58 | 3.2 | 2.4 | 1.6 | 1.9 | 1.2 | 10 | >100 | 9.4 | 7.9 | 8.4 | 10 | >100 | 1 | 0.25 | 0.42 | 8.86 | 0.46 |
| | DH12 | 46 | >100 | 2.6 | 4.3 | >100 | 3.6 | 32 | 2.6 | 3.4 | 21 | 8.3 | 5.6 | >100 | 9.7 | 10 | 38 | 4.1 | >100 | 823 | 0.12 | 0.40 | >100 | 48 |
| | HxB2 | 0.75 | >100 | 0.067 | 0.24 | >100 | 0.098 | 0.72 | 0.043 | 0.12 | 0.26 | 0.17 | 0.10 | >100 | 0.083 | 0.13 | 0.48 | >100 | >100 | 926 | 0.01 | 0.05 | >100 | >100 |
| | JRCSF | 4.6 | >100 | 0.60 | 0.91 | >100 | 1.5 | 1.3 | 0.43 | 1.6 | 0.56 | 0.70 | 0.92 | >100 | 1.4 | 2.7 | 1.6 | 3.3 | >100 | 182 | 0.12 | 0.14 | >100 | 0.43 |
| | JRFL | 0.064 | >100 | 0.022 | 0.055 | >100 | 0.14 | 0.082 | 0.053 | 0.052 | 0.053 | 0.037 | 0.070 | >100 | 0.11 | 0.42 | 0.35 | 0.13 | 2.0 | 2275 | 71.60 | 0.61 | 0.05 | 0.04 |
| B | MN | 0.15 | >100 | 0.12 | 0.088 | >100 | 0.075 | >100 | 0.072 | 0.13 | >100 | >100 | >100 | >100 | 0.28 | 0.18 | 0.49 | >100 | >100 | 496 | 0.03 | 0.09 | >100 | 20 |
| | PVO4 | 1.1 | >100 | 0.28 | 0.32 | 4.48 | 2.6 | 0.35 | 0.47 | 0.30 | 0.23 | 0.19 | 0.68 | >100 | 0.89 | 2.4 | 7.2 | 2.4 | 28 | 402 | 0.19 | 0.35 | 0.29 | 0.41 |
| | QH0692 | 6.0 | >100 | 2.3 | 2.1 | >100 | 12 | 1.4 | 1.8 | 1.3 | 1.4 | 1.0 | 1.9 | >100 | 6.0 | 35 | 16 | 5.0 | >100 | 198 | 3.23 | 1.84 | 7.28 | 4.83 |
| | REJO | 0.13 | >100 | 0.039 | 0.058 | >100 | 0.13 | 0.050 | 0.034 | 0.065 | 0.15 | 0.094 | 0.066 | >100 | 0.13 | 0.15 | 0.096 | 0.42 | >100 | 273 | 0.04 | 0.09 | >100 | 0.79 |
| | RHPA4 | 0.20 | >100 | 0.048 | 0.12 | >100 | 0.15 | 0.030 | 0.050 | 0.074 | 0.029 | 0.022 | 0.052 | >100 | 0.089 | 0.23 | 1.8 | 0.16 | 3.4 | 705 | 21 | 0.04 | 1.37 | 0.04 |
| | SC422 | 0.50 | >100 | 0.12 | 0.36 | >100 | 0.52 | 0.13 | 0.081 | 0.15 | 0.19 | 0.11 | 0.39 | >100 | 0.24 | 0.96 | 1.1 | >100 | >100 | 222 | 0.30 | 0.09 | >100 | 2.70 |
| | SF162 | >100 | >100 | 2.4 | 22 | >100 | 0.39 | >100 | 0.19 | 0.99 | 44 | 12 | 0.89 | >100 | 0.45 | 0.45 | 6.0 | >100 | >100 | 834 | 0.04 | 0.14 | >100 | 0.67 |
| | SS1196 | >100 | >100 | 8.9 | 35 | >100 | 1.1 | >100 | 0.37 | 9.0 | 19 | 13 | 3.6 | >100 | 1.3 | 2.7 | >100 | >100 | >100 | 378 | 0.09 | 0.22 | >100 | >100 |
| | TRJO | >100 | >100 | 272 | >100 | >100 | 0.59 | 0.24 | 0.11 | 62 | 0.080 | 0.080 | 0.12 | >100 | 0.19 | 0.16 | >100 | >100 | >100 | 246 | 0.12 | 0.06 | >100 | 1.25 |
| | TRO11 | 0.37 | >100 | 0.24 | 0.28 | >100 | 0.47 | 0.080 | 0.18 | 0.18 | 0.049 | 0.035 | 0.068 | >100 | 0.31 | 0.79 | 27 | 0.46 | 99 | 439 | 2.84 | 0.52 | 0.26 | 0.22 |
| | WITO | 0.82 | >100 | 0.13 | 0.12 | >100 | 0.24 | 0.092 | 0.086 | 0.085 | 0.051 | 0.048 | 0.062 | >100 | 0.078 | 0.078 | >100 | 0.24 | >100 | 496 | 1.07 | 0.17 | 2.88 | 0.22 |
| | YU2 | 0.13 | >100 | 0.058 | 0.10 | >100 | 0.65 | 0.085 | 0.18 | 0.087 | 0.067 | 0.056 | 0.11 | >100 | 0.60 | 0.92 | 7.4 | 0.17 | 15 | 1170 | 0.05 | 0.09 | 0.15 | 0.05 |
| | 93IN905 | 0.73 | >100 | 0.17 | 0.36 | >100 | 0.34 | 0.063 | 0.090 | 0.21 | 0.035 | 0.014 | 0.056 | >100 | 0.17 | 0.58 | 40 | 0.33 | 0.59 | 701 | 0.06 | 0.13 | 2.28 | 0.06 |
| | CAP210 | >100 | >100 | >100 | >100 | >100 | >100 | >100 | 45 | >100 | >100 | >100 | >100 | >100 | >100 | >100 | >100 | >100 | >100 | 1 | >100 | >100 | >100 | >100 |
| | CAP45 | >100 | >100 | >100 | >100 | >100 | >100 | >100 | 0.053 | >100 | >100 | >100 | >100 | >100 | 0.13 | 0.053 | >100 | >100 | >100 | 1 | >100 | 0.27 | >100 | 0.06 |
| | DU156 | >100 | >100 | 7.9 | 21 | >100 | 0.12 | 0.51 | 0.034 | 6.6 | 0.11 | 0.067 | 1.7 | >100 | 0.070 | 0.15 | >100 | 0.014 | >100 | 654 | 0.05 | 0.06 | 6.78 | 0.03 |
| | DU172 | 4.8 | >100 | 0.37 | 0.75 | >100 | 0.75 | 0.25 | 0.29 | 0.60 | 0.27 | 0.16 | 0.21 | >100 | 0.38 | 0.76 | 67 | 1.5 | 10 | 589 | >100 | >100 | 0.56 | 0.29 |
| | DU422 | >100 | >100 | >100 | >100 | >100 | >100 | >100 | >100 | >100 | >100 | >100 | >100 | >100 | >100 | >100 | >100 | >100 | >100 | 1 | >100 | >100 | >100 | 3.37 |
| C | IAVIC22 | >100 | >100 | 20 | 62 | >100 | 0.066 | 2.6 | 2.6 | 40 | 2.4 | 2.0 | 2.6 | >100 | 7.9 | 21 | >100 | >100 | >100 | 177 | 0.28 | 0.54 | >100 | 67 |
| | ZM53 | 1.1 | >100 | 0.45 | 0.79 | >100 | 1.1 | 0.39 | 0.35 | 0.36 | 0.26 | 0.52 | 0.36 | >100 | 0.69 | 3.6 | >100 | 0.77 | 24 | n.t. | 0.54 | 0.79 | 0.63 | 0.25 |
| | ZM109 | 2.2 | >100 | 0.98 | 1.0 | >100 | 1.3 | 0.49 | 0.62 | 1.4 | 0.40 | 0.44 | 1.0 | >100 | 7.4 | 9.9 | >100 | >100 | >100 | n.t. | 28 | 0.11 | >100 | 5.06 |
| | ZM135 | 3.2 | >100 | 1.3 | 1.9 | >100 | 7.5 | 4.5 | 1.5 | 1.3 | 1.3 | 1.6 | 3.1 | >100 | 7.4 | 14 | >100 | 45 | >100 | 1 | 63 | 1.17 | >100 | >100 |
| | ZM214 | 0.17 | >100 | 0.12 | 0.12 | 0.12 | 0.013 | 0.084 | 0.14 | 0.16 | 0.080 | 0.012 | 0.015 | >100 | 0.19 | 0.14 | 0.74 | 0.021 | 0.46 | 1 | 0.18 | 0.31 | 0.15 | 0.21 |
| | ZM249 | 0.43 | >100 | 0.16 | 0.43 | >100 | 0.15 | 0.055 | 0.080 | 0.14 | 0.046 | 0.044 | 0.058 | >100 | 0.11 | 0.58 | 5.9 | >100 | >100 | 330 | 0.08 | 0.09 | 22 | 0.10 |

Figure 8

B

| Ab name | Breadth (% viruses) IC50 <0.1 µg/mL | IC50 <1 µg/mL | IC50 <10 µg/mL | IC50 <50 µg/mL | GeoMean IC50 (µg/mL) | SHM (VH+JH) | SHM (VK+JK) |
|---|---|---|---|---|---|---|---|
| 66B | 3% | 45% | 70% | 75% | 0.8 | 9.6 | 12.7 |
| 71B | 3% | 3% | 3% | 3% | 0.04 | 9.9 | 11.0 |
| 71C | 15% | 63% | 85% | 88% | 0.50 | 10.8 | 12.4 |
| 71D2b | 10% | 55% | 75% | 83% | 0.73 | 10.5 | 12.7 |
| 71F | 0% | 5% | 8% | 8% | 0.72 | 12.5 | 11.0 |
| 71G | 13% | 58% | 90% | 93% | 0.57 | 13.1 | 12.4 |
| 71H | 23% | 55% | 75% | 83% | 0.48 | 13.1 | 13.0 |
| 71I1a | 30% | 75% | 95% | 98% | 0.28 | 13.7 | 13.0 |
| 71J2a | 15% | 55% | 85% | 88% | 0.56 | 10.8 | 12.7 |
| 71K | 23% | 63% | 80% | 90% | 0.42 | 14.2 | 13.0 |
| 71L | 30% | 63% | 80% | 85% | 0.27 | 14.2 | 13.0 |
| 71M1a | 20% | 58% | 80% | 85% | 0.55 | 14.5 | 12.4 |
| 71N1a | 0% | 0% | 0% | 0% | / | 14.5 | 12.7 |
| 71O | 10% | 65% | 95% | 95% | 0.630 | 16.0 | 12.7 |
| 71P | 8% | 55% | 78% | 95% | 1.1 | 16.0 | 13.0 |
| 77B1b | 5% | 18% | 40% | 58% | 4.2 | 11.3 | 12.7 |
| 77C | 5% | 33% | 53% | 58% | 0.92 | 11.9 | 13.7 |
| 77D | 0% | 5% | 15% | 30% | 7.3 | 13.1 | 12.4 |
| PC63M33 | 25% | 65% | 83% | 88% | 125 | | |
| min VRC01 | 25% | 68% | 78% | 83% | 0.37 | 6.5 | 7.2 |
| VRC01 | 30% | 88% | 93% | 93% | 0.21 | 29.3 | 21.3 |
| min 12A21 | 8% | 33% | 48% | 50% | 0.64 | 8.3 | 3.4 |
| 12A21 | 25% | 65% | 83% | 88% | 0.47 | 21.9 | 12.4 |

| Breadth (viruses neutralized) | Potency mAb (GeoMean IC50 ) | Potency Plasma (GeoMean ID50 ) |
|---|---|---|
| 0-10% | 10-50 µg/mL | / |
| 10-25% | 1-10 µg/mL | 50-100 |
| 25-50% | 0.1-1 µg/mL | 100-300 |
| 50-75% | 0.01-0.1 µg/mL | 300-900 |
| 75-100% | <0.01 µg/mL | >900 |

Figure 8 (cont.)

A

| Time point | | PC63V72 | PC63V78 | PC63V78 | PC63V78 | PC63V81 | PC63V36 | VRC01 | VRC01 | 12A21 | 12A21 |
|---|---|---|---|---|---|---|---|---|---|---|---|
| Ab name | | P2C3 | P2C6 | P1D7#1a | P3B9 | P3B6 | Serum | Min | Mat | Min | Mat |
| Neutralization $IC_{50}$ (mg/mL) | | | | | | | | | | | |
| Subtype | HIV.1 Isolate | PCIN 66B | PCIN 71G | PCIN 71I | PCIN 71L | PCIN 77D | PC63 M33 serum | Min VRC01 | Mat VRC01 | Min 12A21 | Mat 12A21 |
| - | aMLV | >100 | >100 | >100 | >100 | >100 | <20 | >100 | >100 | >100 | >100 |
| A | 0260.v5.c1 | 1.5 | 1.7 | 1.7 | 0.58 | 0.95 | NT | 0.85 | 0.33 | 0.51 | 0.19 |
| | 0330.v4.c3 | 0.45 | 0.29 | 0.19 | 0.077 | 74 | 735 | NT | NT | NT | NT |
| | 191084 B7.19 | 0.86 | 0.21 | 0.17 | 0.19 | >100 | 634 | 0.057 | 0.043 | 7.3 | 0.042 |
| | 191955 A11 | >100 | 1.2 | 0.036 | 6.3 | >100 | **2018** | >100 | >100 | >100 | >100 |
| | 9004SS A3 4 | >100 | >100 | >100 | >100 | >100 | NT | >100 | >100 | >100 | >100 |
| | MS208.A1 | 0.73 | 0.28 | 0.24 | 0.19 | >100 | 530 | >100 | 0.024 | >100 | 6.0 |
| | Q168ENVa2 | NT | NT | NT | NT | NT | NT | NT | NT | NT | NT |
| | Q23ENV17 | 0.36 | 0.18 | 0.15 | 0.080 | 0.17 | 736 | 0.074 | 0.042 | 0.12 | 0.026 |
| | Q259ENVd2.17 | >100 | 0.77 | 0.073 | >100 | >100 | 93 | 0.20 | 0.029 | >100 | 0.10 |
| | Q461ENVe2 | 6.8 | 7.7 | 7.1 | 2.2 | >100 | 57 | 1.2 | 0.27 | 0.29 | 0.087 |
| | Q769ENVd22 | 0.22 | 0.094 | 0.070 | 0.079 | >100 | **1355** | 0.036 | 0.019 | 0.035 | **0.0089** |
| | Q842ENVd12 | >100 | >100 | >100 | >100 | >100 | NT | >100 | >100 | >100 | >100 |
| AC | 3301.v1.c24 | 0.68 | 0.49 | 0.39 | 0.33 | >100 | 558 | 0.11 | 0.14 | >100 | 0.049 |
| | 6041.v3.c23 | 0.063 | 0.066 | 0.057 | 0.022 | 0.097 | <20 | 1.8 | 0.013 | 0.014 | **0.0069** |
| | 6540.v4.c1 | >100 | >100 | >100 | >100 | >100 | 24 | >100 | >100 | >100 | >100 |
| | 6545.v4.c1 | >100 | >100 | >100 | >100 | >100 | 2 | >100 | >100 | >100 | >100 |
| ACD | 0815.v3.c3 | 0.12 | 0.057 | 0.062 | 0.032 | >100 | **1019** | 0.056 | **0.0100** | 0.033 | 0.012 |
| | 3103.v3.c10 | >100 | 4.0 | 6.4 | >100 | >100 | <20 | 4.1 | 1.3 | >100 | 0.47 |
| AE | 620345.c01 | >100 | >100 | >100 | >100 | >100 | 170 | >100 | >100 | >100 | >100 |
| | BJOX009000.02.4 | >100 | 4.2 | 2.9 | 11 | >100 | <20 | 2.9 | 0.64 | >100 | >100 |
| | BJOX010000.06.2 | >100 | 16 | 8.5 | 9.9 | >100 | 57 | 6.5 | 3.9 | >100 | 8.0 |
| | BJOX015000.11.5 | >100 | 1.4 | 0.99 | 0.44 | >100 | 36 | 2.0 | 0.19 | 0.60 | 0.13 |
| | BJOX025000.01.1 | >100 | 0.58 | 0.49 | 26 | 0.16 | 311 | 7.3 | 2.7 | 0.27 | 0.13 |
| | BJOX028000.10.3 | 0.079 | 0.11 | 0.076 | 0.052 | >100 | **1813** | 11 | 0.086 | 0.029 | **0.0091** |
| | C1080.c03 | 46 | 3.7 | 2.1 | 1.2 | >100 | 466 | >100 | 0.55 | 0.33 | 0.11 |
| | C3347.c11 | 5.9 | 0.042 | 0.034 | 0.016 | 0.016 | **3162** | 0.039 | 0.050 | **0.0090** | 0.011 |
| | C4118.c09 | >100 | >100 | >100 | >100 | >100 | 477 | >100 | >100 | >100 | >100 |
| | CNE5 | 4.0 | 0.29 | 0.18 | 0.35 | >100 | 21 | 0.20 | 0.060 | 0.19 | 0.045 |
| | CNE8 | >100 | 0.44 | 0.36 | 0.36 | >100 | 76 | 0.42 | 0.74 | >100 | 0.28 |
| | R1166.c01 | 4.0 | 0.46 | 0.33 | 0.23 | 2.3 | 337 | 0.62 | 0.39 | 0.17 | 0.097 |
| | R2184.c04 | 4.0 | 0.17 | 0.13 | 0.24 | >100 | 594 | 0.030 | 0.024 | 0.84 | 0.027 |
| | R3265.c06 | 0.72 | 0.57 | 0.78 | 0.21 | >100 | 138 | 0.73 | 0.17 | 0.057 | 0.044 |
| AG | 928.28 | 0.42 | 0.69 | 0.39 | 0.13 | >100 | **1116** | 1.1 | 0.22 | 0.42 | 0.20 |
| | T211.9 | 2.1 | 1.3 | 0.88 | 0.48 | >100 | NT | >100 | 0.90 | >100 | >100 |
| | T235.47 | >100 | 0.042 | 0.043 | 0.059 | >100 | 432 | >100 | 0.028 | 0.40 | 0.012 |
| | T250.4 | >100 | >100 | >100 | >100 | >100 | 25 | >100 | >100 | >100 | >100 |
| | T251.18 | 9.7 | 7.3 | 8.8 | 1.9 | >100 | 114 | 1.7 | 1.3 | 1.9 | 0.43 |
| | T255.34 | 0.37 | 0.20 | 0.23 | 0.070 | 1.0 | 264 | 0.71 | 0.39 | 0.072 | 0.028 |
| | T257.31 | 0.57 | 0.96 | 1.2 | 0.22 | >100 | 203 | 0.71 | 0.31 | 0.078 | 0.028 |
| | T263.8 | 0.35 | 0.14 | 0.17 | 0.070 | 1.6 | NT | 0.094 | 0.12 | 0.11 | 0.044 |
| | T278.5 | >100 | >100 | >100 | >100 | >100 | <20 | >100 | >100 | >100 | >100 |
| B | 1006.11.C3.1601 | 0.25 | 0.18 | 0.13 | 0.049 | >100 | **1173** | 2.5 | 0.095 | 0.15 | 0.036 |
| | 1012.11.TC21.3257 | 0.28 | 0.87 | 0.49 | 0.65 | >100 | 146 | 0.035 | 0.070 | >100 | 0.035 |
| | 1054.07.TC4.1499 | 2.2 | 3.3 | 3.1 | 1.9 | >100 | 33 | 0.20 | 0.83 | >100 | 0.50 |
| | 1056.10.TA11.1826 | 2.0 | 1.1 | 0.68 | 0.20 | >100 | 106 | 0.33 | 0.55 | >100 | 0.18 |
| | 62357.14.D3.4589 | 0.29 | 0.19 | 0.10 | 0.083 | 0.029 | **4317** | 0.43 | 0.39 | 0.44 | 0.11 |
| | 6240.08.TA5.4622 | 6.5 | 4.1 | 2.5 | 0.85 | >100 | 71 | 1.6 | 0.60 | 1.2 | 0.39 |
| | 6244.13.B5.4567 | 0.57 | 0.95 | 0.65 | 0.26 | 1.2 | 340 | 0.16 | 0.12 | 0.21 | 0.072 |
| | AC10.0.29 | >100 | 1.9 | 1.0 | >100 | >100 | 79 | 1.6 | 1.1 | 8.3 | 0.63 |
| | CAAN5342.A2 | 0.72 | 2.6 | 2.2 | 0.76 | >100 | 38 | 0.45 | 0.55 | >100 | 0.49 |
| | SC05.8C11.2344 | 22 | 2.3 | 1.8 | 6.7 | >100 | 95 | 0.26 | 0.49 | >100 | 1.8 |
| | TRO.11 | 0.47 | 0.17 | 0.14 | 0.065 | >100 | 649 | 0.79 | 0.25 | 0.20 | 0.077 |
| | WEAU.d15.410.787 | 1.81 | 0.27 | 0.20 | 0.098 | >100 | 214 | 0.027 | 0.046 | 9.98 | 0.012 |
| BC | CNE17 | >100 | 3.7 | 2.6 | 5.93 | >100 | <20 | 0.18 | 0.38 | >100 | 2.7 |
| | CNE19 | 0.092 | 0.12 | 0.098 | 0.036 | 0.41 | 708 | 0.027 | 0.074 | 0.13 | 0.019 |
| | CNE20 | 0.051 | 0.12 | 0.12 | 0.048 | >100 | **1510** | >100 | 1.3 | >100 | **0.0078** |
| | CNE21 | 0.25 | 0.55 | 0.50 | 0.19 | >100 | **1668** | 0.58 | 0.078 | 2.0 | 0.016 |
| | CNE30 | 6.1 | 3.2 | 2.6 | 0.99 | 3.6 | 441 | 0.60 | 0.28 | 0.45 | 0.14 |
| | CNE52 | 0.87 | 0.60 | 0.41 | 0.11 | 1.2 | 630 | 0.10 | 0.084 | 0.092 | 0.025 |
| | CNE53 | 0.10 | 0.11 | 0.069 | 0.057 | 0.061 | **11658** | 0.035 | 0.046 | 0.065 | 0.027 |
| | CNE58 | 0.71 | 0.10 | 0.12 | 0.076 | 1.3 | **2315** | 0.49 | 0.087 | >100 | 0.078 |

Figure 9

A (cont.)

| Time point | | PC63V72 | PC63V78 | PC63V78 | PC63V78 | PC63V81 | PC63V36 | VRC01 | VRC01 | 12A21 | 12A21 |
|---|---|---|---|---|---|---|---|---|---|---|---|
| Ab name | | P2C3 | P2C6 | P1D7#1a | P3B9 | P3B6 | Serum | Min | Mat | Min | Mat |
| Neutralization $IC_{50}$ (mg/mL) | | | | | | | | | | | |
| Subtype | HIV.1 isolate | PCIN 66B | PCIN 71G | PCIN 71I | PCIN 71L | PCIN 77D | PC63 M33 serum | Min VRC01 | Mat VRC01 | Min 12A21 | Mat 12A21 |
| | 1394C9G1(Rev.) | 0.12 | 0.43 | 0.23 | 0.18 | >100 | 465 | 1.2 | 0.15 | 0.058 | 0.058 |
| | 7030102001E5(Rev.) | 12 | 1.4 | 0.91 | 0.39 | >100 | 701 | 0.23 | 0.37 | >100 | 0.22 |
| | 8F1266.431a | 0.68 | 0.56 | 0.056 | 0.13 | >100 | 355 | **0.0079** | **0.0077** | >100 | >100 |
| | Ce0393 C3 | 0.15 | 0.38 | 0.26 | 0.15 | >100 | 299 | >100 | 0.12 | 0.015 | 0.013 |
| | Ce0682 E4 | >100 | >100 | >100 | >100 | >100 | NT | >100 | >100 | >100 | >100 |
| | Ce1086 B2 | >100 | >100 | >100 | >100 | >100 | NT | >100 | >100 | >100 | >100 |
| | Ce1172 H1 | >100 | >100 | >100 | 3.2 | >100 | <20 | >100 | >100 | >100 | >100 |
| | Ce1176 A3 | 4.0 | 1.4 | 1.2 | 0.72 | 68 | 129 | 1.5 | 0.77 | 0.45 | 0.22 |
| | Ce2010 F5 | 1.1 | 0.54 | 0.52 | 0.11 | 6.8 | 208 | 0.31 | 0.19 | 0.42 | 0.22 |
| | Ce2060 G9 | 1.6 | 1.0 | 1.3 | 0.89 | 18 | 203 | 0.34 | 0.14 | 0.25 | 0.11 |
| | Ce703010054 2A2 | >100 | 2.0 | 2.8 | 2.4 | >100 | <20 | 0.99 | 0.43 | >100 | 0.16 |
| | Ce704809221 1B3 | 3.5 | 0.52 | 0.79 | 0.33 | >100 | 58 | 0.32 | 0.24 | 0.29 | 0.20 |
| | Du156.12 | >100 | 0.088 | 0.11 | 0.18 | >100 | 311 | 0.029 | 0.036 | >100 | 0.22 |
| | Du172.17 | 0.73 | 0.22 | 0.12 | 0.097 | 0.40 | 401 | >100 | >100 | 0.017 | 0.068 |
| C | Du422.1 | >100 | >100 | >100 | >100 | >100 | 31 | >100 | >100 | >100 | 2.0 |
| | HIV-0013095.2.11 | 1.7 | 0.52 | 0.56 | 0.46 | >100 | 92 | 0.035 | 0.038 | >100 | 0.048 |
| | HIV-001428.2.42 | 0.45 | 0.062 | 0.058 | 0.077 | >100 | **1077** | **0.0067** | 0.011 | 2.2 | **0.0087** |
| | HIV-16055.2.3 | 0.65 | 0.24 | 0.20 | 0.26 | >100 | 431 | 0.027 | 0.024 | 0.052 | **0.0087** |
| | HIV-16845.2.22 | >100 | >100 | >100 | >100 | >100 | NT | >100 | >100 | >100 | >100 |
| | ZM109F.PB4 | 1.1 | 0.44 | 0.55 | 0.23 | >100 | <20 | 0.29 | 0.035 | >100 | 0.21 |
| | ZM135M.PL10a | 2.2 | 2.0 | 2.3 | 0.62 | >100 | 74 | >100 | 0.57 | >100 | >100 |
| | ZM197M.PB7 | >100 | 0.53 | 0.66 | 0.55 | >100 | 281 | 0.27 | 0.28 | >100 | >100 |
| | ZM214M.PL15 | 1.3 | 1.7 | 2.2 | 0.43 | 1.7 | 199 | 0.48 | 0.36 | 0.31 | 0.085 |
| | ZM233M.PB6 | >100 | 4.0 | 2.3 | >100 | >100 | 57 | >100 | >100 | >100 | >100 |
| | ZM246F.D5 | >100 | 0.77 | 0.87 | 0.22 | >100 | <20 | >100 | 2.2 | >100 | 0.088 |
| | ZM247F.F7 | >100 | >100 | >100 | >100 | >100 | <20 | >100 | 0.16 | >100 | 0.097 |
| | ZM249M.B10 | 0.64 | 0.12 | 0.13 | 0.051 | >100 | 301 | 0.044 | 0.056 | >100 | 0.031 |
| | ZM249M.PL1 | 0.78 | 0.16 | 0.11 | 0.062 | >100 | 313 | 0.044 | 0.073 | >100 | 0.060 |
| | ZM53M.PB12 | 7.2 | 2.7 | 2.9 | 1.7 | 32 | 119 | 0.69 | 0.42 | 0.53 | 0.22 |
| | 3817.v2.c59 | >100 | 2.6 | 3.4 | 3.1 | >100 | 232 | >100 | >100 | 3.8 | 0.82 |
| | 6480.v4.c25 | 0.83 | 0.083 | 0.12 | 0.091 | >100 | 416 | 0.031 | 0.029 | 0.090 | 0.016 |
| CD | 6811.v7.c18 | 1.5 | 0.86 | 1.1 | 0.72 | >100 | 141 | 0.045 | 0.068 | 0.20 | 0.028 |
| | 6952.v1.c20 | >100 | 0.17 | 0.16 | 0.55 | >100 | 230 | 0.063 | 0.020 | >100 | >100 |
| | 89.F1 2 25 | >100 | >100 | >100 | >100 | >100 | NT | >100 | >100 | >100 | >100 |
| | 191821 E6 1 | >100 | >100 | >100 | >100 | >100 | NT | >100 | >100 | >100 | >100 |
| D | 231965.c01 | >100 | 2.3 | 2.8 | >100 | >100 | 59 | 0.25 | 0.32 | >100 | >100 |
| | 3016.v5.c45 | >100 | 0.24 | 0.36 | 4.4 | >100 | NT | 1.7 | 0.068 | 0.23 | 0.048 |
| | A07412M1.vrc12 | 0.23 | 0.29 | 0.18 | 0.18 | >100 | **1037** | 0.11 | 0.088 | 0.027 | 0.016 |
| | P0402 c2 11 | 0.99 | 0.54 | 0.54 | 0.46 | >100 | 431 | 0.050 | 0.038 | 0.052 | 0.056 |
| | P1981 C5 3 | >100 | 4.27 | 4.14 | 15 | >100 | 62 | 0.055 | 0.079 | 14 | 0.19 |
| | X1193 c1 | 0.78 | 0.28 | 0.17 | 0.28 | >100 | 344 | **0.0026** | **0.0013** | 6.46 | 0.066 |
| G | X1254 c3 | >100 | 1.39 | 1.10 | >100 | >100 | 68 | 0.019 | 0.024 | >100 | 0.15 |
| | X1632 S2 B10 | 0.70 | 1.25 | 1.14 | 1.03 | >100 | 193 | **0.0028** | **0.0047** | >100 | 0.055 |
| | X2088 c9 | >100 | >100 | >100 | >100 | >100 | <20 | >100 | >100 | >100 | >100 |
| | X2131 C1 B5 | 3.61 | 0.80 | 0.81 | 2.71 | >100 | 411 | **0.0075** | 0.014 | >100 | 0.26 |

Figure 9 (cont.)

B

| Env Subtype | GeoMean (IC50 mg/mL) | | | | | | | | | |
|---|---|---|---|---|---|---|---|---|---|---|
| | PCIN 66B | PCIN 71G | PCIN 71I | PCIN 71L | PCIN 77D | PC63 M33 serum | Min VRC01 | Mat VRC01 | Min 12A21 | Mat 12A21 |
| A | 0.80 | 0.54 | 0.24 | 0.33 | 2.3 | 476 | 0.18 | 0.058 | 0.34 | 0.100 |
| AC | 0.21 | 0.18 | 0.15 | 0.086 | 0.097 | 30 | 0.45 | 0.042 | 0.014 | 0.018 |
| ACD | 0.12 | 0.48 | 0.63 | 0.032 | / | 1019 | 0.48 | 0.12 | 0.033 | 0.076 |
| AE | 2.7 | 0.64 | 0.48 | 0.59 | 0.18 | 234 | 0.83 | 0.28 | 0.14 | 0.087 |
| AG | 0.92 | 0.50 | 0.48 | 0.18 | 1.3 | 205 | 0.61 | 0.27 | 0.24 | 0.057 |
| B | 1.1 | 0.88 | 0.61 | 0.34 | 0.19 | 192 | 0.34 | 0.29 | 0.84 | 0.15 |
| BC | 0.33 | 0.40 | 0.33 | 0.18 | 0.68 | 1448 | 0.16 | 0.15 | 0.23 | 0.051 |
| C | 1.2 | 0.57 | 0.49 | 0.31 | 7.6 | 208 | 0.15 | 0.13 | 0.17 | 0.092 |
| CD | 1.1 | 0.42 | 0.53 | 0.58 | / | 237 | 0.044 | 0.034 | 0.41 | 0.072 |
| D | 0.23 | 0.54 | 0.56 | 0.90 | / | 246 | 0.36 | 0.12 | 0.079 | 0.028 |
| G | 1.2 | 0.98 | 0.85 | 1.4 | / | 191 | 0.012 | 0.014 | 1.7 | 0.11 |
| Overall | 0.93 | 0.58 | 0.46 | 0.34 | 1.1 | 255 | 0.21 | 0.13 | 0.25 | 0.084 |

| Env Subtype | Breadth (% viruses) | | | | | | | | | |
|---|---|---|---|---|---|---|---|---|---|---|
| | PCIN 66B | PCIN 71G | PCIN 71I | PCIN 71L | PCIN 77D | PC63 M33 serum | Min VRC01 | Mat VRC01 | Min 12A21 | Mat 12A21 |
| A | 64% | 82% | 82% | 73% | 27% | 100% | 60% | 70% | 50% | 70% |
| AC | 50% | 50% | 50% | 50% | 25% | 25% | 50% | 50% | 25% | 50% |
| ACD | 50% | 100% | 100% | 50% | 0% | 50% | 100% | 100% | 50% | 100% |
| AE | 50% | 86% | 86% | 86% | 21% | 79% | 79% | 86% | 64% | 79% |
| AG | 67% | 78% | 78% | 78% | 22% | 71% | 56% | 78% | 67% | 67% |
| B | 92% | 100% | 100% | 92% | 17% | 83% | 100% | 100% | 58% | 100% |
| BC | 88% | 100% | 100% | 100% | 63% | 88% | 88% | 100% | 63% | 100% |
| C | 62% | 79% | 79% | 79% | 21% | 77% | 62% | 76% | 38% | 72% |
| CD | 40% | 80% | 80% | 80% | 0% | 100% | 60% | 60% | 60% | 60% |
| D | 25% | 75% | 75% | 50% | 0% | 100% | 75% | 75% | 50% | 50% |
| G | 57% | 86% | 86% | 71% | 0% | 86% | 86% | 86% | 43% | 86% |
| Overall | 63% | 84% | 84% | 79% | 21% | 80% | 72% | 81% | 51% | 77% |

| Breadth (viruses neutralized) | Potency mAb (GeoMean $IC_{50}$) | Potency Plasma (GeoMean $ID_{50}$) |
|---|---|---|
| 0-10% | 10-50 μg/mL | / |
| 10-25% | 1-10 μg/mL | 50-100 |
| 25-50% | 0.1-1 μg/mL | 100-300 |
| 50-75% | 0.01-0.1 μg/mL | 300-900 |
| 75-100% | <0.01 μg/mL | >900 |

Figure 9 (cont.)

ANTI-HIV ANTIBODIES

CROSS-REFERENCE TO RELATED APPLICATIONS

This application is the U.S. national phase of International Application No. PCT/US2019/057180, filed Oct. 21, 2019, which designated the U.S. and claims the benefit of priority of U.S. Provisional Application No. 62/748,610, filed Oct. 22, 2018, each of which is herein incorporated by reference in its entirety.

GOVERNMENT INTEREST

The invention was made with government support under Grant No. USAID Cooperative Agreement AID-OAA-A-11-00020 awarded by the USAID. The U.S. government has certain rights in the invention.

REFERENCE TO SEQUENCE LISTING SUBMITTED ELECTRONICALLY

The content of the electronically submitted sequence listing (Name: 6765_0310 Sequence_Listing.txt; Size: 270, 480 bytes; and Date of Creation: Apr. 8, 2025) is incorporated herein by reference in its entirety.

FIELD OF THE INVENTION

The field of the invention generally relates to anti-HIV Env antibodies and their use in the treatment or prevention of HIV/AIDS.

BACKGROUND

In 2015, there were approximately 2.1 million new human immunodeficiency virus (HIV) infections, over 36.7 million people living with HIV, and 1.1 million acquired immune deficiency syndrome (AIDS) related deaths. unaids.org/en/resources/fact-sheet (accessed on Jun. 29, 2017) While great progress has been made in the treatment of HIV/AIDS, all individuals living with HIV will have to be treated with anti-retroviral therapy (ART) for the rest of their lives since drug therapy is unable to clear latent viral reservoirs that exist in resting CD4+ T cells at a frequency of about $1/10^6$ cells. See, Eriksson, S. 2013. *PLOS Pathog* 9: e1003174.

HIV isolates can be classified into different groups and clades based on genotype and geographic location. For example, the population episensus (i.e., epitope based consensus sequence) antigen is central to the B clade epidemic in the United States while the population episensus antigen is central to the HIV C clade epidemic in South Africa. Broadly neutralizing anti-Env antibodies, for example PGT-121 can neutralize more than one HIV isolate. U.S. Pat. No. 9,464,131.

Until a vaccine is discovered, many agree that a single product or approach will not completely halt new HIV infections. Accordingly, the use of HIV broadly neutralizing antibodies (bnAbs) has the potential to complement existing prevention methods by addressing important shortfalls or gaps in current product profiles. To achieve the goal of making bnAbs affordable and feasible products for widespread use in HIV prevention efforts, maximizing the potency of current and future bnAb candidates represents a promising and inadequately explored opportunity.

Thus, there remains a need for the development of broadly neutralizing antibodies that can be used in the treatment and prevention of HIV.

BRIEF SUMMARY

In one aspect, provided herein are monoclonal antibodies that specifically bind to HIV Env. In some embodiments, an antibody described herein is a monoclonal antibody. In some embodiments, an antibody described herein is a human antibody. In some embodiments, an antibody described herein is a broadly neutralizing antibody. In some embodiments, an antibody described herein specifically binds the Env of at least one HIV isolate in the indicator virus panels of FIGS. 8 and 9. In some embodiments, an antibody described herein specifically binds the Env of at least two, at least three, at least four, or at least five HIV isolates in the indicator virus panel of FIGS. 8 and 9. In some embodiments, an antibody described herein is a VRCO1 class antibody. In some embodiments, an antibody described herein binds Env at the CD4 receptor binding site (CD4bs) epitope region.

In one aspect, provided herein are pharmaceutical compositions comprising a monoclonal antibody that specifically binds to HIV Env described herein.

In one aspect, provided herein are isolated polynucleotides encoding a monoclonal antibody that specifically binds to HIV Env described herein.

In one aspect, provided herein are methods of producing a monoclonal antibody that specifically binds to HIV Env described herein.

In one aspect, provided herein are methods of neutralizing an HIV virus, comprising contacting the virus with a monoclonal antibody that specifically binds to HIV Env described herein.

In one aspect, provided herein are methods of reducing the likelihood of HIV infection in a subject exposed to HIV comprising administering to the subject a monoclonal antibody that specifically binds to HIV Env described herein.

In one aspect, provided herein are methods of treating HIV/AIDS comprising administering to a subject in need thereof a monoclonal antibody that specifically binds to HIV Env described herein.

In one aspect, provided herein are methods of producing an engineered variant of a monoclonal antibody that specifically binds to HIV Env described herein.

In some embodiments, the disclosure provides:

[1.] An isolated monoclonal antibody that specifically binds to HIV Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D;

[2.] an isolated monoclonal antibody that specifically binds to HIV Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C;

[3.] an isolated monoclonal antibody that specifically binds to HIV Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of PCIN63-71I1a, or PCIN63-71L;

[4.] an isolated monoclonal antibody that specifically binds to HIV Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 37-54;

[5.] an isolated monoclonal antibody that specifically binds to HIV Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 37, 39, 40, 42-48, or 50-53;

[6.] an isolated monoclonal antibody that specifically binds to HIV Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 44 or 47;

[7.] an isolated monoclonal antibody that specifically binds to HIV Env and comprises a VH CDR1, VH CDR2, VH CDR3, VL CDR1, VL CDR2, and VL CDR3, wherein the VH CDR3 comprises the VH CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D comprising 0, 1, 2, 3, 4, or 5 substitutions, insertions, or deletions;

[8.] an isolated monoclonal antibody that specifically binds to HIV Env and comprises a VH CDR1, VH CDR2, VH CDR3, VL CDR1, VL CDR2, and VL CDR3, wherein the VH CDR3 comprises the VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions;

[9.] an isolated monoclonal antibody that specifically binds to HIV Env and comprises a VH CDR1, VH CDR2, VH CDR3, VL CDR1, VL CDR2, and VL CDR3, wherein the VH CDR3 comprises the VH CDR3 of PCIN63-71I1a, or PCIN63-71L comprising 0, 1, 2, 3, 4, or 5 substitutions, insertions, or deletions;

[10.] an isolated monoclonal antibody that specifically binds to HIV Env and comprises a VH CDR1, VH CDR2, VH CDR3, VL CDR1, VL CDR2, and VL CDR3, wherein the VH CDR3 comprises the amino acid sequence of SEQ ID NO: 37-54 comprising 0, 1, 2, 3, 4, or 5 substitutions, insertions, or deletions;

[11.] an isolated monoclonal antibody that specifically binds to HIV Env and comprises a VH CDR1, VH CDR2, VH CDR3, VL CDR1, VL CDR2, and VL CDR3, wherein the VH CDR3 comprises the amino acid sequence of SEQ ID NO: 37, 39, 40, 42-48, or 50-53 comprising 0, 1, 2, 3, 4, or 5 substitutions, insertions, or deletions;

[12.] an isolated monoclonal antibody that specifically binds to HIV Env and comprises a VH CDR1, VH CDR2, VH CDR3, VL CDR1, VL CDR2, and VL CDR3, wherein the VH CDR3 comprises the amino acid sequence of SEQ ID NO: 44 or 47 comprising 0, 1, 2, 3, 4, or 5 substitutions, insertions, or deletions;

[13.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to the VH CDR1 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D;

(b) the VH CDR2 comprises an amino acid sequence that is at least about 90%, 95%, 97%, 98%, 99% or 100% identical to the VH CDR2 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D; and (c) the VH CDR3 comprises an amino acid sequence that is at least about 90%, 95%, 97%, 98%, 99% or 100% identical to the VH CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D;

[14.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to the VH CDR1 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C;

(b) the VH CDR2 comprises an amino acid sequence that is at least about 90%, 95%, 97%, 98%, 99% or 100% identical to the VH CDR2 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C; and (c) the VH CDR3 comprises an amino acid sequence that is at least about 90%, 95%, 97%, 98%, 99% or 100% identical to the VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C;

[15.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to the VH CDR1 of PCIN63-71I1a, or PCIN63-71L;

(b) the VH CDR2 comprises an amino acid sequence that is at least about 90%, 95%, 97%, 98%, 99% or 100% identical to the VH CDR2 of PCIN63-71I1a, or PCIN63-71L; and (c) the VH CDR3 comprises an amino acid sequence that is at least about 90%, 95%, 97%, 98%, 99% or 100% identical to the VH CDR3 of PCIN63-71I1a, or PCIN63-71L;

[16.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to SEQ ID NO: 1-18;

(b) the VH CDR2 comprises an amino acid sequence that is at least about 90%, 95%, 97%, 98%, 99% or 100% identical to SEQ ID NO: 19-36; and (c) the VH CDR3 comprises an amino acid sequence that is at least about 90%, 95%, 97%, 98%, 99% or 100% identical to SEQ ID NO: 37-54;

[17.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to SEQ ID NO: 1, 3, 4, 6-12, or 14-17;

(b) the VH CDR2 comprises an amino acid sequence that is at least about 90%, 95%, 97%, 98%, 99% or 100% identical to SEQ ID NO: 19, 21, 22, 24-30, or 32-35; and (c) the VH CDR3 comprises an amino acid sequence that is at least about 90%, 95%, 97%, 98%, 99% or 100% identical to SEQ ID NO: 37, 39, 40, 42-48, or 50-53;

[18.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to SEQ ID NO: 8 or 11;

(b) the VH CDR2 comprises an amino acid sequence that is at least about 90%, 95%, 97%, 98%, 99% or 100% identical to SEQ ID NO: 26 or 29; and (c) the VH CDR3 comprises an amino acid sequence that is at least about 90%, 95%, 97%, 98%, 99% or 100% identical to SEQ ID NO: 44 or 47;

[19.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D comprising 0, 1, 2, 3, 4, or 5 substitutions, insertions, or deletions;

(b) the VH CDR2 comprises the VH CDR2 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D comprising 0, 1, 2, 3, 4, or 5 substitutions, insertions, or deletions; and (c) the VH CDR3 comprises the VH CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D comprising 0, 1, 2, 3, 4, or 5 substitutions, insertions, or deletions;

[20.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions;

(b) the VH CDR2 comprises the VH CDR2 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions; and (c) the VH CDR3 comprises the VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions;

[21.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of PCIN63-71I1a, or PCIN63-71L comprising 0, 1, 2, 3, 4, or 5 substitutions, insertions, or deletions;

(b) the VH CDR2 comprises the VH CDR2 of PCIN63-71I1a, or PCIN63-71L comprising 0, 1, 2, 3, 4, or 5 substitutions, insertions, or deletions; and (c) the VH CDR3 comprises the VH CDR3 of PCIN63-71I1a, or PCIN63-71L comprising 0, 1, 2, 3, 4, or 5 substitutions, insertions, or deletions;

[22.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein
(a) the VH CDR1 comprises the amino acid sequence of SEQ ID NO: 1-18 comprising 0, 1, 2, 3, 4, or 5 substitutions, insertions, or deletions;
(b) the VH CDR2 comprises the amino acid sequence of SEQ ID NO: 19-36 comprising 0, 1, 2, 3, 4, or 5 substitutions, insertions, or deletions; and
(c) the VH CDR3 comprises the amino acid sequence of SEQ ID NO: 37-54 comprising 0, 1, 2, 3, 4, or 5 substitutions, insertions, or deletions;

[23.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein
(a) the VH CDR1 comprises the amino acid sequence of SEQ ID NO: 1, 3, 4, 6-12, or 14-17 comprising 0, 1, 2, 3, 4, or 5 substitutions, insertions, or deletions;
(b) the VH CDR2 comprises the amino acid sequence of SEQ ID NO: 19, 21, 22, 24-30, or 32-35 comprising 0, 1, 2, 3, 4, or 5 substitutions, insertions, or deletions; and
(c) the VH CDR3 comprises the amino acid sequence of SEQ ID NO: 37, 39, 40, 42-48, or 50-53 comprising 0, 1, 2, 3, 4, or 5 substitutions, insertions, or deletions;

[24.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein
(a) the VH CDR1 comprises the amino acid sequence of SEQ ID NO: 8 or 11 comprising 0, 1, 2, 3, 4, or 5 substitutions, insertions, or deletions;
(b) the VH CDR2 comprises the amino acid sequence of SEQ ID NO: 26 or 29 comprising 0, 1, 2, 3, 4, or 5 substitutions, insertions, or deletions; and
(c) the VH CDR3 comprises the amino acid sequence of SEQ ID NO: 44 or 47 comprising 0, 1, 2, 3, 4, or 5 substitutions, insertions, or deletions;

[25.] An isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein
(a) the VH CDR1 comprises the VH CDR1 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D;
(b) the VH CDR2 comprises the VH CDR2 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D; and
(c) the VH CDR3 comprises the VH CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D;

[26.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein
(a) the VH CDR1 comprises the VH CDR1 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C;
(b) the VH CDR2 comprises the VH CDR2 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C; and
(c) the VH CDR3 comprises the VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C;

[27.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein
(a) the VH CDR1 comprises the VH CDR1 of PCIN63-71I1a, or PCIN63-71L;
(b) the VH CDR2 comprises the VH CDR2 of PCIN63-71I1a, or PCIN63-71L; and
(c) the VH CDR3 comprises the VH CDR3 of PCIN63-71I1a, or PCIN63-71L;

[28.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein
(a) the VH CDR1 comprises the amino acid sequence of SEQ ID NO: 1-18;
(b) the VH CDR2 comprises the amino acid sequence of SEQ ID NO: 19-36; and
(c) the VH CDR3 comprises the amino acid sequence of SEQ ID NO: 37-54;

[29.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein
(a) the VH CDR1 comprises the amino acid sequence of SEQ ID NO: 1, 3, 4, 6-12, or 14-17;
(b) the VH CDR2 comprises the amino acid sequence of SEQ ID NO: 19, 21, 22, 24-30, or 32-35; and
(c) the VH CDR3 comprises the amino acid sequence of SEQ ID NO: 37, 39, 40, 42-48, or 50-53;

[30.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein
(a) the VH CDR1 comprises the amino acid sequence of SEQ ID NO: 8 or 11;

(b) the VH CDR2 comprises the amino acid sequence of SEQ ID NO: 26 or 29; and (c) the VH CDR3 comprises the amino acid sequence of SEQ ID NO: 44 or 47;

[31.] the isolated monoclonal antibody of any one of [1] to comprising a heavy chain variable region (VH) and a light chain variable region (VL), wherein the VH comprises one or more of (a) the amino acid sequence of SEQ ID NO: 109-126 or 310-315 at Kabat positions H31-H37;

(b) the amino acid sequence of SEQ ID NO: 127-144 or 316-318 at Kabat positions H52-H56; and (c) the amino acid sequence of SEQ ID NO: 145-162 at Kabat positions H61-H62;

[32.] the isolated monoclonal antibody of any one of [1] to comprising a heavy chain variable region (VH) and a light chain variable region (VL), wherein the VH comprises (a) the amino acid sequence of SEQ ID NO: 109-126 or 310-315 at Kabat positions H31-H37;

(b) the amino acid sequence of SEQ ID NO: 127-144 or 316-318 at Kabat positions H52-H56; and (c) the amino acid sequence of SEQ ID NO: 145-162 at Kabat positions H61-H62;

[33.] the isolated monoclonal antibody of any one of [1] to [32], wherein (a) the VL CDR1 comprises an amino acid sequence that is at least about 90%, 95%, 97%, 98%, 99% or 100% identical to the VL CDR1 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D;

(b) the VL CDR2 comprises an amino acid sequence that is at least about 90%, 95%, 97%, 98%, 99% or 100% identical to the VL CDR2 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D; and (c) the VL CDR3 comprises an amino acid sequence that is at least about 90%, 95%, 97%, 98%, 99% or 100% identical to the VL CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D;

[34.] the isolated monoclonal antibody of any one of [1] to [32], wherein (a) the VL CDR1 comprises an amino acid sequence that is at least about 90%, 95%, 97%, 98%, 99% or 100% identical to the VL CDR1 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C;

(b) the VL CDR2 comprises an amino acid sequence that is at least about 90%, 95%, 97%, 98%, 99% or 100% identical to the VL CDR2 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C; and (c) the VL CDR3 comprises an amino acid sequence that is at least about 90%, 95%, 97%, 98%, 99% or 100% identical to the VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C;

[35.] the isolated monoclonal antibody of any one of [1] to [32], wherein (a) the VL CDR1 comprises an amino acid sequence that is at least about 90%, 95%, 97%, 98%, 99% or 100% identical to the VL CDR1 of PCIN63-71I1a, or PCIN63-71L;

(b) the VL CDR2 comprises an amino acid sequence that is at least about 90%, 95%, 97%, 98%, 99% or 100% identical to the VL CDR2 of PCIN63-71I1a, or PCIN63-71L; and (c) the VL CDR3 comprises an amino acid sequence that is at least about 90%, 95%, 97%, 98%, 99% or 100% identical to the VL CDR3 of PCIN63-71I1a, or PCIN63-71L;

[36.] the isolated monoclonal antibody of any one of [1] to [32], wherein (a) the VL CDR1 comprises the VL CDR1 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D comprising 0, 1, 2, 3, 4, or 5 substitutions, insertions, or deletions;

(b) the VL CDR2 comprises the VL CDR2 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D comprising 0, 1, 2, 3, 4, or 5 substitutions, insertions, or deletions; and (c) the VL CDR3 comprises the VL CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D comprising 0, 1, 2, 3, 4, or 5 substitutions, insertions, or deletions;

[37.] the isolated monoclonal antibody of any one of [1] to [32], wherein (a) the VL CDR1 comprises the VL CDR1 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions;

(b) the VL CDR2 comprises the VL CDR2 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions; and (c) the VL CDR3 comprises the VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions;

[38.] the isolated monoclonal antibody of any one of [1] to [32], wherein (a) the VL CDR1 comprises the VL CDR1 of PCIN63-71I1a, or PCIN63-71L comprising 0, 1, 2, 3, 4, or 5 substitutions, insertions, or deletions;

(b) the VL CDR2 comprises the VL CDR2 of PCIN63-7111a, or PCIN63-71L comprising 0, 1, 2, 3, 4, or 5 substitutions, insertions, or deletions; and (c) the VL CDR3 comprises the VL CDR3 of PCIN63-71I1a, or PCIN63-71L comprising 0, 1, 2, 3, 4, or 5 substitutions, insertions, or deletions;

[39.] the isolated monoclonal antibody of any one of [1] to [32], wherein (a) the VL CDR1 comprises the VL CDR1 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D;

(b) the VL CDR2 comprises the VL CDR2 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D; and (c) the VL CDR3 comprises the VL CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D;

[40.] the isolated monoclonal antibody of any one of [1] to [32], wherein (a) the VL CDR1 comprises the VL CDR1 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C;

(b) the VL CDR2 comprises the VL CDR2 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C; and (c) the VL CDR3 comprises the VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C;

[41.] the isolated monoclonal antibody of any one of [1] to [32], wherein (a) the VL CDR1 comprises the VL CDR1 of PCIN63-71I1a, or PCIN63-71L;

(b) the VL CDR2 comprises the VL CDR2 of PCIN63-7111a, or PCIN63-71L; and (c) the VL CDR3 comprises the VL CDR3 of PCIN63-71I1a, or PCIN63-71L;

[42.] the isolated monoclonal antibody of any one of [1] to [32], wherein (a) the VL CDR1 comprises an amino acid sequence that is at least about 90%, 95%, 97%, 98%, 99% or 100% identical to SEQ ID NO: 55-72;

(b) the VL CDR2 comprises an amino acid sequence that is at least about 90%, 95%, 97%, 98%, 99% or 100% identical to SEQ ID NO: 73-90; and (c) the VL CDR3 comprises an amino acid sequence that is at least about 90%, 95%, 97%, 98%, 99% or 100% identical to SEQ ID NO: 91-108;

[43.] the isolated monoclonal antibody of any one of [1] to [32], wherein (a) the VL CDR1 comprises an amino acid sequence that is at least about 90%, 95%, 97%, 98%, 99% or 100% identical to SEQ ID NO: 55, 57, 58, 60-66, or 68-71;

(b) the VL CDR2 comprises an amino acid sequence that is at least about 90%, 95%, 97%, 98%, 99% or 100% identical to SEQ ID NO: 73, 75, 76, 78-84, or 86-89; and (c) the VL CDR3 comprises an amino acid sequence that is at least about 90%, 95%, 97%, 98%, 99% or 100% identical to SEQ ID NO: 91, 93, 94, 96-102, or 104-107;

[44.] the isolated monoclonal antibody of any one of [1] to [32], wherein (a) the VL CDR1 comprises an amino acid sequence that is at least about 90%, 95%, 97%, 98%, 99% or 100% identical to SEQ ID NO: 62 or 65;

(b) the VL CDR2 comprises an amino acid sequence that is at least about 90%, 95%, 97%, 98%, 99% or 100% identical to SEQ ID NO: 80 or 83; and (c) the VL CDR3 comprises an amino acid sequence that is at least about 90%, 95%, 97%, 98%, 99% or 100% identical to SEQ ID NO: 98 or 101;

[45.] the isolated monoclonal antibody of any one of [1] to [32], wherein (a) the VL CDR1 comprises the amino acid sequence of SEQ ID NO: 55-72 comprising 0, 1, 2, 3, 4, or 5 substitutions, insertions, or deletions;

(b) the VL CDR2 comprises the amino acid sequence of SEQ ID NO: 73-90 comprising 0, 1, 2, 3, 4, or 5 substitutions, insertions, or deletions; and (c) the VL CDR3 comprises the amino acid sequence of SEQ ID NO: 91-108 comprising 0, 1, 2, 3, 4, or 5 substitutions, insertions, or deletions;

[46.] the isolated monoclonal antibody of any one of [1] to [32], wherein (a) the VL CDR1 comprises the amino acid sequence of SEQ ID NO: 55, 57, 58, 60-66, or 68-71 comprising 0, 1, 2, 3, 4, or 5 substitutions, insertions, or deletions;

(b) the VL CDR2 comprises the amino acid sequence of SEQ ID NO: 73, 75, 76, 78-84, or 86-89 comprising 0, 1, 2, 3, 4, or 5 substitutions, insertions, or deletions; and (c) the VL CDR3 comprises the amino acid sequence of SEQ ID NO: 91, 93, 94, 96-102, or 104-107 comprising 0, 1, 2, 3, 4, or 5 substitutions, insertions, or deletions;

[47.] the isolated monoclonal antibody of any one of [1] to [32], wherein (a) the VL CDR1 comprises the amino acid sequence of SEQ ID NO: 62 or 65 comprising 0, 1, 2, 3, 4, or 5 substitutions, insertions, or deletions;
(b) the VL CDR2 comprises the amino acid sequence of SEQ ID NO: 80 or 83 comprising 0, 1, 2, 3, 4, or 5 substitutions, insertions, or deletions; and
(c) the VL CDR3 comprises the amino acid sequence of SEQ ID NO: 98 or 101 comprising 0, 1, 2, 3, 4, or 5 substitutions, insertions, or deletions;

[48.] the isolated monoclonal antibody of any one of [1] to [32], wherein
(a) the VL CDR1 comprises the amino acid sequence of SEQ ID NO: 55-72;
(b) the VL CDR2 comprises the amino acid sequence of SEQ ID NO: 73-90; and
(c) the VL CDR3 comprises the amino acid sequence of SEQ ID NO: 91-108;

[49.] the isolated monoclonal antibody of any one of [1] to [32], wherein
(a) the VL CDR1 comprises the amino acid sequence of SEQ ID NO: 55, 57, 58, 60-66, or 68-71;
(b) the VL CDR2 comprises the amino acid sequence of SEQ ID NO: 73, 75, 76, 78-84, or 86-89; and
(c) the VL CDR3 comprises the amino acid sequence of SEQ ID NO: 91, 93, 94, 96-102, or 104-107;

[50.] the isolated monoclonal antibody of any one of [1] to [32], wherein
(a) the VL CDR1 comprises the amino acid sequence of SEQ ID NO: 62 or 65;
(b) the VL CDR2 comprises the amino acid sequence of SEQ ID NO: 80 or 83; and
(c) the VL CDR3 comprises the amino acid sequence of SEQ ID NO: 98 or 101;

[51.] the isolated monoclonal antibody of any one of to comprising a heavy chain variable region (VH) and a light chain variable region (VL), wherein the VL comprises one or more of
(a) the amino acid sequence of SEQ ID NO: 163-180 or 319-324 at Kabat positions H26-H34;
(b) the amino acid sequence of SEQ ID NO: 181-198 or 325-334 at Kabat positions H49-H56;
(c) the amino acid sequence of SEQ ID NO: 199-216 or 335-339 at Kabat positions H67-H70; and
(d) the amino acid sequence of SEQ ID NO: 217-234 at Kabat positions H89-H97;

[52.] the isolated monoclonal antibody of any one of to comprising a heavy chain variable region (VH) and a light chain variable region (VL), wherein the VL comprises
(a) the amino acid sequence of SEQ ID NO: 163-180 or 319-324 at Kabat positions H26-H34;
(b) the amino acid sequence of SEQ ID NO: 181-198 or 325-334 at Kabat positions H49-H56;
(c) the amino acid sequence of SEQ ID NO: 199-216 or 335-339 at Kabat positions H67-H70; and
(d) the amino acid sequence of SEQ ID NO: 217-234 at Kabat positions H89-H97;

[53.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D VH CDR1, VH CDR2, VH CDR3, VL CDR1, VL CDR2, and VL CDR3, respectively;

[54.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C VH CDR1, VH CDR2, VH CDR3, VL CDR1, VL CDR2, and VL CDR3, respectively;

[55.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the PCIN63-71I1a, or PCIN63-71L VH CDR1, VH CDR2, VH CDR3, VL CDR1, VL CDR2, and VL CDR3, respectively;

[56.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of
(a) SEQ ID NO: 1, 19, 37, 55, 73, and 91, respectively;
(b) SEQ ID NO: 2, 20, 38, 56, 74, and 92, respectively;
(c) SEQ ID NO: 3, 21, 39, 57, 75, and 93, respectively;
(d) SEQ ID NO: 4, 22, 40, 58, 76, and 94, respectively;
(e) SEQ ID NO: 5, 23, 41, 59, 77, and 95, respectively;
(f) SEQ ID NO: 6, 24, 42, 60, 78, and 96, respectively;
(g) SEQ ID NO: 7, 25, 43, 61, 79, and 97, respectively;
(h) SEQ ID NO: 8, 26, 44, 62, 80, and 98, respectively;
(i) SEQ ID NO: 9, 27, 45, 63, 81, and 99, respectively;
(j) SEQ ID NO: 10, 28, 46, 64, 82, and 100, respectively;
(k) SEQ ID NO: 11, 29, 47, 65, 83, and 101, respectively;
(l) SEQ ID NO: 12, 30, 48, 66, 84, and 102, respectively;
(m) SEQ ID NO: 13, 31, 49, 67, 85, and 103, respectively;
(n) SEQ ID NO: 14, 32, 50, 68, 86, and 104, respectively;
(o) SEQ ID NO: 15, 33, 51, 69, 87, and 105, respectively;
(p) SEQ ID NO: 16, 34, 52, 70, 88, and 106, respectively;
(q) SEQ ID NO: 17, 35, 53, 71, 89, and 107, respectively; or
(r) SEQ ID NO: 18, 36, 54, 72, 90, and 108, respectively;

[57.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of
(a) SEQ ID NO: 1, 19, 37, 55, 73, and 91, respectively;
(b) SEQ ID NO: 3, 21, 39, 57, 75, and 93, respectively;
(c) SEQ ID NO: 4, 22, 40, 58, 76, and 94, respectively;
(d) SEQ ID NO: 6, 24, 42, 60, 78, and 96, respectively;
(e) SEQ ID NO: 7, 25, 43, 61, 79, and 97, respectively;
(f) SEQ ID NO: 8, 26, 44, 62, 80, and 98, respectively;
(g) SEQ ID NO: 9, 27, 45, 63, 81, and 99, respectively;
(h) SEQ ID NO: 10, 28, 46, 64, 82, and 100, respectively;
(i) SEQ ID NO: 11, 29, 47, 65, 83, and 101, respectively;
(j) SEQ ID NO: 12, 30, 48, 66, 84, and 102, respectively;
(k) SEQ ID NO: 14, 32, 50, 68, 86, and 104, respectively;
(l) SEQ ID NO: 15, 33, 51, 69, 87, and 105, respectively;
(m) SEQ ID NO: 16, 34, 52, 70, 88, and 106, respectively; or
(n) SEQ ID NO: 17, 35, 53, 71, 89, and 107, respectively;

[58.] an isolated monoclonal antibody that specifically binds to HIV Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of
(a) SEQ ID NO: 8, 26, 44, 62, 80, and 98, respectively; or
(b) SEQ ID NO: 11, 29, 47, 65, 83, and 101, respectively;

[59.] the isolated monoclonal antibody of any one of to [58], wherein the VH comprises one or more of
(a) the amino acid sequence of SEQ ID NO: 109-126 or 310-315 at Kabat positions H31-H37;
(b) the amino acid sequence of SEQ ID NO: 127-144 or 316-318 at Kabat positions H52-H56; and
(c) the amino acid sequence of SEQ ID NO: 145-162 at Kabat positions H61-H62; and
wherein the VL comprises one or more of
(d) the amino acid sequence of SEQ ID NO: 163-180 or 319-324 at Kabat positions H26-H34;
(e) the amino acid sequence of SEQ ID NO: 181-198 or 325-334 at Kabat positions H49-H56;
(f) the amino acid sequence of SEQ ID NO: 199-216 or 335-339 at Kabat positions H67-H70; and
(g) the amino acid sequence of SEQ ID NO: 217-234 at Kabat positions H89-H97;

[60.] the isolated monoclonal antibody of any one of to [58], wherein the VH comprises the amino acid sequence of SEQ ID NO: 127-144 or 316-318 at Kabat positions H52-H56, and the VL comprises the amino acid sequence of SEQ ID NO: 163-180 or 319-324 at Kabat positions H26-H34, and the amino acid sequence of SEQ ID NO: 199-216 or 335-339 at Kabat positions H67-H70;

[61.] the isolated monoclonal antibody of any one of to [58], wherein the VH comprises
(a) the amino acid sequence of SEQ ID NO: 109-126 or 310-315 at Kabat positions H31-H37;
(b) the amino acid sequence of SEQ ID NO: 127-144 or 316-318 at Kabat positions H52-H56; and
(c) the amino acid sequence of SEQ ID NO: 145-162 at Kabat positions H61-H62; and
wherein the VL comprises
(d) the amino acid sequence of SEQ ID NO: 163-180 or 319-324 at Kabat positions H26-H34;
(e) the amino acid sequence of SEQ ID NO: 181-198 or 325-334 at Kabat positions H49-H56;
(f) the amino acid sequence of SEQ ID NO: 199-216 or 335-339 at Kabat positions H67-H70; and
(g) the amino acid sequence of SEQ ID NO: 217-234 at Kabat positions H89-H97;

[62.] an isolated monoclonal antibody that specifically binds to HIV Env and comprises a heavy chain variable region (VH) and a light chain variable region (VL), wherein the VH comprises an amino acid sequence that is at least about 90%, 95%, 97%, 98%, 99% or 100% identical to the VH of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D;

[63.] an isolated monoclonal antibody that specifically binds to HIV Env and comprises a heavy chain variable region (VH) and a light chain variable region (VL), wherein the VH comprises an amino acid sequence that is at least about 90%, 95%, 97%, 98%, 99% or 100% identical to the VH of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C;

[64.] an isolated monoclonal antibody that specifically binds to HIV Env and comprises a heavy chain variable region (VH) and a light chain variable region (VL), wherein the VH comprises an amino acid sequence that is at least about 90%, 95%, 97%, 98%, 99% or 100% identical to the VH of PCIN63-71I1a, or PCIN63-71L;

[65.] an isolated monoclonal antibody that specifically binds to HIV Env and comprises a heavy chain variable region (VH) and a light chain variable region (VL), wherein the VH comprises an amino acid sequence that is at least about 90%, 95%, 97%, 98%, 99% or 100% identical to SEQ ID NO: 235-252;

[66.] an isolated monoclonal antibody that specifically binds to HIV Env and comprises a heavy chain variable region (VH) and a light chain variable region (VL), wherein the VH comprises an amino acid sequence that is at least about 90%, 95%, 97%, 98%, 99% or 100% identical to SEQ ID NO: 235, 237, 238, 240-246, or 248-251;

[67.] an isolated monoclonal antibody that specifically binds to HIV Env and comprises a heavy chain variable region (VH) and a light chain variable region (VL), wherein the VH comprises an amino acid sequence that is at least about 90%, 95%, 97%, 98%, 99% or 100% identical to SEQ ID NO: 242 or245;

[68.] the isolated monoclonal antibody of any one of to [67], wherein the VH CDR1, VH CDR2, and VH CDR3, comprise the amino acid sequence of the PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D VH CDR1, VH CDR2, and VH CDR3, respectively;

[69.] the isolated monoclonal antibody of any one of to [67], wherein
(a) the VH CDR1 comprises the amino acid sequence of SEQ ID NO: 1-18;
(b) the VH CDR2 comprises the amino acid sequence of SEQ ID NO: 19-36; and
(c) the VH CDR3 comprises the amino acid sequence of SEQ ID NO: 37-54;

[70.] the isolated monoclonal antibody of any one of to [69], wherein the VH comprises one or more of
(a) the amino acid sequence of SEQ ID NO: 109-126 or 310-315 at Kabat positions H31-H37;
(b) the amino acid sequence of SEQ ID NO: 127-144 or 316-318 at Kabat positions H52-H56; and
(c) the amino acid sequence of SEQ ID NO: 145-162 at Kabat positions H61-H62;

[71.] the isolated monoclonal antibody of any one of to [68], wherein the VH comprises
(a) the amino acid sequence of SEQ ID NO: 109-126 or 310-315 at Kabat positions H31-H37;
(b) the amino acid sequence of SEQ ID NO: 127-144 or 316-318 at Kabat positions H52-H56; and
(c) the amino acid sequence of SEQ ID NO: 145-162 at Kabat positions H61-H62;

[72.] the isolated monoclonal antibody of any one of to [71], wherein the VL comprises an amino acid sequence that is at least about 90%, 95%, 97%, 98%, 99% or 100% identical to the VL of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D;

[73.] the isolated monoclonal antibody of any one of to [71], wherein the VL comprises an amino acid sequence that is at least about 90%, 95%, 97%, 98%, 99% or 100% identical to the VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C;

[74.] the isolated monoclonal antibody of any one of to [71], wherein the VL comprises an amino acid sequence that is at least about 90%, 95%, 97%, 98%, 99% or 100% identical to the VL of PCIN63-71I1a, or PCIN63-71L;

[75.] the isolated monoclonal antibody of any one of to [71], wherein the VL comprises an amino acid sequence that is at least about 90%, 95%, 97%, 98%, 99% or 100% identical to SEQ ID NO: 253-270;

[76.] the isolated monoclonal antibody of any one of to [71], wherein the VL comprises an amino acid sequence that is at least about 90%, 95%, 97%, 98%, 99% or 100% identical to SEQ ID NO: 253, 255, 256, 258-264, or 266-269;

[77.] the isolated monoclonal antibody of any one of to [71], wherein the VL comprises an amino acid sequence that is at least about 90%, 95%, 97%, 98%, 99% or 100% identical to SEQ ID NO: 260 or 263;

[78.] the isolated monoclonal antibody of any one of to [77], wherein the VL CDR1, VL CDR2, and VL CDR3 comprise the amino acid sequence of the PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D VL CDR1, VL CDR2, and VL CDR3, respectively;

[79.] the isolated monoclonal antibody of any one of to [77], wherein
(a) the VL CDR1 comprises the amino acid sequence of SEQ ID NO: 55-72;
(b) the VL CDR2 comprises the amino acid sequence of SEQ ID NO: 73-90; and
(c) the VL CDR3 comprises the amino acid sequence of SEQ ID NO: 91-108;

[80.] the isolated monoclonal antibody of any one of to [79], wherein the VL comprises one or more of
(a) the amino acid sequence of SEQ ID NO: 163-180 or 319-324 at Kabat positions H26-H34;
(b) the amino acid sequence of SEQ ID NO: 181-198 or 325-334 at Kabat positions H49-H56;
(c) the amino acid sequence of SEQ ID NO: 199-216 or 335-339 at Kabat positions H67-H70; and
(d) the amino acid sequence of SEQ ID NO: 217-234 at Kabat positions H89-H97;

[81.] the isolated monoclonal antibody of any one of to [79], wherein the VL comprises
(a) the amino acid sequence of SEQ ID NO: 163-180 or 319-324 at Kabat positions H26-H34;
(b) the amino acid sequence of SEQ ID NO: 181-198 or 325-334 at Kabat positions H49-H56;
(c) the amino acid sequence of SEQ ID NO: 199-216 or 335-339 at Kabat positions H67-H70; and
(d) the amino acid sequence of SEQ ID NO: 217-234 at Kabat positions H89-H97;

[82.] an isolated monoclonal antibody that specifically binds to HIV Env and comprises a heavy chain variable region (VH) and light chain variable region (VL), wherein the VH and VL comprise an amino acid sequence that is at least about 90%, 95%, 97%, 98%, 99% or 100% identical to the PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D VH and VL, respectively;

[83.] an isolated monoclonal antibody that specifically binds to HIV Env and comprises a heavy chain variable region (VH) and light chain variable region (VL), wherein the VH and VL comprise an amino acid sequence that is at least about 90%, 95%, 97%, 98%, 99% or 100% identical to the PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C VH and VL, respectively;

[84.] an isolated monoclonal antibody that specifically binds to HIV Env and comprises a heavy chain variable region (VH) and light chain variable region (VL), wherein the VH and VL comprise an amino acid sequence that is at least about 90%, 95%, 97%, 98%, 99% or 100% identical to the PCIN63-71I1a, or PCIN63-71L VH and VL, respectively;

[85.] an isolated monoclonal antibody that specifically binds to HIV Env and comprises a heavy chain variable region (VH) and light chain variable region (VL), wherein the VH comprises an amino acid sequence that is at least about 90%, 95%, 97%, 98%, 99% or 100% identical to SEQ ID NO: 235-252 and the VL comprises an amino acid sequence that is at least about 90%, 95%, 97%, 98%, 99% or 100% identical to SEQ ID NO: 253-270;

[86.] an isolated monoclonal antibody that specifically binds to HIV Env and comprises a heavy chain variable region (VH) and light chain variable region (VL), wherein the VH and VL comprise an amino acid sequence that is at least about 90%, 95%, 97%, 98%, 99% or 100% identical to
(a) SEQ ID NO: 235 and 253, respectively;
(b) SEQ ID NO: 236 and 254, respectively;
(c) SEQ ID NO: 237 and 255, respectively;
(d) SEQ ID NO: 238 and 256, respectively;
(e) SEQ ID NO: 239 and 257, respectively;
(f) SEQ ID NO: 240 and 258, respectively;
(g) SEQ ID NO: 241 and 259, respectively;
(h) SEQ ID NO: 242 and 260, respectively;
(i) SEQ ID NO: 243 and 261, respectively;
(j) SEQ ID NO: 244 and 262, respectively;
(k) SEQ ID NO: 245 and 263, respectively;
(l) SEQ ID NO: 246 and 264, respectively;
(m) SEQ ID NO: 247 and 265, respectively;
(n) SEQ ID NO: 248 and 266, respectively;
(0) SEQ ID NO: 249 and 267, respectively;
(p) SEQ ID NO: 250 and 268, respectively;
(q) SEQ ID NO: 251 and 269, respectively; or
(r) SEQ ID NO: 252 and 270, respectively;

[87.] the isolated monoclonal antibody of any one of to [86], wherein the VH CDR1, VH CDR2, VH CDR3, VL CDR1, VL CDR2, and VL CDR3 comprise the amino acid sequence of the PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D VH CDR1, VH CDR2, VH CDR3, VL CDR1, VL CDR2, and VL CDR3, respectively;

[88.] the isolated monoclonal antibody of any one of to [86], wherein
(a) the VH CDR1 comprises the amino acid sequence of SEQ ID NO: 1-18;
(b) the VH CDR2 comprises the amino acid sequence of SEQ ID NO: 19-36;
(c) the VH CDR3 comprises the amino acid sequence of SEQ ID NO: 37-54,
(d) the VL CDR1 comprises the amino acid sequence of SEQ ID NO: 55-72;
(e) the VL CDR2 comprises the amino acid sequence of SEQ ID NO: 73-90; and
(f) the VL CDR3 comprises the amino acid sequence of SEQ ID NO: 91-108;

[89.] the isolated monoclonal antibody of any one of to [88], wherein the VH comprises one or more of
(a) the amino acid sequence of SEQ ID NO: 109-126 or 310-315 at Kabat positions H31-H37;
(b) the amino acid sequence of SEQ ID NO: 127-144 or 316-318 at Kabat positions H52-H56; and
(c) the amino acid sequence of SEQ ID NO: 145-162 at Kabat positions H61-H62; and
wherein the VL comprises one or more of
(d) the amino acid sequence of SEQ ID NO: 163-180 or 319-324 at Kabat positions H26-H34;
(e) the amino acid sequence of SEQ ID NO: 181-198 or 325-334 at Kabat positions H49-H56;
(f) the amino acid sequence of SEQ ID NO: 199-216 or 335-339 at Kabat positions H67-H70; and
(g) the amino acid sequence of SEQ ID NO: 217-234 at Kabat positions H89-H97;

[90.] the isolated monoclonal antibody of any one of to [88], wherein the VH comprises the amino acid sequence of SEQ ID NO: 127-144 or 316-318 at Kabat positions H52-H56, and the VL comprises the amino acid sequence of SEQ ID NO: 163-180 or 319-324 at Kabat positions H26-H34, and the amino acid sequence of SEQ ID NO: 199-216 or 335-339 at Kabat positions H67-H70;

[91.] the isolated monoclonal antibody of any one of to [88], wherein the VH comprises
(a) the amino acid sequence of SEQ ID NO: 109-126 or 310-315 at Kabat positions H31-H37;
(b) the amino acid sequence of SEQ ID NO: 127-144 or 316-318 or 316-318 at Kabat positions H52-H56; and
(c) the amino acid sequence of SEQ ID NO: 145-162 at Kabat positions H61-H62; and
wherein the VL comprises
(d) the amino acid sequence of SEQ ID NO: 163-180 or 319-324 at Kabat positions H26-H34;
(e) the amino acid sequence of SEQ ID NO: 181-198 or 325-334 at Kabat positions H49-H56;
(f) the amino acid sequence of SEQ ID NO: 199-216 or 335-339 at Kabat positions H67-H70; and
(g) the amino acid sequence of SEQ ID NO: 217-234 at Kabat positions H89-H97;

[92.] the isolated antibody of any one of [1] to [91], wherein the antibody is not PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D;

[93.] the isolated antibody of any one of [1] to [91], wherein the antibody is not PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C;

[94.] the isolated antibody of any one of [1] to [91], wherein the antibody is not PCIN63-71I1a, or PCIN63-71L;

[95.] the monoclonal antibody of any one of [1] to [94, further comprising a heavy and/or light chain constant region;

[96.] the monoclonal antibody of any one of [1] to [94], further comprising a human heavy and/or light chain constant region;

[97.] the antibody of or [96], wherein the heavy chain constant region is selected from the group consisting of a human immunoglobulin IgG1, IgG2, IgG3, IgG4, IgA1, and IgA2 constant region;

[98.] the antibody of any one of to [97], wherein the heavy chain constant region comprises a native amino acid sequence;

[99.] the antibody of any one of to [97], wherein the heavy chain constant region comprises a variant amino acid sequence;

[100.] the isolated monoclonal antibody of any one of [1] to [99], wherein the antibody is a recombinant antibody, a chimeric antibody, a human antibody, an antibody fragment, a bispecific antibody, or a trispecific antibody;

[101.] the isolated monoclonal antibody of [100], wherein the antibody fragment comprises a single-chain Fv (scFv), F (ab) fragment, F(ab') 2 fragment, or an isolated VH domain;

[102.] the monoclonal antibody of any one of [1] to [101], wherein the antibody is capable of neutralizing at least two cross-clade isolates of HIV;
[103.] the monoclonal antibody of any one of [1] to [101], wherein the antibody is capable of neutralizing at least one clade A HIV isolate, at least one clade B HIV isolate, and at least one clade C HIV isolate;
[104.] the antibody of [102], wherein the antibody is capable of neutralizing at least about 40%, 50%, 60%, 70%, 80%, 90%, or 100% of cross-clade HIV isolates in the indicator virus panel of FIG. 8;
[105.] the antibody of [102], wherein the antibody is capable of neutralizing at least about 40%, 50%, 60%, 70%, 80%, 90%, or 100% of cross-clade HIV isolates in the indicator virus panel of FIG. 9;
[106.] the antibody of or [105], wherein the antibody is capable of neutralizing the cross-clade HIV isolates with a median IC50 equal to or less than about 1 microg/ml, about 0.8 microg/ml, 0.5 microg/ml, or 0.3 microg/ml;
[107.] the antibody of or [105], wherein the antibody is capable of neutralizing the cross-clade HIV isolates with a mean IC50 equal to or less than about 1 microg/ml, about 0.8 microg/ml, 0.5 microg/ml, or 0.3 microg/ml;
[108.] a pharmaceutical composition comprising the monoclonal antibody of any one of [1] to and a pharmaceutically acceptable excipient;
[109.] the pharmaceutical composition of [108], which is lyophilized;
[110.] an isolated polynucleotide encoding the heavy chain variable region or heavy chain of the antibody of any one of [1] to [101];
[111.] an isolated polynucleotide encoding the light chain variable region or light chain of the antibody of any one of [1] to [101];
[112.] an isolated polynucleotide encoding the heavy chain variable region or heavy chain of the antibody of any one of [1] to and the light chain variable region or light chain of the antibody of any one of [1] to [101];
[113.] the isolated polynucleotide of of or [112], wherein the polynucleotide encodes a heavy chain variable region comprising the amino acid sequence of SEQ ID NO: 235-252;
[114.] the isolated polynucleotide of of or [112], wherein the polynucleotide encodes a light chain variable region comprising the amino acid sequence of SEQ ID NO: 253-270;
[115.] the isolated polynucleotide of any one of to [114], which is a DNA;
[116.] the isolated polynucleotide of any one of to [114], which is an mRNA;
[117.] the isolated polynucleotide of [116], wherein the mRNA comprises a modified nucleotide;
[118.] an isolated vector comprising the polynucleotide of any one of to [114]; [119.] the isolated vector of [117], wherein the vector is a viral vector;
[120.] a recombinant virus comprising the polynucleotide of any one of to [114]; [121.] the recombinant virus of [119], which is a recombinant adeno-associated virus (AAV);
[122.] a host cell comprising the polynucleotide of any one of to [115], the vector of or [119], or a first vector comprising the nucleic acid of and a second vector comprising the nucleic acid of [111];
[123.] the host cell of [122], which is selected from the group consisting of E. coli, *Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture;
[124.] a method of producing an antibody that binds to HIV comprising culturing the host cell of so that the polynucleotide is expressed and the antibody is produced;
[125.] an isolated antibody that specifically binds to HIV Env and is encoded by the isolated polynucleotide of any one of to [117];
[126.] a method of neutralizing an HIV virus comprising contacting the virus with a sufficient amount of the antibody of any one of [1] to [101], or the pharmaceutical composition of [108];
[127.] a method of reducing the likelihood of HIV infection in a subject exposed to HIV comprising administering to the subject a therapeutically sufficient amount of the antibody of any one of [1] to [101], or of the pharmaceutical composition of [108];
[128.] a method of reducing the risk of a subject becoming infected with HIV comprising administering to the subject in need thereof an effective amount of the antibody of any one of [1] to [101], or the pharmaceutical composition of [108];
[129.] a method for passively immunizing a subject comprising administering to the subject in need thereof an effective amount of the antibody of any one of [1] to [101], or the pharmaceutical composition of [108];
[130.] a method of preventing HIV infection comprising administering to a subject in need thereof a therapeutically sufficient amount of the antibody of any one of [1] to [101], the pharmaceutical composition of [108], the isolated polynucleotide of any one of to [117], or the recombinant virus of any or [121];
[131.] a method of treating HIV/AIDS comprising administering to a subject in need thereof a therapeutically sufficient amount of the antibody of any one of [1] to [101], the pharmaceutical composition of [108], the isolated polynucleotide of any one of to [117], or the recombinant virus of any or [121];
[132.] the method of any one of to [131], wherein the administering to the subject is by at least one mode selected from oral, parenteral, subcutaneous, intramuscular, intravenous, vaginal, rectal, buccal, sublingual, and transdermal;
[133.] the method of any one of to [132], further comprising administering at least one additional therapeutic agent;
[134.] the method of [133], wherein the additional therapeutic agent is an antiretroviral agent or a second antibody;
[135.] the method of [134], wherein the additional therapeutic agent comprises a broadly neutralizing antibody;
[136.] the method of [134], wherein the additional therapeutic agent comprises two broadly neutralizing antibodies;
[137.] the method of [134], wherein the additional therapeutic agent comprises three broadly neutralizing antibodies;
[138.] a method for detecting HIV in a sample comprising contacting the sample with the antibody of any one of [1] to [101];
[139.] a method of purifying HIV from a sample comprising contacting the sample with the antibody of any one of [1] to [101];

[140.] a kit comprising the antibody of any one of [1] to [101], or the pharmaceutical composition of and a) a detection reagent, b) an HIV antigen, c) a notice that reflects approval for use or sale for human administration, or d) any combination thereof;

[141.] the antibody of any one of [1] to [101], wherein the antibody specifically binds the Env of at least one HIV isolate in the indicator virus panel of FIG. 8;

[142.] the antibody of any one of [1] to [101], wherein the antibody specifically binds the Env of at least two, at least three, at least four, or at least five HIV isolates in the indicator virus panel of FIG. 8;

[143.] the antibody of any one of [1] to [101], wherein the antibody specifically binds the Env of at least one HIV isolate in the indicator virus panel of FIG. 9;

[144.] the antibody of any one of [1] to [101], wherein the antibody specifically binds the Env of at least two, at least three, at least four, or at least five HIV isolates in the indicator virus panel of FIG. 9;

[145.] a method of producing an engineered variant of a PCIN63 antibody comprising (a) substituting one or more amino acid residues of the VH; and/or substituting one or more amino acid residues of the VL to create an engineered variant antibody, and (b) and producing the engineered variant antibody, wherein the PCIN63 antibody is i. PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D;

ii. PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C; or PCIN63-71I1a, or PCIN63-71L.

Figure 1:
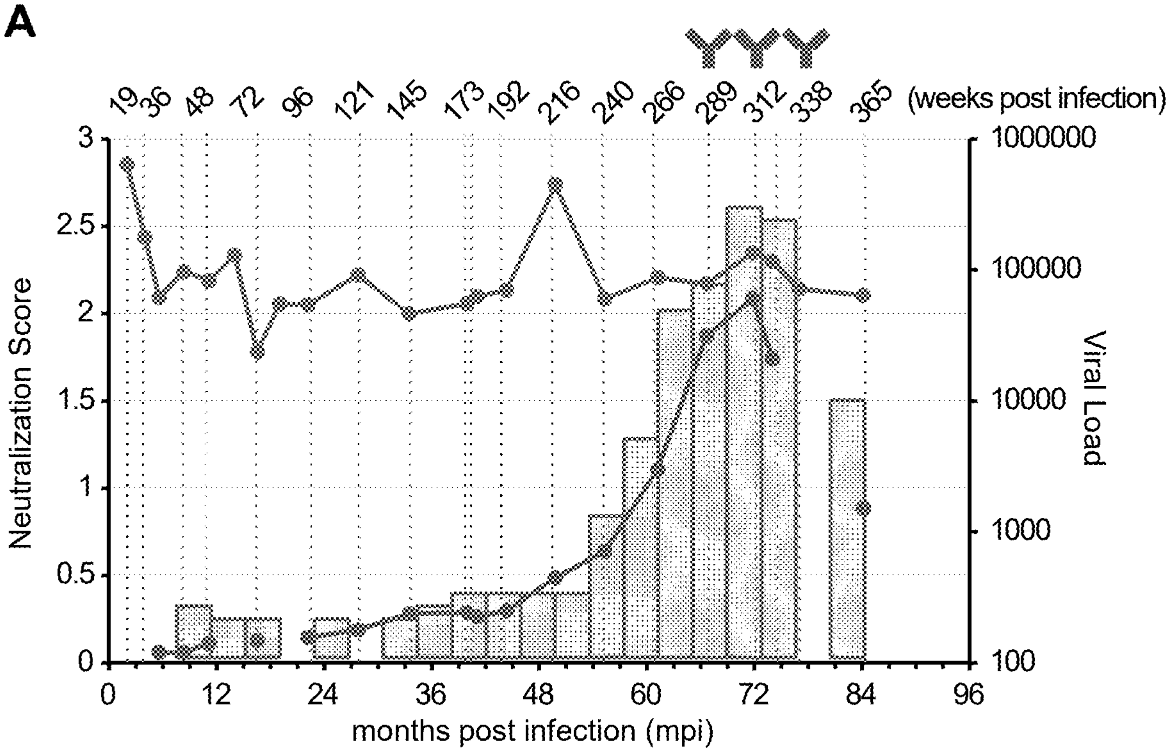
FIG. 1. PCIN63 antibodies define a minimally mutated VRC01-like bnAb lineage. (A) Longitudinal plasma samples from donor PC063 were tested for neutralization against heterologous pseudoviruses. The percent of viruses neutralized (>50% inhibition of infectivity at the lowest plasma dilution, 1:50) from a cross-clade (A, B, C) 37-virus panel is shown as shaded bars. The lower line represents the neutralization score calculated for each sample and taking into account breadth and potency (see Landais et al, 2016). The evolution of the viral load (top line) in the plasma is also plotted. The time points at which PCIN63 antibodies were isolated are indicated by antibody symbols. See also FIG. 6A, 6B. (B) Comparison of CD4bs Abs genetic characteristics. Antibodies are listed by classes as defined in Zhou et al., 2016: PCIN63, DRVI07, VRC01-class bnAbs, HCDR3 dominated bnAbs, VH1-46+bnAbs. Top left inlet: Heavy (VH) and light chains (VL) putative V-genes nucleotide variation from IMGT database reference (% SHM). Top right inlet: light chain V-gene usage. Bottom left inlet: length the HCDR3s, with mean±SEM showed as lines. Bottom right inlet: Logogram of the LCDR3 amino acid sequences for PCIN63 (Q (V/A) (L/Y/F/V) (E/Q) (T/S/W) (SEQ ID NO: 533)) and other VRC01-class Abs ((Q/A/N) (Q/V/A/C/I) (Y/L/F/I) (E/Q) (F/T/A/S/W) (SEQ ID NO: 534)). Residues common or unique to each category are shown. See also FIGS. 6C, 6D, 7, 13. (C) Comparison of PCIN63-71b, min12A21, 12A21, VRC01 and minVRC01 Abs neutralization breadth and potency on a 120-virus panel (Seaman et al, 2010). See also FIGS. 8 and 9. (D) Comparison of the PCIN63 Ab lineage development kinetics with other bnAbs lineages isolated as reported in original publications. Time to maturation (Mat.) is defined as the time between first detection of the lineage in the periphery (Init.) and peak neutralization breadth in plasma. See also FIG. 10A.
Figure 1:
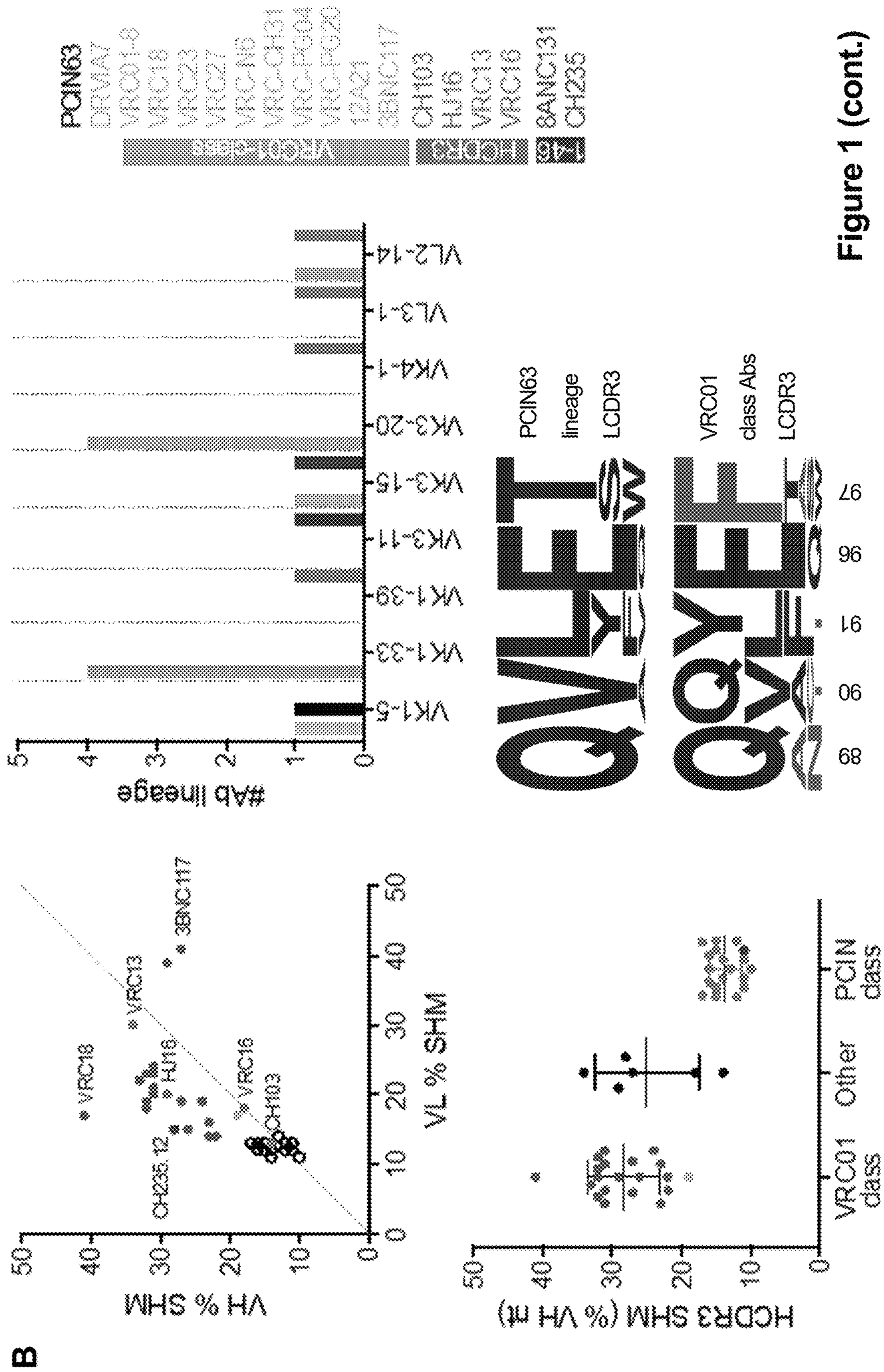
Figure 1:
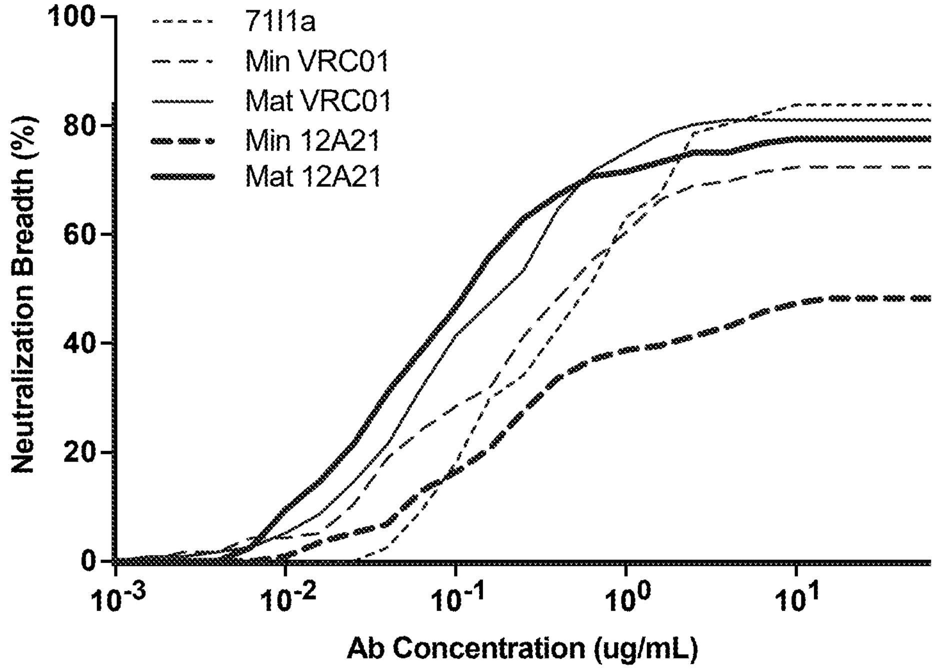
Figure 1:
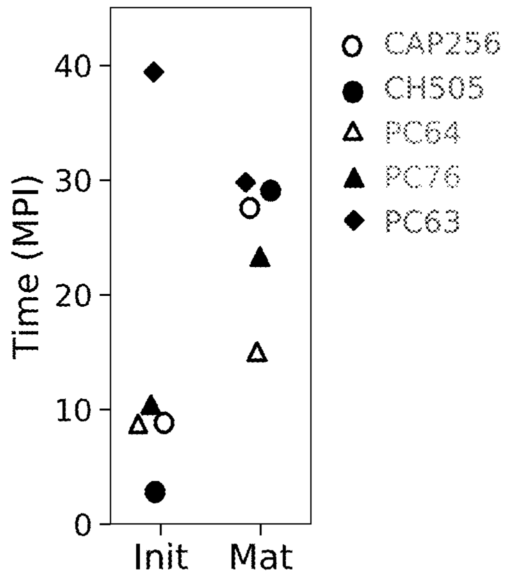

432), 71P-LC (SEQ ID NO: 433), 77B1b-LC (SEQ ID NO: 434), 77C-LC (SEQ ID NO: 435), 77D-LC (SEQ ID NO: 436), VRC01-LC (SEQ ID NO: 437), minVRC01-LC (SEQ ID NO: 438), 12A21-LC (SEQ ID NO: 439), and min12A21-LC (SEQ ID NO: 440).

FIG. 8. Neutralization breadth and potency in the PCIN63 lineage on a medium cross-clade pseudovirus panel. (A) The neutralization $IC_{50}$s (Ab concentration in μg/mL allowing 50% loss of infectivity) of PCIN63 mAbs, PC063-M66 plasma sample and other VR01-class bnAbs on a medium cross-clade pseudotyped virus panel (N=40) are tabulated and shown as indicated. PCIN63 Abs are organized from least to most mutated. (B) Neutralization breadth (% virus neutralized for the indicated $IC_{50}$ threshold) and potency (GeoMean $IC_{50}$ in μg/mL) are tabulated and shown as indicated FIG. 9. Neutralization breadth and potency in the PCIN63 lineage on a large cross-clade pseudovirus panel. (A) The neutralization of PCIN63 mAbs, PC063-M66 plasma sample and other VRC01-class bnAbs was evaluated on a large cross-clade pseudotyped virus panel (N=120) (Seaman et al., 2010). Viruses are organized by subtypes while Abs are organized by level of somatic hypermutation from least to most mature. (B) Neutralization breadth (% virus neutralized at 10 μg/mL) and potency (GeoMean $IC_{50}$ in μg/mL) are tabulated and shown as indicated. (C) Neutralization breadth (% virus neutralized) of the indicated Abs is plotted as a function of neutralization $IC_{50}$ in μg/mL FIG. 10. Emergence and maturation of the PCIN63 bnAb lineage (A) Comparison of the PCIN63 Ab lineage development kinetics with other bnAbs lineages isolated from two Protocol C participants (PC076: high-mannose patch targeting PCDN lineage; PC064: V2-apex targeting PCT64 lineage) as detected in the periphery. Lineage sequences frequencies are plotted as a percentage of total lineage sequences from all time points. Plasma neutralization score (see (Landais et al., 2016)) from a heterologous medium panel is plotted as a dashed line. Related to FIG. 1D. (B) Somatic hypermutation frequency was calculated for each timepoint as divergence (number of amino acid changes compared to LMCA). Data are presented as whisker plot showing mean, 95% upper and lower quartiles, standard deviation and outliers. (C) Longitudinal phylogeny of PCIN63 heavy chain and light chain NGS sequences (mpi). (D) Identification of PCIN63 lineage precursor sequences. The CDR3 of putative PCIN63-UCA NGS sequences (100% identity to PCIN63 Abs HC and LC germline V+J genes) are aligned with IMGT $V_H$1-2*02, $D_H$6*13, $J_H$5*03, Vκ1-5*03 and Jκ1*01 germline genes sequences. The N regions of the junctions are indicated. For putative PCIN63-UCA-KCs, the number of sequences found in the NGS dataset and the corresponding CDRL3 amino-acid sequences are also indicated. Residues previously described as important for binding to the HIV Env CD4bs are shown. Nucleotide sequences shown are VH1-2*02 (SEQ ID NO: 441), DH6*13 (SEQ ID NO: 442), JH5*02 (SEQ ID NO: 443), PCIN63-UCA-VH (SEQ ID NO: 444), VK1-5*03 (SEQ ID NO: 445), JK1*01 (SEQ ID NO: 446), PCIN63-UCA-K1 (SEQ ID NO: 447), PCIN63-UCA-K2 (SEQ ID NO: 448), PCIN63-UCA-K3 (SEQ ID NO: 449), PCIN63-UCA-K4 (SEQ ID NO: 450), PCIN63-UCA-K5 (SEQ ID NO: 451), PCIN63-UCA-K6 (SEQ ID NO: 452), PCIN63-UCA-K7 (SEQ ID NO: 453), PCIN63-UCA-K8 (SEQ ID NO: 454), PCIN63-UCA-K9 (SEQ ID NO: 455), PCIN63-UCA-K10 (SEQ ID NO: 456), PCIN63-UCA-K11 (SEQ ID NO: 457), PCIN63-UCA-K12 (SEQ ID NO: 458), PCIN63-UCA-K13 (SEQ ID NO: 459), PCIN63-UCA-K14 (SEQ ID NO: 460), PCIN63-UCA-K15 (SEQ ID NO: 461), PCIN63-UCA-K16 (SEQ ID NO: 462), PCIN63-UCA-K17 (SEQ ID NO: 463), and PCIN63-UCA-K18 (SEQ ID NO: 464)). Amino acid sequences shown are CARDSSRQQELWWF (SEQ ID NO: 465), TFGQGT (SEQ ID NO: 466), QQSEA (SEQ ID NO: 467), QLYET (SEQ ID NO: 468), QQSRT (SEQ ID NO: 469), QQQET (SEQ ID NO: 470), HHRRL (SEQ ID NO: 471), QQYRT (SEQ ID NO: 472), RQSEA (SEQ ID NO: 473), QQSGA (SEQ ID NO: 474), QQYNS (SEQ ID NO: 475), QHYRT (SEQ ID NO: 476), QHGWT (SEQ ID NO: 477), QQYKT (SEQ ID NO: 478), QHSGA (SEQ ID NO: 479), QHFGA (SEQ ID NO: 480), QQYNR (SEQ ID NO: 481), QQTGT (SEQ ID NO: 482), QQYET (SEQ ID NO: 483), and QQQGT (SEQ ID NO: 484). (E) Binding affinity of PCIN63 mature and putative UCA Abs and VRC01-class inferred germline (VRC01, VRC03, VRC07, 12A12, 12A21, 3BNC60, 3BNC117, VRC-PG04, VRC-CH31) and mature Abs (minVRC01, VRC01, VRC03, VRC07, VRC23, VRC27, 12A12, min12A21, 12A21, 3BNC117, VRC-PG19, VRC-CH31, VRC-N6) for the indicated previously described VH1-2 germline targeting immunogens, as measured by SPR.

Figure 10:
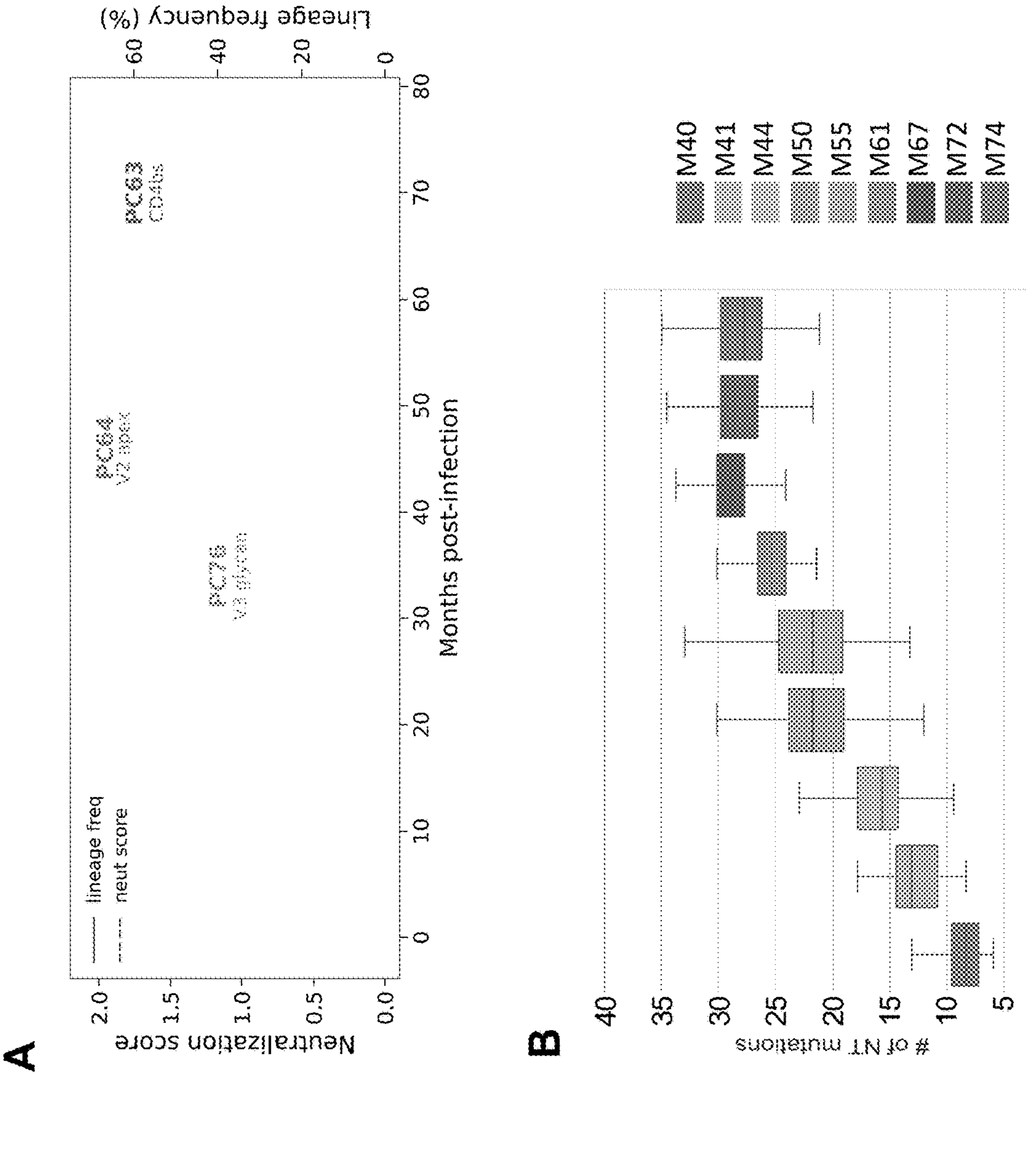
Figure 10:
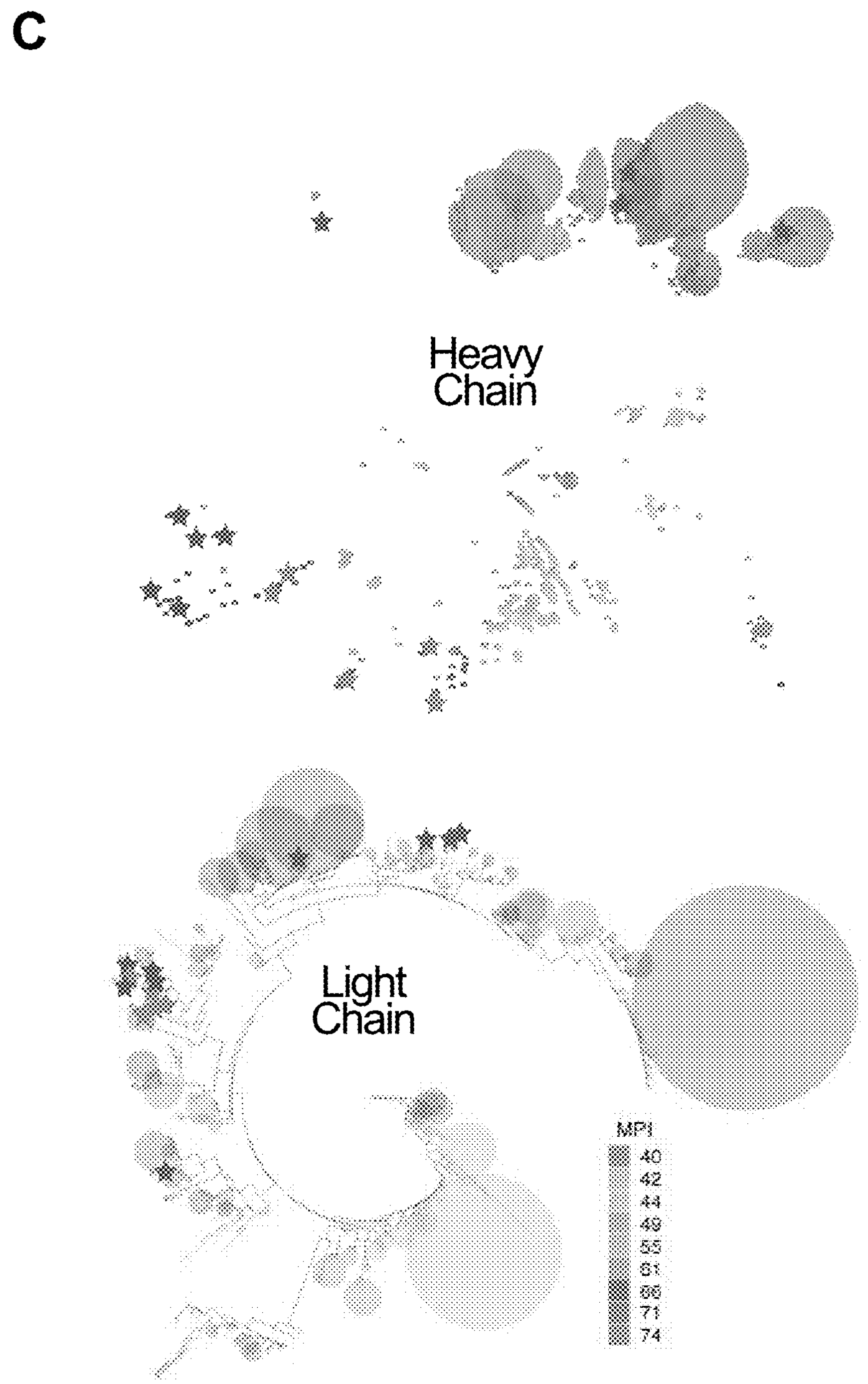
Figure 10:
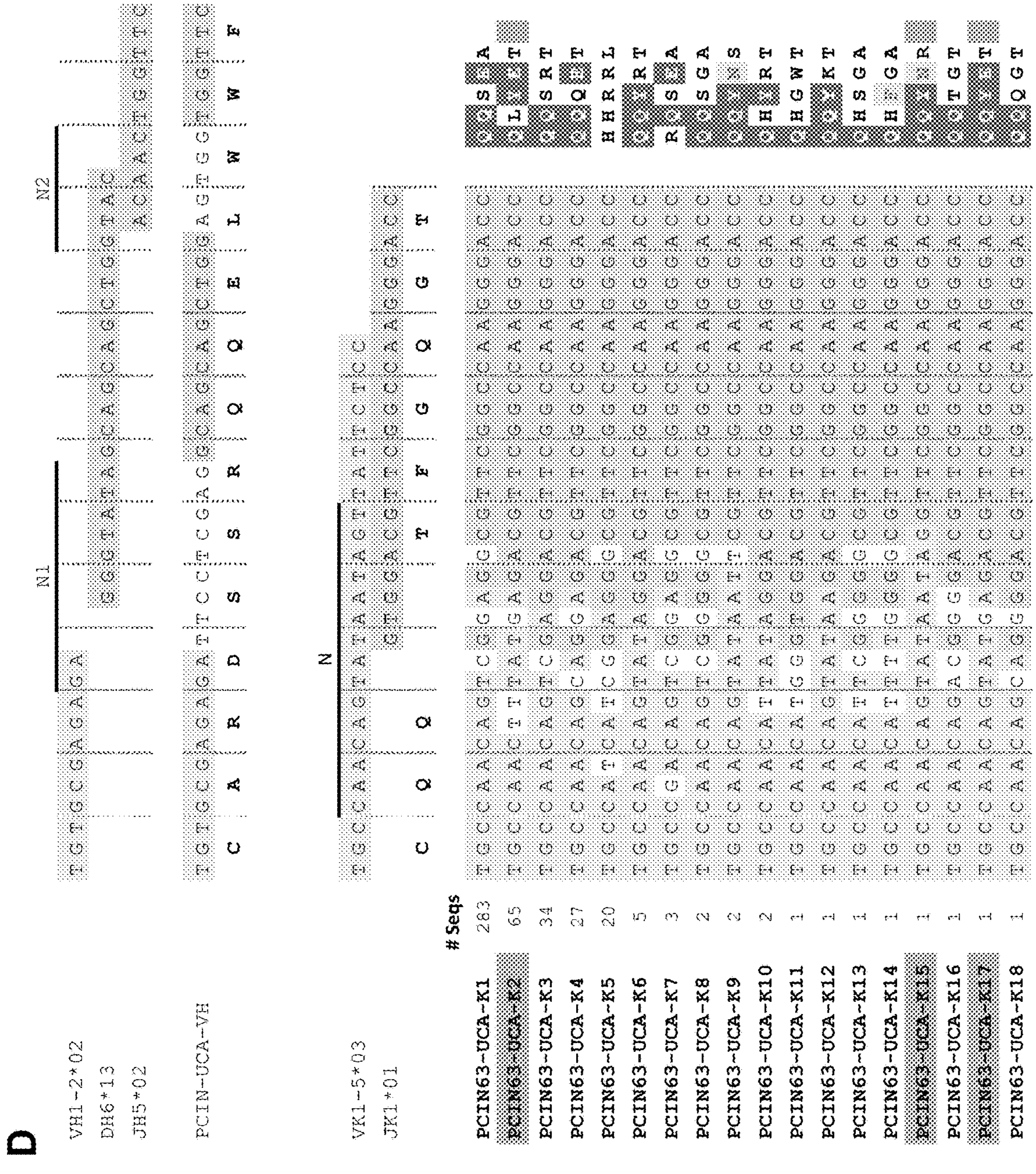
Figure 10:
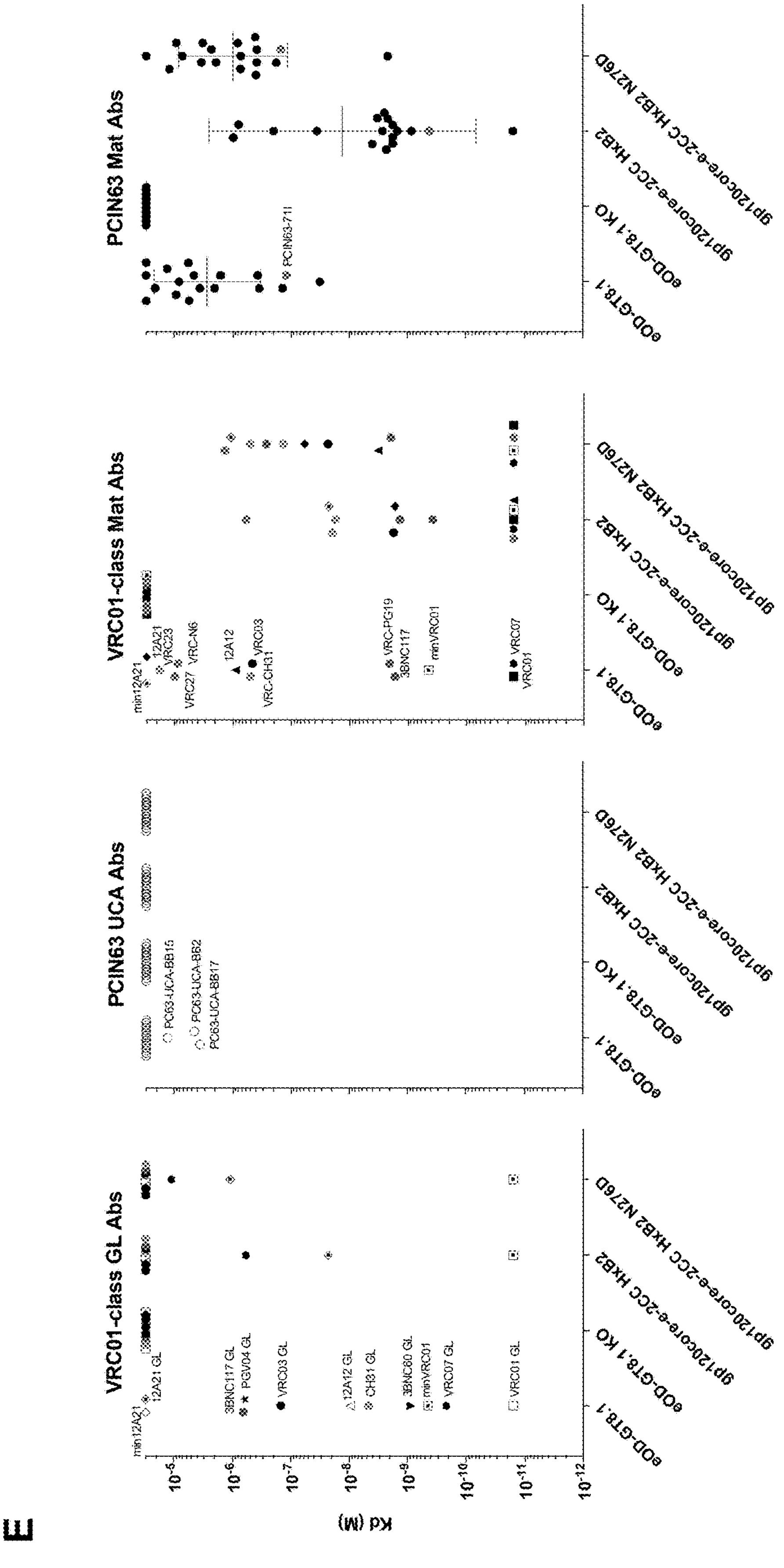
Figure 11:
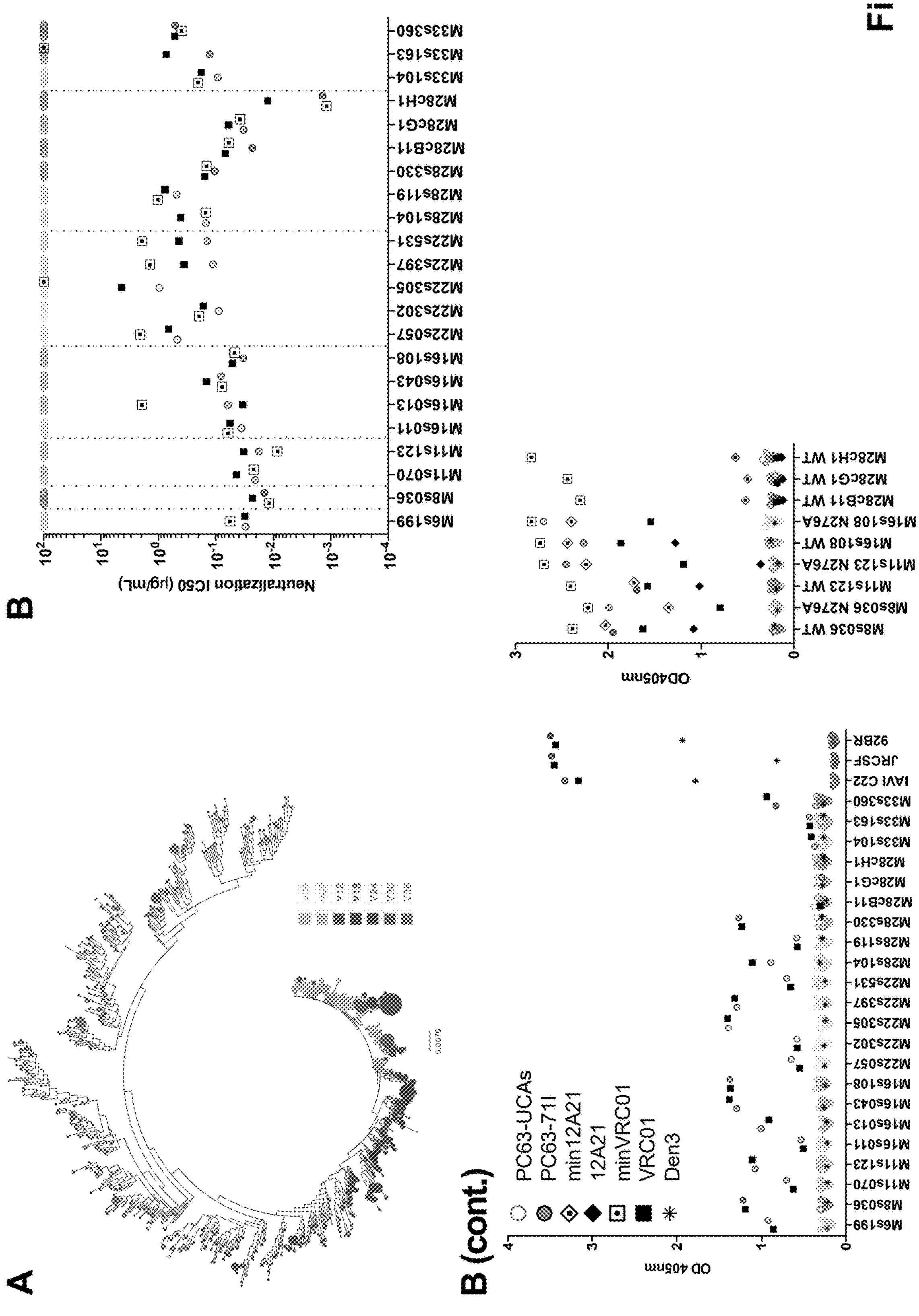
Figure 11:
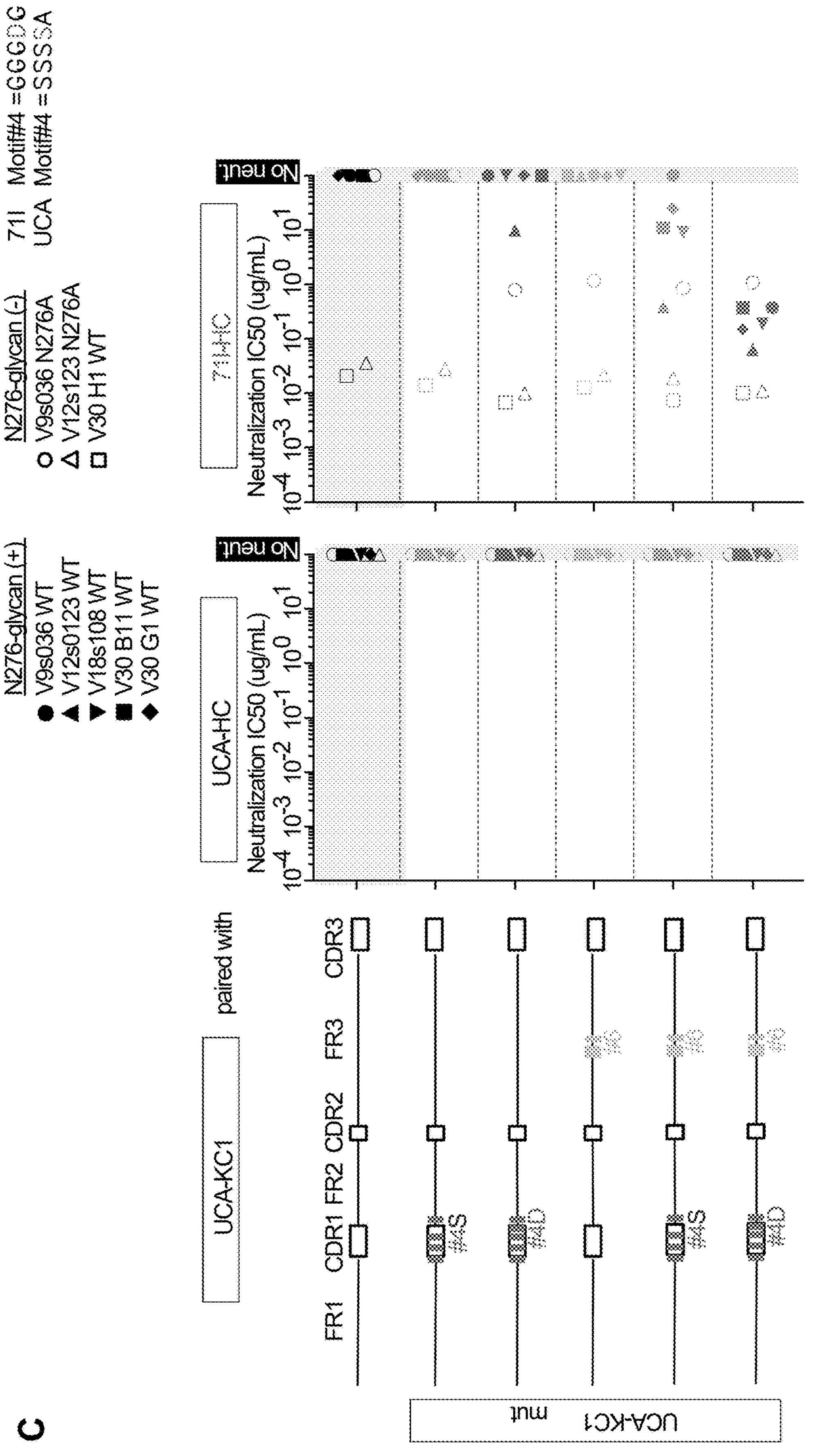
Figure 11:
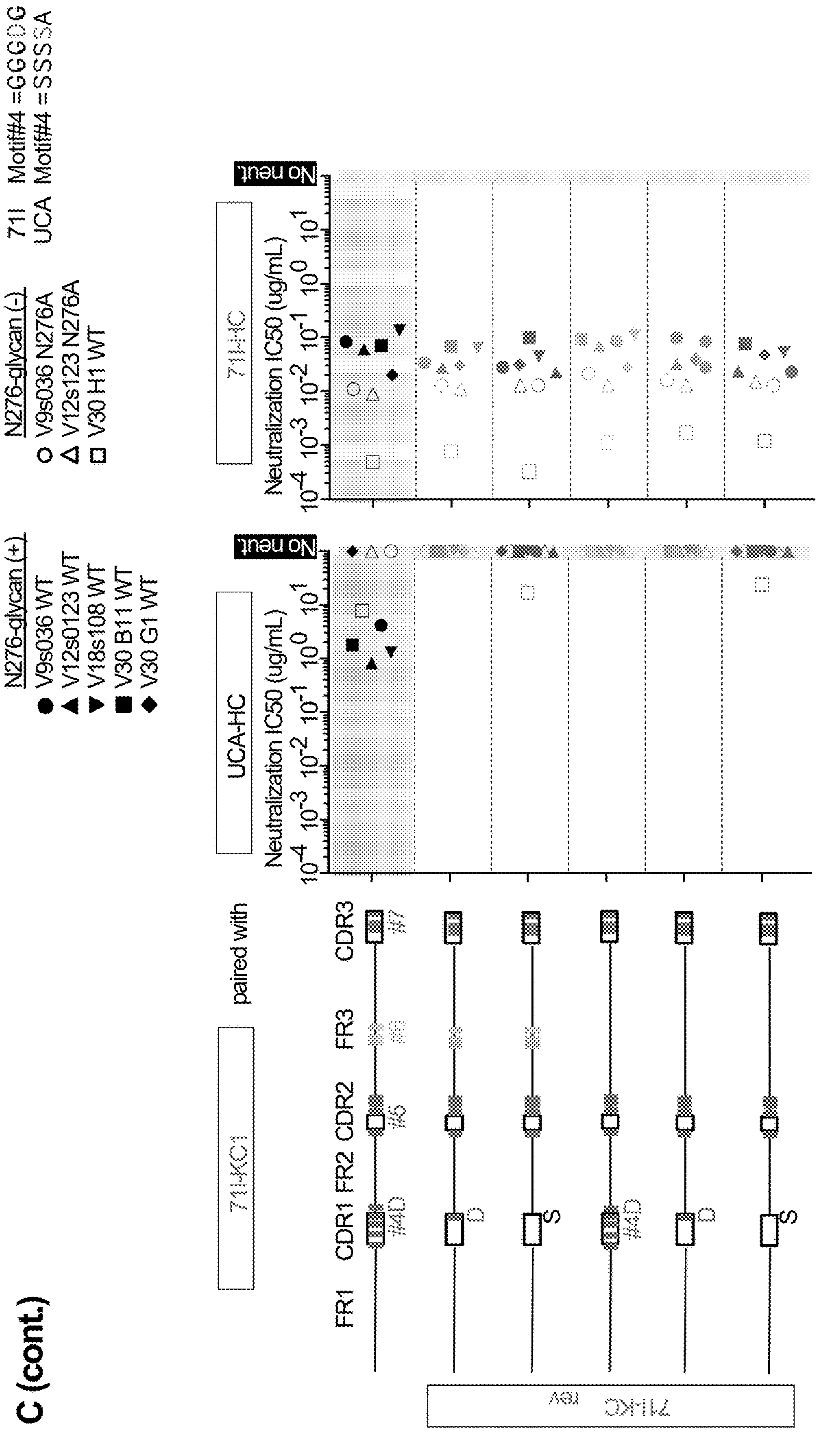

FIG. 11. PCIN63 Ab lineage elicitation by the autologous virus donor PC063. (A) Phylogeny of PC063 HIV subtype C env, estimated by maximum likelihood from full-length env PacBio high-quality consensus sequences (HQCSs) obtained by next-generation sequencing of longitudinal plasma samples (with bubbles representing sample proportion), and organized by samples date. (B) PCIN63 UCA sequences were inferred from the NGS dataset (see FIG. 10D). All possible corresponding PCIN63-UCA Abs were expressed and tested for neutralization (upper panel) of representative pseudotyped autologous Env clones, selected from all time points prior to detection of the PCIN63 lineage in the periphery, and binding to captured gp120 from corresponding pseudovirus stock lysates (lower left panel) or recombinantly expressed (lower right panel). (C) PCIN63-71I-KC SHM Motifs were either introduced into the PCIN63-UCA-KCl (top panels) or reverted to germline (bottom panels), individually or in combination. Motifs are shown and their sequence position on the LC is indicated with a diagram. Motif #4 variants details are also indicated. Mutated constructs were paired with WT PCIN63-UCA (left) or PCIN63-71 (right) HC. The chimeric Abs were tested for neutralization of the indicated WT and N276A autologous Env clones sensitive to neutralization by PCIN63-71I. Related to FIG. 3. 71I Motif #4=GGGDG (SEQ D NO: 485), UCA Motif #4+SSSSA (SEQ ID NO: 486).

Figure 12:
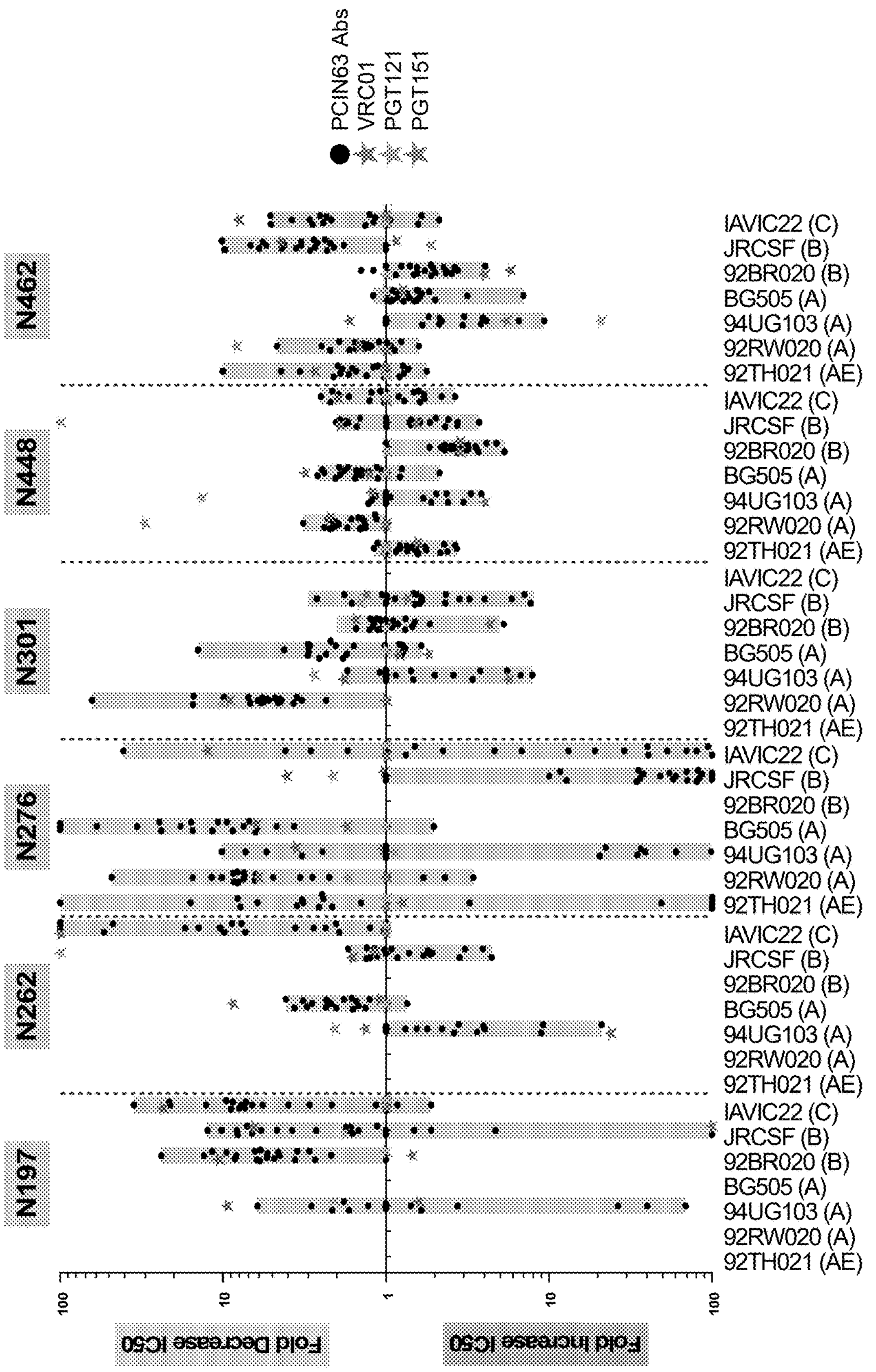
Figure 12:
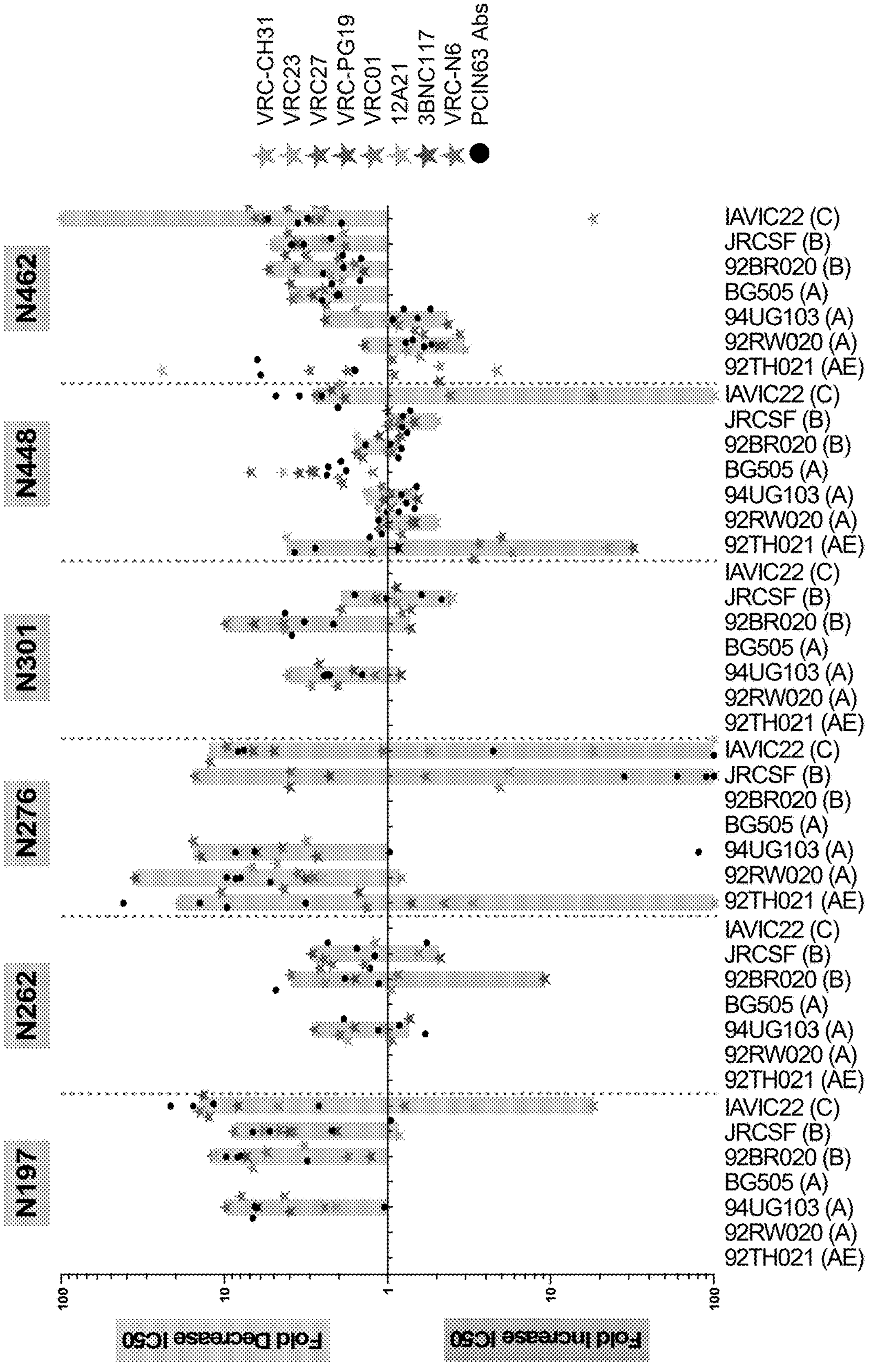

FIG. 12. Effect of CD4bs N-glycan removal on neutralization by PCIN63 Abs. PCIN63 Abs, VRC01-class, PGT151 and PGT121 Abs were tested for neutralizing activity against the indicated pseudoviruses carrying the indicated CD4bs N-glycan single mutation. The fold decrease or increase in neutralization $IC_5$, is plotted. The gray bars indicate the range of variation for the PCIN63 Abs only (upper panel) or VRC01-class reference Abs (lower panel).

Figure 13:
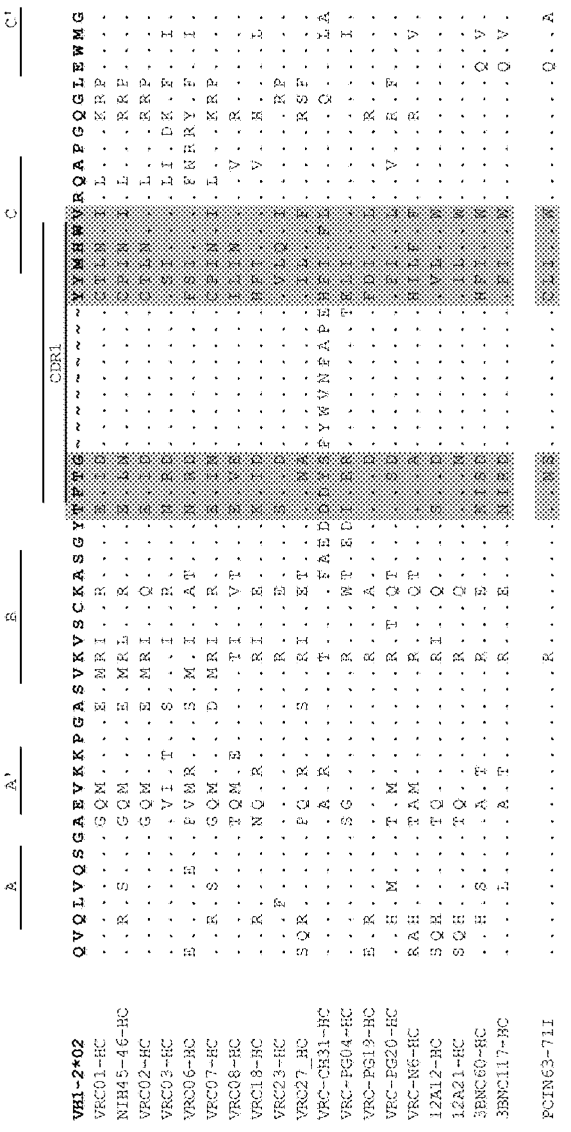
Figure 13:
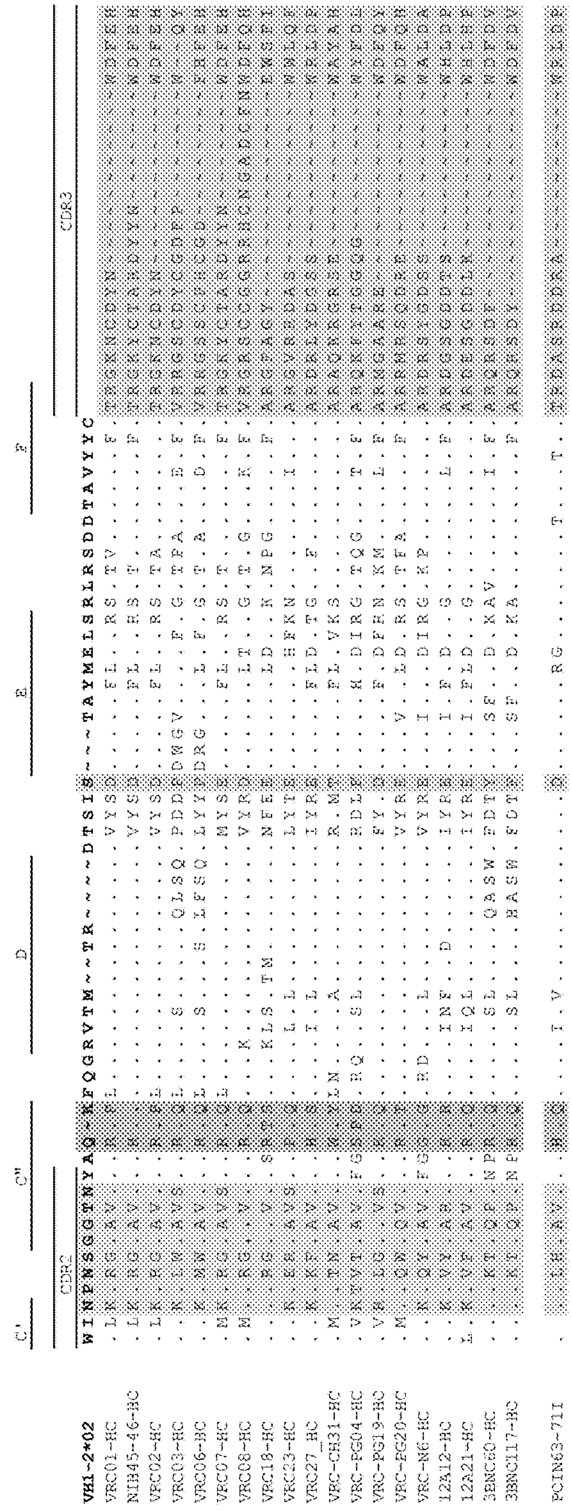
Figure 13:
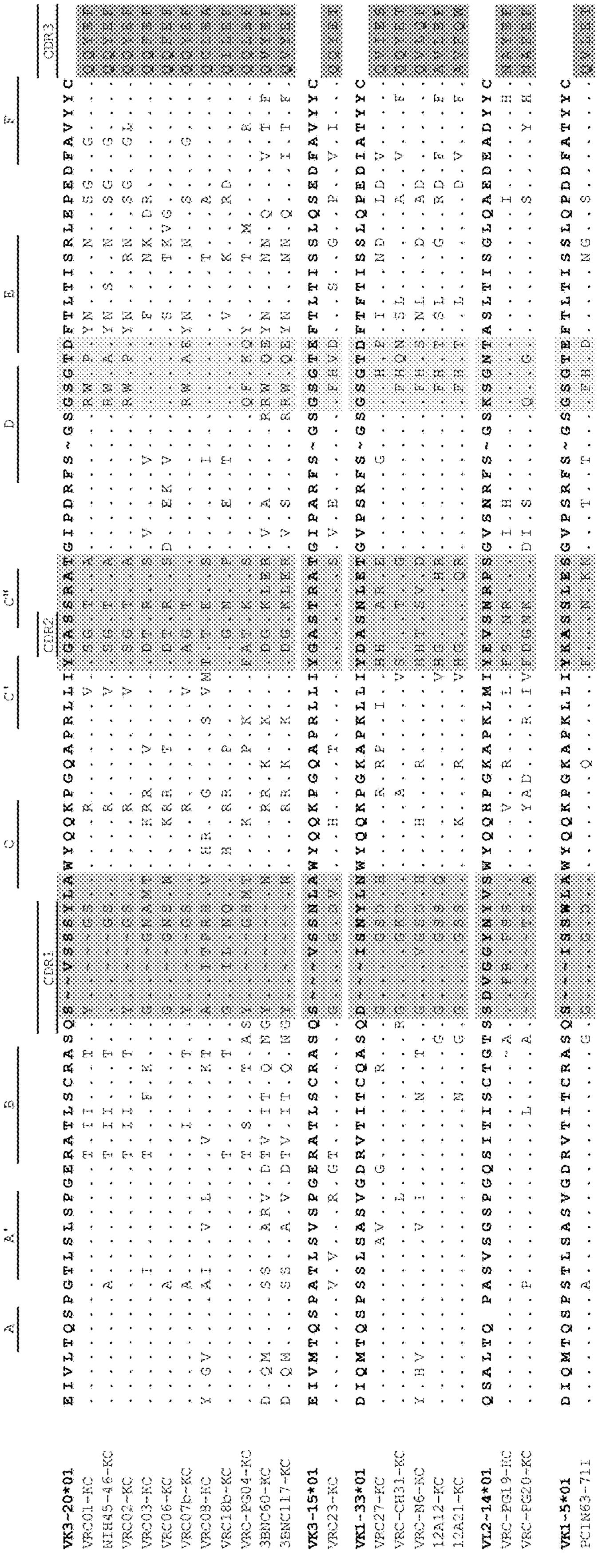

FIG. 13. VRC01-class Abs sequence alignment. (A) VRC01-class bnAbs heavy chain and light chain amino acid alignments with putative germline V-genes. CDR3 Sequences are highlighted in grey. Motifs (as defined in FIG. 2) are highlighted. Sequences shown are VH1-2*02 (SEQ ID NO: 487), VRC01-HC (SEQ ID NO: 488), NIH45-46-HC (SEQ ID NO: 489), VRC02-HC (SEQ ID NO: 490), VRC03-HC (SEQ ID NO: 491), VRC06-HC (SEQ ID NO: 492), VRC07-HC (SEQ ID NO: 493), VRC08-HC (SEQ ID NO: 494), VRC18-HC (SEQ ID NO: 495), VRC23-HC (SEQ ID NO: 496), VRC27_HC (SEQ ID NO: 497), VRC-CH31-HC (SEQ ID NO: 498), VRC-PG04-HC (SEQ ID NO: 499), VRC-PG19-HC (SEQ ID NO: 500), VRC-PG20-HC (SEQ ID NO: 501), VRC-N6-HC (SEQ ID NO: 502), 12A12-HC (SEQ ID NO: 503), 12A21-HC (SEQ ID NO: 504), 3BNC60-HC (SEQ ID NO: 505), 3BNC117-HC (SEQ ID NO: 506), PCIN63-71I-HC (SEQ ID NO: 507), VK3-20*01 (SEQ ID NO: 508), VRC01-KC (SEQ ID NO: 509), NIH45-46-KC (SEQ ID NO: 510), VRC02-KC (SEQ ID NO: 511), VRC03-KC (SEQ ID NO: 512), VRC06-KC (SEQ ID NO: 513), VRC07b-KC (SEQ ID NO: 514), VRC08-KC (SEQ ID NO: 515), VRC18b-KC (SEQ ID NO: 516), VRC-PG04-KC (SEQ ID NO: 517), 3BNC60-KC (SEQ ID NO: 518), 3BNC117-KC (SEQ ID NO: 519), VK3-15*01 (SEQ ID NO: 520), VRC23-KC (SEQ ID NO: 521), VK1-33*01 (SEQ ID NO: 522), VRC27-KC (SEQ ID NO: 523), VRC-CH31-KC (SEQ ID NO: 524), VRC-N6-KC (SEQ ID NO: 525), 12A12-KC (SEQ ID NO: 526), 12A21-KC (SEQ ID NO: 527), VL2-14*01 (SEQ ID NO: 528), VRC-PG19-KC (SEQ ID NO: 529), VRC-PG20-KC (SEQ ID NO: 530), VK1-5*01 (SEQ ID NO: 531), and PCIN63-71I-KC (SEQ ID NO: 532).

DETAILED DESCRIPTION

In one aspect, provided herein are anti-HIV Env antibodies generated from a HIV subtype C infected human patient and variants of the antibodies. In some embodiments, an antibody described herein has the hallmark VRC01-class features and demonstrates similar neutralization breath to the prototype VRC01 antibody. In another aspect, the present disclosure relates to nucleotide sequences encoding, compositions comprising, and kits comprising an antibody described herein. In another aspect, the present disclosure relates to methods of treatment and prevention of HIV using an antibody described herein. In another aspect, the present disclosure relates to methods of diagnosing and monitoring of HIV infection using an antibody described herein.

I. Definitions

To facilitate an understanding of the present invention, a number of terms and phrases are defined below.

The terms "human immunodeficiency virus" or "HIV," as used herein, refer generally to a retrovirus that is the causative agent for acquired immunodeficiency syndrome (AIDS), variants thereof (e.g., simian acquired immunodeficiency syndrome, SAIDS), and diseases, conditions, or opportunistic infections associated with AIDS or its variants, and includes HIV-Type 1 (HIV-1) and HIV-Type 2 (HIV-2) of any clade or strain therein, related retroviruses (e.g., simian immunodeficiency virus (SIV)), and variants thereof (e.g., engineered retroviruses, e.g., chimeric HIV viruses, e.g., simian-human immunodeficiency viruses (SHIVs)). In some embodiments, an HIV virus is an HIV-Type-1 virus. Previous names for HIV include human T-lymphotropic virus-III (HTLV-III), lymphadenopathy-associated virus (LAV), and AIDS-associated retrovirus (ARV).

As used herein, the term "clade" refers to related human immunodeficiency viruses (HIVs) classified according to their degree of genetic similarity. There are currently four known groups of HIV-1 isolates: M, N, O, and P. Group M (major strains) viruses are responsible for the majority of the global HIV epidemic. The other three groups, i.e., N, O and P are quite uncommon and only occur in Cameroon, Gabon and Equatorial Guinea. In some embodiments, an HIV virus is a Group M HIV virus. Within group M there are known to be at least nine genetically distinct subtypes or clades of HIV-1: subtypes or clades A, B, C, D, F, G, H, J and K. Additionally, different subtypes can combine genetic material to form a hybrid virus, known as a 'circulating recombinant form' (CRFs). Subtype/clade B is the dominant HIV subtype in the Americas, Western Europe and Australasia. Subtype/clade C is very common in the high AIDS prevalence countries of Southern Africa, as well as in the horn of Africa and India. Just under half of all people living with HIV have subtype C. In certain exemplary embodiments, methods described herein can be used to treat a subject (e.g., a human) infected with HIV (e.g., HIV-1) or to block or prevent HIV (e.g., HIV-1) infection in subject (e.g., a human) at risk of HIV transmission. The HIV may be of two, three, four, five, six, seven, eight, nine, ten, or more clades and/or two or more groups of HIV.

Acquired immune deficiency syndrome ("AIDS") is a disease caused by the human immunodeficiency virus, or HIV.

Figure 9:
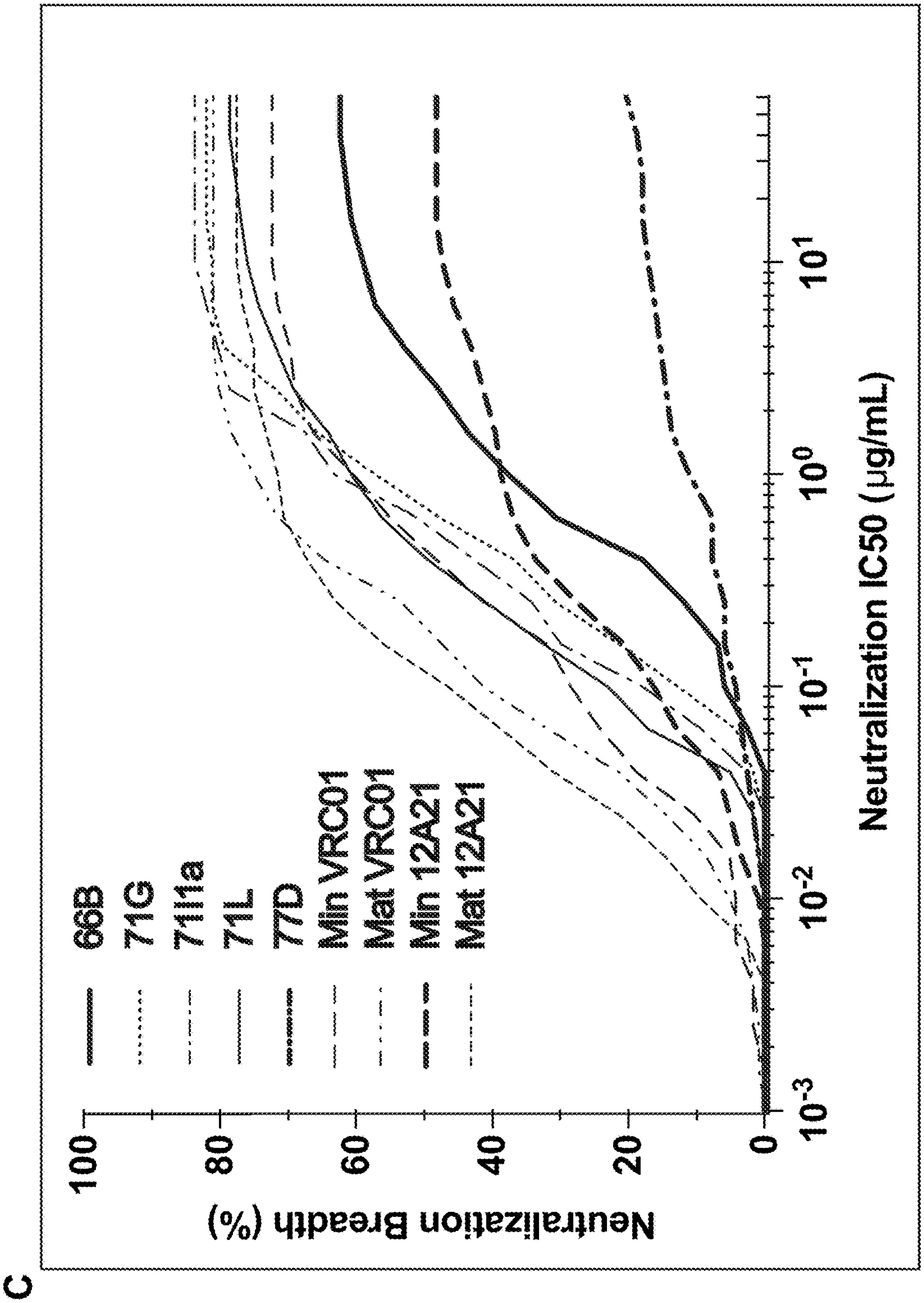

As used herein, the term "envelope glycoprotein" or "Env" refers to the glycoprotein that is expressed on the surface of the envelope of HIV virions and the surface of the plasma membrane of HIV infected cells. "Envelope glycoprotein" or "Env" encompass, but are not limited to, native Env, an isoform of Env, or a recombinant variant of Env (e.g., SOSIP) derived from an HIV isolate. Env is the sole virally encoded gene product on the surface of the virus and, as such, is the only target of neutralizing antibodies. Env is a trimer of heterodimers composed of two non-covalently associated subunits: the receptor-binding gp120 and the fusion machinery-containing gp41. Each subunit is derived from a gp160 precursor glycoprotein following cleavage by cellular furins. HIV-1 gp120 binds the CD4 molecule on the surface of human target T cells to initiate the viral entry process, and following co-receptor engagement, fusion is mediated by gp41. gp140 env is the uncleaved ectodomain of gp160. In some embodiments, the Env is a clade A Env. In some embodiments, the Env is a clade B Env. In some embodiments, the Env is a clade C Env. In some embodiments, the Env is a clade A Env from the indicator virus panel as shown in FIG. 8 or FIG. 9. In some embodiments, the Env is a clade B Env from the indicator virus panel as shown in FIG. 8 or FIG. 9. In some embodiments, the Env is a clade C Env from the indicator virus panel as shown in FIG. 8 or FIG. 9. In some embodiments, the Env is the Env of a virus from the indicator virus panel as shown in FIG. 8 or FIG. 9. In some embodiments, the Env is a BG505, 92BR020, JR-FL, YU-2, or JR-CSF Env polypeptide. In some embodiments, the Env is a BG505 Env polypeptide. UniProtKB accession number Q2NOS5-1, Q2NOS6-1, and Q2NOS7-1 provide BG505 env gp160 polypeptide sequences. In some embodiments, the Env is a well-ordered Env trimer.

The term "well-ordered Env trimer" or "well-ordered trimer" as used herein refers to an envelope glycoprotein trimer comprising three cleaved gp140 polypeptides that closely mimics the quaternary structure of the Env ectodomain on the surface of the envelope of HIV or SIV virions and the surface of the plasma membrane of HIV or SIV infected cells. In some embodiments, the gp120 and gp41 ectodomain is linked by a covalent linkage, for example, a disulfide bond. In some embodiments, the gp140 polypeptide comprises one or more mutations to promote trimer formation. In some embodiments, the gp140 polypeptide comprises one or more mutations to promote disulfide formation. In some embodiments, the well-ordered trimer is an SOSIP gp140 trimer. Well-ordered SOSIP trimers have been disclosed in US Patent Appl. Pub. No. 2014/0212458, Sanders, R. W. et al., *PLOS Pathog.* 9, e1003618 (2013) and Guenaga J., et al., *Immunity* 46 (5): 792-803.e3 (2017), each of which is incorporated by reference herein in its entirety. In some embodiments, a well ordered trimer is formed from a clade A Env. In some embodiments, a well ordered trimer is formed from a clade B Env. In some embodiments, a well ordered trimer is formed from a clade C Env. In some embodiments, a well ordered trimer is formed from a circulating recombinant form Env. In some embodiments, a well ordered trimer is YU-2 gp140. In some embodiments, a well ordered trimer is BG505 SOSIP as disclosed in International Application No. PCT/US2018/041729, filed Jul. 12, 2018, which is incorporated herein by reference in its entirety for all purposes. In some embodiments, a well-ordered Env trimer is a native flexibly linked (NFL) trimer as described in Sharna, et al., Cell Reports, 11 (4): 539-50 (2015). In some embodiments, a well-ordered Env trimer is a DS-SOSIP as described in Chuang, et al., J. Virology, 91 (10) pii: e02268-16 (2017). In some embodiments, a well ordered trimer is formed from a SIV Env. In some embodiments, a well ordered trimer is an SIV Env SOSIP. In some embodiments, a well ordered trimer is formed from an Env comprising a mutation (e.g., substitution or deletion) in the CD4 binding site. In some embodiments, a well ordered trimer is YU-2 gp140 comprising the D368R substitution. In some embodiments, a well ordered trimer is formed from an Env comprising a mutation (e.g., substitution or deletion) in the CD4 binding site wherein the mutation reduces or disrupts the binding between Env and CD4. In some embodiments, a well ordered trimer is a CRF or C108 SOSIP. See, e.g., Andrabi et al, *Immunity* 43 (5): 959-973 (2015). In some embodiments, the gp120 and gp41 ectodomain is linked by a peptide linker, for example, a Gly-Ser linker, as described in Georgiev I S, et al., *J. Virology* 89 (10): 5318-5329 (2015). In some embodiments, the well-ordered Env trimer is stable. In some embodiments, the BG50S Env has the amino acid sequence of SEQ ID NO: 340.

The term “antibody” means an immunoglobulin molecule (or a group of immunoglobulin molecules) that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the terms “antibody” and “antibodies” are terms of art and can be used interchangeably herein and refer to a molecule with an antigen-binding site that specifically binds an antigen.

Antibodies can include, for example, monoclonal antibodies, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), affybodies, Fab fragments, F(ab') 2 fragments, disulfide-linked Fvs (sdFv), anti-idiotypic (anti-Id) antibodies (including, e.g., anti-anti-Id antibodies), bispecific antibodies, and multi-specific antibodies. In certain embodiments, antibodies described herein refer to polyclonal antibody populations. Antibodies can be of any type (e.g., IgG, IgE, IgM, IgD, IgA, or IgY), any class (e.g., $IgG_1$, $IgG_2$, $IgG_3$, $IgG_4$, IgA1, or IgA2), or any subclasses (isotypes) thereof (e.g. $IgG_1$, $IgG_2$, $IgG_3$, $IgG_4$, IgA1 and IgA2), of immunoglobulin molecule, based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated or fused to other molecules such as toxins, radioisotopes, other polypeptides etc.

As used herein, the terms “antigen-binding domain,” “antigen-binding region,” “antigen-binding site,” and similar terms refer to the portion of antibody molecules which comprises the amino acid residues that confer on the antibody molecule its specificity for the antigen (e.g., HIV Env). The antigen-binding region can be derived from any animal species, such as mouse and humans.

As used herein, the terms “variable region” or “variable domain” are used interchangeably and are common in the art. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen (e.g., HIV Env). In certain embodiments, the variable region is a human variable region. In certain embodiments, the variable region comprises human CDRs and human framework regions (FRs). In certain embodiments, the variable region comprises human CDRs and primate (e.g., non-human primate) framework regions (FRs).

There are several approaches for determining CDRs. One approach is based on cross-species sequence variability (i.e., Kabat et al., *Sequences of Proteins of Immunological Interest*, (5th ed., 1991, National Institutes of Health, Bethesda Md.), “Kabat”). A second approach was developed by the MGT, the international ImMunoGeneTics database (imgt.cines.fr) as a high quality integrated information system specializing in immunoglobulins (IG), T cell receptors (TR) and major histocompatibility complex (MHC) of human and other vertebrates. Lefranc, M.-P., The Immunologist, 7, 132-136 (1999). The IMGT unique numbering defined for the IG and TR variable regions and domains of all jawed vertebrates has allowed a redefinition of the limits of the framework (FR-IMGT) and complementarity determining regions (CDR-IMGT), leading to a standardized description of mutations, allelic polymorphisms, 2D representations (Colliers de Perles) and 3D structures, whatever the antigen receptor, the chain type, or the species. A third approach is based on crystallographic studies of antigen-antibody complexes (Al-lazikani et al, *J. Molec. Biol.* 273:927-948 (1997)). In addition, combinations of these approaches are sometimes used in the art to determine CDRs. In some embodiments, the CDR regions are determined according to Kabat. In some embodiments, the CDR regions are determined according to IMGT.

The Kabat numbering system is generally used when referring to a residue in the variable domain (approximately residues 1-107 of the light chain and residues 1-113 of the heavy chain) (e.g., Kabat et al., *Sequences of Immunological Interest*. (5th Ed., 1991, National Institutes of Health, Bethesda, Md.) (“Kabat”).

The amino acid position numbering as in Kabat, refers to the numbering system used for heavy chain variable domains or light chain variable domains of the compilation of antibodies in Kabat et al. (*Sequences of Immunological Interest*. (5th Ed., 1991, National Institutes of Health, Bethesda, Md.), "Kabat"). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. In some embodiments, the CDR regions are determined according to Kabat. In some embodiments, the CDR regions are determined according to IMGT. In some embodiments, the CDR regions are determined according to Chothia. In some embodiments, the CDR regions are determined according to AbM.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The terms "VL" and "VL domain" are used interchangeably to refer to the light chain variable region of an antibody.

The terms "VH" and "VH domain" are used interchangeably to refer to the heavy chain variable region of an antibody.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab') 2, and Fv fragments, linear antibodies, and single chain antibodies.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab') 2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "polyclonal antibody" describes a composition of different (diverse) antibody molecules which are capable of binding to or reacting with several different specific antigenic determinants on the same or on different antigens. Usually, the variability of a polyclonal antibody is located in the so-called variable regions of the polyclonal antibody, in particular in the CDR regions. In the present disclosure a mixture of two or more polyclonal antibodies (a polycomposition) is produced in one mixture from a polyclonal polycomposition cell line, which is produced from two or more parental polyclonal cell lines each expressing antibody molecules which are capable of binding to a distinct target, but it may also be a mixture of two or more polyclonal antibodies produced separately. A mixture of monoclonal antibodies providing the same antigen/epitope coverage as a polyclonal antibody described herein will be considered as an equivalent of a polyclonal antibody. When stating that a member of a polyclonal antibody binds to an antigen, it is herein meant to be binding with a binding constant below 100 nM, preferably below 10 nM, even more preferred below 1 nM.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g. murine) that have the desired specificity, affinity, and capability ("CDR grafted") (Jones et al., *Nature* 321:522-525 (1986); Riechmann et al., *Nature* 332:323-327 (1988); Verhoeyen et al., *Science* 239:1534-1536 (1988)). In some instances, the Fv framework region (FR) residues of a human immunoglobulin are replaced with the corresponding residues in an antibody or fragment from a non-human species (e.g., murine) that has the desired specificity, affinity, and capability. The humanized antibody or antigen-binding fragment thereof can be further modified by the substitution of additional residues either in the Fv framework region and/or within the replaced non-human residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., *Proc. Natl. Acad. Sci., USA,* 91 (3): 969-973 (1994), and Roguska et al., *Protein Eng.* 9 (10): 895-904 (1996). In some embodiments, a “humanized antibody” is a resurfaced antibody.

The term “chimeric” antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g., mouse) with the desired specificity, affinity, and capability while the constant regions are homologous to the sequences in antibodies or antigen-binding fragments thereof derived from another (usually human) to avoid eliciting an immune response in that species.

The term “epitope” or “antigenic determinant” are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

“Binding affinity” generally refers to the strength of the sum total of non-covalent interactions between a single binding site of a molecule (e.g., an antibody) and its binding partner (e.g., an antigen). Unless indicated otherwise, as used herein, “binding affinity” refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

“Or better” when used herein to refer to binding affinity refers to a stronger binding between a molecule and its binding partner. “Or better” when used herein refers to a stronger binding, represented by a smaller numerical Kd value. For example, an antibody which has an affinity for an antigen of “0.6 nM or better”, the antibody’s affinity for the antigen is <0.6 nM, i.e. 0.59 nM, 0.58 nM, 0.57 nM etc. or any value less than 0.6 nM.

As used herein, the terms “immunospecifically binds,” “immunospecifically recognizes,” “specifically binds,” and “specifically recognizes” are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), or other assays known in the art. In a specific embodiment, molecules that immunospecifically bind to an antigen bind to the antigen with a Kd that is at least 2 logs, 2.5 logs, 3 logs, or 4 logs lower than the Kd when the molecules bind non-specifically to another antigen. In one example, the antibody may specifically bind to the BG505 Env. In some embodiments, the BG505 Env has the amino acid sequence of SEQ ID NO: 340. In one example, the antibody may specifically bind to a BG505 SOSIP trimer. In one example, the antibody may specifically bind to JR-FL Env. In one example, the antibody may specifically bind to JR-FL SOSIP. In one example, the antibody may specifically bind to YU2 gp140. The antibody may bind to JR-FL SOSIP, BG505 SOSIP, or YU2 gp140 with a Kd at least 2 logs, 2.5 logs, 3 logs, or 4 logs lower than Kd of binding to other viral or non-viral polypeptides. An antibody that specifically binds to Env encompass, but are not limited to, antibodies that specifically bind to native Env, an isoform of Env, or a variant of Env (e.g., SOSIP) derived from an HIV isolate, for example, JR-FL, BG505, or YU2. In some embodiments, the antibody specifically binds to JR-FL Env. In some embodiments, the antibody specifically binds to JR-FL SOSIP. In some embodiments, the antibody specifically binds to BG505 Env. In some embodiments, the antibody specifically binds to BG505 SOSIP. In some embodiments, the antibody specifically binds to YU2 Env. In some embodiments, the antibody specifically binds to YU2 SOSIP.

By “preferentially binds,” it is meant that the antibody specifically binds to an epitope more readily than it would bind to a related, similar, homologous, or analogous epitope. Thus, an antibody which “preferentially binds” to a given epitope would more likely bind to that epitope than to a related epitope, even though such an antibody may cross-react with the related epitope.

An antibody is said to “competitively inhibit” binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The term “broadly neutralizing antibody” or “bnAb,” as used herein, with respect to HIV (e.g., HIV-1), refers to an antibody that recognizes HIV Env of more than one isolate or strain of HIV and inhibits or prevents receptor binding of target cells as evaluated in an in vitro neutralization assay. In some embodiments, a broadly neutralizing antibody inhibits infection of a susceptible target cell by HIV. In some embodiments, a broadly neutralizing antibody specifically binds an HIV Env and inhibits infection of a susceptible target cell (e.g., TZM-bl) by an HIV pseudovirus comprising an Env polypeptide. HIV pseudovirus neutralization assays have been disclosed in the art, for example, in Walker, L. M. et al., *Nature* 477, 466-470 (2011), Li M., et al., J. Virol. 79:10108-10125 (2005), each of which is incorporated herein by reference in its entirety for all purposes. In some embodiments, a broadly neutralizing antibody neutralizes 2, 3, 4, 5, 6, 7, 8, 9, or more HIV strains or pseudoviruses. In some embodiments, a broadly neutralizing antibody neutralizes 2, 3, 4, 5, 6, 7, 8, 9, or more HIV strains or pseudoviruses that belong to the same or different clades. In some embodiments, a broadly neutralizing antibody is capable of neutralizing HIV strains or pseudoviruses from at least two different clades. In some embodiments, a broadly neutralizing antibody is capable of neutralizing HIV at least one clade B strain or pseudovirus and one clade C strain or pseudovirus. In some embodiments, a broadly neutralizing antibody is capable of neutralizing HIV more than one clade B strain or pseudovirus and more than one clade C strain or pseudovirus.

In some embodiments, the breadth of neutralization is tested on an indicator virus panel comprising cross-clade HIV isolates. In some embodiments, the virus panel comprises the cross-clade isolates as shown in FIG. 8. In some embodiments, the virus panel comprises the cross-clade isolates as shown in FIG. 9 In some embodiments, a broadly neutralizing antibody is capable of neutralizing at least about 50%, 60%, 70%, 80%, 90%, 95%, or 100% of cross-clade HIV isolates in the 106-member indicator virus panel. In some embodiments, a broadly neutralizing antibody is capable of neutralizing at least about 60% of cross-clade HIV isolates in the 106-member indicator virus panel. In some embodiments, a broadly neutralizing antibody is capable of neutralizing at least about 70% of cross-clade HIV isolates in the 106-member indicator virus panel. In some embodiments, a broadly neutralizing antibody is capable of neutralizing at least about 75% of cross-clade HIV isolates in the 106-member indicator virus panel. In some embodiments, a broadly neutralizing antibody is capable of neutralizing at least about 80% of cross-clade HIV isolates in the 106-member indicator virus panel. In some embodiments, a broadly neutralizing antibody is capable of neutralizing at least about 90% of cross-clade HIV isolates in the 106-member indicator virus panel. In some embodiments, a broadly neutralizing antibody is capable of neutralizing at least about 95% of cross-clade HIV isolates in the 106-member indicator virus panel. In some embodiments, a broadly neutralizing antibody is capable of neutralizing at least about 40%, 50%, 60%, 70%, 80%, 90%, 95%, or 100% of cross-clade HIV isolates in the indicator virus panel as shown in FIG. 8 or FIG. 9. In some embodiments, a broadly neutralizing antibody is capable of neutralizing at least about 40% of cross-clade HIV isolates in the indicator virus panel as shown in FIG. 8 or FIG. 9. In some embodiments, a broadly neutralizing antibody is capable of neutralizing at least about 50% of cross-clade HIV isolates in the indicator virus panel as shown in FIG. 8 or FIG. 9. In some embodiments, a broadly neutralizing antibody is capable of neutralizing at least about 60% of cross-clade HIV isolates in the indicator virus panel as shown in FIG. 8 or FIG. 9. In some embodiments, a broadly neutralizing antibody is capable of neutralizing at least about 70% of cross-clade HIV isolates in the indicator virus panel as shown in FIG. 8 or FIG. 9. In some embodiments, a broadly neutralizing antibody is capable of neutralizing at least about 75% of cross-clade HIV isolates in the indicator virus panel as shown in FIG. 8 or FIG. 9. In some embodiments, a broadly neutralizing antibody is capable of neutralizing at least about 80% of cross-clade HIV isolates in the indicator virus panel as shown in FIG. 8 or FIG. 9. In some embodiments, a broadly neutralizing antibody is capable of neutralizing at least about 90% of cross-clade HIV isolates in the indicator virus panel as shown in FIG. 8 or FIG. 9. In some embodiments, a broadly neutralizing antibody is capable of neutralizing at least about 95% of cross-clade HIV isolates in the indicator virus panel as shown in FIG. 8 or FIG. 9.

In some embodiments, the potency of neutralization by a broadly neutralizing antibody is expressed as the median $IC_{50}$ neutralization activity against a virus panel, for example, the indicator virus panel as shown in FIG. 8 or FIG. 9.

In some embodiments, a broadly neutralizing antibody is capable of neutralizing at least about 40%, 50%, 60%, 70%, 80%, 90%, 95%, or 100% of cross-clade HIV isolates in the indicator virus panel as shown in FIG. 8 or FIG. 9 with a median $IC_{50}$ equal to or less than about 1 μg/ml, 0.8 μg/ml, 0.5 μg/ml, 0.3 μg/ml, 0.1 μg/ml, 0.07 μg/ml, 0.06 μg/ml, 0.05 μg/ml, 0.025 μg/ml, 0.01 μg/ml or 0.005 μg/ml. In some embodiments, a broadly neutralizing antibody is capable of neutralizing at least about 70% of cross-clade HIV isolates in the indicator virus panel as shown in FIG. 8 or FIG. 9 with a median $IC_{50}$ equal to or less than 0.8 μg/ml. In some embodiments, a broadly neutralizing antibody is capable of neutralizing at least about 75% of cross-clade HIV isolates in the indicator virus panel as shown in FIG. 8 or FIG. 9 with a median $IC_{50}$ equal to or less than 0.8 μg/ml. In some embodiments, a broadly neutralizing antibody is capable of neutralizing at least about 80% of cross-clade HIV isolates in the indicator virus panel as shown in FIG. 8 or FIG. 9 with a median $IC_{50}$ equal to or less than 0.8 μg/ml. In some embodiments, a broadly neutralizing antibody is capable of neutralizing at least about 70% of cross-clade HIV isolates in the indicator virus panel as shown in FIG. 8 or FIG. 9 with a median $IC_{50}$ equal to or less than 0.5 μg/ml. In some embodiments, a broadly neutralizing antibody is capable of neutralizing at least about 75% of cross-clade HIV isolates in the indicator virus panel as shown in FIG. 8 or FIG. 9 with a median $IC_{50}$ equal to or less than 0.5 μg/ml. In some embodiments, a broadly neutralizing antibody is capable of neutralizing at least about 80% of cross-clade HIV isolates in the indicator virus panel as shown in FIG. 8 or FIG. 9 with a median $IC_{50}$ equal to or less than 0.5 μg/ml.

The term "$IC_{50}$" refers to the half maximal inhibitory concentration of an inhibitor, e.g., a broadly neutralizing antibody. For example, $IC_{50}$ is the concentration of an inhibitor, e.g., a broadly neutralizing antibody, where the response, e.g., infection by virus or pseudovirus, is reduced by 50%.

The phrase "substantially similar," or "substantially the same", as used herein, denotes a sufficiently high degree of similarity between two numeric values (generally one associated with an antibody described herein and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides described herein are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, *Proc. Natl. Acad. Sci.,* 87:2264-2268 (1990), as modified in Karlin et al., *Proc. Natl. Acad. Sci.,* 90:5873-5877 (1993), and incorporated into the NBLAST and XBLAST programs (Altschul et al., *Nucleic Acids Res.,* 25:3389-3402 (1991)). In certain embodiments, Gapped BLAST can be used as described in Altschul et al., *Nucleic Acids Res.* 25:3389-3402 (1997). BLAST-2, WU-BLAST-2 (Altschul et al., *Methods in Enzymology,* 266:460-480 (1996)), ALIGN, ALIGN-2 (Genentech, South San Francisco, California) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48): 444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (*CABIOS,* 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, WI 53711). Bestfit uses the local homology algorithm of Smith and Waterman (*Advances in Applied Mathematics* 2:482 489 (1981)) to find the best segment of homology between two sequences. When using Bestfit or any other sequence alignment program to determine whether a particular sequence is, for instance, 95% identical to a reference sequence described herein, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides described herein are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value there between, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies described herein do not abrogate the binding of the polypeptide or antibody containing the amino acid sequence, to the antigen(s). Methods of identifying nucleotide and amino acid conservative substitutions which do not eliminate antigen binding are well-known in the art (see, e.g., Brummell et al., *Biochem.* 32:1180-1 187 (1993); Kobayashi et al., *Protein Eng.* 12 (10): 879-884 (1999); and Burks et al., *Proc. Natl. Acad. Sci. USA* 94: 412-417 (1997)).

Vectors that can be used include, but are not limited to, plasmids, bacterial vectors, and viral vectors. Viral vectors include cytomegalovirus (CMV) vectors. An advantage of these CMV vectors for use in therapeutic vaccine delivery is that they create a new CD8+ T cell epitope paradigm and induce more potent and enduring responses. It has been shown in animal models that vaccines based on these viral vectors can clear viral infections (Hansen, S. G. 2013. *Science* 340:1237874), and so these approaches have promise for a therapeutic vaccine, a setting in which tailored vaccines can be useful.

Other viral vectors can include poxvirus (vaccinia), including vaccinia Ankara and canarypox; adenoviruses, including adenovirus type 5 (Ad5); rubella; sendai virus; rhabdovirus; alphaviruses; and adeno-associated viruses. Alternatively, the vaccine antigens could be delivered as DNA, RNA or protein components of a vaccine.

As used herein, the terms "treatment" or "therapy" (as well as different forms thereof, including curative or palliative) refer to treatment of an infected person. As used herein, the term "treating" includes alleviating or reducing at least one adverse or negative effect or symptom of a condition, disease or disorder. This condition, disease or disorder can be HIV infection.

Terms such as "treating" or "treatment" or "to treat" or "alleviating" or "to alleviate" refer to therapeutic measures that cure, slow down, lessen symptoms of, and/or halt progression of a diagnosed pathologic condition or disorder, such as HIV or AIDS. Thus, those in need of treatment include those already diagnosed with or suspected of having the disorder. In certain embodiments, a subject is successfully "treated" for the disorder according to the methods described herein if the patient shows one or more of the following: a reduction in the number of or complete absence of viral load; a reduction in the viral burden; inhibition of or an absence of the virus into peripheral organs; relief of one or more symptoms associated with the disorder; reduced morbidity and mortality; improvement in quality of life; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

As used herein, the terms "prevention" or "prophylaxis" refer to preventing a subject from becoming infected with, or reducing the risk of a subject from becoming infected with, or halting transmission of, or the reducing the risk of transmission of a virus. Prophylactic or preventative measures refer to measures that prevent and/or slow the development of a targeted pathological condition or disorder. Thus, those in need of prophylactic or preventative measures include those prone to have the disorder and those in whom the disorder is to be prevented. In some embodiments, prevention encompasses passive immunization of a subject in need thereof comprising administering an effective amount of an antibody described herein.

As employed above and throughout the disclosure the term "effective amount" refers to an amount effective, at dosages, and for periods of time necessary, to achieve the desired result with respect to the treatment of the relevant disorder, condition, or side effect. An "effective amount" can be determined empirically and in a routine manner, in relation to the stated purpose. It will be appreciated that the effective amount of components of the present invention will vary from patient to patient not only with the particular vaccine, component or composition selected, the route of administration, and the ability of the components to elicit a desired result in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide the improved therapeutic response. An effective amount is also one in which any toxic or detrimental effects of the components are outweighed by the therapeutically beneficial effects.

The term "therapeutically effective amount" refers to an amount of an antibody, immunoconjugate, or other drug effective to "treat" a disease or disorder in a subject or mammal. To the extent an antibody can prevent growth and/or kill existing cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "subject," "individual," and "patient" are used interchangeably herein, and refer to an animal, for example a human, to whom treatment, including prophylactic treatment, with the antibody or pharmaceutical composition according to the present disclosure, is provided. In some embodiments, the subject, individual, or patient has been infected with HIV. In some embodiments, the subject, individual, or patient suffers from AIDS. In some embodiments, the subject, individual, or patient has been exposed to HIV. In some embodiments, the subject, individual, or patient is at risk of being exposed to HIV.

Administration "in combination with" one or more further therapeutic agents includes simultaneous (concurrent) or consecutive administration in any order.

The terms "pharmaceutically composition," "pharmaceutical formulation," "pharmaceutically acceptable formulation," or "pharmaceutically acceptable composition" all of which are used interchangeably, refer to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. "Pharmaceutically acceptable" or "pharmaceutical formulation" refers to a preparation which is in such form as to permit the biological activity of the active ingredient to be effective, and which contains no additional components which are unacceptably toxic to a subject to which the formulation would be administered. The formulation can be sterile.

The term "antiretroviral therapy" or "ART," as used herein, refers to any of the therapies used to manage progression of a retrovirus (e.g., HIV) infection in a subject (e.g., a human), including, for example, nucleoside reverse transcriptase inhibitors (NRTIs), non-nucleoside reverse transcriptase inhibitors (NNRTIs), protease inhibitors (PIs), fusion inhibitors, entry inhibitors, maturation inhibitors, cellular inhibitors, integrase strand transfer inhibitors, and multi-class combinations. Such drugs include, but are not limited to, lamivudine and zidovudine, emtricitabine (FTC), zidovudine (ZDV), azidothymidine (AZT), lamivudine (3TC), zalcitabine, dideoxycytidine (ddC), tenofovir disoproxil fumarate (TDF), didanosine (ddl), stavudine (d4T), abacavir sulfate (ABC), etravirine, delavirdine (DLV), efavirenz (EFV), nevirapine (NVP), amprenavir (APV), tipranavir (TPV), indinavir (IDV), saquinavir, saquinavir mesylate (SQV), lopinavir (LPV), ritonavir (RTV), fosamprenavir calcium (FOS-APV), ritonavir, RTV, darunavir, atazanavir sulfate (ATV), nelfinavir mesylate (NFV), enfuvirtide, T-20, maraviroc and raltegravir. ART drugs can also include antibodies that target HIV proteins or cellular proteins associated with disease progression. Also included are immune-based therapies, such as IL-2, IL-12, and alpha-epibromide. Each of these drugs can be administered alone or in combination with any other ART drug or any HIV-specific neutralizing antibody, such as a broadly neutralizing antibody, which is incorporated by reference herein in its entirety for all purposes.

The term "immunomodulator," as used herein, refers to an agent, such as an antibody or peptide, which is capable of increasing, inducing, or extending an immune response (e.g., a cell-mediated immune response and/or a humoral immune response) when administered to a subject (e.g., a human, e.g., a human infected with HIV or at risk of an HIV infection or transmission). Immunomodulators include, but are not limited to immune checkpoint inhibitors, for example, a PD-1, PD-L1, LAG-3, or TIGIT antagonist. In some embodiments, an immunomodulator used in the methods described herein comprises an anti-PD-1 antibody, anti-PD-L1 antibody, anti-LAG3 antibody, or an anti-TIGIT antibody. An immunomodulator can be administered in conjunction with (e.g., prior to, concurrently with, or subsequent to, or within the context of a treatment regimen that includes the administration of a broadly neutralizing antibody described herein.

As used in this specification and the appended claims, the singular forms "a," "an," and "the" include plural referents unless the content clearly dictates otherwise. Thus, for example, reference to "a cell" includes a combination of two or more cells, and the like.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "about" as used herein when referring to a measurable value such as an amount, a temporal duration, and the like, is meant to encompass variations of up to +20% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope described herein are approximations, the numerical values set forth in the specific examples are reported as precisely as possible. Any numerical value, however, inherently contain certain errors necessarily resulting from the standard deviation found in their respective testing measurements.

It is understood that wherever embodiments are described herein with the language "comprising," otherwise analogous embodiments described in terms of "consisting of" and/or "consisting essentially of" are also provided.

II. Anti-HIV Antibodies

In one aspect, provided herein are anti-HIV antibodies that bind to Env. In some embodiments, an antibody described herein is a monoclonal antibody. In some embodiments, an antibody described herein is a human antibody. In some embodiments, an antibody described herein is a broadly neutralizing antibody. In some embodiments, an antibody described herein specifically binds the Env of at least one HIV isolate in the indicator virus panels of FIGS. 8 and 9. In some embodiments, an antibody described herein specifically binds the Env of at least two, at least three, at least four, or at least five HIV isolates in the indicator virus panel of FIGS. 8 and 9. In some embodiments, an antibody described herein is a VRCO1 class antibody. In some embodiments, an antibody described herein binds Env at the CD4 receptor binding site (CD4bs) epitope region. In some embodiments, an antibody described herein binds to wild type Env, but does not bind a mutant variant of Env comprising a substitution or deletion in the CD4 receptor binding site. In some embodiments, the Env is a clade A Env. In some embodiments, the Env is a clade B Env. In some embodiments, the Env is a clade C Env. In some embodiments, the Env is a clade A Env from the indicator virus panel as shown in FIG. 8 or FIG. 9. In some embodiments, the Env is a clade B Env from the indicator virus panel as shown in FIG. 8 or FIG. 9. In some embodiments, the Env is a clade C Env from the indicator virus panel as shown in FIG. 8 or FIG. 9. In some embodiments, the Env is the Env of a virus from the indicator virus panel as shown in FIG. 8 or FIG. 9. In some embodiments, the Env is BG505, JR-FL, YU-2, or JR-CSF r92RW020, BG505, or JR-FL Env.

In some embodiments, an isolated monoclonal antibody described herein comprises a VH, a VL, or a VH and VL as shown in the section titled "SEQUENCES."

In some embodiments, an isolated monoclonal antibody described herein comprises one, two, three, four, five or six of the VH CDR1, VH CDR2, VH CDR3, VL CDR1, VL CDR2, and VL CDR3 sequences as shown in the section titled "SEQUENCES."

In some embodiments, an isolated monoclonal antibody described herein comprises a VH CDR3 sequence as shown in the section titled "SEQUENCES."

In some embodiments, an isolated monoclonal antibody described herein comprises a VH CDR1, VH CDR2, VH CDR3, VL CDR1, VL CDR2, and VL CDR3 sequence as shown in the section titled "SEQUENCES."

Also provided herein are polypeptides that comprise an amino acid sequence having at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence, or is identical to the sequences listed in the section titled "SEQUENCES."

In some embodiments, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D. In some embodiments, the antibody is a human antibody. In some embodiments, the antibody comprises the VH CDR1, VH CDR2, VL CDR1, VL CDR2, and VL CDR3 of an antibody described herein. In some embodiments, the antibody comprises the VH CDR1, VH CDR2, VL CDR1, VL CDR2, and VL CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D.

In some embodiments, an isolated monoclonal antibody described herein specifically binds to Env and comprises a $V_H$ CDR1, $V_H$ CDR2, $V_H$ CDR3, VL CDR1, VL CDR2, and VL CDR3, wherein the $V_H$ CDR3 comprises an amino acid sequence that is at least about 90%, 95%, 97%, 98%, 99% or 100% identical to the $V_H$ CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody is a human antibody. In some embodiments, the antibody comprises the $V_H$ CDR1, $V_H$ CDR2, VL CDR1, VL CDR2, and VL CDR3 of an antibody described herein. In some embodiments, the antibody comprises the $V_H$ CDR1, $V_H$ CDR2, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C.

In some embodiments, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of PCIN63-71I1a, or PCIN63-71L. In some embodiments, the antibody is a human antibody. In some embodiments, the antibody comprises the VH CDR1, VH CDR2, VL CDR1, VL CDR2, and VL CDR3 of an antibody described herein. In some embodiments, the antibody comprises the VH CDR1, VH CDR2, VL CDR1, VL CDR2, and VL CDR3 of PCIN63-71I1a, or PCIN63-71L.

In some embodiments, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 37-54. In some embodiments, the antibody comprises the VH CDR1, VH CDR2, VL CDR1, VL CDR2, and VL CDR3 of an antibody described herein. In some embodiments, the antibody comprises the VH CDR1, VH CDR2, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VL CDR1, VL CDR2, and VL CDR3 of PCIN63-71I1a, or PCIN63-71L.

In some embodiments, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 37, 39, 40, 42-48, or 50-53. In some embodiments, the antibody comprises the VH CDR1, VH CDR2, VL CDR1, VL CDR2, and VL CDR3 of an antibody described herein. In some embodiments, the antibody comprises the VH CDR1, VH CDR2, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VL CDR1, VL CDR2, and VL CDR3 of PCIN63-71I1a, or PCIN63-71L.

In some embodiments, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 44 or 47. In some embodiments, the antibody comprises the VH CDR1, VH CDR2, VL CDR1, VL CDR2, and VL CDR3 of an antibody described herein. In some embodiments, the antibody comprises the VH CDR1, VH CDR2, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VL CDR1, VL CDR2, and VL CDR3 of PCIN63-71I1a, or PCIN63-71L.

In some embodiments, an isolated monoclonal antibody described herein specifically binds to Env and comprises a VH CDR1, VH CDR2, VH CDR3, VL CDR1, VL CDR2, and VL CDR3, wherein the VH CDR3 comprises the VH CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D comprising 0, 1, 2, 3, 4, or 5 substitutions, insertions, or deletions. In some embodiments, the antibody is a human antibody. In some embodiments, the antibody comprises the VH CDR1, VH CDR2, VL CDR1, VL CDR2, and VL CDR3 of an antibody described herein. In some embodiments, the antibody comprises the VH CDR1, VH CDR2, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VL CDR1, VL CDR2, and VL CDR3 of PCIN63-71I1a, or PCIN63-71L.

In some embodiments, an isolated monoclonal antibody described herein specifically binds to Env and comprises a VH CDR1, VH CDR2, VH CDR3, VL CDR1, VL CDR2, and VL CDR3, wherein the VH CDR3 comprises the VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions. In some embodiments, the antibody is a human antibody. In some embodiments, the antibody comprises the VH CDR1, VH CDR2, VL CDR1, VL CDR2, and VL CDR3 of an antibody described herein. In some embodiments, the antibody comprises the VH CDR1, VH CDR2, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VL CDR1, VL CDR2, and VL CDR3 of PCIN63-71I1a, or PCIN63-71L.

In some embodiments, an isolated monoclonal antibody described herein specifically binds to Env and comprises a VH CDR1, VH CDR2, VH CDR3, VL CDR1, VL CDR2, and VL CDR3, wherein the VH CDR3 comprises the VH CDR3 of PCIN63-71I1a, or PCIN63-71L comprising 0, 1, 2, 3, 4, or 5 substitutions, insertions, or deletions. In some embodiments, the antibody is a human antibody. In some embodiments, the antibody comprises the VH CDR1, VH CDR2, VL CDR1, VL CDR2, and VL CDR3 of an antibody described herein. In some embodiments, the antibody comprises the VH CDR1, VH CDR2, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VL CDR1, VL CDR2, and VL CDR3 of PCIN63-71I1a, or PCIN63-71L.

In some embodiments, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 37-54 comprising 0, 1, 2, 3, 4, or 5 substitutions, insertions, or deletions. In some embodiments, the antibody is a human antibody. In some embodiments, the antibody comprises the VH CDR1, VH CDR2, VL CDR1, VL CDR2, and VL CDR3 of an antibody described herein. In some embodiments, the antibody comprises the VH CDR1, VH CDR2, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VL CDR1, VL CDR2, and VL CDR3 of PCIN63-71I1a, or PCIN63-71L.

In some embodiments, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 37, 39, 40, 42-48, or 50-53 comprising 0, 1, 2, 3, 4, or 5 substitutions, insertions, or deletions. In some embodiments, the antibody is a human antibody. In some embodiments, the antibody comprises the VH CDR1, VH CDR2, VL CDR1, VL CDR2, and VL CDR3 of an antibody described herein. In some embodiments, the antibody comprises the VH CDR1, VH CDR2, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VL CDR1, VL CDR2, and VL CDR3 of PCIN63-71I1a, or PCIN63-71L.

In some embodiments, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 44 or 47 comprising 0, 1, 2, 3, 4, or 5 substitutions, insertions, or deletions. In some embodiments, the antibody is a human antibody. In some embodiments, the antibody comprises the VH CDR1, VH CDR2, VL CDR1, VL CDR2, and VL CDR3 of an antibody described herein. In some embodiments, the antibody comprises the VH CDR1, VH CDR2, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to the VH CDR1 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D; (b) the VH CDR2 comprises an amino acid sequence that is at least about 90%, 95%, 97%, 98%, 99% or 100% identical to the VH CDR2 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D; and (c) the VH CDR3 comprises an amino acid sequence that is at least about 90%, 95%, 97%, 98%, 99% or 100% identical to the VH CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to the VH CDR1 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C; (b) the VH CDR2 comprises an amino acid sequence that is at least about 90%, 95%, 97%, 98%, 99% or 100% identical to the VH CDR2 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C; and (c) the VH CDR3 comprises an amino acid sequence that is at least about 90%, 95%, 97%, 98%, 99% or 100% identical to the VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to the VH CDR1 of PCIN63-71I1a, or PCIN63-71L; (b) the VH CDR2 comprises an amino acid sequence that is at least about 90%, 95%, 97%, 98%, 99% or 100% identical to the VH CDR2 of PCIN63-71I1a, or PCIN63-71L; and (c) the VH CDR3 comprises an amino acid sequence that is at least about 90%, 95%, 97%, 98%, 99% or 100% identical to the VH CDR3 of PCIN63-71I1a, or PCIN63-71L. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to SEQ ID NO: 1-18; (b) the VH CDR2 comprises an amino acid sequence that is at least about 90%, 95%, 97%, 98%, 99% or 100% identical to SEQ ID NO: 19-36; and (c) the VH CDR3 comprises an amino acid sequence that is at least about 90%, 95%, 97%, 98%, 99% or 100% identical to SEQ ID NO: 37-54. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to SEQ ID NO: 1, 3, 4, 6-12, or 14-17; (b) the VH CDR2 comprises an amino acid sequence that is at least about 90%, 95%, 97%, 98%, 99% or 100% identical to SEQ ID NO: 19, 21, 22, 24-30, or 32-35; and (c) the VH CDR3 comprises an amino acid sequence that is at least about 90%, 95%, 97%, 98%, 99% or 100% identical to SEQ ID NO: 37, 39, 40, 42-48, or 50-53. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to SEQ ID NO: 8 or 11; (b) the VH CDR2 comprises an amino acid sequence that is at least about 90%, 95%, 97%, 98%, 99% or 100% identical to SEQ ID NO: 26 or 29; and (c) the VH CDR3 comprises an amino acid sequence that is at least about 90%, 95%, 97%, 98%, 99% or 100% identical to SEQ ID NO: 44 or 47. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D comprising 0, 1, 2, 3, 4, or 5 substitutions, insertions, or deletions; (b) the VH CDR2 comprises the VH CDR2 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D comprising 0, 1, 2, 3, 4, or 5 substitutions, insertions, or deletions; and (c) the VH CDR3 comprises the VH CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D comprising 0, 1, 2, 3, 4, or 5 substitutions, insertions, or deletions. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions; (b) the VH CDR2 comprises the VH CDR2 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions; and (c) the VH CDR3 comprises the VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of PCIN63-71I1a, or PCIN63-71L comprising 0, 1, 2, 3, 4, or 5 substitutions, insertions, or deletions; (b) the VH CDR2 comprises the VH CDR2 of PCIN63-71I1a, or PCIN63-71L comprising 0, 1, 2, 3, 4, or 5 substitutions, insertions, or deletions; and (c) the VH CDR3 comprises the VH CDR3 of PCIN63-71I1a, or PCIN63-71L comprising 0, 1, 2, 3, 4, or 5 substitutions, insertions, or deletions. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the amino acid sequence of SEQ ID NO: 1-18 comprising 0, 1, 2, 3, 4, or 5 substitutions, insertions, or deletions; (b) the VH CDR2 comprises the amino acid sequence of SEQ ID NO: 19-36 comprising 0, 1, 2, 3, 4, or 5 substitutions, insertions, or deletions; and (c) the VH CDR3 comprises the amino acid sequence of SEQ ID NO: 37-54 comprising 0, 1, 2, 3, 4, or 5 substitutions, insertions, or deletions. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the amino acid sequence of SEQ ID NO: 1, 3, 4, 6-12, or 14-17 comprising 0, 1, 2, 3, 4, or 5 substitutions, insertions, or deletions; (b) the VH CDR2 comprises the amino acid sequence of SEQ ID NO: 19, 21, 22, 24-30, or 32-35 comprising 0, 1, 2, 3, 4, or 5 substitutions, insertions, or deletions; and (c) the VH CDR3 comprises the amino acid sequence of SEQ ID NO: 37, 39, 40, 42-48, or 50-53 comprising 0, 1, 2, 3, 4, or 5 substitutions, insertions, or deletions. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the amino acid sequence of SEQ ID NO: 8 or 11 comprising 0, 1, 2, 3, 4, or 5 substitutions, insertions, or deletions; (b) the VH CDR2 comprises the amino acid sequence of SEQ ID NO: 26 or 29 comprising 0, 1, 2, 3, 4, or 5 substitutions, insertions, or deletions; and (c) the VH CDR3 comprises the amino acid sequence of SEQ ID NO: 44 or 47 comprising 0, 1, 2, 3, 4, or 5 substitutions, insertions, or deletions. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-

77B1b, PCIN63-77C, or PCIN63-77D; (b) the VH CDR2 comprises the VH CDR2 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D; and (c) the VH CDR3 comprises the VH CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C; (b) the VH CDR2 comprises the VH CDR2 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C; and (c) the VH CDR3 comprises the VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of PCIN63-71I1a, or PCIN63-71L; (b) the VH CDR2 comprises the VH CDR2 of PCIN63-71I1a, or PCIN63-71L; and (c) the VH CDR3 comprises the VH CDR3 of PCIN63-71I1a, or PCIN63-71L. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the amino acid sequence of SEQ ID NO: 1-18; (b) the VH CDR2 comprises the amino acid sequence of SEQ ID NO: 19-36; and (c) the VH CDR3 comprises the amino acid sequence of SEQ ID NO: 37-54. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the amino acid sequence of SEQ ID NO: 1, 3, 4, 6-12, or 14-17; (b) the VH CDR2 comprises the amino acid sequence of SEQ ID NO: 19, 21, 22, 24-30, or 32-35; and (c) the VH CDR3 comprises the amino acid sequence of SEQ ID NO: 37, 39, 40, 42-48, or 50-53. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the amino acid sequence of SEQ ID NO: 8 or 11; (b) the VH CDR2 comprises the amino acid sequence of SEQ ID NO: 26 or 29; and (c) the VH CDR3 comprises the amino acid sequence of SEQ ID NO: 44 or 47. In some embodiments, the antibody comprises the VL CDR1, VL CDR2, and VL CDR3 of an antibody described herein. In some embodiments, the antibody comprises the VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL CDR1, VL CDR2, and VL CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises an amino acid sequence that is at least about 90%, 95%, 97%, 98%, 99% or 100% identical to the VL CDR1 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D; (b) the VL CDR2 comprises an amino acid sequence that is at least about 90%, 95%, 97%, 98%, 99% or 100% identical to the VL CDR2 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D; and (c) the VL CDR3 comprises an amino acid sequence that is at least about 90%, 95%, 97%, 98%, 99% or 100% identical to the VL CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises an amino acid sequence that is at least about 90%, 95%, 97%, 98%, 99% or 100% identical to the VL CDR1 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C; (b) the VL CDR2 comprises an amino acid sequence that is at least about 90%, 95%, 97%, 98%, 99% or 100% identical to the VL CDR2 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C; and (c) the VL CDR3 comprises an amino acid sequence that is at least about 90%, 95%, 97%, 98%, 99% or 100% identical to the VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises an amino acid sequence that is at least about 90%, 95%, 97%, 98%, 99% or 100% identical to the VL CDR1 of PCIN63-71I1a, or PCIN63-71L; (b) the VL CDR2 comprises an amino acid sequence that is at least about 90%, 95%, 97%, 98%, 99% or 100% identical to the VL CDR2 of PCIN63-71I1a, or PCIN63-71L; and (c) the VL CDR3 comprises an amino acid sequence that is at least about 90%, 95%, 97%, 98%, 99% or 100% identical to the VL CDR3 of PCIN63-71I1a, or PCIN63-71L. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the VL CDR1 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D comprising 0, 1, 2, 3, 4, or 5 substitutions, insertions, or deletions; (b) the VL CDR2 comprises the VL CDR2 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D comprising 0, 1, 2, 3, 4, or 5 substitutions, insertions, or deletions; and (c) the VL CDR3 comprises the VL CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D comprising 0, 1, 2, 3, 4, or 5 substitutions, insertions, or deletions. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the VL CDR1 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C comprising 0, 1, 2, 3, 4, or 5 substitutions, insertions, or deletions; (b) the VL CDR2 comprises the VL CDR2 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions; and (c) the VL CDR3 comprises the VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C comprising 0, 1, 2, 3, 4, or 5 substitutions, insertions, or deletions. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the VL CDR1 of PCIN63-71I1a, or PCIN63-71L comprising 0, 1, 2, 3, 4, or 5 substitutions, insertions, or deletions; (b) the VL CDR2 comprises the VL CDR2 of PCIN63-71I1a, or PCIN63-71L comprising 0, 1, 2, 3, 4, or 5 substitutions, insertions, or deletions; and (c) the VL CDR3 comprises the VL CDR3 of PCIN63-71I1a, or PCIN63-71L comprising 0, 1, 2, 3, 4, or 5 substitutions, insertions, or deletions. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the VL CDR1 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D; (b) the VL CDR2 comprises the VL CDR2 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D; and (c) the VL CDR3 comprises the VL CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the VL CDR1 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C; (b) the VL CDR2 comprises the VL CDR2 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C; and (c) the VL CDR3 comprises the VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the VL CDR1 of PCIN63-71I1a, or PCIN63-71L; (b) the VL CDR2 comprises the VL CDR2 of PCIN63-71I1a, or PCIN63-71L; and (c) the VL CDR3 comprises the VL CDR3 of PCIN63-71I1a, or PCIN63-71L. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises an amino acid sequence that is at least about 90%, 95%, 97%, 98%, 99% or 100% identical to SEQ ID NO: 55-72; (b) the VL CDR2 comprises an amino acid sequence that is at least about 90%, 95%, 97%, 98%, 99% or 100% identical to SEQ ID NO: 73-90; and (c) the VL CDR3 comprises an amino acid sequence that is at least about 90%, 95%, 97%, 98%, 99% or 100% identical to SEQ ID NO: 91-108. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises an amino acid sequence that is at least about 90%, 95%, 97%, 98%, 99% or 100% identical to SEQ ID NO: 55, 57, 58, 60-66, or 68-71; (b) the VL CDR2 comprises an amino acid sequence that is at least about 90%, 95%, 97%, 98%, 99% or 100% identical to SEQ ID NO: 73, 75, 76, 78-84, or 86-89; and (c) the VL CDR3 comprises an amino acid sequence that is at least about 90%, 95%, 97%, 98%, 99% or 100% identical to SEQ ID NO: 91, 93, 94, 96-102, or 104-107. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises an amino acid sequence that is at least about 90%, 95%, 97%, 98%, 99% or 100% identical to SEQ ID NO: 62 or 65; (b) the VL CDR2 comprises an amino acid sequence that is at least about 90%, 95%, 97%, 98%, 99% or 100% identical to SEQ ID NO: 80 or 83; and (c) the VL CDR3 comprises an amino acid sequence that is at least about 90%, 95%, 97%, 98%, 99% or 100% identical to SEQ ID NO: 98 or 101. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the amino acid sequence of SEQ ID NO: 55-72 comprising 0, 1, 2, 3, 4, or 5 substitutions, insertions, or deletions; (b) the VL CDR2 comprises the amino acid sequence of SEQ ID NO: 73-90 comprising 0, 1, 2, 3, 4, or 5 substitutions, insertions, or deletions; and (c) the VL CDR3 comprises the amino acid sequence of SEQ ID NO: 91-108 comprising 0, 1, 2, 3, 4, or 5 substitutions, insertions, or deletions. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the amino acid sequence of SEQ ID NO: 55, 57, 58, 60-66, or 68-71 comprising 0, 1, 2, 3, 4, or 5 substitutions, insertions, or deletions; (b) the VL CDR2 comprises the amino acid sequence of SEQ ID NO: 73, 75, 76, 78-84, or 86-89 comprising 0, 1, 2, 3, 4, or 5 substitutions, insertions, or deletions; and (c) the VL CDR3 comprises the amino acid sequence of SEQ ID NO: 91, 93, 94, 96-102, or 104-107 comprising 0, 1, 2, 3, 4, or 5 substitutions, insertions, or deletions. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the amino acid sequence of SEQ ID NO: 62 or 65 comprising 0, 1, 2, 3, 4, or 5 substitutions, insertions, or deletions; (b) the VL CDR2 comprises the amino acid sequence of SEQ ID NO: 80 or 83 comprising 0, 1, 2, 3, 4, or 5 substitutions, insertions, or deletions; and (c) the VL CDR3 comprises the amino acid sequence of SEQ ID NO: 98 or 101 comprising 0, 1, 2, 3, 4, or 5 substitutions, insertions, or deletions. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the amino acid sequence of SEQ ID NO: 55-72; (b) the VL CDR2 comprises the amino acid sequence of SEQ ID NO: 73-90; and (c) the VL CDR3 comprises the amino acid sequence of SEQ ID NO: 91-108. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the amino acid sequence of SEQ ID NO: 55, 57, 58, 60-66, or 68-71; (b) the VL CDR2 comprises the amino acid sequence of SEQ ID NO: 73, 75, 76, 78-84, or 86-89; and (c) the VL CDR3 comprises the amino acid sequence of SEQ ID NO: 91, 93, 94, 96-102, or 104-107. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the amino acid sequence of SEQ ID NO: 62 or 65; (b) the VL CDR2 comprises the amino acid sequence of SEQ ID NO: 80 or 83; and (c) the VL CDR3 comprises the amino acid sequence of SEQ ID NO: 98 or 101. In some embodiments, the antibody comprises the VH CDR1, VH CDR2, and VH CDR3 of an antibody described herein. In some embodiments, the antibody comprises the VH CDR1, VH CDR2, and VH CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, and VH CDR3 of PCIN63-71I1a, or PCIN63-71L.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D VH CDR1, VH CDR2, VH CDR3, VL CDR1, VL CDR2, and VL CDR3, respectively.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C VH CDR1, VH CDR2, VH CDR3, VL CDR1, VL CDR2, and VL CDR3, respectively.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the PCIN63-71I1a, or PCIN63-71L VH CDR1, VH CDR2, VH CDR3, VL CDR1, VL CDR2, and VL CDR3, respectively.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of (a) SEQ ID NO: 1, 19, 37, 55, 73, and 91, respectively; (b) SEQ ID NO: 2, 20, 38, 56, 74, and 92, respectively; (c) SEQ ID NO: 3, 21, 39, 57, 75, and 93, respectively; (d) SEQ ID NO: 4, 22, 40, 58, 76, and 94, respectively; (e) SEQ ID NO: 5, 23, 41, 59, 77, and 95, respectively; (f) SEQ ID NO: 6, 24, 42, 60, 78, and 96, respectively; (g) SEQ ID NO: 7, 25, 43, 61, 79, and 97, respectively; (h) SEQ ID NO: 8, 26, 44, 62, 80, and 98, respectively; (i) SEQ ID NO: 9, 27, 45, 63, 81, and 99, respectively; (j) SEQ ID NO: 10, 28, 46, 64, 82, and 100, respectively; (k) SEQ ID NO: 11, 29, 47, 65, 83, and 101, respectively; (1) SEQ ID NO: 12, 30, 48, 66, 84, and 102, respectively; (m) SEQ ID NO: 13, 31, 49, 67, 85, and 103, respectively; (n) SEQ ID NO: 14, 32, 50, 68, 86, and 104, respectively; (o) SEQ ID NO: 15, 33, 51, 69, 87, and 105, respectively; (p) SEQ ID NO: 16, 34, 52, 70, 88, and 106, respectively; (q) SEQ ID NO: 17, 35, 53, 71, 89, and 107, respectively; or (r) SEQ ID NO: 18, 36, 54, 72, 90, and 108, respectively.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of (a) SEQ ID NO: 1, 19, 37, 55, 73, and 91, respectively; (b) SEQ ID NO: 3, 21, 39, 57, 75, and 93, respectively; (c) SEQ ID NO: 4, 22, 40, 58, 76, and 94, respectively; (d) SEQ ID NO: 6, 24, 42, 60, 78, and 96, respectively; (e) SEQ ID NO: 7, 25, 43, 61, 79, and 97, respectively; (f) SEQ ID NO: 8, 26, 44, 62, 80, and 98, respectively; (g) SEQ ID NO: 9, 27, 45, 63, 81, and 99, respectively; (h) SEQ ID NO: 10, 28, 46, 64, 82, and 100, respectively; (i) SEQ ID NO: 11, 29, 47, 65, 83, and 101, respectively; (j) SEQ ID NO: 12, 30, 48, 66, 84, and 102, respectively; (k) SEQ ID NO: 14, 32, 50, 68, 86, and 104, respectively; (1) SEQ ID NO: 15, 33, 51, 69, 87, and 105, respectively; (m) SEQ ID NO: 16, 34, 52, 70, 88, and 106, respectively; or (n) SEQ ID NO: 17, 35, 53, 71, 89, and 107, respectively.

In some embodiments, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of (a) SEQ ID NO: 8, 26, 44, 62, 80, and 98, respectively; or (b) SEQ ID NO: 11, 29, 47, 65, 83, and 101, respectively.

In some embodiments, an isolated monoclonal antibody described herein specifically binds to Env and comprises a heavy chain variable region (VH) and a light chain variable region (VL), wherein the VH comprises an amino acid sequence that is at least about 90%, 95%, 97%, 98%, 99% or 100% identical to the VH of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VL of an antibody described herein. In some embodiments, the antibody comprises the VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VL of PCIN63-71I1a, or PCIN63-71L.

In some embodiments, an isolated monoclonal antibody described herein specifically binds to Env and comprises a heavy chain variable region (VH) and a light chain variable region (VL), wherein the VH comprises an amino acid sequence that is at least about 90%, 95%, 97%, 98%, 99% or 100% identical to the VH of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VL of an antibody described herein. In some embodiments, the antibody comprises the VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VL of PCIN63-71I1a, or PCIN63-71L.

In some embodiments, an isolated monoclonal antibody described herein specifically binds to Env and comprises a heavy chain variable region (VH) and a light chain variable region (VL), wherein the VH comprises an amino acid sequence that is at least about 90%, 95%, 97%, 98%, 99% or 100% identical to the VH of PCIN63-71I1a, or PCIN63-71L. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VL of an antibody described herein. In some embodiments, the antibody comprises the VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VL of PCIN63-71I1a, or PCIN63-71L.

In some embodiments, an isolated monoclonal antibody described herein specifically binds to Env and comprises a heavy chain variable region (VH) and a light chain variable region (VL), wherein the VH comprises an amino acid sequence that is at least about 90%, 95%, 97%, 98%, 99% or 100% identical to SEQ ID NO: 235-252. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VL of an antibody described herein. In some embodiments, the antibody comprises the VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VL of PCIN63-71I1a, or PCIN63-71L.

In some embodiments, an isolated monoclonal antibody described herein specifically binds to Env and comprises a heavy chain variable region (VH) and a light chain variable region (VL), wherein the VH comprises an amino acid sequence that is at least about 90%, 95%, 97%, 98%, 99% or 100% identical to SEQ ID NO: 235, 237, 238, 240-246, or 248-251. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-

71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VL of an antibody described herein. In some embodiments, the antibody comprises the VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL of PCIN63-71I1a, or PCIN63-71L.

In some embodiments, an isolated monoclonal antibody described herein specifically binds to Env and comprises a heavy chain variable region (VH) and a light chain variable region (VL), wherein the VH comprises an amino acid sequence that is at least about 90%, 95%, 97%, 98%, 99% or 100% identical to SEQ ID NO: 242 or245. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VL of an antibody described herein. In some embodiments, the antibody comprises the VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VL of PCIN63-71I1a, or PCIN63-71L.

In some embodiments, an isolated monoclonal antibody described herein specifically binds to Env and comprises a heavy chain variable region (VH) and a light chain variable region (VL), wherein the VL comprises an amino acid sequence that is at least about 90%, 95%, 97%, 98%, 99% or 100% identical to the VL of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH of an antibody described herein. In some embodiments, the antibody comprises the VH of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH of PCIN63-71I1a, or PCIN63-71L.

In some embodiments, an isolated monoclonal antibody described herein specifically binds to Env and comprises a heavy chain variable region (VH) and a light chain variable region (VL), wherein the VL comprises an amino acid sequence that is at least about 90%, 95%, 97%, 98%, 99% or 100% identical to the VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH of an antibody described herein. In some embodiments, the antibody comprises the VH of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH of PCIN63-71I1a, or PCIN63-71L.

In some embodiments, an isolated monoclonal antibody described herein specifically binds to Env and comprises a heavy chain variable region (VH) and a light chain variable region (VL), wherein the VL comprises an amino acid sequence that is at least about 90%, 95%, 97%, 98%, 99% or 100% identical to the VL of PCIN63-7111a, or PCIN63-71L. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH of an antibody described herein. In some embodiments, the antibody comprises the VH of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH of PCIN63-71I1a, or PCIN63-71L.

In some embodiments, an isolated monoclonal antibody described herein specifically binds to Env and comprises a heavy chain variable region (VH) and a light chain variable region (VL), wherein the VL comprises an amino acid sequence that is at least about 90%, 95%, 97%, 98%, 99% or 100% identical to SEQ ID NO: 253-270. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH of an antibody described herein. In some embodiments, the antibody comprises the VH of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH of PCIN63-71I1a, or PCIN63-71L.

In some embodiments, an isolated monoclonal antibody described herein specifically binds to Env and comprises a heavy chain variable region (VH) and a light chain variable region (VL), wherein the VL comprises an amino acid sequence that is at least about 90%, 95%, 97%, 98%, 99% or 100% identical to SEQ ID NO: 253, 255, 256, 258-264, or 266-269. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH of an antibody described herein. In some embodiments, the antibody comprises the VH of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH of PCIN63-71I1a, or PCIN63-71L.

In some embodiments, an isolated monoclonal antibody described herein specifically binds to Env and comprises a heavy chain variable region (VH) and a light chain variable region (VL), wherein the VL comprises an amino acid sequence that is at least about 90%, 95%, 97%, 98%, 99% or 100% identical to SEQ ID NO: 260 or 263. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH of an antibody described herein. In some embodiments, the antibody comprises the VH of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH of PCIN63-71I1a, or PCIN63-71L.

In some embodiments, an isolated monoclonal antibody described herein specifically binds to Env and comprises a heavy chain variable region (VH) and a light chain variable region (VL), wherein the VH and VL comprise an amino acid sequence that is at least about 90%, 95%, 97%, 98%, 99% or 100% identical to the PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D VH and VL, respectively. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L.

In some embodiments, an isolated monoclonal antibody described herein specifically binds to Env and comprises a heavy chain variable region (VH) and a light chain variable region (VL), wherein the VH and VL comprise an amino acid sequence that is at least about 90%, 95%, 97%, 98%, 99% or 100% identical to the PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C VH and VL, respectively. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L.

In some embodiments, an isolated monoclonal antibody described herein specifically binds to Env and comprises a heavy chain variable region (VH) and a light chain variable region (VL)), wherein the VH and VL comprise an amino acid sequence that is at least about 90%, 95%, 97%, 98%, 99% or 100% identical to the PCIN63-71I1a, or PCIN63-71L VH and VL, respectively. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L.

In some embodiments, an isolated monoclonal antibody described herein specifically binds to Env and comprises a heavy chain variable region (VH) and a light chain variable region (VL), wherein the VH comprises an amino acid sequence that is at least about 90%, 95%, 97%, 98%, 99% or 100% identical to SEQ ID NO: 235-252 and the VL comprises an amino acid sequence that is at least about 90%, 95%, 97%, 98%, 99% or 100% identical to SEQ ID NO: 253-270. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L.

In some embodiments, an isolated monoclonal antibody described herein specifically binds to Env and comprises a heavy chain variable region (VH) and a light chain variable region (VL), wherein the VH and VL comprise an amino acid sequence that is at least about 90%, 95%, 97%, 98%, 99% or 100% identical to (a) SEQ ID NO: 235 and 253, respectively; (b) SEQ ID NO: 236 and 254, respectively; (c) SEQ ID NO: 237 and 255, respectively; (d) SEQ ID NO: 238 and 256, respectively; (e) SEQ ID NO: 239 and 257, respectively; (f) SEQ ID NO: 240 and 258, respectively; (g) SEQ ID NO: 241 and 259, respectively; (h) SEQ ID NO: 242 and 260, respectively; (i) SEQ ID NO: 243 and 261, respectively; (j) SEQ ID NO: 244 and 262, respectively; (k) SEQ ID NO: 245 and 263, respectively; (1) SEQ ID NO: 246 and 264, respectively; (m) SEQ ID NO: 247 and 265, respectively; (n) SEQ ID NO: 248 and 266, respectively; (o) SEQ ID NO: 249 and 267, respectively; (p) SEQ ID NO: 250 and 268, respectively; (q) SEQ ID NO: 251 and 269, respectively; or (r) SEQ ID NO: 252 and 270, respectively. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L.

In some embodiments, an isolated monoclonal antibody described herein specifically binds to Env and comprises a heavy chain variable region (VH) and a light chain variable region (VL), wherein the VH comprises an amino acid sequence comprising one or more of Motif #1, Motif #2, and Motif #3. In some embodiments, the VH comprises an amino acid sequence comprising Motif #1, Motif #2, and Motif #3. In some embodiments, Motif #1 comprises the amino acid sequence of SEQ ID NO: 109-126 or 310-315 at Kabat positions H31-H37. In some embodiments, Motif #1 comprises the amino acid sequence of SEQ ID NO: 109-126 at Kabat positions H31-H37. In some embodiments, Motif #1 comprises the amino acid sequence of SEQ ID NO: 310-315 at Kabat positions H31-H37. In some embodiments, Motif #1 comprises the amino acid sequence of SEQ ID NO: 310 at Kabat positions H31-H37. In some embodiments, Motif #1 comprises the amino acid sequence of SEQ ID NO: 311 at Kabat positions H31-H37. In some embodiments, Motif #1 comprises the amino acid sequence of SEQ ID NO: 312 at Kabat positions H31-H37. In some embodiments, Motif #1 comprises the amino acid sequence of SEQ ID NO: 313 at Kabat positions H31-H37. In some embodiments, Motif #1 comprises the amino acid sequence of SEQ ID NO: 314 at Kabat positions H31-H37. In some embodiments, Motif #1 comprises the amino acid sequence of SEQ ID NO: 315 at Kabat positions H31-H37. In some embodiments, Motif #2 comprises the amino acid sequence of SEQ ID NO: 127-144 or 316-318 at Kabat positions H52-H56. In some embodiments, Motif #2 comprises the amino acid sequence of SEQ ID NO: 127-144 at Kabat positions H52-H56. In some embodiments, Motif #2 comprises the amino acid sequence of SEQ ID NO: 316-318 at Kabat positions H52-H56. In some embodiments, Motif #2 comprises the amino acid sequence of SEQ ID NO: 316 at Kabat positions H52-H56. In some embodiments, Motif #2 comprises the amino acid sequence of SEQ ID NO: 317 at Kabat positions H52-H56. In some embodiments, Motif #2 comprises the amino acid sequence of SEQ ID NO: 318 at Kabat positions H52-H56. In some embodiments, Motif #3 comprises the amino acid sequence of SEQ ID NO: 145-162 at Kabat positions H61-H62. In some embodiments, Motif #3 comprises the amino acid sequence of SEQ ID NO: 145 at Kabat positions H61-H62. In some embodiments, Motif #3 comprises the amino acid sequence of SEQ ID NO: 146 at Kabat positions H61-H62. In some embodiments, Motif #3 comprises the amino acid sequence of SEQ ID NO: 147 at Kabat positions H61-H62. In some embodiments, Motif #3 comprises the amino acid sequence of SEQ ID NO: 149 at Kabat positions H61-H62. In some embodiments, Motif #3 comprises the amino acid sequence of SEQ ID NO: 150 at Kabat positions H61-H62. In some embodiments, Motif #3 comprises the amino acid sequence of SEQ ID NO: 151 at Kabat positions H61-H62. In some embodiments, Motif #3 comprises the amino acid sequence of SEQ ID NO: 156 at Kabat positions H61-H62. In some embodiments, Motif #3 comprises the amino acid sequence of SEQ ID NO: 157 at Kabat positions H61-H62. In some embodiments, Motif #3 comprises the amino acid sequence of SEQ ID NO: 161 at Kabat positions H61-H62. In some embodiments, the VH comprises an amino acid sequence comprising (a) VH CDR1, VH CDR2, and VH CDR3, and (b) one or more of Motif #1, Motif #2, and Motif #3, wherein the sequence of VH CDR1, VH CDR2, VH CDR3, Motif #1, Motif #2, and Motif #3 is derived from the same antibody described herein. In some embodiments, the VH comprises an amino acid sequence comprising (a) VH CDR1, VH CDR2, and VH CDR3, and (b) Motif #1, Motif #2, and Motif #3, wherein the sequence of VH CDR1, VH CDR2, VH CDR3, Motif #1, Motif #2, and Motif #3 is derived from the same antibody described herein. In some embodiments, the sequence of VH CDR1, VH CDR2, VH CDR3, Motif #1, Motif #2, and Motif #3 is derived from PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the sequence of VH CDR1, VH CDR2, VH CDR3, Motif #1, Motif #2, and Motif #3 is derived from PCIN63-71I1a, or PCIN63-71L. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-

71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH and VL of an antibody described herein. In some embodiments, the antibody comprises the VH and VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH and VL of PCIN63-71I1a, or PCIN63-71L.

In some embodiments, an isolated monoclonal antibody described herein specifically binds to Env and comprises a heavy chain variable region (VH) and a light chain variable region (VL), wherein the VH comprises an amino acid sequence comprising one or more of (a) the amino acid sequence of SEQ ID NO: 109-126 or 310-315 at Kabat positions H31-H37; (b) the amino acid sequence of SEQ ID NO: 127-144 or 316-318 at Kabat positions H52-H56; and (c) the amino acid sequence of SEQ ID NO: 145-162 at Kabat positions H61-H62. In some embodiments, an isolated monoclonal antibody described herein specifically binds to Env and comprises a heavy chain variable region (VH) and a light chain variable region (VL), wherein the VH comprises an amino acid sequence comprising (a) the amino acid sequence of SEQ ID NO: 109-126 or 310-315 at Kabat positions H31-H37; (b) the amino acid sequence of SEQ ID NO: 127-144 or 316-318 at Kabat positions H52-H56; and (c) the amino acid sequence of SEQ ID NO: 145-162 at Kabat positions H61-H62. In some embodiments, the VH comprises an amino acid sequence comprising (a) VH CDR1, VH CDR2, and VH CDR3, and (b) one or more of Motif #1, Motif #2, and Motif #3, wherein the sequence of VH CDR1, VH CDR2, VH CDR3, Motif #1, Motif #2, and Motif #3 is derived from the same antibody described herein. In some embodiments, the VH comprises an amino acid sequence comprising (a) VH CDR1, VH CDR2, and VH CDR3, and (b) Motif #1, Motif #2, and Motif #3, wherein the sequence of VH CDR1, VH CDR2, VH CDR3, Motif #1, Motif #2, and Motif #3 is derived from the same antibody described herein. In some embodiments, the sequence of VH CDR1, VH CDR2, VH CDR3, Motif #1, Motif #2, and Motif #3 is derived from PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the sequence of VH CDR1, VH CDR2, VH CDR3, Motif #1, Motif #2, and Motif #3 is derived from PCIN63-71I1a, or PCIN63-71L. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH and VL of an antibody described herein. In some embodiments, the antibody comprises the VH and VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH and VL of PCIN63-71I1a, or PCIN63-71L.

In some embodiments, an isolated monoclonal antibody described herein specifically binds to Env and comprises a heavy chain variable region (VH) and a light chain variable region (VL), wherein the VH comprises an amino acid sequence comprising one or more of (a) the amino acid sequence of SEQ ID NO: 310-315 at Kabat positions H31-H37; (b) the amino acid sequence of SEQ ID NO: 316-318 at Kabat positions H52-H56; and (c) the amino acid sequence of SEQ ID NO: 145-162 at Kabat positions H61-H62. In some embodiments, an isolated monoclonal antibody described herein specifically binds to Env and comprises a heavy chain variable region (VH) and a light chain variable region (VL), wherein the VH comprises an amino acid sequence comprising (a) the amino acid sequence of SEQ ID NO: 310-315 at Kabat positions H31-H37; (b) the amino acid sequence of SEQ ID NO: 316-318 at Kabat positions H52-H56; and (c) the amino acid sequence of SEQ ID NO: 145-162 at Kabat positions H61-H62. In some embodiments, the VH comprises an amino acid sequence comprising (a) VH CDR1, VH CDR2, and VH CDR3, and (b) one or more of Motif #1, Motif #2, and Motif #3, wherein the sequence of VH CDR1, VH CDR2, VH CDR3, Motif #1, Motif #2, and Motif #3 is derived from the same antibody described herein. In some embodiments, the VH comprises an amino acid sequence comprising (a) VH CDR1, VH CDR2, and VH CDR3, and (b) Motif #1, Motif #2, and Motif #3, wherein the sequence of VH CDR1, VH CDR2, VH CDR3, Motif #1, Motif #2, and Motif #3 is derived from the same antibody described herein. In some embodiments, the sequence of VH CDR1, VH CDR2, VH CDR3, Motif #1, Motif #2, and Motif #3 is derived from PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the sequence of VH CDR1, VH CDR2, VH CDR3, Motif #1, Motif #2, and Motif #3 is derived from PCIN63-71I1a, or PCIN63-71L. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH and VL of an antibody described herein. In some embodiments, the antibody comprises the VH and VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH and VL of PCIN63-71I1a, or PCIN63-71L.

In some embodiments, an isolated monoclonal antibody described herein specifically binds to Env and comprises a heavy chain variable region (VH) and a light chain variable region (VL), wherein the VL comprises an amino acid sequence comprising one or more of Motif #4, Motif #5, Motif #6, and Motif #7. In some embodiments, the VL comprises an amino acid sequence comprising of Motif #4, Motif #5, Motif #6, and Motif #7. In some embodiments, Motif #4 comprises the amino acid sequence of SEQ ID NO: 163-180 or 319-324 at Kabat positions H26-H34. In some embodiments, Motif #4 comprises the amino acid sequence of SEQ ID NO: 163-180 at Kabat positions H26-H34. In some embodiments, Motif #4 comprises the amino acid sequence of SEQ ID NO: 319-324 at Kabat positions H26-H34. In some embodiments, Motif #4 comprises the amino acid sequence of SEQ ID NO: 319 at Kabat positions H26-H34. In some embodiments, Motif #4 comprises the amino acid sequence of SEQ ID NO: 320 at Kabat positions H26-H34. In some embodiments, Motif #4 comprises the amino acid sequence of SEQ ID NO: 321 at Kabat positions H26-H34. In some embodiments, Motif #4 comprises the amino acid sequence of SEQ ID NO: 322 at Kabat positions H26-H34. In some embodiments, Motif #4 comprises the amino acid sequence of SEQ ID NO: 323 at Kabat positions H26-H34. In some embodiments, Motif #4 comprises the amino acid sequence of SEQ ID NO: 323 at Kabat positions H26-H34. In some embodiments, Motif #5 comprises the amino acid sequence of SEQ ID NO: 181-198 or 325-334 at Kabat positions H49-H56. In some embodiments, Motif #5 comprises the amino acid sequence of SEQ ID NO: 181-198 at Kabat positions H49-H56. In some embodiments, Motif #5 comprises the amino acid sequence of SEQ ID NO: 325-334 at Kabat positions H49-H56. In some embodiments, Motif #5 comprises the amino acid sequence of SEQ ID NO: 325 at Kabat positions H49-H56. In some embodiments, Motif #5 comprises the amino acid sequence of SEQ ID NO: 326 at Kabat positions H49-H56. In some embodiments, Motif #5 comprises the amino acid sequence of SEQ ID NO: 327 at Kabat positions H49-H56. In some embodiments, Motif #5 comprises the amino acid sequence of SEQ ID NO: 328 at Kabat positions H49-H56. In some embodiments, Motif #5 comprises the amino acid sequence of SEQ ID NO: 329 at Kabat positions H49-H56. In some embodiments, Motif #5 comprises the amino acid sequence of SEQ ID NO: 330 at Kabat positions H49-H56. In some embodiments, Motif #5 comprises the amino acid sequence of SEQ ID NO: 331 at Kabat positions H49-H56. In some embodiments, Motif #5 comprises the amino acid sequence of SEQ ID NO: 332 at Kabat positions H49-H56. In some embodiments, Motif #5 comprises the amino acid sequence of SEQ ID NO: 333 at Kabat positions H49-H56. In some embodiments, Motif #5 comprises the amino acid sequence of SEQ ID NO: 334 at Kabat positions H49-H56. In some embodiments, Motif #6 comprises the amino acid sequence of SEQ ID NO: 199-216 or 335-339 at Kabat positions H67-H70. In some embodiments, Motif #6 comprises the amino acid sequence of SEQ ID NO: 199-216 at Kabat positions H67-H70. In some embodiments, Motif #6 comprises the amino acid sequence of SEQ ID NO: 335-339 at Kabat positions H67-H70. In some embodiments, Motif #6 comprises the amino acid sequence of SEQ ID NO: 335 at Kabat positions H67-H70. In some embodiments, Motif #6 comprises the amino acid sequence of SEQ ID NO: 336 at Kabat positions H67-H70. In some embodiments, Motif #6 comprises the amino acid sequence of SEQ ID NO: 337 at Kabat positions H67-H70. In some embodiments, Motif #6 comprises the amino acid sequence of SEQ ID NO: 338 at Kabat positions H67-H70. In some embodiments, Motif #6 comprises the amino acid sequence of SEQ ID NO: 339 at Kabat positions H67-H70. In some embodiments, Motif #7 comprises the amino acid sequence of SEQ ID NO: 217-234 at Kabat positions H89-H97. In some embodiments, Motif #7 comprises the amino acid sequence of SEQ ID NO: 217 at Kabat positions H89-H97. In some embodiments, Motif #7 comprises the amino acid sequence of SEQ ID NO: 218 at Kabat positions H89-H97. In some embodiments, Motif #7 comprises the amino acid sequence of SEQ ID NO: 222 at Kabat positions H89-H97. In some embodiments, Motif #7 comprises the amino acid sequence of SEQ ID NO: 224 at Kabat positions H89-H97. In some embodiments, Motif #7 comprises the amino acid sequence of SEQ ID NO: 229 at Kabat positions H89-H97. In some embodiments, Motif #7 comprises the amino acid sequence of SEQ ID NO: 234 at Kabat positions H89-H97. In some embodiments, the VL comprises an amino acid sequence comprising (a) VL CDR1, VL CDR2, and VL CDR3, and (b) one or more of Motif #4, Motif #5, Motif #6, and Motif #7, wherein the sequence of VL CDR1, VL CDR2, VL CDR3, Motif #4, Motif #5, Motif #6, and Motif #7 is derived from the same antibody described herein. In some embodiments, the VL comprises an amino acid sequence comprising (a) VL CDR1, VL CDR2, and VL CDR3, and (b) Motif #4, Motif #5, Motif #6, and Motif #7, wherein the sequence of VL CDR1, VL CDR2, VL CDR3, Motif #4, Motif #5, Motif #6, and Motif #7 is derived from the same antibody described herein. In some embodiments, the sequence of VL CDR1, VL CDR2, VL CDR3, Motif #4, Motif #5, Motif #6, and Motif #7 is derived from PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the sequence of VL CDR1, VL CDR2, VL CDR3, Motif #4, Motif #5, Motif #6, and Motif #7 is derived from PCIN63-71I1a, or PCIN63-71L. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH and VL of an antibody described herein. In some embodiments, the antibody comprises the VH and VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH and VL of PCIN63-71I1a, or PCIN63-71L.

In some embodiments, an isolated monoclonal antibody described herein specifically binds to Env and comprises a heavy chain variable region (VH) and a light chain variable region (VL), wherein the VL comprises an amino acid sequence comprising one or more of (a) the amino acid sequence of SEQ ID NO: 163-180 or 319-324 at Kabat positions H26-H34; (b) the amino acid sequence of SEQ ID NO: 181-198 or 325-334 at Kabat positions H49-H56; (c) the amino acid sequence of SEQ ID NO: 199-216 or 335-339 at Kabat positions H67-H70; and (d) the amino acid sequence of SEQ ID NO: 217-234 at Kabat positions H89-H97. In some embodiments, an isolated monoclonal antibody described herein specifically binds to Env and comprises a heavy chain variable region (VH) and a light chain variable region (VL), wherein the VL comprises an amino acid sequence comprising (a) the amino acid sequence of SEQ ID NO: 163-180 or 319-324 at Kabat positions H26-H34; (b) the amino acid sequence of SEQ ID NO: 181-198 or 325-334 at Kabat positions H49-H56; (c) the amino acid sequence of SEQ ID NO: 199-216 or 335-339 at Kabat positions H67-H70; and (d) the amino acid sequence of SEQ ID NO: 217-234 at Kabat positions H89-H97. In some embodiments, the VL comprises an amino acid sequence comprising (a) VL CDR1, VL CDR2, and VL CDR3, and (b) one or more of Motif #4, Motif #5, Motif #6, and Motif #7, wherein the sequence of VL CDR1, VL CDR2, VL CDR3, Motif #4, Motif #5, Motif #6, and Motif #7 is derived from the same antibody described herein. In some embodiments, the VL comprises an amino acid sequence comprising (a) VL CDR1, VL CDR2, and VL CDR3, and (b) Motif #4, Motif #5, Motif #6, and Motif #7, wherein the sequence of VL CDR1, VL CDR2, VL CDR3, Motif #4, Motif #5, Motif #6, and Motif #7 is derived from the same antibody described herein. In some embodiments, the sequence of VL CDR1, VL CDR2, VL CDR3, Motif #4, Motif #5, Motif #6, and Motif #7 is derived from PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the sequence of VL CDR1, VL CDR2, VL CDR3, Motif #4, Motif #5, Motif #6, and Motif #7 is derived from PCIN63-71I1a, or PCIN63-71L. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH and VL of an antibody described herein. In some embodiments, the antibody comprises the VH and VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH and VL of PCIN63-71I1a, or PCIN63-71L.

In some embodiments, an isolated monoclonal antibody described herein specifically binds to Env and comprises a heavy chain variable region (VH) and a light chain variable region (VL), wherein the VL comprises an amino acid sequence comprising one or more of (a) the amino acid sequence of SEQ ID NO: 319-324 at Kabat positions H26-H34; (b) the amino acid sequence of SEQ ID NO: 325-334 at Kabat positions H49-H56; (c) the amino acid sequence of SEQ ID NO: 335-339 at Kabat positions H67-H70; and (d) the amino acid sequence of SEQ ID NO: 217-234 at Kabat positions H89-H97. In some embodiments, an isolated monoclonal antibody described herein specifically binds to Env and comprises a heavy chain variable region (VH) and a light chain variable region (VL), wherein the VL comprises an amino acid sequence comprising (a) the amino acid sequence of SEQ ID NO: 319-324 at Kabat positions H26-H34; (b) the amino acid sequence of SEQ ID NO: 325-334 at Kabat positions H49-H56; (c) the amino acid sequence of SEQ ID NO: 335-339 at Kabat positions H67-H70; and (d) the amino acid sequence of SEQ ID NO: 217-234 at Kabat positions H89-H97. In some embodiments, the VL comprises an amino acid sequence comprising (a) VL CDR1, VL CDR2, and VL CDR3, and (b) one or more of Motif #4, Motif #5, Motif #6, and Motif #7, wherein the sequence of VL CDR1, VL CDR2, VL CDR3, Motif #4, Motif #5, Motif #6, and Motif #7 is derived from the same antibody described herein. In some embodiments, the VL comprises an amino acid sequence comprising (a) VL CDR1, VL CDR2, and VL CDR3, and (b) Motif #4, Motif #5, Motif #6, and Motif #7, wherein the sequence of VL CDR1, VL CDR2, VL CDR3, Motif #4, Motif #5, Motif #6, and Motif #7 is derived from the same antibody described herein. In some embodiments, the sequence of VL CDR1, VL CDR2, VL CDR3, Motif #4, Motif #5, Motif #6, and Motif #7 is derived from PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the sequence of VL CDR1, VL CDR2, VL CDR3, Motif #4, Motif #5, Motif #6, and Motif #7 is derived from PCIN63-71I1a, or PCIN63-71L. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH and VL of an antibody described herein. In some embodiments, the antibody comprises the VH and VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH and VL of PCIN63-71I1a, or PCIN63-71L.

In some embodiments, an isolated monoclonal antibody described herein specifically binds to Env and comprises a heavy chain variable region (VH) and a light chain variable region (VL), wherein (a) the VH comprises an amino acid sequence comprising one or more of Motif #1, Motif #2, and Motif #3, and/or (b) the VL comprises an amino acid sequence comprising one or more of Motif #4, Motif #5, Motif #6, and Motif #7. In some embodiments, an isolated monoclonal antibody described herein specifically binds to Env and comprises a heavy chain variable region (VH) and a light chain variable region (VL), wherein (a) the VH comprises an amino acid sequence comprising Motif #2 and (b) the VL comprises an amino acid sequence comprising Motif #4, and Motif #6. In some embodiments, an isolated monoclonal antibody described herein specifically binds to Env and comprises a heavy chain variable region (VH) and a light chain variable region (VL), wherein (a) the VH comprises an amino acid sequence comprising Motif #1, Motif #2, and Motif #3, and (b) the VL comprises an amino acid sequence comprising Motif #4, Motif #5, Motif #6, and Motif #7. In some embodiments, Motif #1 comprises the amino acid sequence of SEQ ID NO: 109-126 or 310-315 at Kabat positions H31-H37. In some embodiments, Motif #1 comprises the amino acid sequence of SEQ ID NO: 109-126 at Kabat positions H31-H37. In some embodiments, Motif #1 comprises the amino acid sequence of 310-315 at Kabat positions H31-H37. In some embodiments, Motif #2 comprises the amino acid sequence of SEQ ID NO: 127-144 or 316-318 at Kabat positions H52-H56. In some embodiments, Motif #2 comprises the amino acid sequence of SEQ ID NO: 127-144 at Kabat positions H52-H56. In some embodiments, Motif #2 comprises the amino acid sequence of SEQ ID NO: 316-318 at Kabat positions H52-H56. In some embodiments, Motif #3 comprises the amino acid sequence of SEQ ID NO: 145-162 at Kabat positions H61-H62. In some embodiments, Motif #4 comprises the amino acid sequence of SEQ ID NO: 163-180 or 319-324 at Kabat positions H26-H34. In some embodiments, Motif #4 comprises the amino acid sequence of SEQ ID NO: 163-180 at Kabat positions H26-H34. In some embodiments, Motif #4 comprises the amino acid sequence of SEQ ID NO: 319-324 at Kabat positions H26-H34. In some embodiments, Motif #5 comprises the amino acid sequence of SEQ ID NO: 181-198 or 325-334 at Kabat positions H49-H56. In some embodiments, Motif #5 comprises the amino acid sequence of SEQ ID NO: 181-198 at Kabat positions H49-H56. In some embodiments, Motif #5 comprises the amino acid sequence of SEQ ID NO: 325-334 at Kabat positions H49-H56. In some embodiments, Motif #6 comprises the amino acid sequence of SEQ ID NO: 199-216 or 335-339 at Kabat positions H67-H70. In some embodiments, Motif #6 comprises the amino acid sequence of SEQ ID NO: 199-216 at Kabat positions H67-H70. In some embodiments, Motif #6 comprises the amino acid sequence of SEQ ID NO: 335-339 at Kabat positions H67-H70. In some embodiments, Motif #7 comprises the amino acid sequence of SEQ ID NO: 217-234 at Kabat positions H89-H97. In some embodiments, the VH comprises an amino acid sequence comprising (a) VH CDR1, VH CDR2, and VH CDR3, and (b) one or more of Motif #1, Motif #2, and Motif #3 and the VL comprises an amino acid sequence comprising (d) VL CDR1, VL CDR2, and VL CDR3, and (e) one or more of Motif #4, Motif #5, Motif #6, and Motif #7, wherein the sequence of VH CDR1, VH CDR2, VH CDR3, VL CDR1, VL CDR2, VL CDR3, Motif #1, Motif #2, Motif #3, Motif #4, Motif #5, Motif #6, and Motif #7 is derived from the same antibody described herein. In some embodiments, the VH comprises an amino acid sequence comprising (a) VH CDR1, VH CDR2, and VH CDR3, and (b) one or more of Motif #1, Motif #2, and Motif #3 and the VL comprises an amino acid sequence comprising (d) VL CDR1, VL CDR2, and VL CDR3, and (e) one or more of Motif #4, Motif #5, Motif #6, and Motif #7, wherein the sequence of VH CDR1, VH CDR2, VH CDR3, VL CDR1, VL CDR2, VL CDR3, Motif #1, Motif #2, Motif #3, Motif #4, Motif #5, Motif #6, and Motif #7 is derived from the same antibody described herein. In some embodiments, the sequence of VH CDR1, VH CDR2, VH CDR3, VL CDR1, VL CDR2, VL CDR3, Motif #1, Motif #2, Motif #3, Motif #4, Motif #5, Motif #6, and Motif #7 is derived from PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the sequence of VH CDR1, VH CDR2, VH CDR3, VL CDR1, VL CDR2, VL CDR3, Motif #1, Motif #2, Motif #3, Motif #4, Motif #5, Motif #6, and Motif #7 is derived from PCIN63-71I1a, or PCIN63-71L. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH and VL of an antibody described herein. In some embodiments, the antibody comprises the VH and VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH and VL of PCIN63-71I1a, or PCIN63-71L.

In some embodiments, an isolated monoclonal antibody described herein specifically binds to Env and comprises a heavy chain variable region (VH) and a light chain variable region (VL), wherein the VH comprises an amino acid sequence comprising one or more of (a) the amino acid sequence of SEQ ID NO: 109-126 or 310-315 at Kabat positions H31-H37; (b) the amino acid sequence of SEQ ID NO: 127-144 or 316-318 at Kabat positions H52-H56; and (c) the amino acid sequence of SEQ ID NO: 145-162 at Kabat positions H61-H62 and/or the VL comprises an amino acid sequence comprising one or more of (d) the amino acid sequence of SEQ ID NO: 163-180 or 319-324 at Kabat positions H26-H34; (e) the amino acid sequence of SEQ ID NO: 181-198 or 325-334 at Kabat positions H49-H56; (f) the amino acid sequence of SEQ ID NO: 199-216 or 335-339 at Kabat positions H67-H70; and (g) the amino acid sequence of SEQ ID NO: 217-234 at Kabat positions H89-H97. In some embodiments, an isolated monoclonal antibody described herein specifically binds to Env and comprises a heavy chain variable region (VH) and a light chain variable region (VL), wherein the VH comprises an amino acid sequence comprising the amino acid sequence of SEQ ID NO: 127-144 or 316-318 at Kabat positions H52-H56; and the VL comprises an amino acid sequence comprising (a) the amino acid sequence of SEQ ID NO: 163-180 or 319-324 at Kabat positions H26-H34 and (b) the amino acid sequence of SEQ ID NO: 199-216 or 335-339 at Kabat positions H67-H70. In some embodiments, an isolated monoclonal antibody described herein specifically binds to Env and comprises a heavy chain variable region (VH) and a light chain variable region (VL), wherein the VH comprises an amino acid sequence comprising (a) the amino acid sequence of SEQ ID NO: 109-126 or 310-315 at Kabat positions H31-H37; (b) the amino acid sequence of SEQ ID NO: 127-144 or 316-318 at Kabat positions H52-H56; and (c) the amino acid sequence of SEQ ID NO: 145-162 at Kabat positions H61-H62, and the VL comprises an amino acid sequence comprising (a) the amino acid sequence of SEQ ID NO: 163-180 or 319-324 at Kabat positions H26-H34; (b) the amino acid sequence of SEQ ID NO: 181-198 or 325-334 at Kabat positions H49-H56; (c) the amino acid sequence of SEQ ID NO: 199-216 or 335-339 at Kabat positions H67-H70; and (d) the amino acid sequence of SEQ ID NO: 217-234 at Kabat positions H89-H97. In some embodiments, the VH comprises an amino acid sequence comprising (a) VH CDR1, VH CDR2, and VH CDR3, and (b) one or more of Motif #1, Motif #2, and Motif #3 and the VL comprises an amino acid sequence comprising (d) VL CDR1, VL CDR2, and VL CDR3, and (e) one or more of Motif #4, Motif #5, Motif #6, and Motif #7, wherein the sequence of VH CDR1, VH CDR2, VH CDR3, VL CDR1, VL CDR2, VL CDR3, Motif #1, Motif #2, Motif #3, Motif #4, Motif #5, Motif #6, and Motif #7 is derived from the same antibody described herein. In some embodiments, the VH comprises an amino acid sequence comprising (a) VH CDR1, VH CDR2, and VH CDR3, and (b) one or more of Motif #1, Motif #2, and Motif #3 and the VL comprises an amino acid sequence comprising (d) VL CDR1, VL CDR2, and VL CDR3, and (e) one or more of Motif #4, Motif #5, Motif #6, and Motif #7, wherein the sequence of VH CDR1, VH CDR2, VH CDR3, VL CDR1, VL CDR2, VL CDR3, Motif #1, Motif #2, Motif #3, Motif #4, Motif #5, Motif #6, and Motif #7 is derived from the same antibody described herein. In some embodiments, the sequence of VH CDR1, VH CDR2, VH CDR3, VL CDR1, VL CDR2, VL CDR3, Motif #1, Motif #2, Motif #3, Motif #4, Motif #5, Motif #6, and Motif #7 is derived from PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the sequence of VH CDR1, VH CDR2, VH CDR3, VL CDR1, VL CDR2, VL CDR3, Motif #1, Motif #2, Motif #3, Motif #4, Motif #5, Motif #6, and Motif #7 is derived from PCIN63-71I1a, or PCIN63-71L. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH and VL of an antibody described herein. In some embodiments, the antibody comprises the VH and VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH and VL of PCIN63-71I1a, or PCIN63-71L.

In some embodiments, an isolated monoclonal antibody described herein specifically binds to Env and comprises a heavy chain variable region (VH) and a light chain variable region (VL), wherein the VH comprises an amino acid sequence comprising one or more of (a) the amino acid sequence of SEQ ID NO: 310-315 at Kabat positions H31-H37; (b) the amino acid sequence of SEQ ID NO: 316-318 at Kabat positions H52-H56; and (c) the amino acid sequence of SEQ ID NO: 145-162 at Kabat positions H61-H62 and/or the VL comprises an amino acid sequence comprising one or more of (d) the amino acid sequence of SEQ ID NO: 319-324 at Kabat positions H26-H34; (e) the amino acid sequence of SEQ ID NO: 325-334 at Kabat positions H49-H56; (f) the amino acid sequence of SEQ ID NO: 335-339 at Kabat positions H67-H70; and (g) the amino acid sequence of SEQ ID NO: 217-234 at Kabat positions H89-H97. In some embodiments, an isolated monoclonal antibody described herein specifically binds to Env and comprises a heavy chain variable region (VH) and a light chain variable region (VL), wherein the VH comprises an amino acid sequence comprising the amino acid sequence of SEQ ID NO: 316-318 at Kabat positions H52-H56; and the VL comprises an amino acid sequence comprising (a) the amino acid sequence of SEQ ID NO: 319-324 at Kabat positions H26-H34 and (b) the amino acid sequence of SEQ ID NO: 335-339 at Kabat positions H67-H70. In some embodiments, an isolated monoclonal antibody described herein specifically binds to Env and comprises a heavy chain variable region (VH) and a light chain variable region (VL), wherein the VH comprises an amino acid sequence comprising (a) the amino acid sequence of SEQ ID NO: 310-315 at Kabat positions H31-H37; (b) the amino acid sequence of SEQ ID NO: 316-318 at Kabat positions H52-H56; and (c) the amino acid sequence of SEQ ID NO: 145-162 at Kabat positions H61-H62, and the VL comprises an amino acid sequence comprising (d) the amino acid sequence of SEQ ID NO: 319-324 at Kabat positions H26-H34; (e) the amino acid sequence of SEQ ID NO: 325-334 at Kabat positions H49-H56; (f) the amino acid sequence of SEQ ID NO: 335-339 at Kabat positions H67-H70; and (g) the amino acid sequence of SEQ ID NO: 217-234 at Kabat positions H89-H97. In some embodiments, the VH comprises an amino acid sequence comprising (a) VH CDR1, VH CDR2, and VH CDR3, and (b) one or more of Motif #1, Motif #2, and Motif #3 and the VL comprises an amino acid sequence comprising (d) VL CDR1, VL CDR2, and VL CDR3, and (e) one or more of Motif #4, Motif #5, Motif #6, and Motif #7, wherein the sequence of VH CDR1, VH CDR2, VH CDR3, VL CDR1, VL CDR2, VL CDR3, Motif #1, Motif #2, Motif #3, Motif #4, Motif #5, Motif #6, and Motif #7 is derived from the same antibody described herein. In some embodiments, the VH comprises an amino acid sequence comprising (a) VH CDR1, VH CDR2, and VH CDR3, and (b) one or more of Motif #1, Motif #2, and Motif #3 and the VL comprises an amino acid sequence comprising (d) VL CDR1, VL CDR2, and VL CDR3, and (e) one or more of Motif #4, Motif #5, Motif #6, and Motif #7, wherein the sequence of VH CDR1, VH CDR2, VH CDR3, VL CDR1, VL CDR2, VL CDR3, Motif #1, Motif #2, Motif #3, Motif #4, Motif #5, Motif #6, and Motif #7 is derived from the same antibody described herein. In some embodiments, the sequence of VH CDR1, VH CDR2, VH CDR3, VL CDR1, VL CDR2, VL CDR3, Motif #1, Motif #2, Motif #3, Motif #4, Motif #5, Motif #6, and Motif #7 is derived from PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the sequence of VH CDR1, VH CDR2, VH CDR3, VL CDR1, VL CDR2, VL CDR3, Motif #1, Motif #2, Motif #3, Motif #4, Motif #5, Motif #6, and Motif #7 is derived from PCIN63-71I1a, or PCIN63-71L. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the antibody comprises the VH CDR1, VH CDR2, VH CDR3, VL CDR1, VL CDR2, and VL CDR3 of PCIN63-71I1a, or PCIN63-71L. In some embodiments, the antibody comprises the VH and VL of an antibody described herein. In some embodiments, the antibody comprises the VH and VL of PCIN63-

66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-71O, PCIN63-71P, PCIN63-77B1b, or PCIN63-77C. In some embodiments, the antibody comprises the VH and VL of PCIN63-71I1a, or PCIN63-71L.

In some embodiments, an antibody described herein is not identical to PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D.

In some embodiments, an antibody described herein is markedly different from PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D.

In some embodiments, an antibody described herein comprises a VH CDR3 comprising a sequence that is not identical to the VHCDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D.

In some embodiments, an antibody described herein comprises a VH CDR1, VH CDR2, or VH CDR3 comprising an amino acid sequence that is not identical to the amino acid sequence of VH CDR1, VH CDR2, or VH CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D.

In some embodiments, an antibody described herein comprises a VL CDR1, VL CDR2, or VL CDR3 comprising an amino acid sequence that is not identical to the amino acid sequence of VL CDR1, VL CDR2, or VL CDR3 of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D.

In some embodiments, an antibody described herein comprises a VH comprising an amino acid sequence that is not identical to the amino acid sequence of VH PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D.

In some embodiments, an antibody described herein comprises a VL comprising an amino acid sequence that is not identical to the amino acid sequence of VL PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D.

In some embodiments, an antibody described herein comprises at least one substitution, insertion, or deletion compared to the corresponding amino acid sequence of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-71O, PCIN63-71P, PCIN63-77B1b, PCIN63-77C, or PCIN63-77D.

In some embodiments, an isolated monoclonal antibody described herein further comprises heavy and/or light chain constant regions.

In some embodiments, an isolated monoclonal antibody described herein further comprises human heavy and/or light chain constant regions.

In some embodiments, the heavy chain constant region is selected from the group consisting of human immunoglobulins IgG1, IgG2, IgG3, IgG4, IgA1, and IgA2.

In some embodiments, the heavy chain constant region comprises a native amino acid sequence.

In some embodiments, the heavy chain constant region comprises a variant amino acid sequence.

In some embodiments, the antibody is a recombinant antibody, a chimeric antibody, a human antibody, an antibody fragment, a bispecific antibody, a trispecific antibody, or a multispecific antibody.

In some embodiments, an antibody described herein is a multispecific antibody, e.g. a bispecific antibody. Multispecific antibodies are monoclonal antibodies that have binding specificities for at least two different sites. In some embodiments, one of the binding specificities is for HIV Env and the other is for any other antigen. In some embodiments, bispecific antibodies bind to two different epitopes of HIV Env. Bispecific antibodies can be prepared as full length antibodies or antibody fragments.

Techniques for making multispecific antibodies, e.g., bispecific antibodies include, but are not limited to, recombinant co-expression of two immunoglobulin heavy chain-light chain pairs having different specificities (see Milstein and Cuello, Nature 305:537 (1983)), WO 93/08829, and Traunecker et al., EMBO J. 10:3655 (1991)), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229:81 (1985)); using leucine zippers to produce bi-specific antibodies (see, e.g., Kostelny et al., J. Immunol., 148 (5): 1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see,e.g. Gruber et al., J. Immunol., 152:5368 (1994)); and preparing trispecific antibodies as described, e.g., in Tutt et al. J. Immunol. 147:60 (1991). Engineered antibodies with three or more functional antigen binding sites, including "Octopus antibodies" and dual variable domain (DVD) immunoglobulins are also included herein (see, e.g. US 2006/0025576A1 and U.S. Pat. No. 10,093,733). The antibody or fragment disclosed herein also includes a "Dual Acting Fab" or "DAF" comprising an antigen binding site that binds to different epitopes, e.g., two different HIV Env epitopes (see, US 2008/0069820, for example).

In some embodiments, an antibody described herein is a multispecific antibody, e.g. a bispecific antibody comprising a first antigen binding domain comprising a VH domain or VH and VL domains disclosed herein, and a second antigen binding region capable of binding an HIV Env epitope. In one embodiment, the second antigen binding region binds to an HIV Env epitope region different from the HIV Env epitope region bound by an antibody disclosed herein. In one embodiment, the second antigen binding region binds to the high-mannose patch epitope region, V1/V2-glycan site (V2g) epitope region, or gp41 MPER epitope region. In some embodiments, the second antigen binding region binds to the high-mannose patch epitope region (e.g., PGT-121 or an engineered variant thereof). In some embodiments, the second antigen binding region binds to the high-mannose patch epitope region disclosed in International Appl. No. PCT/US2019/43578, filed on Jul. 26, 2016, which is incorporated herein by reference in its entirety for all purposes. In some embodiments, the second antigen binding region binds to the V1/V2-glycan site (V2g) epitope region. In some embodiments, the second antigen binding region binds to the gp41 MPER epitope region.

In some embodiments, the antibody fragment comprises a single-chain Fv (scFv), F(ab) fragment, F(ab')2 fragment, or an isolated VH domain.

In some embodiments, the antibody is capable of neutralizing at least two cross-clade isolates of HIV.

In some embodiments, an antibody described herein specifically binds the Env of at least one HIV isolate in the indicator virus panel of FIG. 8. In some embodiments, an antibody described herein specifically binds the Env of at least two, at least three, at least four, or at least five HIV isolates in the indicator virus panel of FIG. 8. In some embodiments, an antibody described herein specifically binds the Env of 1, 2, 3, 4, 5, 10, 15, 20, or 25 HIV isolates in the indicator virus panel of FIG. 8. In some embodiments, an antibody described herein specifically binds the Env of at least 50%, 60%, 70%, 80%, 90%, or 95% of the HIV isolates in the indicator virus panel of FIG. 8. In some embodiments, an antibody described herein specifically binds the Env of the 100% of HIV isolates in the indicator virus panel of FIG. 8. In some embodiments, an antibody described herein binds Env at the CD4 receptor binding site (CD4bs) epitope region. In some embodiments, an antibody described herein binds to wild type Env, but does not bind a mutant variant of Env comprising a substitution or deletion in the CD4 receptor binding site.

In some embodiments, an antibody described herein specifically binds the Env of at least one HIV isolate in the indicator virus panel of FIG. 9. In some embodiments, an antibody described herein specifically binds the Env of at least two, at least three, at least four, or at least five HIV isolates in the indicator virus panel of FIG. 9. In some embodiments, an antibody described herein specifically binds the Env of 1, 2, 3, 4, 5, 10, 15, 20, or 25 HIV isolates in the indicator virus panel of FIG. 9. In some embodiments, an antibody described herein specifically binds the Env of at least 50%, 60%, 70%, 80%, 90%, or 95% of the HIV isolates in the indicator virus panel of FIG. 9. In some embodiments, an antibody described herein specifically binds the Env of the 100% of HIV isolates in the indicator virus panel of FIG. 9. In some embodiments, an antibody described herein binds Env at the CD4 receptor binding site (CD4bs) epitope region. In some embodiments, an antibody described herein binds to wild type Env, but does not bind a mutant variant of Env comprising a substitution or deletion in the CD4 receptor binding site.

In some embodiments, an antibody described herein is capable of neutralizing at least one HIV isolate in the indicator virus panel of FIG. 8. In some embodiments, an antibody described herein is capable of neutralizing at least two, at least three, at least four, or at least five HIV isolates in the indicator virus panel of FIG. 8. In some embodiments, an antibody described herein is capable of neutralizing 1, 2, 3, 4, 5, 10, 15, 20, or 25 HIV isolates in the indicator virus panel of FIG. 8. In some embodiments, an antibody described herein is capable of neutralizing at least 50%, 60%, 70%, 80%, 90%, or 95% of the HIV isolates in the indicator virus panel of FIG. 8. In some embodiments, an antibody described herein is capable of neutralizing the 100% of HIV isolates in the indicator virus panel of FIG. 8. In some embodiments, the IC50 for neutralizing an HIV isolate is higher than the IC50 of neutralizing a corresponding HIV isolate comprising the N276A substitution. In some embodiments, the IC50 for neutralizing an HIV isolate is the same as the IC50 of neutralizing a corresponding HIV isolate comprising the N276A substitution. In some embodiments, the IC50 for neutralizing an HIV isolate is lower than the IC50 of neutralizing a corresponding HIV isolate comprising the N276A substitution.

In some embodiments, an antibody described herein is capable of neutralizing at least one HIV isolate in the indicator virus panel of FIG. 9. In some embodiments, an antibody described herein is capable of neutralizing at least two, at least three, at least four, or at least five HIV isolates in the indicator virus panel of FIG. 9. In some embodiments, an antibody described herein is capable of neutralizing 1, 2, 3, 4, 5, 10, 15, 20, or 25 HIV isolates in the indicator virus panel of FIG. 9. In some embodiments, an antibody described herein is capable of neutralizing at least 50%, 60%, 70%, 80%, 90%, or 95% of the HIV isolates in the indicator virus panel of FIG. 9. In some embodiments, an antibody described herein is capable of neutralizing the 100% of HIV isolates in the indicator virus panel of FIG. 9. In some embodiments, the IC50 for neutralizing an HIV isolate is higher than the IC50 of neutralizing a corresponding HIV isolate comprising the N276A substitution. In some embodiments, the IC50 for neutralizing an HIV isolate is the same as the IC50 of neutralizing a corresponding HIV isolate comprising the N276A substitution. In some embodiments, the IC50 for neutralizing an HIV isolate is lower than the IC50 of neutralizing a corresponding HIV isolate comprising the N276A substitution.

In some embodiments, an antibody described herein specifically binds to Env and is capable of neutralizing at least two isolates of HIV. In some embodiments, an antibody described herein is a broadly neutralizing antibody. In some embodiments, the two isolates are two cross-clade isolates. In some embodiments, an antibody described herein is capable of neutralizing at least one clade A HIV isolate, at least one clade B HIV isolate, and at least one clade C HIV isolate. In some embodiments, an antibody described herein is capable of neutralizing at least about 40%, 50%, 60%, 70%, 80%, 90%, or 100% of cross-clade HIV isolates in the indicator virus panel of FIG. 8. In some embodiments, an antibody described herein is capable of neutralizing at least about 40%, 50%, 60%, 70%, 80%, 90%, or 100% of cross-clade HIV isolates in the indicator virus panel of FIG. 9. In some embodiments, an antibody described herein is capable of neutralizing the cross-clade HIV isolates with a median IC50 equal to or less than about 1 μg/ml, about 0.8 μg/ml, 0.5 μg/ml, or 0.3 μg/ml. In some embodiments, an antibody described herein is capable of neutralizing the cross-clade HIV isolates with a mean IC50 equal to or less than about 1 μg/ml, about 0.8 μg/ml, 0.5 μg/ml, or 0.3 μg/ml. In some embodiments, an antibody described herein is capable of neutralizing at least about 40%, 50%, 60%, 70%, 80%, 90%, or 100% of cross-clade HIV isolates in the indicator virus panel of FIG. 8 with a mean IC50 equal to or less than about 1 μg/ml, about 0.8 μg/ml, 0.5 μg/ml, or 0.3 μg/ml. In some embodiments, an antibody described herein is capable of neutralizing at least about 40%, 50%, 60%, 70%, 80%, 90%, or 100% of cross-clade HIV isolates in the indicator virus panel of FIG. 8 with a mean IC50 equal to or less than about 0.8 μg/ml. In some embodiments, an antibody described herein is capable of neutralizing at least about 40%, 50%, 60%, 70%, 80%, 90%, or 100% of cross-clade HIV isolates in the indicator virus panel of FIG. 8 with a mean IC50 equal to or less than 0.5 μg/ml. In some embodiments, an antibody described herein is capable of neutralizing at least about 80% of cross-clade HIV isolates in the indicator virus panel of FIG. 8 with a mean IC50 equal to or less than about 1 μg/ml, about 0.8 μg/ml, 0.5 μg/ml, or 0.3 μg/ml. In some embodiments, an antibody described herein is capable of neutralizing at least about 40%, 50%, 60%, 70%, 80%, 90%, or 100% of cross-clade HIV isolates in the indicator virus panel of FIG. 9 with a mean IC50 equal to or less than about 1 μg/ml, about 0.8 μg/ml, 0.5 μg/ml, or 0.3 μg/ml. In some embodiments, an antibody described herein is capable of neutralizing at least about 40%, 50%, 60%, 70%, 80%, 90%, or 100% of cross-clade HIV isolates in the indicator virus panel of FIG. 9 with a mean IC50 equal to or less than about 0.8 μg/ml. In some embodiments, an antibody described herein is capable of neutralizing at least about 40%, 50%, 60%, 70%, 80%, 90%, or 100% of cross-clade HIV isolates in the indicator virus panel of FIG. 9 with a mean IC50 equal to or less than about 0.5 μg/ml. In some embodiments, an antibody described herein is capable of neutralizing at least about 80% of cross-clade HIV isolates in the indicator virus panel of FIG. 9 with a mean IC50 equal to or less than about 1 μg/ml, about 0.8 μg/ml, 0.5 μg/ml, or 0.3 μg/ml.

In some embodiments, the IC50 for neutralizing an HIV isolate is higher than the IC50 of neutralizing a corresponding HIV isolate comprising the N276A substitution. In some embodiments, the IC50 for neutralizing an HIV isolate is the same as the IC50 of neutralizing a corresponding HIV isolate comprising the N276A substitution. In some embodiments, the IC50 for neutralizing an HIV isolate is lower than the IC50 of neutralizing a corresponding HIV isolate comprising the N276A substitution.

In another aspect, provided herein are antibodies that bind the same or an overlapping epitope of Env (e.g., an epitope of BG505, JR-FL, YU-2, and JR-CSF Env) as an antibody described herein (e.g., PCIN63-71I1a, or PCIN63-71L). In certain embodiments, the epitope of an antibody can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50 (Pt 4): 339-350; McPherson A (1990) Eur J Biochem 189:1-23; Chayen N E (1997) Structure 5:1269-1274; McPherson A (1976) J Biol Chem 251:6300-6303). Antibody: antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49 (Pt 1): 37-60; Bricogne G (1997) Meth Enzymol 276A: 361-423, ed Carter C W; Roversi P et al., (2000) Acta Crystallogr D Biol Crystallogr 56 (Pt 10): 1316-1323). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. Usually, binding to the antigen is reduced or disrupted when a residue within the epitope is substituted to alanine. In some embodiments, the Kd of binding to the antigen is increased by about 5-fold, 10-fold, 20-fold, 10-fold or more when a residue within the epitope is substituted for alanine. In some embodiments, binding affinity is determined by ELISA. In addition, antibodies that recognize and bind to the same or overlapping epitopes of Env (e.g., an epitope of BG505, YU-2, JR-FL, and JR-CSF Env) can be identified using routine techniques such as an immunoassay, for example, by showing the ability of one antibody to block the binding of another antibody to a target antigen, i.e., a competitive binding assay.

In some embodiments, provided herein is an antibody, which immunospecifically binds to the same epitope as an antibody comprising a heavy chain variable region (VH) and light chain variable region (VL) of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D. In some embodiments, provided herein is an antibody, which immunospecifically binds to the same epitope as an antibody comprising a VH and VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, provided herein is an antibody, which immunospecifically binds to the same epitope as an antibody comprising a VH and VL of PCIN63-71I1a, or PCIN63-71L. In some embodiments, provided herein is an antibody, which immunospecifically binds to the same epitope as an antibody comprising the VH and VL of SEQ ID NO 242 and 260, respectively. In some embodiments, provided herein is an antibody, which immunospecifically binds to the same epitope as an antibody comprising the VH and VL of 245 and 263, respectively. In some embodiments, provided herein is an antibody, which immunospecifically binds to the same epitope as an antibody comprising a VH and VL of PCIN63-71I1a, or PCIN63-71L for specific binding to Env. Assays known to one of skill in the art or described herein (e.g., X-ray crystallography, hydrogen/deuterium exchange coupled with mass spectrometry (e.g., liquid chromatography electrospray mass spectrometry), alanine scanning, ELISA assays, etc.) can be used to determine if two antibodies bind to the same epitope.

In another aspect, provided herein are antibodies that compete (e.g., in a dose dependent manner) for binding to Env (e.g., an epitope of BG505, YU-2, JR-FL, and JR-CSF Env) with an antibody described herein (e.g., PCIN63-71I1a, or PCIN63-71L), as determined using assays known to one of skill in the art or described herein (e.g., ELISA competitive assays or surface plasmon resonance). In another aspect, provided herein are antibodies that competitively inhibit (e.g., in a dose dependent manner) an antibody described herein (e.g., PCIN63-71I1a, or PCIN63-71L) from binding to Env (e.g., an epitope of BG505, YU-2, JR-FL, and JR-CSF Env), as determined using assays known to one of skill in the art or described herein (e.g., ELISA competitive assays, or suspension array or surface plasmon resonance assay).

In some embodiments, an antibody described herein competes for binding to Env with an antibody disclosed herein.

In some embodiments, an antibody described herein competes for binding to Env with an antibody comprising the VH and VL of PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D. In some embodiments, an antibody described herein competes for binding to Env with an antibody comprising the VH and VL of PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, an antibody described herein competes for binding to Env with an antibody comprising the VH and VL of PCIN63-71I1a, or PCIN63-71L. In some embodiments, an antibody described herein competes for binding to Env with an antibody comprising the VH and VL of SEQ ID NO 242 and 260, respectively. In some embodiments, an antibody described herein competes for binding to Env with an antibody comprising the VH and VL of 245 and 263, respectively. In some embodiments, the Env is BG505 Env. In some embodiments, the Env is YU-2 Env. In some embodiments, the Env is JR-FL Env. In some embodiments, the Env is JR-CSF Env.

In certain embodiments, the epitope of an antibody described herein is used as an immunogen to produce antibodies.

In one aspect, provided herein are methods for producing an engineered variant of an antibody described herein. In some embodiments, a method for producing an engineered variant comprises directed-evolution and yeast display. Methods for producing an engineered antibody are known to those skilled in the art, for example, as described in International Appl. No. PCT/US2019/43578, filed on Jul. 26, 2016, which is incorporated herein by reference in its entirety for all purposes. In some embodiments, an engineered antibody possesses one or more improved properties, for example, higher binding affinity to target antigen, higher binding affinity to target antigen at low pH, increased median neutralization IC50 potency, and increased breadth of neutralization compared to the parent antibody.

In some embodiments, a method of producing an engineered variant of a parent antibody comprises substituting one or more amino acid residues of the VH; and/or substituting one or more amino acid residues of the VL to create an engineered variant antibody, and producing the engineered variant antibody. In some embodiments, the parent antibody is an antibody described herein. In some embodiments, the parent antibody is PCIN63-66B, PCIN63-71B, PCIN63-71C, PCIN63-71D2b, PCIN63-71F, PCIN63-71G, PCIN63-71H, PCIN63-71I1a, PCIN63-71J2a, PCIN63-71K, PCIN63-71L, PCIN63-71M1a, PCIN63-71N1a, PCIN63-710, PCIN63-71P, PCIN63-77B1b, PCIN63-77C, or PCIN63-77D. In some embodiments, the parent antibody is PCIN63-66B, PCIN63-71C, PCIN63-71D2b, PCIN63-71G, PCIN63-71H, PCIN63-71I1a, PCIN63-71J2a, PCIN63-71K, PCIN63-71L, PCIN63-71M1a, PCIN63-710, PCIN63-71P, PCIN63-77B1b, or PCIN63-77C. In some embodiments, the parent antibody is PCIN63-71I1a, or PCIN63-71L. In some embodiments, the method further comprises determining that the engineered variant antibody has improved properties, for example, by determining the engineered variant antibody's binding affinity to target antigen, binding affinity to target antigen at low pH, median neutralization IC50 potency, or breadth of neutralization compared to the parent antibody.

The affinity or avidity of an antibody or fusion polypeptide for an antigen can be determined experimentally using any suitable method well known in the art, e.g., flow cytometry, enzyme-linked immunoabsorbent assay (ELISA), or radioimmunoassay (RIA), or kinetics (e.g., BIACORE™ analysis). Direct binding assays as well as competitive binding assay formats can be readily employed. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., Kd, Kon, Koff) are made with standardized solutions of antibody and antigen, and a standardized buffer, as known in the art and such as the buffer described herein.

In some embodiments, the broadly neutralizing anti-Env antibody described herein is a monoclonal antibody. Monoclonal antibodies can be prepared using hybridoma methods, such as those described by Kohler and Milstein (1975) Nature 256:495. Using the hybridoma method, a bovine host (e.g., cow) is immunized to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g., radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid using any method known in the art.

Alternatively monoclonal antibodies can also be made using recombinant DNA methods as described in U.S. Pat. No. 4,816,567. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antibody binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the antigen and other favorable biological properties. To achieve this goal, humanized (or human) or engineered antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

Humanization, resurfacing or engineering of antibodies described herein can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151:2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567; PCT/: US98/16280; US96/18978; US91/09630; US91/05939; US94/01234; GB89/01334; GB91/01134; GB92/01755; WO90/14443; WO90/14424; WO90/14430; EP 229246; 7,557,189; 7,538,195; and 7,342,110, each of which is entirely incorporated herein by reference, including the references cited therein.

In certain alternative embodiments, the antibody is a human antibody. Human antibodies can be directly prepared using various techniques known in the art. Human antibodies can be isolated from suitable donors following the methods described herein. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1): 86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi: 10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

In certain embodiments an antibody fragment is provided. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from antibody phage libraries. The antibody fragment can also be linear antibodies as described in U.S. Pat. No. 5,641,870, for example, and can be monospecific or bispecific. Other techniques for the production of antibody fragments will be apparent to the skilled practitioner.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It may not be necessary to replace all of the CDRs with the complete CDRs from the donor variable region to transfer the antigen-binding capacity of one variable domain to another. Rather, it may only be necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies described herein will comprise antibodies (e.g., full-length antibodies or immunoreactive fragments thereof) in which at least a fraction of one or more of the constant region domains has been deleted or otherwise altered so as to provide desired biochemical characteristics such as increased serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies described herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain will be replaced by a short amino acid spacer (e.g., 10 residues) that provides some of the molecular flexibility typically imparted by the absent constant region.

It will be noted that in certain embodiments, the modified antibodies can be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies described herein can be provided by the partial deletion or substitution of a few or even a single amino acid. For example, it may be desirable to simply delete that part of one or more constant region domains that control the effector function (e.g., complement C1Q binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The half-life of an IgG is mediated by its pH-dependent binding to the neonatal receptor FcRn. In some embodiments, an antibody described herein comprises a variant Fc region that has been modified to enhance binding to FcRn (see, e.g., Petkova et al., Int. Immunol. 18:1759-1769 (2006); Dall'Acqua et al., J. Immunol.169:5171-5180 (2002); Oganesyan et al., Mol. Immunol. 46:1750-1755 (2009); Dall'Acqua et al., J. Biol. Chem. 281:23514-23524 (2006), Hinton et al., J. Immunol. 176:346-356 (2006); Datta-Mannan et al., Drug Metab. Dispos. 35:86-94 (2007); Datta-Mannan et al., J. Biol. Chem. 282:1709-1717 (2007); WO 06/130834; Strohl, Curr. Op. Biotechnol. 20:685-691 (2009); and Yeung et al., J. Immunol. 182:7663-7671 (2009), the contents of each of which is herein incorporated by reference in its entirety).

In some embodiments, an antibody described herein comprises a variant Fc region that has been modified to have a selective affinity for FcRn at pH 6.0, but not pH 7.4. By way of example, the variant Fc region contains one or more of the following modifications that increase half-life: IgG1-M252Y, S254T, T256E; IgG1-T250Q, M428L; IgG1-M428L and N434S (the "LS" mutation); IgG1-H433K, N434Y; IgG1-N434A; and IgG1-T307A, E380A, N434A; wherein the numbering of the residues is that of the EU index of Kabat et al. (Kabat et al., Sequences of Proteins of Immunological Interest, 1991 Fifth edition, herein incorporated by reference).

In some embodiments, an antibody described herein comprises a variant Fc region that has been modified to reduce its effector functions. In some embodiments, the variant Fc region comprises the L234A, L235A hinge region substitutions, wherein the numbering of the residues is that of the EU index of Kabat et al.

In some embodiments, an antibody described herein comprises an Fc region having a carbohydrate structure that lacks fucose attached (directly or indirectly) to the Fc region or has a reduced level of fucosylation. In some embodiments, a fucosylation variant antibody has improved ADCC function. See, e.g., US Patent Publication Nos. US 2003/0157108; US 2004/0093621, each of which is incorporated by reference herein in its entirety. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87:614 (2004), each of which is incorporated by reference herein in its entirety. Examples of cell lines capable of producing defucosylated antibodies include Lec 13 CHO cells deficient in protein fucosylation (Ripka et al. Arch. Biochem. Biophys. 249:533-545 (1986); US Pat Appl No US 2003/0157108 A1; and WO 2004/056312), and knockout cell lines, such as alpha-1,6-fucosyltransferase gene, FUT8, knockout CHO cells (see, e.g., Yamane-Ohnuki et al. Biotech. Bioeng. 87:614 (2004); Kanda, Y. et al., Biotechnol. Bioeng., 94 (4): 680-688 (2006); and WO2003/085107), each of which is incorporated by reference herein in its entirety.

In some embodiment, an antibody described herein comprises bisected oligosaccharides, in which a biantennary oligosaccharide attached to the Fc region of the antibody is bisected by GlcNAc. In some embodiment, an antibody comprising bisected oligosaccharides has reduced fucosylation and/or improved ADCC function. See, e.g., WO 2003/011878; U.S. Pat. No. 6,602,684; and US 2005/0123546, each of which is incorporated by reference herein in its entirety. In some embodiment, an antibody described herein comprises at least one galactose residue in the oligosaccharide attached to the Fc region. Such antibody variants may have improved CDC function. See, e.g., in WO 1997/30087; WO 1998/58964; and WO 1999/22764, each of which is incorporated by reference herein in its entirety.

In some embodiments, an antibody described herein comprises a variant Fc region comprising a combination of substitutions with increased binding to FcRn and Fc gamma RIIIa. The combinations increase antibody half-life and ADCC. For example, such combination include antibodies with the following amino acid substitution in the Fc region: (1) S239D/I332E and T250Q/M428L; (2) S239D/I332E and M428L/N434S; (3) S239D/I332E and N434A; (4) S239D/I332E and T307A/E380A/N434A; (5) S239D/I332E and M252Y/S254T/T256E; (6) S239D/A330L/I332E and 250Q/M428L; (7) S239D/A330L/I332E and M428L/N434S; (8) S239D/A330L/I332E and N434A; (9) S239D/A330L/I332E and T307A/E380A/N434A; or (10) S239D/A330L/I332E and M252Y/S254T/T256E, wherein the numbering of the residues is that of the EU index of Kabat et al. In some embodiments, an antibody comprising the variant Fc region is directly cytotoxic to infected cells, or uses natural defenses such as complement, antibody dependent cellular cytotoxicity (ADCC), or phagocytosis by macrophages.

The present invention further embraces variants and equivalents which are substantially homologous to the chimeric, humanized and human antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides provided herein can be recombinant polypeptides, natural polypeptides, or synthetic polypeptides comprising an antibody, or fragment thereof. It will be recognized in the art that some amino acid sequences described herein can be varied without significant effect of the structure or function of the protein. Thus, the invention further includes variations of the polypeptides which show substantial activity or which include regions of an antibody, or fragment thereof, against a human folate receptor protein. Such mutants include deletions, insertions, inversions, repeats, and type substitutions.

The polypeptides and analogs can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in REMINGTON'S PHARMACEUTICAL SCIENCES, 21th ed., Mack Publishing Co., Easton, PA (2005).

III. Polynucleotides

In certain aspects, provided herein are polynucleotides comprising a nucleotide sequence or nucleotide sequences encoding a broadly neutralizing anti-Env antibody described herein or a fragment thereof and vectors, e.g., vectors comprising such polynucleotides. In some embodiments, the vectors can be used for recombinant expression of an antibody described herein in host cells (e.g., *E. coli* and mammalian cells). In some embodiments, the vectors can be used for administration of an antibody described herein to a patient in need thereof.

In one aspect, provided herein are isolated polynucleotides encoding the heavy chain variable region or heavy chain of an antibody described herein.

In one aspect, provided herein are isolated polynucleotides encoding the light chain variable region or light chain of an antibody described herein.

In one aspect, provided herein are isolated polynucleotides encoding the heavy chain variable region or heavy chain of an antibody described herein and the light chain variable region or light chain of an antibody described herein.

In some embodiments, the polynucleotide encodes a heavy chain variable region comprising the amino acid sequence of SEQ ID NO: 235-252.

In some embodiments, the polynucleotide encodes a light chain variable region comprising the amino acid sequence of SEQ ID NO: 253-270.

In some embodiments, an isolated polynucleotide described herein encodes a broadly neutralizing antibody described herein and comprises an mRNA. In some embodiments, the mRNA comprises at least one modified nucleotide. In some embodiments, a modified mRNA encoding an antibody described herein is for administering to a subject to treat or prevent HIV infection.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody or fusion polypeptide described herein is isolated or purified.

In particular aspects, provided herein are polynucleotides comprising nucleotide sequences encoding antibodies described herein, as well as antibodies that compete with such antibodies for binding to HIV, or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL of antibodies described herein. The polynucleotides can comprise nucleotide sequences encoding a heavy chain comprising the VH of antibodies described herein. In specific embodiments, a polynucleotide described herein encodes a VH domain comprising the amino acid sequence set forth in SEQ ID NO: 235-252. In specific embodiments, a polynucleotide described herein encodes a VL domain comprising the amino acid sequence set forth in SEQ ID NO: 253-270. In some embodiments, the antibody is a human antibody. In some embodiments, the antibody is a chimeric antibody.

In particular embodiments, provided herein are polynucleotides comprising a nucleotide sequence encoding a broadly neutralizing anti-Env antibody comprising three VL chain CDRs, e.g., containing VL CDR1, VL CDR2, and VL CDR3 of any one of antibodies described herein. In specific embodiments, provided herein are polynucleotides comprising three VH chain CDRs, e.g., containing VH CDR1, VH CDR2, and VH CDR3 of any one of antibodies described herein. In specific embodiments, provided herein are polynucleotides comprising a nucleotide sequence encoding an anti-Env antibody comprising three VL CDRs, e.g., containing VL CDR1, VL CDR2, and VL CDR3 of any one of antibodies described herein and three VH chain CDRs, e.g., containing VH CDR1, VH CDR2, and VH CDR3 of any one of antibodies described herein. In some embodiments, the antibody is a human antibody.

In particular embodiments, provided herein are polynucleotides comprising a nucleotide sequence encoding a broadly neutralizing anti-Env antibody comprising three VL chain CDRs, e.g., containing VL CDR1, VL CDR2, and VL CDR3 of any one of antibodies described herein. In some embodiment, the antibody comprises a VL, wherein the VL comprises an amino acid sequence comprising one or more of Motifs #4, #5, #6, and #7 (comprising the amino acid sequence of SEQ ID NO: 163-180 or 319-324, 181-198 or 325-334, 199-216 or 335-339, and 217-234, respectively). In some embodiment, the antibody comprises a VL, wherein the VL comprises an amino acid sequence comprising Motifs #4, #5, #6, and #7.

In particular embodiments, provided herein are polynucleotides comprising a nucleotide sequence encoding a broadly neutralizing anti-Env antibody comprising three VH chain CDRs, e.g., containing VH CDR1, VH CDR2, and VH CDR3 of any one of antibodies described herein. In some embodiment, the antibody comprises a VH, wherein the VH comprises an amino acid sequence comprising one or more of Motifs #1, #2, and #3 (comprising the amino acid sequence of SEQ ID NO: 109-126 or 310-315, 127-144 or 316-318, and 145-162, respectively). In some embodiment, the antibody comprises a VH, wherein the VH comprises an amino acid sequence comprising Motifs #1, #2, and #3.

In particular embodiments, provided herein are polynucleotides comprising a nucleotide sequence encoding a broadly neutralizing anti-Env antibody comprising three VL CDRs, e.g., containing VL CDR1, VL CDR2, and VL CDR3 of any one of antibodies described herein and three VH chain CDRs, e.g., containing VH CDR1, VH CDR2, and VH CDR3 of any one of antibodies described herein. In some embodiment, the antibody comprises a VL and a VH, wherein the VL comprises an amino acid sequence comprising one or more of Motifs #4, #5, #6, and #7 (comprising the amino acid sequence of SEQ ID NO: 163-180 or 319-324, 181-198 or 325-334, 199-216 or 335-339, and 217-234, respectively), and/or the VH comprises an amino acid sequence comprising one or more of Motifs #1, #2, and #3 (comprising the amino acid sequence of SEQ ID NO: 109-126 or 310-315, 127-144 or 316-318, and 145-162, respectively). In some embodiment, the antibody comprises a VL and a VH, wherein the VL comprises an amino acid sequence comprising Motifs #4, and #6, and the VH comprises an amino acid sequence comprising Motifs #2. In some embodiment, the antibody comprises a VL and a VH, wherein the VL comprises an amino acid sequence comprising Motifs #4, #5, #6, and #7 (comprising the amino acid sequence of SEQ ID NO: 163-180 or 319-324, 181-198 or 325-334, 199-216 or 335-339, and 217-234, respectively), and the VH comprises an amino acid sequence comprising Motifs #1, #2, and #3 (comprising the amino acid sequence of SEQ ID NO: 109-126 or 310-315, 127-144 or 316-318, and 145-162, respectively).

In some embodiments, provided herein are polynucleotides comprising a nucleotide sequence encoding a broadly neutralizing anti-Env antibody comprising the VH CDR3 of an antibody described herein. In some embodiments, the VH CDR3 comprises the amino acid sequence of SEQ ID NO: 37-54. In some embodiments, the antibody is a human antibody.

In specific embodiments, a polynucleotide provided herein comprises a nucleotide sequence encoding an antibody or fragment thereof described herein comprising: framework regions (e.g., framework regions of the VL domain and VH domain) that are human framework regions, wherein the antibody immunospecifically binds Env. In certain embodiments, a polynucleotide provided herein comprises a nucleotide sequence encoding an antibody or fragment thereof (e.g., CDRs or variable domain) described herein.

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an antibody, which immunospecifically binds to Env, wherein the antibody comprises a light chain, and wherein the amino acid sequence of the VL domain can comprise the amino acid sequence set forth herein, and wherein the constant region of the light chain comprises the amino acid sequence of a human kappa light chain constant region. In another particular embodiment, a polynucleotide provided herein comprises a nucleotide sequence encoding an antibody, which immunospecifically binds to Env, and comprises a light chain, wherein the amino acid sequence of the VL domain can comprise the amino acid sequence set forth herein, and wherein the constant region of the light chain comprises the amino acid sequence of a human lambda light chain constant region. For example, human constant region sequences can be those described in U.S. Pat. No. 5,693,780.

In a particular embodiment, a polynucleotide provided herein comprises a nucleotide sequence encoding an antibody described herein, which immunospecifically binds to Env, wherein the antibody comprises a heavy chain, wherein the amino acid sequence of the VH domain can comprise the amino acid sequence of SEQ ID NO: 235-252, and wherein the constant region of the heavy chain comprises the amino acid sequence of a human alpha or gamma heavy chain constant region.

In yet another specific embodiment, a polynucleotide provided herein comprises a nucleotide sequence encoding an antibody described herein, which immunospecifically binds Env, wherein the antibody comprises a VL domain and a VH domain comprising any amino acid sequences described herein, and wherein the constant regions comprise the amino acid sequences of the constant regions of a human $IgA_1$, human $IgA_2$' human $IgG_1$ (e.g., allotype 1, 17, or 3), human $IgG_2$, or human $IgG_4$.

In yet another specific embodiment, a polynucleotide provided herein comprises a nucleotide sequences encoding an anti-Env antibody or a fragment thereof that are optimized, e.g., by codon/RNA optimization, replacement with heterologous signal sequences, and elimination of mRNA instability elements. Methods to generate optimized nucleic acids encoding an anti-Env antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid.

In certain embodiments, an optimized polynucleotide sequence encoding an anti-Env antibody described herein or a fragment thereof (e.g., VL domain or VH domain) can hybridize to an antisense (e.g., complementary) polynucleotide of an unoptimized polynucleotide sequence encoding an anti-Env antibody described herein or a fragment thereof (e.g., VL domain or VH domain). In specific embodiments, an optimized nucleotide sequence encoding an anti-Env antibody described herein or a fragment hybridizes under high stringency conditions to antisense polynucleotide of an unoptimized polynucleotide sequence encoding an anti-Env antibody described herein or a fragment thereof. In a specific embodiment, an optimized nucleotide sequence encoding an anti-Env antibody described herein or a fragment thereof hybridizes under high stringency, intermediate or lower stringency hybridization conditions to an antisense polynucleotide of an unoptimized nucleotide sequence encoding an anti-Env antibody described herein or a fragment thereof. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17:242-246), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody or fragment thereof described herein can be generated from nucleic acid from a suitable source (e.g., PBMCs) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody or fragment thereof is not available, but the sequence of the antibody molecule or fragment thereof is known, a nucleic acid encoding the immunoglobulin or fragment can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-Env antibodies described herein can be readily isolated and sequenced using conventional procedures (e.g., by using oligonucleotide probes that are capable of binding specifically to genes encoding the heavy and light chains of the anti-Env antibodies). PBMCs can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-Env antibodies in the recombinant host cells.

The DNA also can be modified, for example, by substituting the coding sequence for human heavy and light chain constant domains with a coding sequence for a non-immunoglobulin polypeptide, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

IV. Vectors, Cells, and Methods of Producing a Broadly Neutralizing Agent

In certain aspects, provided herein are cells (e.g., host cells) expressing (e.g., recombinantly) antibodies described herein which specifically bind to Env and related polynucleotides and expression vectors. Provided herein are vectors (e.g., expression vectors) comprising polynucleotides comprising nucleotide sequences encoding anti-Env antibodies or a fragment thereof described herein. In some embodiments, the vectors can be used for recombinant expression of an antibody described herein in host cells (e.g., mammalian cells). In some embodiments, the vectors can be used for administration of an antibody described herein to a patient in need thereof. Also provided herein are host cells comprising such vectors for recombinantly expressing anti-Env antibodies described herein. In a particular aspect, provided herein are methods for producing an antibody described herein, comprising expressing such antibody in a host cell. In one embodiment, the antibody comprises PCIN63-71I1a. In one embodiment, the antibody comprises or PCIN63-71L.

In certain aspects, provided herein is an isolated vector comprising a polynucleotide described herein. In some embodiments, the vector is a viral vector.

In certain aspects, provided herein is a recombinant virus comprising a polynucleotide described herein. In some embodiments, the recombinant virus encodes an antibody described herein. In one embodiment, the recombinant virus encodes a bispecific antibody described herein. In one embodiment, the recombinant virus is a replication defective virus. Suitable replication defective viral vectors are known to those skilled in the art, for example, as disclosed in U.S. Pat. Nos. 7,198,784, 9,408,905, 9,862,931, 8,067,156, U.S. Pat. Appl. Pub. Nos. 20150291935, 20120220492, 20180291351, and 20170175137, each of which is incorporated herein by reference in its entirety. In one embodiment, the recombinant virus is a retrovirus or retroviral vector, for example, a lentivirus or lentiviral vector. In one embodiment, the recombinant virus is an adenovirus or adenoviral vector, HSV or HSV vector, or influenza virus or viral vector. In one embodiment, the recombinant virus is an adeno-associated virus (AAV). In one embodiment, the recombinant virus is for administration to a subject to prevent or treat HIV infection. In one embodiment, the recombinant virus is an adeno-associated virus (AAV) for administration to a subject to prevent or treat HIV infection. Recombinant AAV particles encoding an antibody that binds to HIV Env and methods for producing thereof are known to one skilled in the art, for example, as disclosed in U.S. Pat. No. 8,865,881 and US20190031740, each of which is incorporated by reference herein in its entirety for all purposes. See also, Lin and Balazs, Retrovirology 15:66 (2018) and van den berg et al., Molecular Therapy: methods & Clinical Development 14:100-112 (2019), each of which is incorporated by reference herein in its entirety for all purposes. In one embodiment, the antibody comprises PCIN63-71I1a. In one embodiment, the antibody comprises or PCIN63-71L.

In certain aspects, provided herein is a host cell comprising a polynucleotide described herein, or a vector described herein. In some embodiments, the vector encodes an antibody described herein. In some embodiments, a vector described herein comprises a first vector encoding a VH described herein and a second vector encoding a VL described herein. In some embodiments, a vector described herein comprises a first nucleotide sequence encoding a VH described herein and a second nucleotide sequence encoding a VL described herein.

In some embodiments, the host cell is selected from the group consisting of *E. coli, Pseudomonas, Bacillus, Streptomyces*, yeast, CHO, YB/20, NS0, PER-C6, HEK-293T, NIH-3T3, Helga, BHK, Hep G2, SP2/0, R1.1, B-W, L-M, COS 1, COS 7, BSC1, BSC40, BMT10 cell, plant cell, insect cell, and human cell in tissue culture. In some embodiments, the host cell is CHO.

In certain aspects, provided herein is a method of producing an antibody that binds to HIV comprising culturing a host cell described herein so that the polynucleotide is expressed and the antibody is produced. In some embodiments, the method further comprises recovering the antibody.

The isolated polypeptides, i.e., anti-HIV Env antibodies described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies or fragments thereof. Recombinant expression vectors are replicable DNA constructs which have synthetic or cDNA-derived DNA fragments encoding a polypeptide chain of an antibody or fragment thereof operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7030, HsS78Bst, Helga, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45:101-105; and Cockett M I et al., (1990) Biotechnology 8:662-667). In certain embodiments, antibodies described herein are produced by CHO cells or NS0 cells. In a specific embodiment, the expression of nucleotide sequences encoding antibodies described herein which immunospecifically bind Env is regulated by a constitutive promoter, inducible promoter or tissue specific promoter.

For applications where it is desired that the antibodies described herein be expressed in vivo, for example in a subject in need of treatment with an antibody described herein, any vector that allows for the expression of the antibodies and is safe for use in vivo may be used. In some embodiments, the vector is a viral vector. Viral vectors can include poxvirus (vaccinia), including vaccinia Ankara and canarypox; adenoviruses, including adenovirus type 5 (Ad5); rubella; Sendai virus; rhabdovirus; alphaviruses; and adeno-associated viruses. In some embodiments, the viral vector is an adeno-associated virus. Alternatively, a polynucleotide encoding the antibody could be delivered as DNA or RNA to the subject for in vivo expression of the antibody.

Suitable host cells for expression of a polypeptide of interest such as an antibody described herein include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express a recombinant protein such as an antibody described herein. Expression of recombinant proteins in mammalian cells can be performed because such proteins are generally correctly folded, appropriately modified and completely functional. Examples of suitable mammalian host cell lines include but are not limited to CHO, VERO, BHK, Hela, MDCK, HEK 293, NIH 3T3, W138, BT483, Hs578T, HTB2, BT20 and T47D, NS0 (a murine myeloma cell line that does not endogenously produce any immunoglobulin chains), CRL7030, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein, e.g., an antibody, into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further an agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody. When the polypeptide (e.g., antibody described herein) is recombinantly produced, it is also generally substantially free of culture medium, i.e., culture medium represents less than about 20%, 10%, 2%, 1%, 0.5%, or 0.1% of the volume of the protein preparation. When the polypeptide (e.g., antibody described herein) is produced by chemical synthesis, it is generally substantially free of chemical precursors or other chemicals, i.e., it is separated from chemical precursors or other chemicals which are involved in the synthesis of the protein. Accordingly, such preparations of the polypeptide (e.g., antibody described herein) have less than about 30%, 20%, 10%, or 5% (by dry weight) of chemical precursors or compounds other than the polypeptide of interest. In some embodiments, antibodies described herein are isolated or purified.

V. Pharmaceutical Compositions

Compositions comprising the antibodies or antigen-binding fragments described herein are also provided. Further provided herein are compositions comprising a polynucleotide or polynucleotides encoding the antibodies or antigen-binding fragments described herein. In some embodiments, the polynucleotide comprises mRNA. In some embodiments, the composition is a pharmaceutical composition.

In some embodiments, the composition is a lyophilized composition. In some embodiments, the composition is formulated for topical administration, and in certain embodiments the composition is formulated for vaginal or rectal administration.

In certain aspects, provided herein is a pharmaceutical composition comprising an antibody described herein and a pharmaceutically acceptable excipient. In some embodiments, the antibody is an intact antibody. In some embodiments, the antibody is an antigen binding antibody fragment. In some embodiments, the composition is formulated for topical administration, and in certain embodiments the composition is formulated for vaginal or rectal administration.

In another embodiment, the disclosure provides a pharmaceutical composition comprising an antibody described herein. Such compositions are intended for prevention and treatment of HIV infection.

In further embodiments of the present disclosure, a composition comprising the antibody described herein can additionally be combined with other compositions for the treatment of HIV infection or the prevention of HIV transmission.

In some embodiments, an antibody described herein may be administered within a pharmaceutically-acceptable diluent, carrier, or excipient, in unit dose form. Conventional pharmaceutical practice may be employed to provide suitable formulations or compositions to administer to individuals being treated for HIV infection. In some embodiments, the administration is prophylactic. Any appropriate route of administration may be employed, for example, administration may be parenteral, intravenous, intra-arterial, subcutaneous, intramuscular, intraperitoneal, intranasal, aerosol, suppository, oral administration, vaginal, or anal.

The pharmaceutical compositions described herein are prepared in a manner known per se, for example, by means of conventional dissolving, lyophilizing, mixing, granulating or confectioning processes. The pharmaceutical compositions may be formulated according to conventional pharmaceutical practice (see for example, in Remington: The Science and Practice of Pharmacy (21st ed.), ed. A. R. Gennaro, 2005, Lippincott Williams & Wilkins, Philadelphia, PA, and Encyclopedia of Pharmaceutical Technology, eds. J. Swarbrick and J. C. Boylan, 2013, Marcel Dekker, New York, NY).

The injection compositions are prepared in customary manner under sterile conditions; the same applies also to introducing the compositions into ampoules or vials and sealing the containers.

Pharmaceutical compositions according to the invention may be, for example, in unit dose form, such as in the form of ampoules, vials, suppositories, tablets, pills, or capsules. The formulations can be administered to human individuals in therapeutically or prophylactic effective amounts (e.g., amounts which prevent, eliminate, or reduce a pathological condition) to provide therapy for a disease or condition. The preferred dosage of therapeutic agent to be administered is likely to depend on such variables as the type and extent of the disorder, the overall health status of the particular patient, the formulation of the compound excipients, and its route of administration.

In certain embodiments, the compositions described herein can be formulated for topical administration, and in certain embodiments the composition is formulated for vaginal or rectal administration. The composition may be formulated as a gel, or formulated as a topical cream, ointment, lotion or foam formulation. Useful formulations are known in the art, for example, as disclosed in U.S. Patent Appl. Pub. No. 20130022619, which is incorporated by reference herein in its entirety for all purposes.

In certain embodiments, the composition may further comprise a pharmaceutically acceptable excipient, a lubricant, or an antiviral agent.

The topical formulations of the present invention can be used to prevent HIV infection in a human, or to inhibit transmission of the HIV virus from an infected human to another human. The topical formulations of the present invention can inhibit the growth or replication of HIV. The topical formulations are useful in the prophylactic treatment of humans who are at risk for HIV infection. The topical formulations also can be used to treat objects or materials, such as contraceptive devices (for example condoms or intrauterine devices), medical equipment, supplies, or fluids, including biological fluids, such as blood, blood products, and tissues, to prevent or inhibit viral infection of a human. Such topical formulations also are useful to prevent transmission, such as sexual transmission of viral infections, e.g., HIV, which is the primary way in which HIV is transmitted globally. The methods of prevention or inhibition or retardation of transmission of viral infection, e.g., HIV infection, in accordance with the present invention, comprise vaginal, rectal, penile or other topical treatment with an antiviral effective amount of a topical preparation of the present invention, alone or in combination with another antiviral compound as described herein.

In some embodiments the composition is in the form of a cream, lotion, gel, or foam that is applied to the affected skin or epithelial cavity, and preferably spread over the entire skin or epithelial surface which is at risk of contact with bodily fluids. Such formulations, which are suitable for vaginal or rectal administration, may be present as aqueous or oily suspensions, solutions or emulsions (liquid formulations) containing in addition to the active ingredient, such carriers as are known in the art to be appropriate. These formulations are useful to protect not only against sexual transmission of HIV, but also to prevent infection of a baby during passage through the birth canal. Thus the vaginal administration can take place prior to sexual intercourse, during sexual intercourse, and immediately prior to childbirth.

As a vaginal formulation, the active ingredient may be used in conjunction with a spermicide and may be employed with a condom, diaphragm, sponge or other contraceptive device. Examples of suitable spermicides include nonylphenoxypolyoxyethylene glycol (nonoxynol 9), benzethonium chloride, and chlorindanol. Suitably, the pH of the composition is 4.5 to 8.5. Vaginal compositions preferably have a pH of 4.5 to 6, most preferably about 5.

Vaginal formulations include suppositories (for example, gel-covered creams), tablets and films. The suppositories can be administered by insertion with an applicator using methods well known in the art.

Vaginal formulations further include vaginal ring devices formulated for sustained release. See, e.g., Morrow et al., Eur J Pharm Biopharm. 77 (1): 3-10 (2011), Zhao et al., Antimicrob Agents Chemother. 61 (7) pii: e02465-16 (2017).

Buccal formulations include creams, ointments, gels, tablets or films that comprise ingredients that are safe when administered via the mouth cavity. Buccal formulations can also comprise a taste-masking or flavoring agent.

The present compositions may be associated with a contraceptive device or article, such as a vaginal ring device, an intrauterine device (IUD), vaginal diaphragm, vaginal sponge, pessary, condom, etc.

In some embodiments the compositions described herein are used in conjunction with condoms, to enhance the risk-reducing effectiveness of condoms and provide maximum protection for users. The composition can either be coated onto condoms during manufacture, and enclosed within conventional watertight plastic or foil packages that contain one condom per package, or it can be manually applied by a user to either the inside or the outside of a condom, immediately before use. As used herein, “condom” refers to a barrier device which is used to provide a watertight physical barrier between male and female genitalia during sexual intercourse, and which is removed after intercourse. This term includes conventional condoms that cover the penis; it also includes so-called “female condoms” which are inserted into the vaginal cavity prior to intercourse.

In another embodiment a composition described herein is in the form of an intra-vaginal pill, an intra-rectal pill, or a suppository. The suppository or pill should be inserted into the vaginal or rectal cavity in a manner that permits the suppository or pill, as it dissolves or erodes, to coat the vaginal or rectal walls with a prophylactic layer of an antibody described herein.

In certain embodiments, the composition may further comprise a pharmaceutically acceptable excipient, a lubricant, or an antiviral agent.

Compositions used in the methods of this invention may also comprise other active agents, such as another agent to prevent HIV infection, and agents that protect individuals from conception and other sexually transmitted diseases. Thus, in another embodiment the compositions used in this invention further comprise a second anti-HIV agent, a virucide effective against viral infections other than HIV, and/or a spermicide.

The compositions used in this invention may also contain a lubricant that facilitates application of the composition to the desired areas of skin and epithelial tissue, and reduces friction during sexual intercourse. In the case of a pill or suppository, the lubricant can be applied to the exterior of the dosage form to facilitate insertion.

In the cream or ointment embodiments of the present invention, the topical formulation comprises one or more lubricants. The gels and foams of the present invention optionally can include one or more lubricants.

Non-limiting examples of useful lubricants include cetyl esters wax, hydrogenated vegetable oil, magnesium stearate, methyl stearate, mineral oil, polyoxyethylene-polyoxypropylene copolymer, polyethylene glycol, polyvinyl alcohol, sodium lauryl sulfate, white wax, or mixtures of two or more of the above.

The gel formulations of the present invention comprise one or more gelling agents. Non-limiting examples of useful gelling agents include carboxylic acid polymers including acrylic acid polymers crosslinked with cross links such as allyl ethers of sucrose (e.g. carbomer brand thickeners), cetostearyl alcohol, hydroxymethyl cellulose, polyoxyethylene-polyoxypropylene copolymer, sodium carboxymethylcellulose, polyvinyl pyrrolidone, or mixtures of two or more thereof.

VI. Uses and Methods

Therapeutic Uses and Methods:

In one aspect, provided herein is a method of treating HIV or inhibiting transmission of HIV. In some embodiments, the method of inhibiting transmission of HIV comprises administering to a subject in need thereof an effective amount of an antibody described herein (e.g., a bispecific or multispecific antibody), a pharmaceutical composition described herein, an isolated polynucleotide described herein, or a recombinant virus described herein (e.g., recombinant AAV). In some embodiments, the method of inhibiting transmission of HIV comprises administering to a subject in need thereof an effective amount of an antibody described herein. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject that has been exposed to HIV or is at risk of being exposed to HIV is a newborn. In one embodiment, the antibody comprises PCIN63-71I1a. In one embodiment, the antibody comprises or PCIN63-71L.

In one aspect, provided herein is a method of reducing the risk of a subject becoming infected with HIV comprising administering to the subject in need thereof an effective amount of an antibody described herein, a pharmaceutical composition described herein, an isolated polynucleotide described herein, or a recombinant virus described herein. In some embodiments, the subject is administered an antibody described herein. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject that has been exposed to HIV or is at risk of being exposed to HIV is a newborn. In one aspect, provided herein is an antibody, a pharmaceutical composition, an isolated polynucleotide, or a recombinant virus for reducing the risk of a subject becoming infected with HIV. In one embodiment, the antibody is a multispecific, such as bispecific antibody. In one embodiment, the antibody comprises PCIN63-71I1a. In one embodiment, the antibody comprises or PCIN63-71L.

In one aspect, provided herein is a method for passively immunizing a subject comprising administering to the subject in need thereof an effective amount of an antibody described herein, a pharmaceutical composition described herein, an isolated polynucleotide described herein, or a recombinant virus described herein. In some embodiments, the subject is administered an antibody described herein. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject that has been exposed to HIV or is at risk of being exposed to HIV is a newborn. In one aspect, provided herein is provided herein is an antibody, a pharmaceutical composition, an isolated polynucleotide, or a recombinant virus for passively immunizing a subject. In one embodiment, the antibody is a multispecific, such as bispecific antibody. In one embodiment, the antibody comprises PCIN63-71I1a. In one embodiment, the antibody comprises or PCIN63-71L.

Further provided herein is a method of neutralizing an HIV virus comprising contacting the virus with an effective amount of an antibody described herein. In some embodiments, the virus is comprised by a composition, for example, a fluid, including a biological fluid, such as blood or blood product. In certain embodiments, the method comprises adding an antibody described herein to a composition comprising HIV in a sufficient amount or concentration to neutralize the HIV. In one embodiment, the antibody is a multispecific, such as bispecific antibody. In one embodiment, the antibody comprises PCIN63-71I1a. In one embodiment, the antibody comprises or PCIN63-71L.

Further provided herein is a method of reducing viral load comprising administering to a subject in need thereof an effective amount of an antibody (e.g., bispecific antibody) described herein, a pharmaceutical composition described herein, an isolated polynucleotide described herein, or a recombinant virus described herein. In one embodiment, the method comprises administering to a subject in need thereof an effective amount of an antibody (e.g., a bispecific antibody) described herein. In one embodiment, the method comprises administering to a subject in need thereof an effective amount of a recombinant AAV encoding an antibody (e.g., a bispecific antibody) described herein. In one embodiment, the antibody is a multispecific, such as bispecific antibody. In one embodiment, the antibody comprises PCIN63-71I1a. In one embodiment, the antibody comprises or PCIN63-71L.

In some embodiments of a method described herein, the antibody can be a chimeric antibody, engineered antibody, recombinant antibody, or a monoclonal antibody described herein. In some embodiments, the antibody is a full antibody, an F(ab) fragment, or an F(ab) 2 fragment described herein. In a specific embodiment, the antibody is an engineered monoclonal antibody described herein. In a specific embodiment, the antibody is a recombinant monoclonal antibody described herein. In a specific embodiment, the antibody is a chimeric monoclonal antibody described herein. In a specific embodiment, the antibody is a F(ab) described herein. In a specific embodiment, the antibody is a F(ab')2 fragment described herein.

In some embodiments, a method of preventing HIV infection provided herein comprises administering to a subject in need thereof a therapeutically sufficient amount of an antibody described herein, a pharmaceutical composition described herein, an isolated polynucleotide described herein, or a recombinant virus described herein. In one embodiment, the antibody is a multispecific, such as bispecific antibody. In one embodiment, the antibody comprises PCIN63-71I1a. In one embodiment, the antibody comprises or PCIN63-71L.

In some embodiments, a method of treating HIV/AIDS provided herein comprises administering to a subject in need thereof a therapeutically sufficient amount of an antibody described herein, a pharmaceutical composition described herein, an isolated polynucleotide described herein, or a recombinant virus described herein. In some embodiments, a method of treating HIV/AIDS comprises administering an antibody described herein. In some embodiments, a method of treating HIV/AIDS comprises administering a pharmaceutical composition described herein. In some embodiments, a method of treating HIV/AIDS comprises administering an isolated polynucleotide described herein. In some embodiments, a method of treating HIV/AIDS comprises administering a recombinant virus described herein. In one aspect, provided herein is an antibody, a pharmaceutical composition, an isolated polynucleotide, or a recombinant virus for treating HIV/AIDS. In one embodiment, the antibody is a multispecific, such as bispecific antibody. In one embodiment, the antibody comprises PCIN63-71I1a. In one embodiment, the antibody comprises or PCIN63-71L.

In some embodiments, the administering to the subject is by at least one mode selected from oral, parenteral, subcutaneous, intramuscular, intravenous, vaginal, rectal, buccal, sublingual, and transdermal In some embodiments, a method of treatment described herein further comprises administering at least one additional therapeutic agent. In some embodiments, the additional therapeutic agent comprises an antiretroviral therapy (ART) agent, a reservoir activator, an immunomodulator, a second antibody, or a second and third antibody. In some embodiments, the additional therapeutic agent comprises a second antibody. In some embodiments, the additional therapeutic agent comprises a second and third antibody. In some embodiments, the additional therapeutic agent comprises a second and optionally third antibody which is an anti-HIV antibody. In some embodiments, the additional therapeutic agent comprises a second and optionally third antibody which is an anti-HIV Env antibody. In some embodiments, the additional therapeutic agent comprises a second and optionally third anti-HIV Env antibody which binds to an HIV Env epitope region different from the HIV Env epitope region bound by an antibody described herein. In some embodiments, the additional therapeutic agent comprises a second and optionally third anti-HIV Env antibody which binds to the high-mannose patch epitope region, V1/V2-glycan site (V2g) epitope region, or gp41 MPER epitope region. In some embodiments, the additional therapeutic agent comprises a second anti-HIV Env antibody which binds to the high-mannose patch epitope region (e.g., PGT-121 or an engineered variant thereof). In some embodiments, the additional therapeutic agent comprises a second anti-HIV Env antibody which binds to the high-mannose patch epitope region disclosed in International Appl. No. PCT/US2019/43578, filed on Jul. 26, 2016, which is incorporated herein by reference in its entirety for all purposes. In some embodiments, the additional therapeutic agent comprises a second anti-HIV Env antibody which binds to the V1/V2-glycan site (V2g) epitope region. In some embodiments, the additional therapeutic agent comprises a second anti-HIV Env antibody which binds to the gp41 MPER epitope region.

In certain embodiments, the subject is at risk for exposure to HIV. In some embodiments, the subject is infected with HIV. In some embodiments, the subject is diagnosed with AIDS. In certain embodiments, the subject at risk for exposure to HIV is a health care worker. In certain embodiments, the subject at risk for exposure to HIV is a sex worker. In certain embodiments, the subject at risk for exposure to HIV is a sexual partner of an HIV infected individual. In certain embodiments, the subject at risk for exposure to HIV is a newborn.

The invention also features methods of blocking HIV infection in a subject (e.g., a human) at risk of HIV transmission. For example, in one aspect, the subject may be a fetus of an HIV-infected pregnant female and the method includes administering to the HIV-infected pregnant female an antibody described herein, thereby blocking the HIV infection in the fetus. In other instances, the subject is a newborn having an HIV-infected mother, a subject at risk of HIV transmission following a needle stick injury, or a subject at risk of HIV transmission following a sexual exposure to an HIV-infected individual.

In instances when the subject is a newborn having an HIV-infected mother, the newborn can be administered an antibody described herein peripartum and/or postpartum, for example, prior to, during, and/or following breastfeeding from the HIV-infected mother, in order to block an HIV infection in the newborn. In one embodiment, the antibody is a multispecific, such as bispecific antibody. In one embodiment, the antibody comprises PCIN63-71I1a. In one embodiment, the antibody comprises or PCIN63-71L.

In instances when the subject is at risk of HIV transmission following a sexual exposure to an HIV-infected individual, the subject can be administered an antibody described herein following the sexual exposure in order to block an HIV infection in the subject. In one embodiment, the antibody is a multispecific, such as bispecific antibody. In one embodiment, the antibody comprises PCIN63-71I1a. In one embodiment, the antibody comprises or PCIN63-71L.

In some embodiments, an antibody described herein can be used as a microbicides to prevent mucosal HIV acquisition. In some embodiments, an antibody described herein is used to prevent vaginal or rectal acquisition of HIV. In some embodiments, an antibody described herein can be used as a microbicides to reduce the likelihood of mucosal HIV acquisition. In some embodiments, an antibody described herein is used to reduce the likelihood of vaginal or rectal acquisition of HIV.

In any of the methods described above, further administration of ART and/or an immunomodulator and/or a second antibody is contemplated. For example, the ART and/or immunomodulator and/or a second antibody can be administered in conjunction with, prior to, concurrently with, subsequent to, or within the context of a treatment regimen that includes administration of an antibody described herein.

An antibody described herein, or a pharmaceutical composition described herein can be delivered to a subject by a variety of routes, such as oral, parenteral, subcutaneous, intravenous, intradermal, transdermal, intranasal, vaginal, or anal. In some embodiments, the antibody or pharmaceutical composition is administered intravenously, vaginally, or anally.

The amount of an antibody described herein, or a pharmaceutical composition described herein which will be effective in the treatment and/or prevention of a condition will depend on the nature of the disease, and can be determined by standard clinical techniques.

The precise dose to be employed in a pharmaceutical composition will also depend on the route of administration, and the seriousness of the disease, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Detection & Diagnostic Uses

An antibody described herein can be used to detect HIV and/or assay HIV levels in a biological sample using classical immunohistological methods known to those of skill in the art, including immunoassays, such as the enzyme linked immunosorbent assay (ELISA), immunoprecipitation, or Western blotting. An antibody described herein can also be used as an imaging agent, for example, a tissue-penetrating imaging agent. In some embodiments, an antibody described herein is conjugated with a detectable label. Suitable assay labels are known in the art and include enzyme labels, such as, glucose oxidase; radioisotopes, such as iodine ($^{125}I$, $^{121}I$), carbon ($^{14}C$), sulfur ($^{35}S$), tritium ($^{3}H$), indium ($^{121}In$), and technetium ($^{99}Tc$); luminescent labels, such as luminol; and fluorescent labels, such as fluorescein and rhodamine, and biotin. Such labels can be used to label an antibody or fusion polypeptide described herein. Alternatively, a second antibody that recognizes an antibody described herein can be labeled and used in combination with the antibody described herein to detect HIV levels.

As used herein, the term "biological sample" refers to any biological sample obtained from a subject, cell line, tissue, or other source potentially comprising HIV. Methods for obtaining tissue biopsies and body fluids from animals (e.g., humans) are well known in the art.

In another embodiment, an antibody described herein can be used to detect levels of HIV, which levels can then be linked to certain disease symptoms. An antibody described herein may carry a detectable or functional label. An antibody described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An antibody described herein can carry a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{117}Lu$, $^{121}I$, $^{124}I$, $^{125}I$, $^{131}I$, $^{198}Au$, $^{211}At$, $^{213}Bi$, $^{225}Ac$ and $^{186}Re$. When radioactive labels are used, currently available counting procedures known in the art may be utilized to identify and quantitate the specific binding of an antibody described herein to HIV. In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an antibody described herein under conditions that allow for the formation of a complex between the antibody and HIV. Any complexes formed between the antibody and HIV are detected and compared in the sample and the control. An antibody described herein can also be used to purify HIV via immunoaffinity purification.

In some aspects, provided herein are methods for in vitro detecting HIV in a sample, comprising contacting said sample with an antibody described herein. In some aspects, provided herein is the use of an antibody described herein, for in vitro detecting HIV in a sample. In one aspect, provided herein is an antibody or pharmaceutical composition described herein for use in the detection of HIV in a subject. In one aspect, provided herein is an antibody or pharmaceutical composition described herein for use as a diagnostic. In one preferred embodiment, the antibody comprises a detectable label. In some embodiments, the subject is a human. In some embodiments, the method of detecting HIV in a sample comprises contacting the sample with an antibody described herein.

In some embodiments, the present disclosure provides methods of purifying HIV from a sample. In some embodiments, the method of purifying HIV from a sample comprises contacting the sample with an antibody described herein under conditions that allow the antibody to bind to HIV. In some embodiments, the antibody comprises a tag, for example, hexa-histidine tag or FLAG-tag to facilitate the purification of HIV.

VII. Kits

Provided herein are kits comprising one or more antibodies described herein. In some embodiments, a pharmaceutical pack or kit described herein comprises one or more containers filled with one or more of the ingredients of the pharmaceutical compositions described herein, such as one or more antibodies described herein. In some embodiments, a kit contains an antibody described herein or a pharmaceutical composition described herein, and a second prophylactic or therapeutic agent used in the treatment or prevention of HIV. In some embodiments, the second agent is an antiretroviral agent. In some embodiments, the second agent is an immunomodulator. In some embodiments, the second agent is one or more anti-HIV antibody. In some embodiments, the second agent is one or more anti-HIV Env antibody that binds to an HIV Env epitope region different from the HIV Env epitope region bound by an antibody described herein. In some embodiments, the second agent is one or more anti-HIV Env antibody that binds to the high-mannose patch epitope region, V1/V2-glycan site (V2g) epitope region, or gp41 MPER epitope region. In some embodiments, a kit contains an antibody described herein or a pharmaceutical composition described herein, and a reagent used in the detection of HIV. In some embodiments, the detection reagent comprises DNA primers for the detection of HIV. Optionally associated with such container(s) can be a notice in the form prescribed by a governmental agency regulating the manufacture, use or sale of pharmaceuticals or biological products, which notice reflects approval by the agency of manufacture, use or sale for human administration.

In some embodiments, a kit described herein comprises an antibody described herein or a pharmaceutical composition described herein and a) a detection reagent, b) an HIV antigen, c) a notice that reflects approval for use or sale for human administration, or d) any combination thereof.

In some embodiments, a kit described herein comprises a fusion polypeptide described herein or a pharmaceutical composition described herein and a) a detection reagent, b) an HIV antigen, c) a notice that reflects approval for use or sale for human administration, or d) any combination thereof.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

All documents, patent, and patent applications cited herein are hereby incorporated by reference, and may be employed in the practice described herein.

EXAMPLES

Example 1. Fast and Focused Maturation of a VH1-2-Restricted HIV-Env CD4 Binding Site Targeting bnAb Lineage Involves Direct Binding to the N276-Glycan The VH1-2 restricted VRC01-class antibodies targeting the HIV Env CD4 binding-site (CD4bs) is a major focus of HIV vaccine strategies. While enormous progress has been made in the elicitation VRC01-class antibody precursors by immunization, challenges remain in understanding how to drive such responses towards the neutralization profile characteristic to this family of antibodies. To inform these strategies, described here is the rapid development of a VRC01-class antibody lineage in the subtype C infected IAVI-Protocol C neutralizer PC063. PCIN63 antibodies have the hallmark VRC01-class features and demonstrates similar neutralization breath to the prototype VRC01 antibody, but are 3 to 4-fold less mutated. Maturation occurred rapidly within ~24 months of emergence and was focused on key contact residues. This first longitudinal study of broadly neutralizing VRC01-class Abs reveals compelling nuances in the recognition of the CD4bs in the context of the surrounding glycan fence.

Elicitation of broadly neutralizing antibodies (bnAbs) targeting the HIV envelope glycoprotein (Env) is thought be a key component of a successful HIV-1 vaccine (Fauci, 2017). VRC01-class antibodies, which target the highly conserved CD4 receptor binding site (CD4bs), are among the broadest neutralizing antibodies. However, these bnAbs typically display exceptionally high level of somatic hypermutation (SHM) (Falkowska et al., 2012; Huang et al., 2016; Scheid et al., 2011; Wu et al., 2010; Zhou et al., 2015) and often require years to develop during natural infection (Landais et al., 2016; Lynch et al., 2012). These features suggest that VRC01-class antibodies not only undergo a long and complex affinity maturation process (Wu et al., 2015) and may be highly difficult to elicit by immunization.

VRC01-like antibodies have been isolated from several chronically HIV infected individuals and display up to 42% nucleotide difference in sequence but share common features (Wu et al., 2010; Zhou et al., 2015) (Huang et al., 2016, Sajadi et al., 2018) including being derived from a VH1-2 variable gene, having a 5-amino acid LCDR3 and a short/flexible LCDR1. These shared features can serve as targets to elicit by vaccination, making such bnAbs amenable for rationally designed germline-targeting immunogens (Jardine et al., 2013; McGuire et al., 2013). Such immunogens have succeeded in eliciting narrowly neutralizing antibody responses with VRC01-like characteristics in transgenic mice models (Briney et al., 2016b; Dosenovic et al., 2015; Jardine et al., 2015; McGuire et al., 2016; Sok et al., 2016; Tian et al., 2016). Comparison of mature VRC01-class antibodies has also highlighted the functional role of key "patches" of SHM that contribute to neutralization breadth and potency (Briney et al., 2016b; Jardine et al., 2013; McGuire et al., 2013). The importance of these mutations was confirmed by the narrowly neutralizing DRVI07 antibody lineage which harbored all the distinguishing features of VRC01-class antibodies except for the SHM mutations in the light chain needed to accommodate of the N276- and N462-glycans (Kong et al., 2016). These data indicate that adaptation to the glycans surrounding the CD4bs is the major hurdle for acquiring neutralization breadth for this class of antibodies.

A detailed analysis of VRC01-like antibody development during infection has been limited by the rare nature of these responses during natural infection and the lack of longitudinal sampling. Furthermore, although germline-targeting immunogens have enabled isolation and characterization of naïve precursors B-cells with VRC01-like features (Jardine et al., 2016a, Havenar-Daughton et al., 2018), whether these precursors are representative of naïve B-cells that will eventually lead to bnAbs is not known. Moreover, there is no clear pathway for how VRC01-like-class precursors might quickly acquire breadth and/or whether key mutations should be acquired in a particular order.

Described herein is the rapid development of VRC01-like bnAbs in a subtype-C infected Protocol C participant, PC063, with clear CD4bs-targeting broadly neutralizing plasma activity (Landais et al., 2016).

PCIN63 Antibodies Define a Minimally Mutated VRC01-Like bnAb Lineage.

Broadly neutralizing antibody activity was first detected in PC063 plasma at 54 months post infection (mpi), approximately two years later than observed for most Protocol C broad neutralizers, and reached a peak at 72 mpi (FIG. 1A). To isolate the antibodies contributing to the plasma neutralization breadth in this donor, we used the previously described recombinant HIV Env (rgp140F) WT and D368R (CD4bs epitope knock-out) proteins for antibody isolation (Li et al., 2012). These proteins differentially adsorbed the broad neutralizing activity from the plasma (Figure S1A) and were used as fluorescent baits to sort CD4bs-specific memory B-cells from peripheral blood mononuclear cells (PMBCs) samples collected at 66, 71 and 77 mpi (FIG. 1A).

Figure 6:
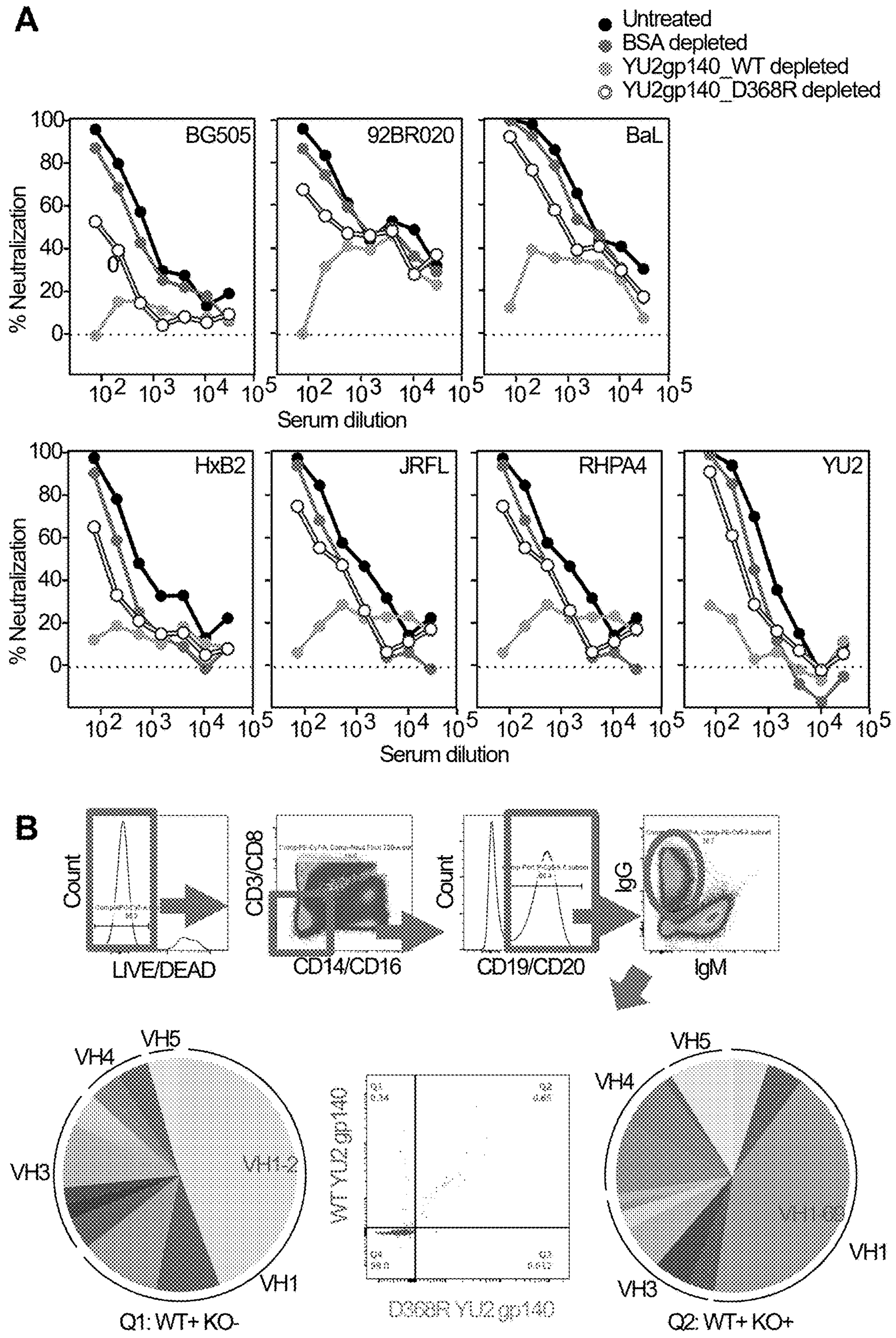
FIG. 6. Isolation of CD4bs-specific antibodies in participant PC063. (A) Neutralization of HIV-1 pseudoviruses by titrated amount of PC063 month-66 (M66) untreated plasma or after adsorption on BSA- or rgp140-coated beads. (B) Fluorescence Activated Cell Sorting (FACS) cell plots highlighting cell selection strategy for CD4bs specific B-cell isolation from PC063. Pie charts detail the distribution of VH-gene IMGT assignment of IgG amplicons generated from rgp140 WT+D368R− and rgp140 WT+D368R+ single sorted cells in (Quadrant #1, Q1, left) and (Quadrant #2, Q2, right). (C) Statistics for the PCIN63 heavy chain and light chain sequences obtained from the VH1-2+ single B-cell isolated in (B) (ARDSSRDETNWWLDP (SEQ ID NO: 364), ARDSSREETNWWLDP (SEQ ID NO: 365), TRDASRDDRAWRLDP (SEQ ID NO: 366), TRDSSRDETNWWLDP (SEQ ID NO: 367), TRDSSRDNLEWRLDP (SEQ ID NO: 368), TRDSSRGDTEWRLDP (SEQ ID NO: 369), TRDSSRGNTEWRLDP (SEQ ID NO: 370), TRDSSRQQRDWWLDP (SEQ ID NO: 371), TRDSSRRDLEWRLDP (SEQ ID NO: 372), TRDSSRRDTNWWLDP (SEQ ID NO: 373), TTHSSRRDFQWSLDP (SEQ ID NO: 374), TTHSSSRDFQWSLDP (SEQ ID NO: 375), QAYES (SEQ ID NO: 376), QVFEW (SEQ ID NO: 377), QVLET (SEQ ID NO: 378), QVVEW (SEQ ID NO: 379), QVYES (SEQ ID NO: 380), QVYQT (SEQ ID NO: 381), QVVQW (SEQ ID NO: 382)). The percent of somatic hyper mutations at the nucleotide (nt) and amino-acid (aa) levels compared to the IMGT database germline gene sequences and NGS-identified unmutated common ancestor (UCA) (see FIG. 10D), were calculated for V and J heavy chain (VH+JH) and light chain (VK+JK) segments. The CDR3 definitions are based on IMGT database guidelines. (D) Logogram of the HCDR3 amino acid sequences for PCIN63 ((T/A) (R/T) (D/H) (S/A) S(R/S) (DRQGE) (DENQ) (TLRF) (NEADQ) W(WRS) (LF) DP (SEQ ID NO: 383)) and VRC01-class ((A/T/V) R (G/D/Q/R/A/M) K(Y/G) (C/G/K/S) (R/S/T/E/F/G/M/Q) (K/S/A/C/L/R/V/Y) (R/G/N/Y/D/P/S/T) (D/G/R/C/A/F/H/Q/Y) (D/A/C/G/S/Y/R) (Y/G/S/D/R/A/L/Q/T) (N/S/E/D/Y/F/G/K) (W/F/E) (D/H/A/W/P/R/Y) (F/L/S/W/Y) (D/E/Q/A/F/H) (H/P/V/Y/A/F/I/L) (SEQ ID NO: 555)) Abs. (E) Frequency of 5-amino acid LCDR3 immunoglobulin sequences in the naïve repertoire of PC63 (from Zambia) at different time points compared to HIV negative individuals from the United States (Southern California) and sub-Saharan Africa (Protocol C clinical research site in Zambia, Uganda, Rwanda and South Africa).
Figure 6:
Figure 6:
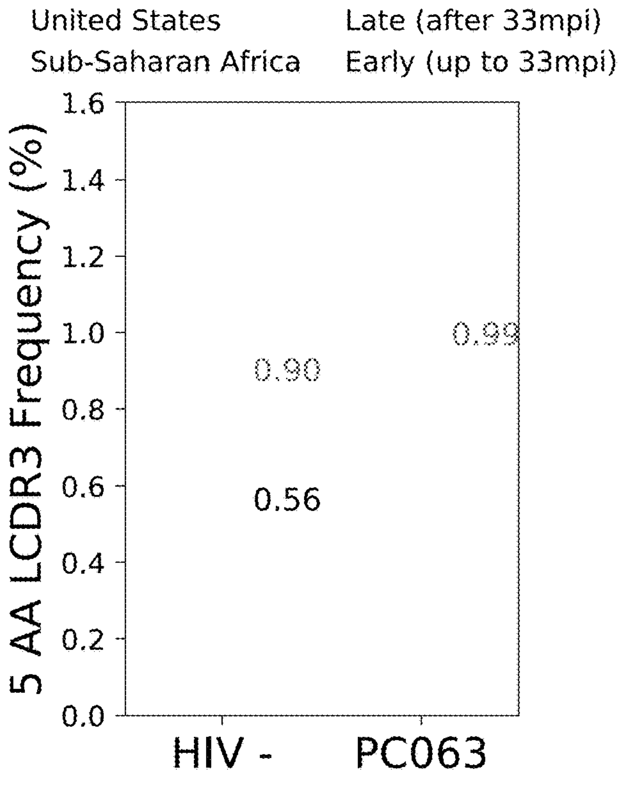

A dominant IGHV1-2*02/IGHJ5*02+IGKV1-5*03/IGKJ1*01 subset of 18 mAbs, which defined the PCIN63 lineage, was identified from the rpg140 $WT^{pos}$ $D368R^{neg}$ B cells (FIG. 6B). PCIN63 Abs exhibited characteristic features of VRC01-class bnAbs, including a 5-amino acid LCDR3 QxxEx Motif, a flexible Gly-rich LCRD1 and a 15-aa HCDR3 containing a WxxxDx Motif upstream of HFR4 (FIGS. 1B, 6C, 6D, 7). Notably, the frequency of 5-aa LCDR3 B cells in the naïve repertoire of PC063, although higher than what was found in normal blood donors from the United States (California), was comparable to HIV negative individuals screened at African Protocol C sites (FIG. 6E).

Figure 7:
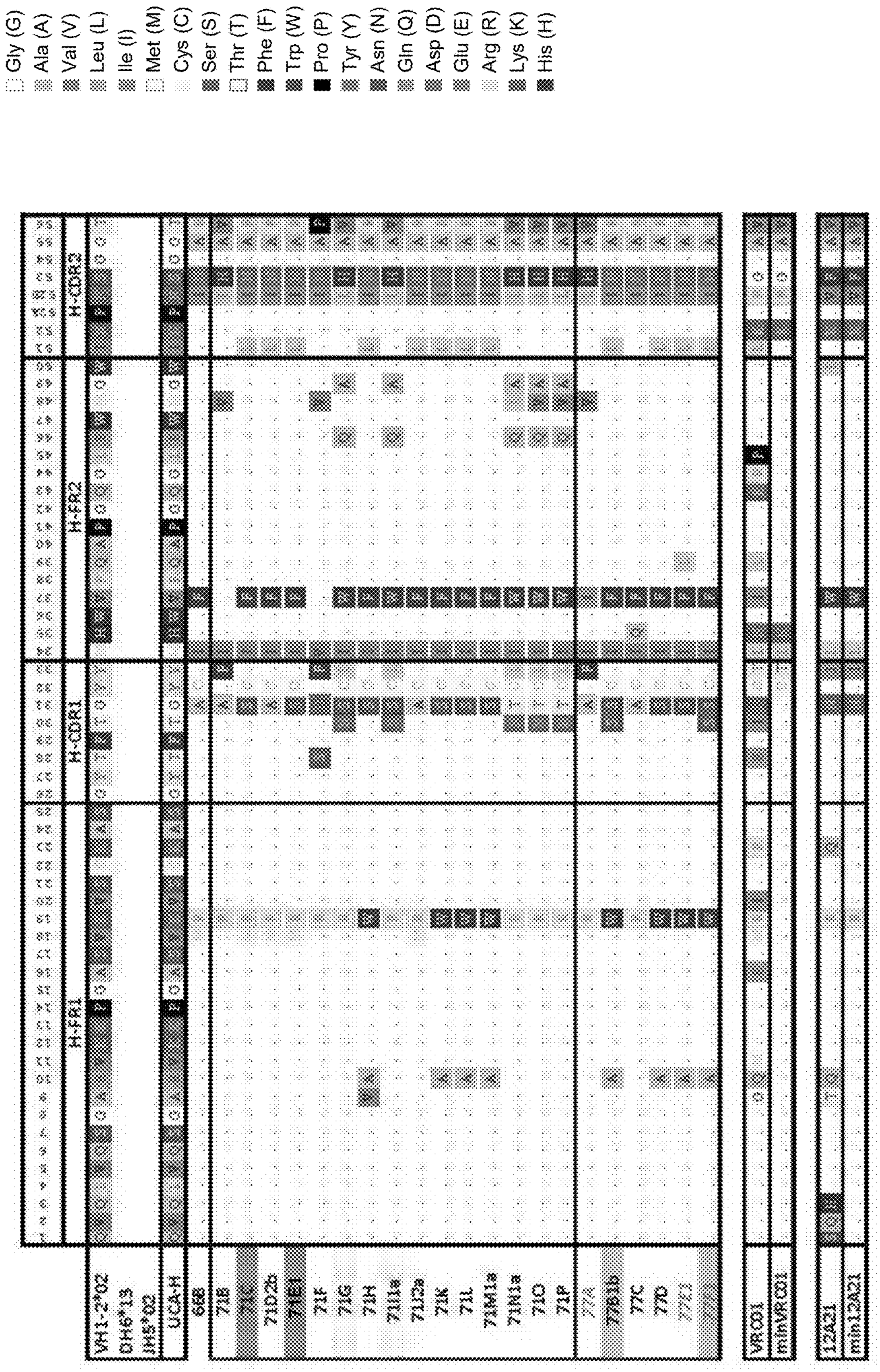
FIG. 7. PCIN63 mAbs heavy chain and light chain amino acid alignments with putative germline genes. PCIN63 mAbs HC (top) and LC (bottom) amino-acid sequences are aligned to the IMGT database $V_H$1-2*02, $D_H$6-13, $J_H$5*02, Vκ1-5*03 and Jκ1*01 sequences and compared to alignment with VRC01, minVRC01, 12A21 and min12A21 amino-acid sequences. Identical residues are marked as a dot and somatically mutated residues are specified using one-letter coding. Deletions are marked by a ~ symbol. CDR regions are indicated. Sequences shown are VH1-2*02 (SEQ ID NO: 384), $D_H$6*13 (SEQ ID NO: 385), $J_H$5*02 (SEQ ID NO: 386), UCA-H (SEQ ID NO: 387), 66B-HC (SEQ ID NO: 388), 71B-HC (SEQ ID NO: 389), 71C-HC (SEQ ID NO: 390), 71D2b-HC (SEQ ID NO: 391), 71E1-HC (SEQ ID NO: 392), 71F-HC (SEQ ID NO: 393), 71G-HC (SEQ ID NO: 394), 71H-HC (SEQ ID NO: 395), 71I1a-HC (SEQ ID NO: 396), 71J2a-HC (SEQ ID NO: 397), 71K-HC (SEQ ID NO: 398), 71L-HC (SEQ ID NO: 399), 71M1a-HC (SEQ ID NO: 400), 71N1a-HC (SEQ ID NO: 401), 710-HC (SEQ ID NO: 402), 71P-HC (SEQ ID NO: 403), 77A-HC (SEQ ID NO: 404), 77B1b-HC (SEQ ID NO: 405), 77C-HC (SEQ ID NO: 406), 77D-HC (SEQ ID NO: 407), 77E1-HC (SEQ ID NO: 408), 77F1-HC (SEQ ID NO: 409), VRC01-HC (SEQ ID NO: 410), minVRC01-HC (SEQ ID NO: 411), 12A21-HC (SEQ ID NO: 412), min12A21-HC (SEQ ID NO: 413), VK1-5*03 (SEQ ID NO: 414), JK1*01 (SEQ ID NO: 415), UCA-K2 (SEQ ID NO: 416), 66Aa-LC (SEQ ID NO: 417), 66B-LC (SEQ ID NO: 418), 71Aa-LC (SEQ ID NO: 419), 71B-LC (SEQ ID NO: 420), 71C-LC (SEQ ID NO: 421), 71D2b-LC (SEQ ID NO: 422), 71F-LC (SEQ ID NO: 423), 71G-LC (SEQ ID NO: 424), 71H-LC (SEQ ID NO: 425), 71I1a-LC (SEQ ID NO: 426), 71J2a-LC (SEQ ID NO: 427), 71K-LC (SEQ ID NO: 428), 71L-LC (SEQ ID NO: 429), 71M1a-LC (SEQ ID NO: 430), 71N1a-LC (SEQ ID NO: 431), 710-LC (SEQ ID NO.
Figure 7:
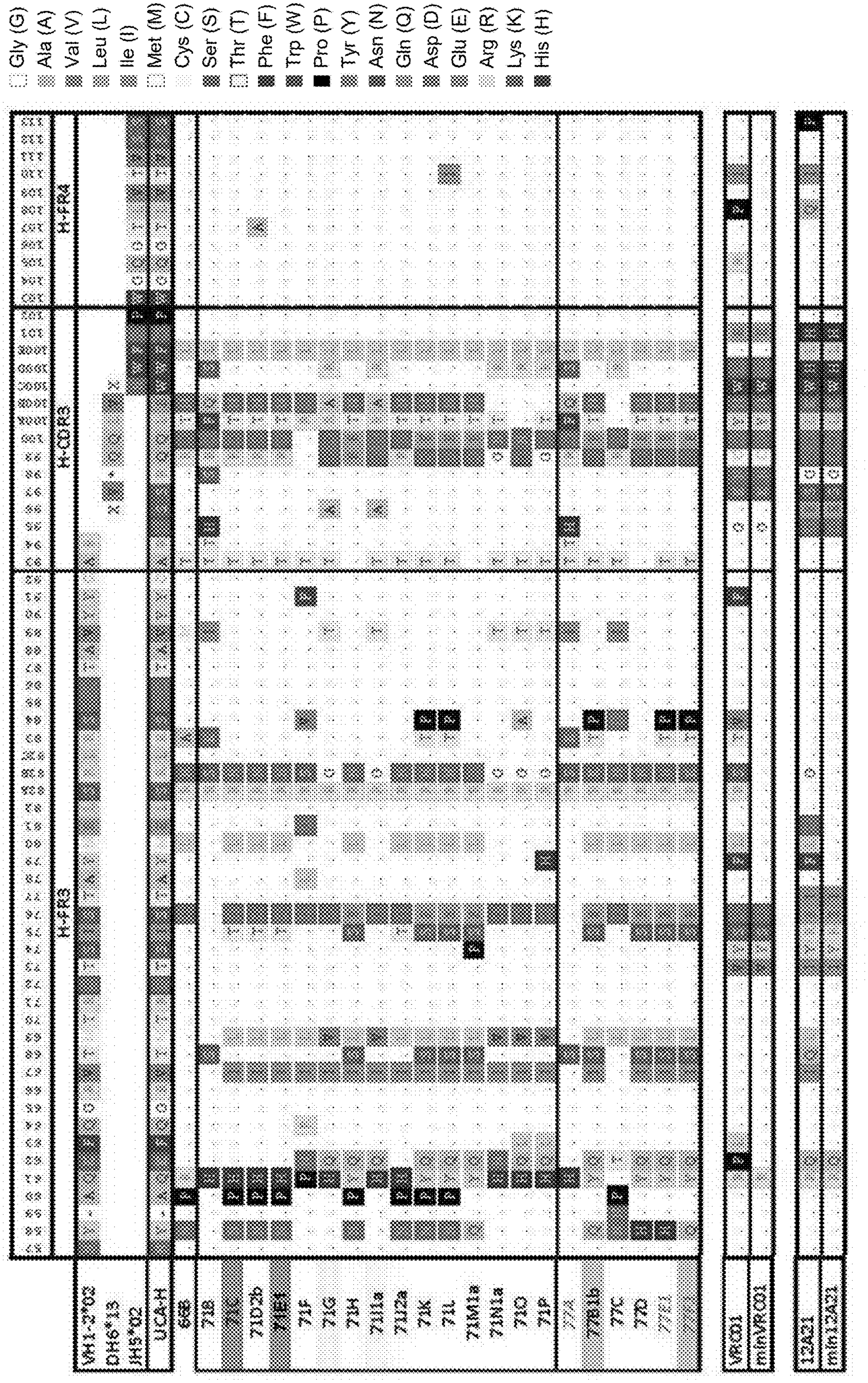
Figure 7:
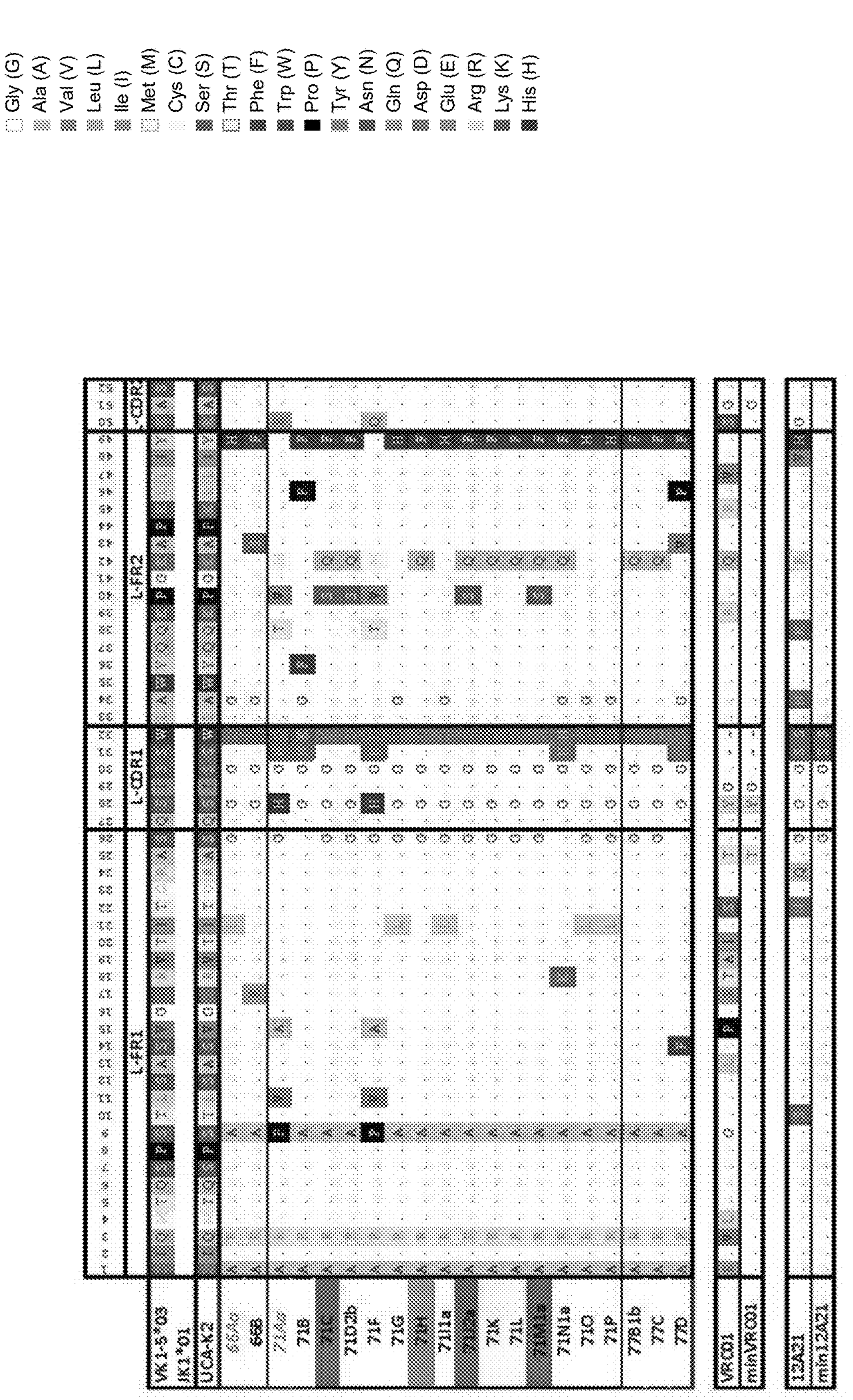
Figure 7:
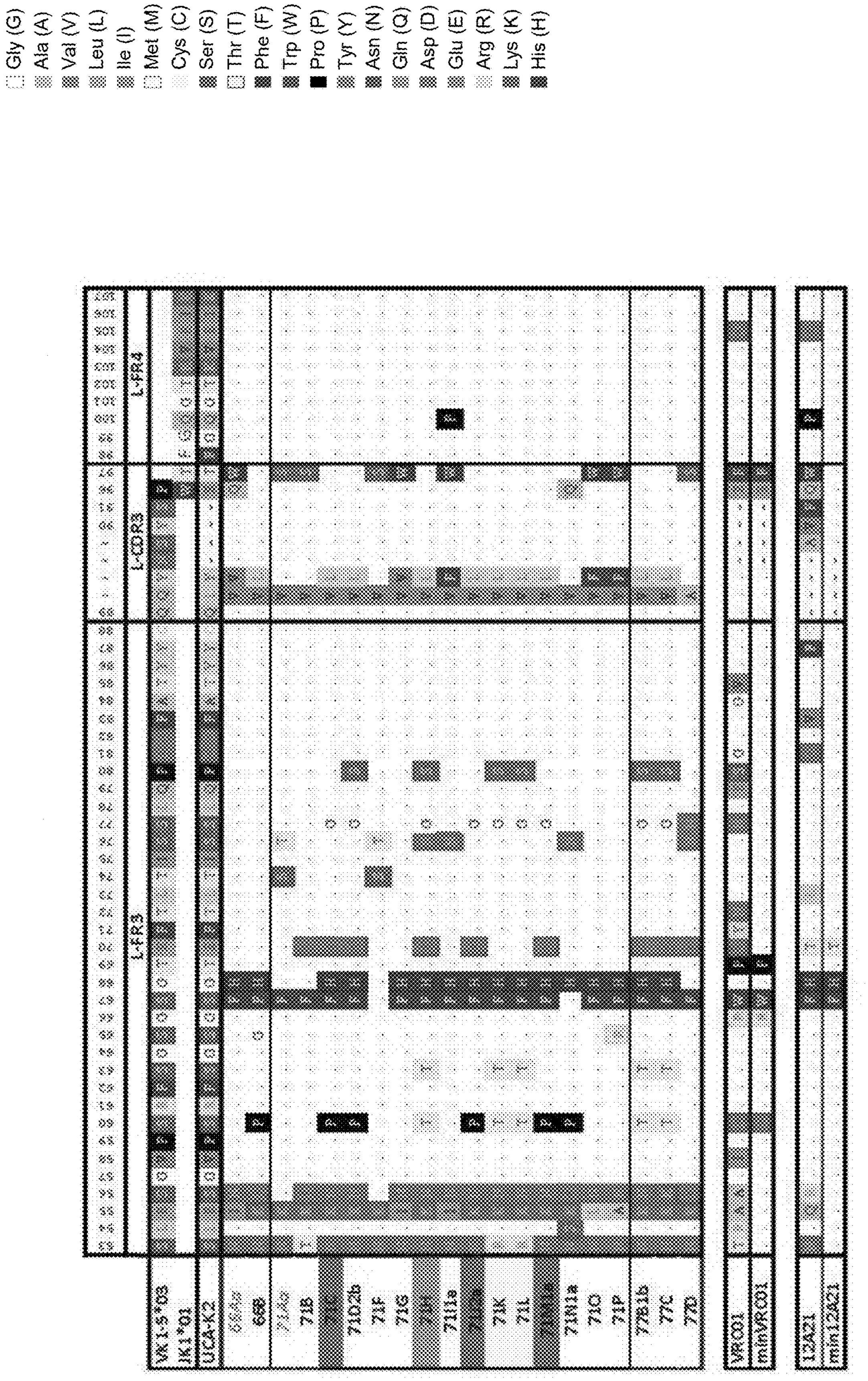

The SHM frequency of the PCIN63 lineage, ranging from 9.6% to 16.0% ($V_H$+$J_H$) and 10.0% to 13.7% ($V_K$+$J_K$) nucleotide mutation for the heavy (HC) and light (LC) chains, respectively, is notably 3-4-fold lower compared to other VRC01-class bnAbs (FIG. 1B, FIG. 6C). Alignment of PCIN63 mAbs amino-acid sequences showed that the SHMs were enriched at positions previously shown to be key epitope contact residues for this class of bNAbs. These include the HCDR1 and HCDR2 mutations important for high affinity binding to the gp120-Loop D and CD4bs-loop, and light chain mutations in LCDR1 and LFR3 that reduce the clash with the N276- and N462 glycans on Env (FIG. 7). Moreover, select PCIN63 bnAbs levels of neutralization breadth and potency are equivalent to VRC01 on a large cross-clade panel of pseudoviruses (N=134) despite being 3 to 4-fold less mutated (FIG. 1C, FIG. 8, 9). In fact, PCIN63 mAbs have striking similarities to mAb min12A12, a minimally mutated but broad version of the CD4bs 12A21 bnAb designed by Schief and colleagues (FIG. 7, 8) (Jardine et al., 2016b).

Fast Maturation of the PCIN63 bnAb Lineage

To better understand the focused maturation of the PCIN63 lineage, next-generation sequencing (NGS) of the circulating IgG+ B-cell repertoire was performed at 17 time points between 4 and 77 mpi. PCIN63 lineage HC and KC sequences were first detected at 40 mpi, followed by two waves of expansion at 44 and 61 mpi (FIGS. 10A-C), with a transient decline in frequency at 50 and 55 mpi, during which the lineage appeared to affinity mature at a constant rate (FIG. 10B). Interestingly, while the emergence of the PCIN63 bnAb lineage was substantially delayed compared to bnAb lineages, the affinity maturation time needed to achieve neutralization breadth was overall equivalent (FIG. 1D). The fast and focused maturation of PCIN63 Abs did not appear to be associated with a particular enrichment in AID hotspots that might have rapidly favored such selection (not shown).

The PCIN63 unmutated common ancestor (UCA) was defined next. For the HC, an unmutated common ancestor (PCIN63-UCA-HC) was identified from the 40 mpi timepoint. However, for the light chain, lineage assignment solely based on $V_K$+$J_K$ gene usage and 5-aa LCDR3 criteria identified 18 possible germline (GL) light chains, among which PCIN63-UCA-KC1 with a QQSEA LCDR3 was the most frequent (FIG. 10D). While none of the PCIN63 LC sequences detected at 40 mpi were 100% identical to $V_K$1-5 and $J_K$1-1 germline genes, all had an identical LCDR3 (QLYET) which was the second most frequent GL light chain sequence identified (PCIN63-UCA-KC2) (FIG. 10D). To functionally characterize these putative UCAs, all 18 light chain variants were subsequently paired with the HC UCA and first evaluated for binding to eOD-GT8, a VRC01-class germline targeting immunogen (FIG. 10E). Only three, including UCA-KC2 bound to eOG-GT8 with affinities similar to recently described putative VRC01-like bnAb precursors (Havenar-Daughton et al., 2018). All putative PCIN63-UCAs were tested against representative autologous Env sequences identified by NGS and SGA at all time points before 40 mpi, including one rare viral variant lacking both the N276- and N462-glycans (M28-H1) (FIG. 11A). None of the putative PCIN63-UCA Abs neutralized any of the autologous Env clones tested and no binding could be detected to the corresponding pseudoviruses lysates derived gp120s or recombinant gp120 from selected representative Env clones (FIG. 11B), although gp120s from Env variants isolated at 28 and 33 mpi did not expressed sufficiently well to be evaluated.

Delineating the order in which SHM Motifs are selected may inform the elicitation of similar antibodies by vaccination. Accordingly, the emergence and frequency of up to 7 SHM Motifs were tracked over the course of infection to qualitatively determine the contributions of each to the expansion of the antibody lineage (FIG. 2A). Longitudinal analysis revealed early selection of the HCDR2-Motif #2, typically a key contact with the CD4bs-loop, and LCDR2-Motif #5 (FIGS. 2B, 2C). It was followed by HCDR1-Motif #1 (stabilizing HCDR2) at 42 mpi, HFWR3-Motif #3 (V5 loop contact), LCDR2-Motif #5 and LCDR1-Motif #4 (adaptation to N276-glycan) at 44 mpi and HFWR3-Motif #6 (adaptation to N276-glycan), and finally LCDR3-Motif #7 (contact with Loop D) at 49 mpi (FIG. 2A). Notably, LC Motifs, especially the LCDR1, appeared to be fixed in sequence almost immediately after selection was initiated while HC Motifs (#1 and #2 in particular), sampled a greater diversity. Although PCIN63 lineage maturation later selected an additional Gly residue, the sudden selection of the triple Gly+D32$_{LC}$ mutations, altogether at once, in LCDR1-Motif #4 at 44 mpi was most striking. Concomitantly, HFWR3-Motif #3 and LCDR2-Motif #5 reached equilibrium of two dominant Motif variations, followed by fixation of HCDR2-Motif #2 and HFWR3-Motif #3 at 55 mpi and finally HCDR1-Motif #1 and LCDR3-Motif #7 at 66 mpi. Overall, the results highlight that less diversity is permissible in the light chain for epitope recognition whereas the heavy chain may be more "tunable" to further drive affinity maturation.

Dependence of SHM Motifs in the PCIN63 bnAb Lineage for Neutralization

Next assessed was the functional relevance of each SHM Motif to antibody neutralization. Antibody variants were generated by introducing individual SHM Motifs to the UCA HC+KC pair and evaluated each variant for neutralization against autologous virus with and without the N276 glycan (FIG. 3A). Pairing of the UCA-HC variants with affinity mature 71I-KC results in cross-neutralization of WT and N276A viruses, particularly when Motifs #2 is introduced to the UCA-HC. Interestingly, the combined LC SHMs alone allowed weak neutralization of all N276-glycan bearing autologous Env but not their N276-glycan lacking counterparts. In contrast, the UCA-KC paired with the affinity-matured 71I-HC predominantly neutralized viruses lacking the N276 glycan site except with the introduction of Motifs #4 and #6 to the UCA-KC, with a critical role of D32$_{LC}$ (FIG. 11C). These observations not only confirm the critical role of the LC mutations in adaptation to the N276-glycan but also suggest direct engagement between the LC and this glycan.

Additionally, antibody variants were created where individual SHM Motifs on the affinity mature antibody PCIN63-71I were reverted back to germline and subsequently evaluated for neutralization on the same viruses (FIG. 3B). Overall, individual reversions of SHM Motifs in either the HC or the KC had minimal effects the variants were paired with affinity-mature KC or HC, indicating a level of redundancy across the SHM Motifs for epitope recognition and that single SHM Motifs are not essential for neutralization. Overall, it is apparent that HCDR2-Motif #2, LCDR1-Motif4 and LFWR3-Motif #6 are sufficient but not necessary for autologous neutralization by PCIN63 Ab.

PCIN63 bnAbs Engage the N276-Glycan of Some Env Strains

Figure 4:
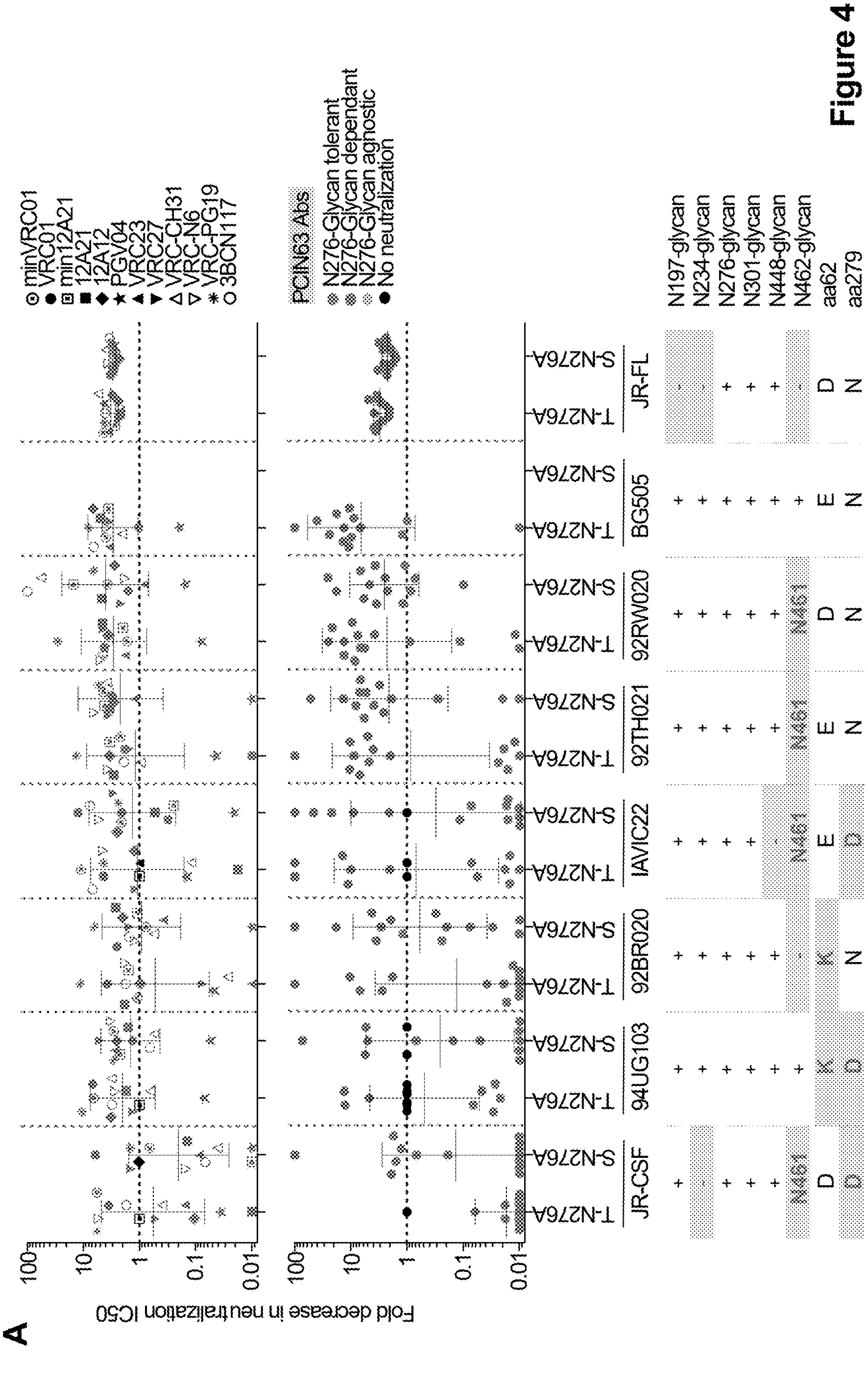
FIG. 4. N276-glycan dependent neutralization of PCIN63 Abs and other VRC01-like Abs. (A) Fold decrease in neutralization $IC_{50}$ of PCIN63 Abs (Lower panel) and the listed VRC01-class Abs (Upper panel) for N276A mutant of the indicated pseudotyped Env strains produced in 293-T or 293-S(GtnI−/1) cells compared to WT. The geomean with standard deviation are indicated. Relevant features of the selected Env strains are indicated above. Symbols are coded according to the permissive versus obstructive potential regarding access to the CD4bs. See also FIG. 12. (B) Logogram of the PCIN63 SHM Motifs amino acid sequences for PCIN63 Abs segregated according to their sensitivity to N276-glycan removal (A) and compared to corresponding sequences of 12A12, 12A21 and min12A21 Abs (TNYILW (SEQ ID NO: 357), VFAV (SEQ ID NO: 358), GGGSN (SEQ ID NO: 359), HNQR (SEQ ID NO: 360), AVFQW (SEQ ID NO: 361), (N/T) (S/T)(C(L/Y)I(W/F) (SEQ ID NO: 547), (L/T)(H/N)A(Y/H) (SEQ ID NO: 548), (G/S)GG(D/K)G (SEQ ID NO: 549), (H/F)(N/T)(I/K/A)(N/D) (SEQ ID NO: 550), Q(V/A)(F/V/Y)E(W/S) (SEQ ID NO: 551), (T/S)(S/A)CYIF (SEQ ID NO: 362), INA(N/Q) (SEQ ID NO: 552), (G/S)GGD(A/G) (SEQ ID NO: 553), F(N/R)K(N/D/K) (SEQ ID NO:554), QVLET (SEQ ID NO: 363)). Residues common to 12A21 and PCIN63 N276-glycan tolerant Abs are shown in light grey. Residues shared between 12A21 and all PCIN63 Abs are shown in dark grey. SHM Motifs are shown as in FIG. 2 and their position is indicated with diagrams. See also FIG. 7, 13.
Figure 4:
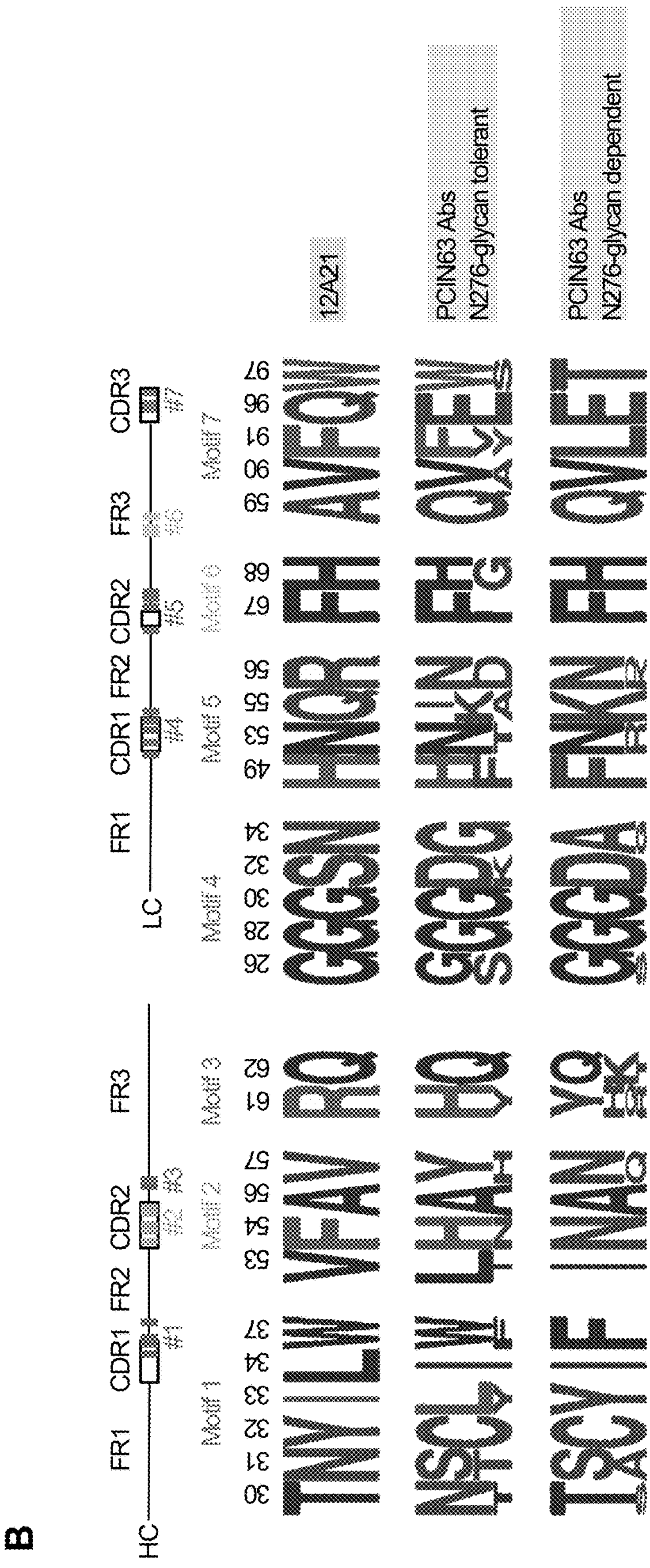

To better understand how this antibody lineage might interact with the N276 and other surrounding glycans, neutralization against WT and corresponding N276A viruses were tested. The data revealed a glycan hierarchy of importance for neutralization by PCIN63 Abs, with N276≥N197>N262≈N301>N462/N463>N448 (FIG. 12). This trend is overall consistent with effect on neutralization by other VRC01-class bnAbs, particularly 12A21 and other Abs bearing a glycine-rich LCDR1 loop (VRC23, VRC27, VRC-CH31) with the exception of VRC-N6 (FIG. 12, 13). Important variations were observed between viral strains for PCIN63 Abs neutralization as well as among PCIN63 bnAbs variants for neutralization of the same viral strain (FIG. 4A). These variations were still apparent, although to a lesser extent, when pseudoviruses were produced in GnT I−/− cells (293-S) yielding predominant Man5 glycans on HIV Env (FIG. 4A). The negative effect of N276-glycan removal was particularly striking and suggests that PCIN63 Abs may directly contact the N276-glycan in the context of some Env strain such as JR-CSF (FIG. 4A). Other components of the epitope including surrounding glycans as well as key contact residues on Env evaluated, and a general trend in dependency on the N276 glycan was observed when other obstructive features are present (JR-CSF) and tolerance of the N276 glycan when surrounding obstructive features are missing (JR-FL), such as a N461-glycan closer to the Ab and the lack of N197- and N234-glycans (FIG. 4A). Comparably, an alignment of PCIN63 antibody sequences that are N276 glycan-tolerant revealed similar features with the glycan-tolerant 12A21 sequence that are not present among the PCIN63 glycan-dependent sequences (FIG. 4B). In fact, these two categories of PCIN63 Abs appeared to segregate into separate branches of the lineage phylogenetic tree (FIG. 10D).

Modelling PCIN63 Maturation

Figure 2:
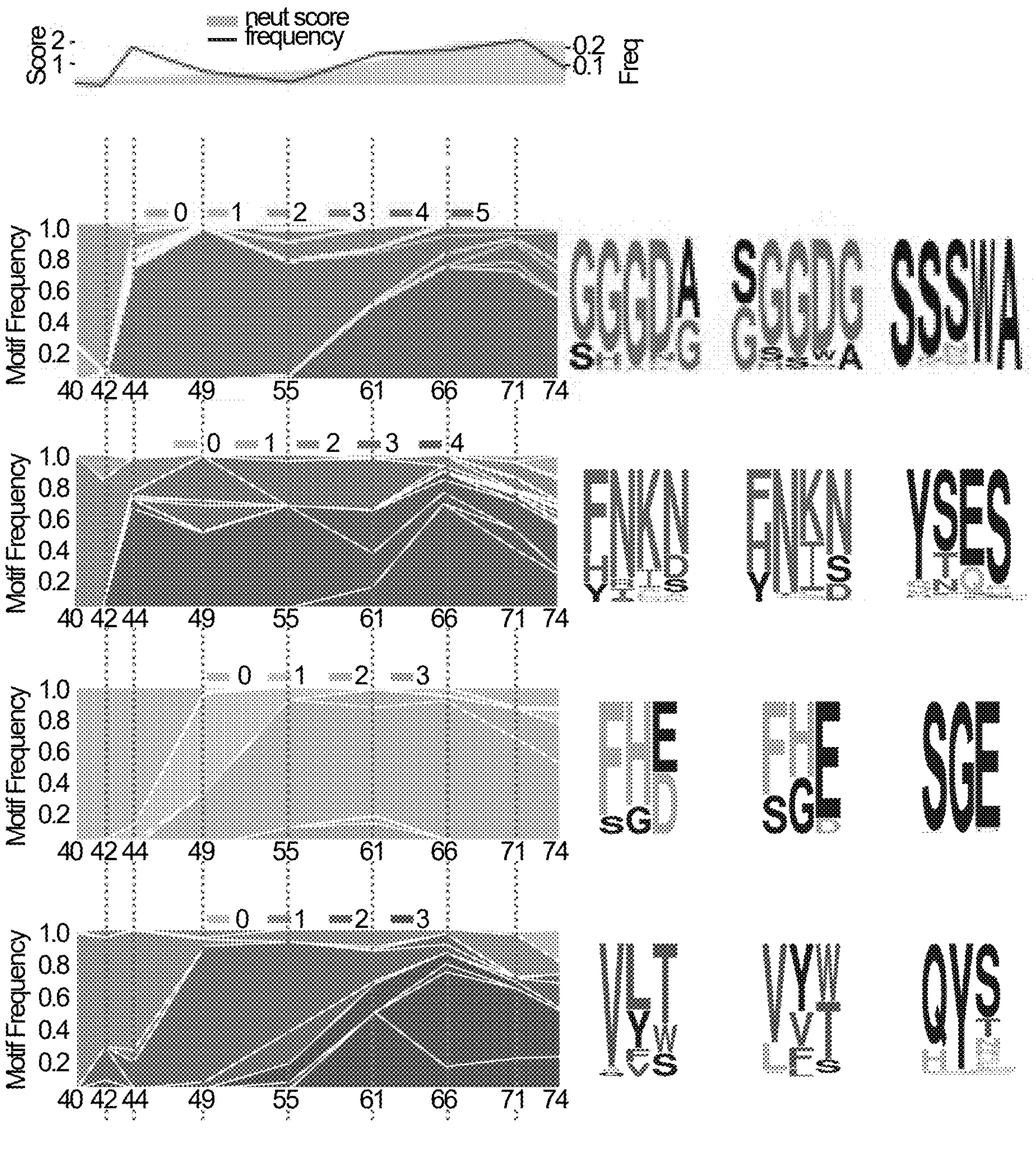
FIG. 2. SHM Motifs are selected sequentially in the PCIN63 bnAb lineage. PC063 IgG libraries prepared from total PBMCs were amplified with IgG-specific primers for all human VH gene families. See FIG. 10A-C. (A) Delineation of PCIN63 Ab SHM Motifs on heavy (HC) and light (KC) chains V-segments amino-acid sequences of mature VRC01, minVRC01, 12A21 and min12A21 and respective germlines. Sequences shown are IGHVI-2*02 SEQ ID NO: 344, min12A21-HC SEQ ID NO: 345, 12A12-HC SEQ ID NO: 346, 12A21-HC SEQ ID NO: 347, minVRC01-HC SEQ ID NO: 348, VRC01-HC SEQ ID NO: 349, IGKVI-33*01 SEQ ID NO: 350, min12A21-KC SEQ ID NO: 351, 12A21-KC SEQ ID NO: 352, 12A12-KC SEQ ID NO: 353, IGKV3-11*01 SEQ ID NO: 354, min VRC01-KC SEQ ID NO: 355, and VRC01-KC SEQ ID NO: 356. Residues varying from VH1-2 and VL putative germlines are indicated by a single letter code. (B, C) Longitudinal frequency of PCIN63 Ab lineage NGS sequences containing 1-5 Motif residues mutated from germline to any of the amino-acid found in the isolated mature PCIN63 Abs. (B) Left Panel: Motifs containing the same number of SHMs but varying in aa sequence are separated by white lines within each shade of the Motif. Motifs are arranged from top to bottom based on the extent of maturation, i.e. the number of intermediate versions, necessary to achieve fixation of the mature sequence found in the PCIN63 mAbs. Right panel: Logogram representing the distribution of amino-acids at each position of the Motif for the isolated mature PCIN63 Abs, the entire PCIN63 lineage NGS sequences and random Ab sequences from the same NGS dataset. Germline residues are indicated in black while mutated amino-acids found in the isolated matured PCIN63 Abs are shown using the pattern defined in (A) ((G/S) (G/S) G (D/N) (A/G) (SEQ ID NO; 535), (S/G) (G/S/H) G (D/W) (G/A) (SEQ ID NO: 536), S(S/N) (S/N) WA (SEQ ID NO: 537), (F/H/Y) (N/R/T/S) (K/I/A/L/Q) (N/D/S/A/K) (SEQ ID NO: 538), (F/H/Y) (N/T) (K/I/L) (N/S/D) (SEQ ID NO: 539), (Y/S/H) (S/T/N/I) (E/Q) (S/R/G/N) (SEQ ID NO: 540), N(I/L) (N/H) A (R/V/P) (SEQ ID NO: 541), N(L/I/N) (H/N) (A/G) (V/P/T/R) (SEQ ID NO: 542), N(N/K/D/Y) (S/T/N) (G/D/A/V) T (SEQ ID NO: 543), (S/A/T/D) (Y/L/F) (I/V) F/W/V/I) (SEQ ID NO: 544), (T/A/S/G/D) (L/Y/F) (I/M/L/V) (W/V/F/L) (SEQ ID NO: 545), (G/D/A/S) (Y/F) (M/I/L) V (SEQ ID NO: 546)). (C) Motifs are grouped based on time between emergence of first mutation to fully mutated sequence (thick line), as found in the PCIN63 mAbs.
Figure 2:
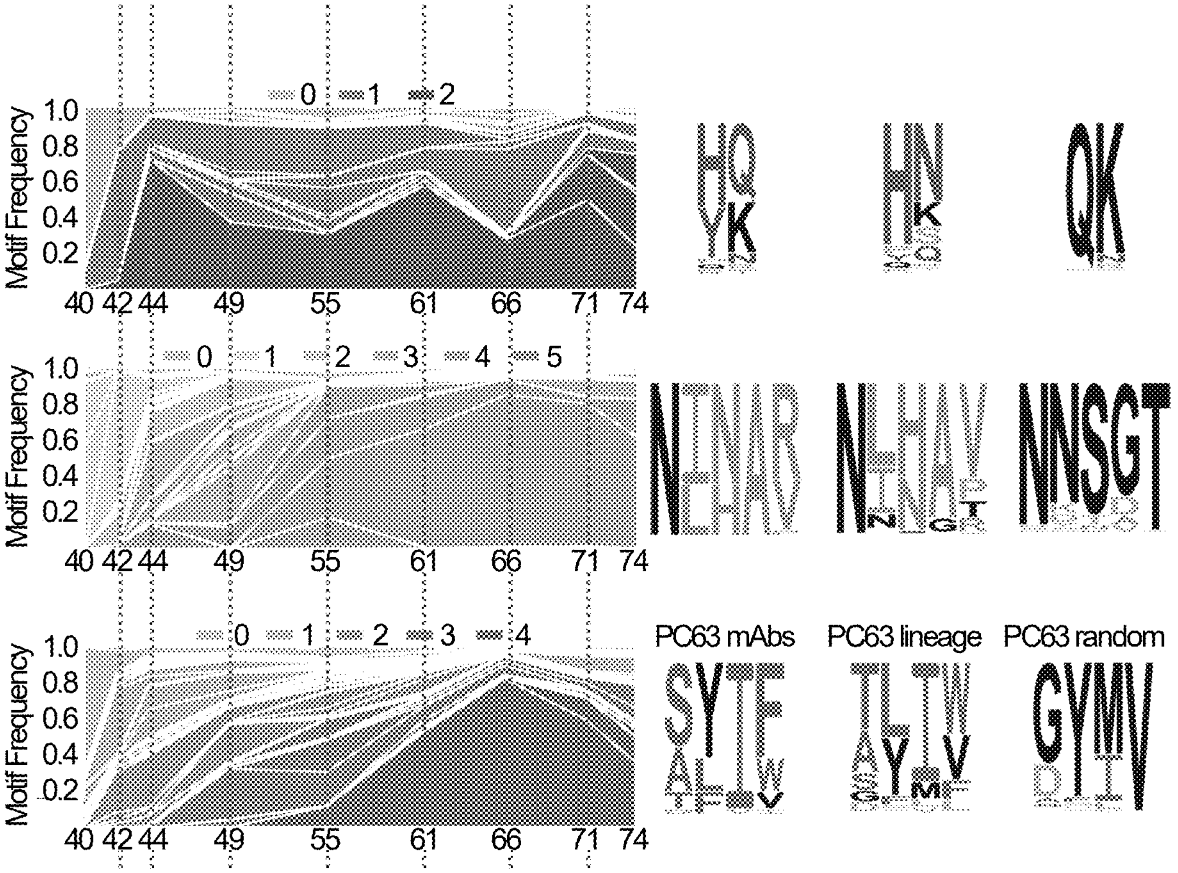
Figure 2:
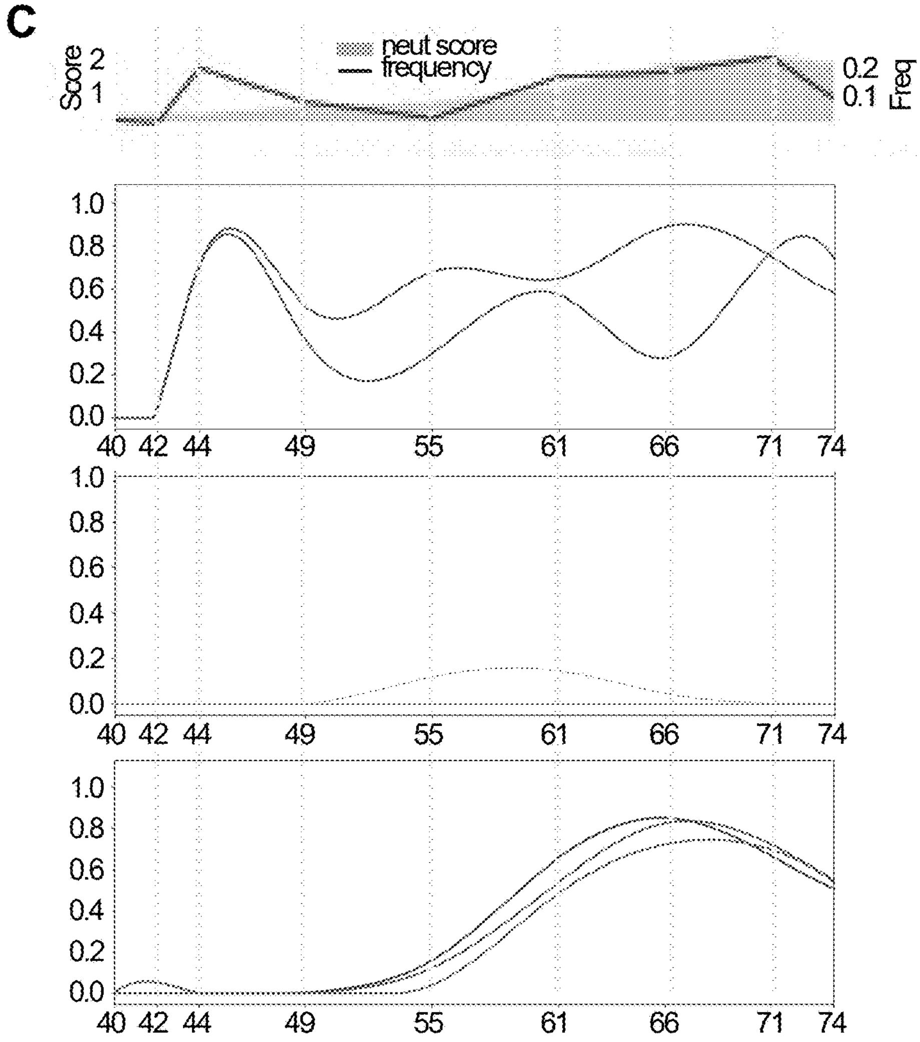
Figure 2:
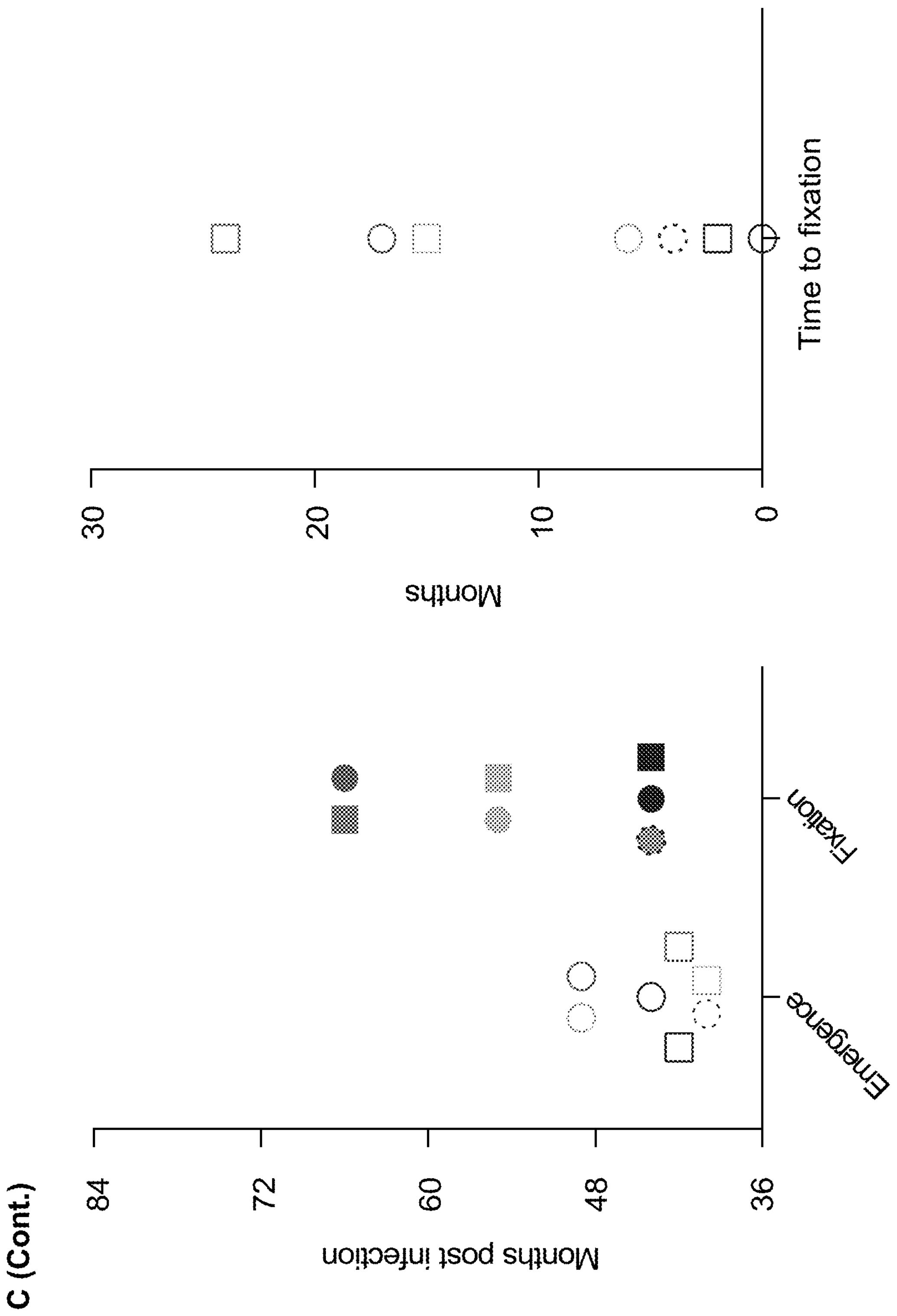
Figure 3:
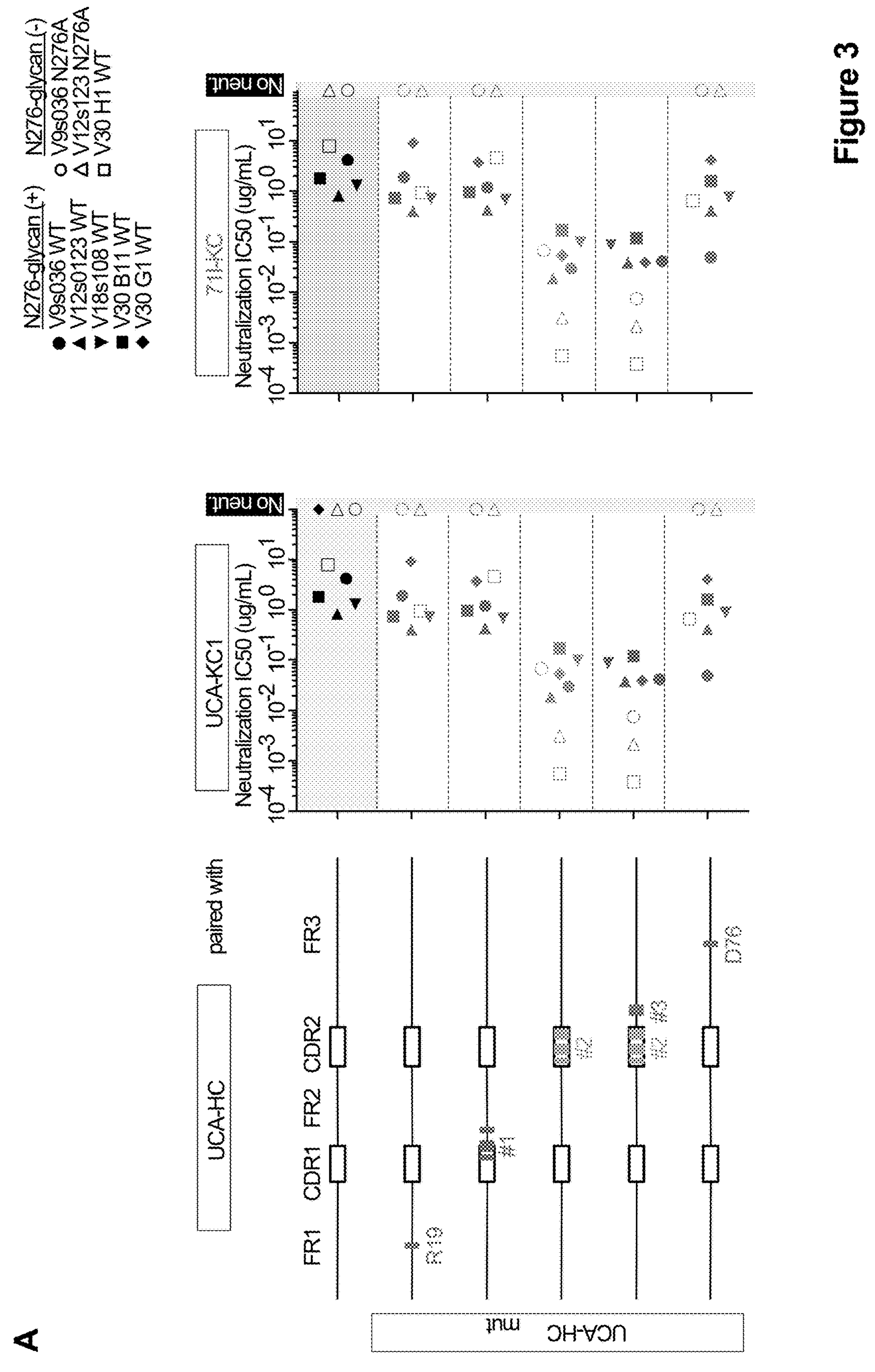
FIG. 3. Role of SHM Motifs in acquisition of neutralization by PCIN63 lineage. PCIN63-71I HC and KC SHM Motifs were either introduced into the PCIN63-UCA-HC and PCIN63-UCA-KCl (mut) (A) or reverted to germline (rev) (B). SHM Motifs are shown as in FIG. 2 and their position is indicated with diagrams. Mutated constructs were paired with WT PCIN63-UCA (left) or PCIN63-71 (right) HC or LC. The chimeric Abs were tested for neutralization of the indicated WT and N276A autologous Env clones sensitive to neutralization by PCIN63-71I. See also FIGS. 10D, 10E, 11.
Figure 3:
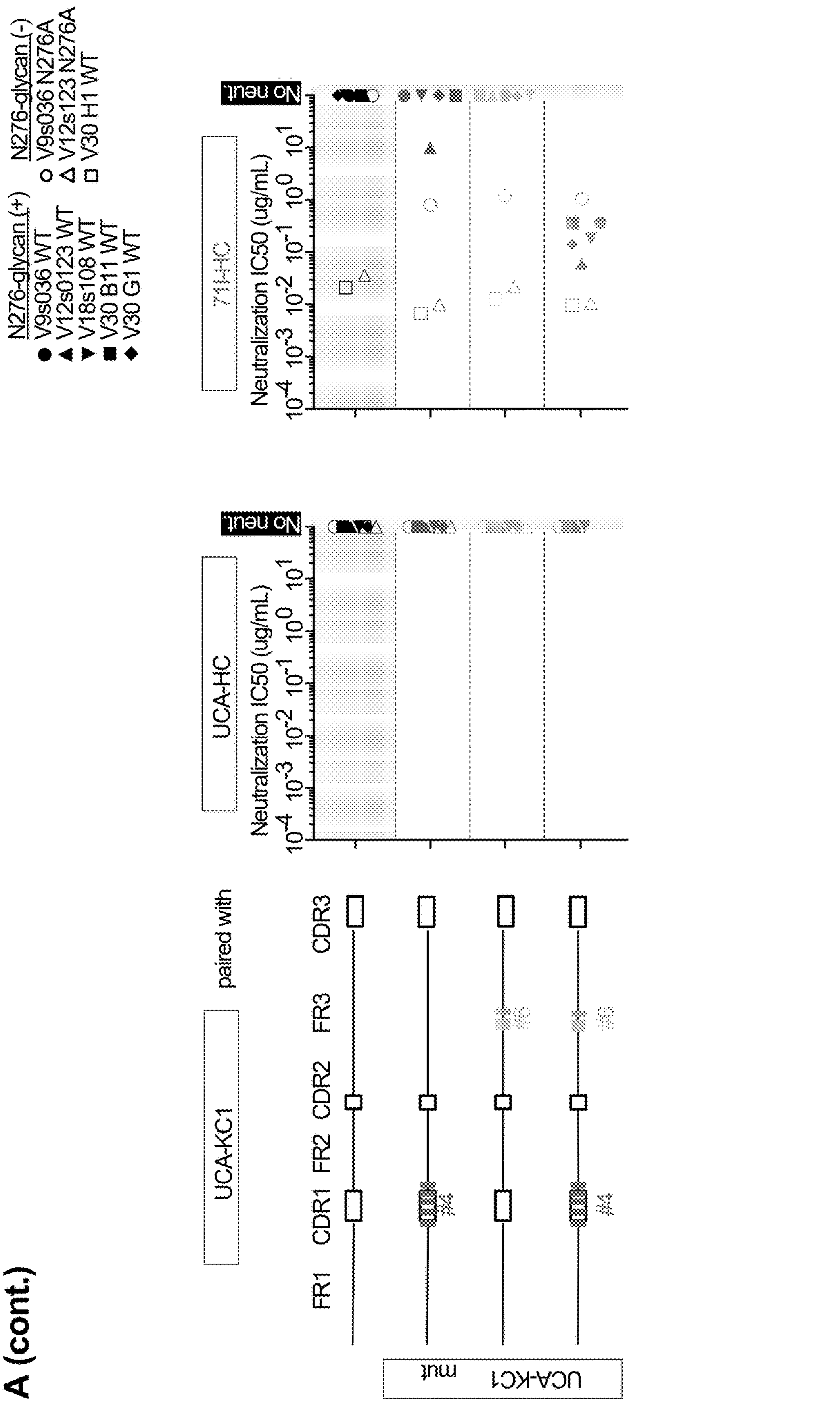
Figure 3:
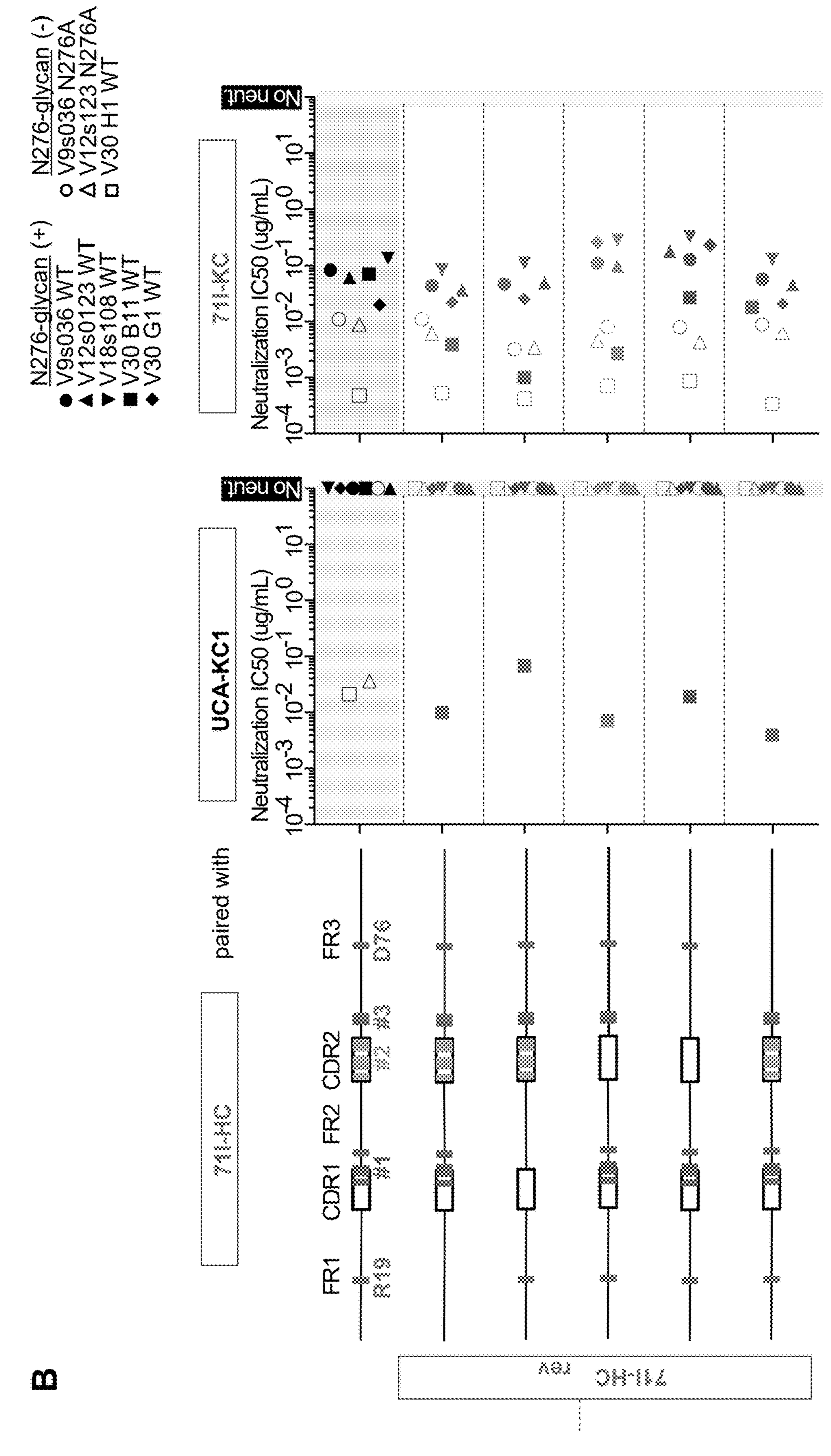
Figure 3:
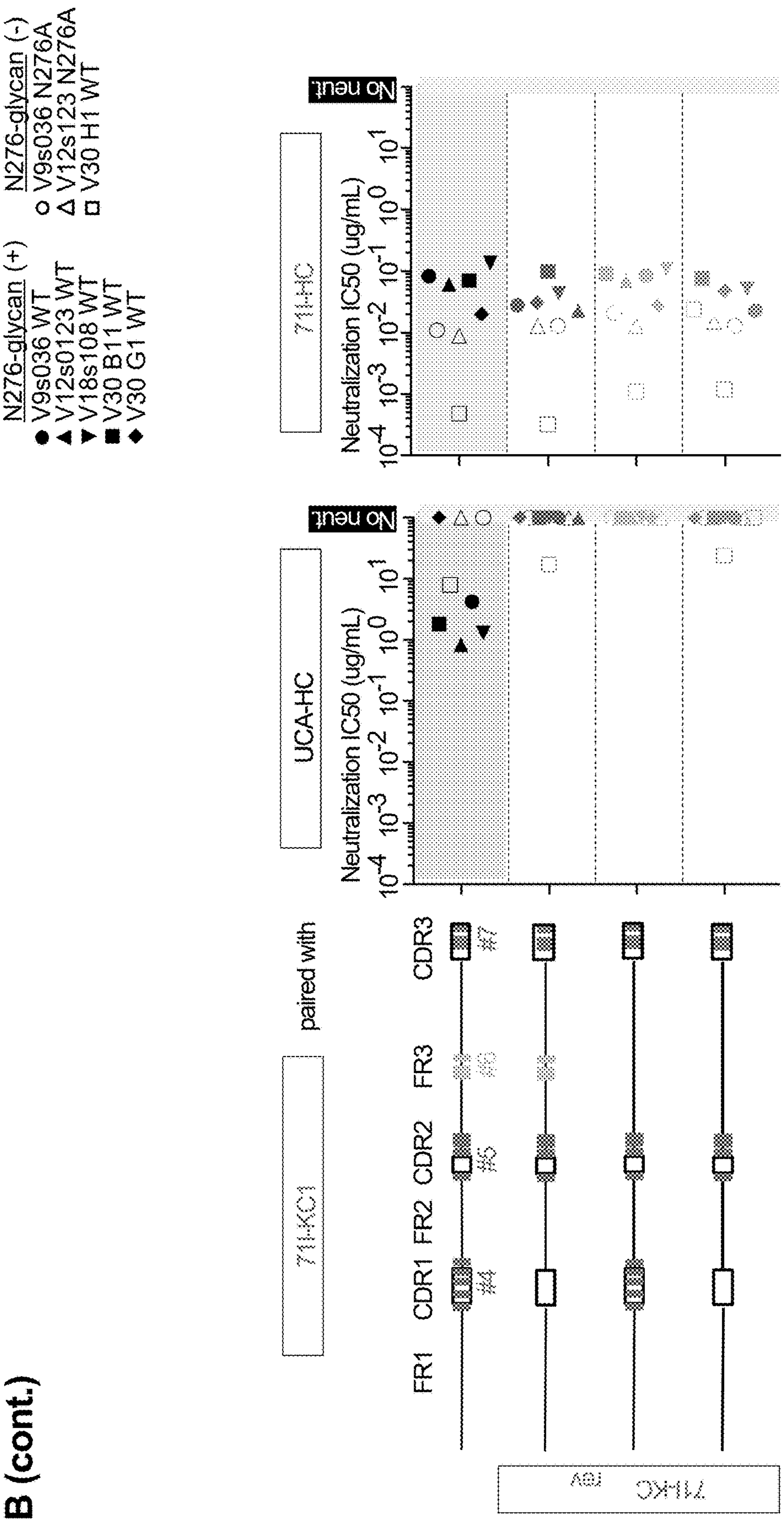
Figure 5:
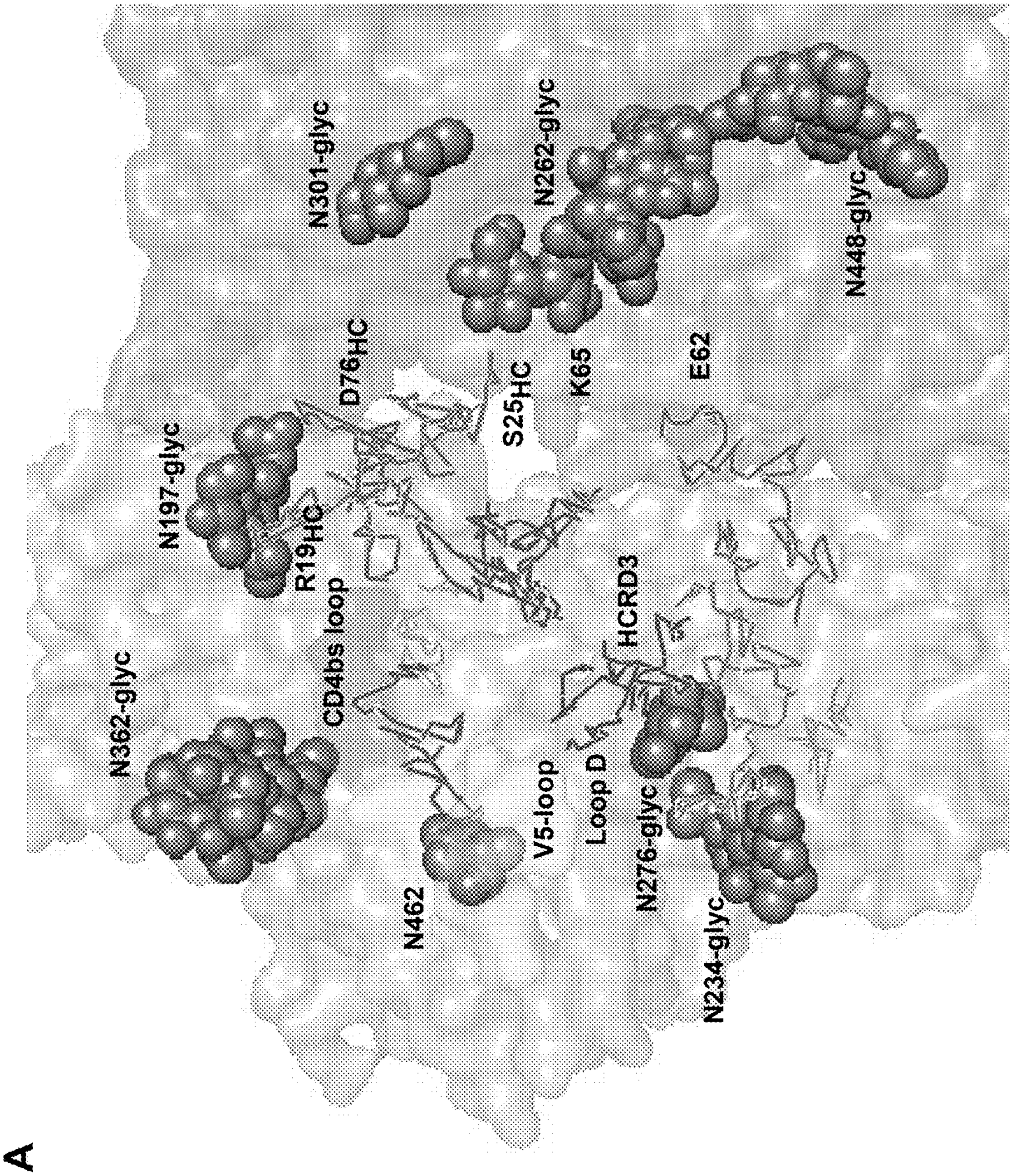
FIG. 5. Modelling PCIN63 maturation. (A) In silico modelling of 12A21 bound to BG505 SOSIP.664 using the published structures of 12A21 bound to gp120 (PDB ID: 4JPW) (Klein et al, 2013) and glycosylated BG505 SOSIP.664 bound to 35022 and PGT122 (PDB ID: 6DE7) (Zhang et al, 2018). Two of the three Env protomers are displayed in shades of gray as transparent surfaces highlighting the CD4bs loop, loop D, the V5 loop on one protomer and other putative contact residues on the second protomer. Glycans surrounding the CD4bs protruding from both protomers are shown as spheres and labeled. 12A21 HC and LC residues corresponding to PCIN63 SHM Motifs are shown as ribbon and shown as defined in FIG. 2A and represented in a diagram (B). Additional Motifs in HFR1 (aa19-25) and HRF3 (aa71-76) are also highlighted. (B) PC63 infection timeline summary showing the evolution of viral load, serum neutralization breadth and potency (score), and overall PCIN63 Ab lineage frequency in the periphery. PCIN63 Ab lineage maturation is further detailed above for each SHM Motif as shaded bars from unmutated to fully mature (full Motif) according to the kinetic analysis detailed in FIG. 2. Putative functional impact of SHM Motifs maturation regarding contact with Env (gray filled boxes) or internal structural stabilization (open boxes) inferred from the model in (A) are indicated.
Figure 5:
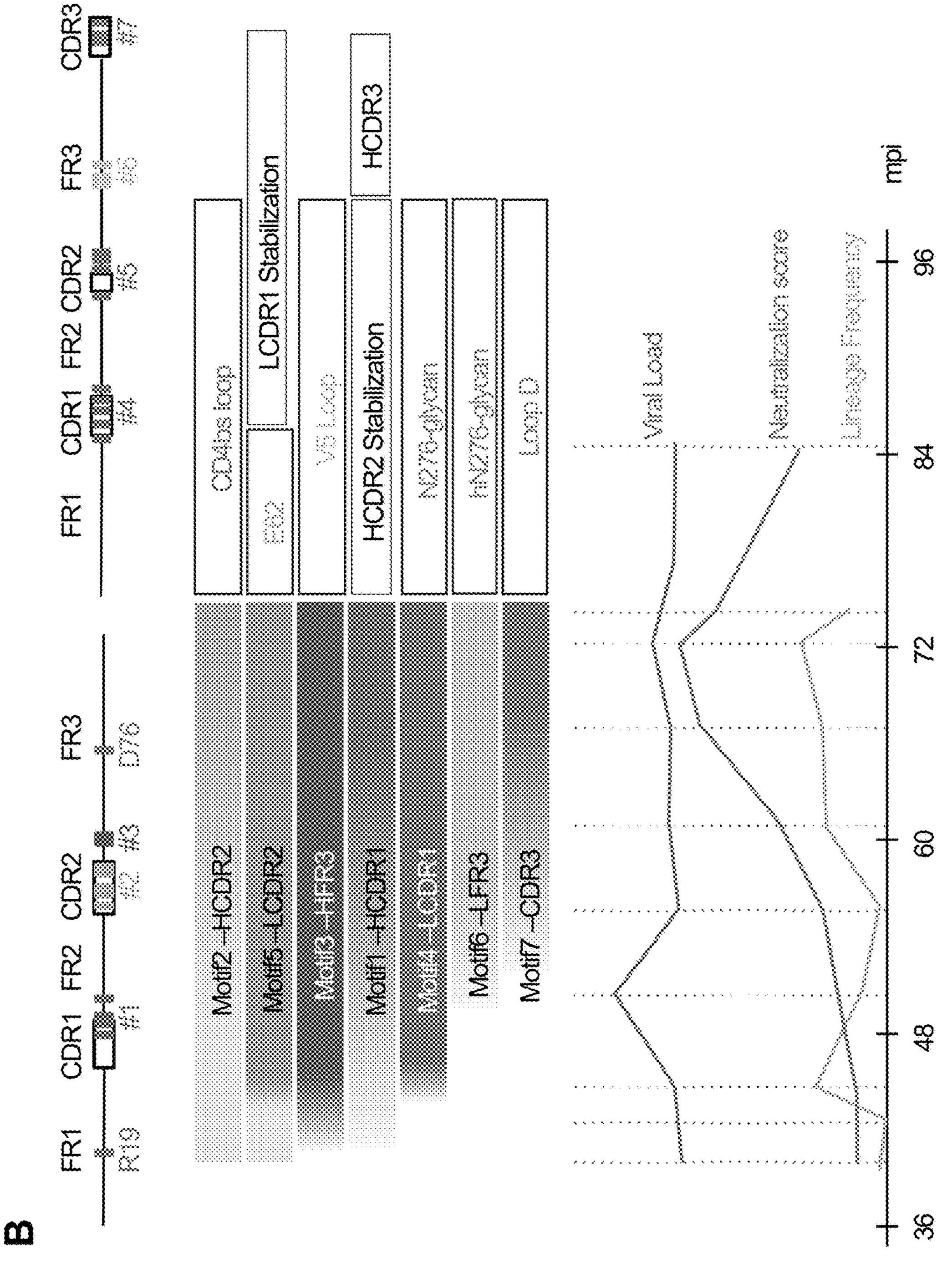

To better understand the putative interactions between PCIN63 Abs and the Env trimer, an in silico model of 12A21 bound to BG505 SOSIP.664 was constructed using the published structures of 12A21 bound to gp120 (PDB ID: 4JPW) (Klein et al, 2013) and glycosylated BG505 SOSIP.664 bound to 35022 and PGT122 (PDB ID: 6DE7) (Zhang et al, 2018) (FIG. 5). We evaluated this model in the context of PCIN63 maturation (FIGS. 2 and 3). This model suggests contacts between E62 and HCDR2-N57HC, and N279 and LCDR3-E96Lc consistent with the strain-specific N276-glycan dependent variations observed in FIG. 4A. Similarly, the N276-glycan dependent PCIN63 Abs carried SHM Motifs possibly sub-optimal for high affinity contacts with the CD4bs loop (non-aromatic residue $N54_{HC}$) and V5 loop ($Y61_{HC}$), while N276-glycan tolerant PCIN63 mAbs carried a fourth Gly in LCDR1-Motif #4 ($G34_{LC}$) and a more canonical LCDR3-Motif #7 with aromatic residues at position 91 and 97 optimal for loop D and V5 loop binding (FIG. 4B). Interestingly, all PCIN63 mAbs also carried $R/W19_{HC}$ and $E/D76_{HC}$ mutations possibly involved in N197-glycan interactions. Overall, these data support a critical role for direct contact of the N276-glycan when the CD4bs loop is less accessible and Env protein contacts sub-optimal.

The late onset of plasma neutralization breadth in PC063 is consistent with previous studies reporting that CD4bs-specific bnAbs appear to require more time to develop than bnAbs targeting other Env epitopes, a hypothesis also supported by the high levels of SHMs typically found among VRC01-class antibodies. In contrast, PCIN63 bnAbs appeared to have acquired neutralization breadth in less than two years and with minimal levels of SHM. While DRVIA7 narrowly neutralizing Abs also derived from the VK1-5 variable gene (Kong et al., 2016) the neutralization breadth of this lineage was limited compared to typical VRC01-class antibodies. Accordingly, the PCIN63 lineage is the first case where a VRC01-class antibody lineage with high levels of neutralization breadth and potency was followed longitudinally from germline to affinity-mature antibody (FIG. 1B) (Wu et al., 2010, Jardine et al., 2015, Zhou et al., 2015). Together with the recent finding that VK1-5+ subclass of VRC01-class precursors were nearly as common as the most frequent VK3-20+ precursors in naïve donor repertoires, (Havenar-Daughton et al., 2018), the isolation of the first VK1-5+ VRC01-class bnAb lineage suggests i) that the naive B-cells isolated using germline targeting immunogens may indeed represent true bnAbs precursors and ii) that this particular subclass of bnAbs serve as favorable targets for vaccine design because of their relatively higher frequency. Furthermore, the absence of enrichment in AID hotspots for this lineage suggests that the rapid affinity maturation of the PCIN63 lineage is not unique and might therefore be similarly recapitulated by vaccination.

The heavy chain of the PCIN63 lineage, particularly HC Motifs #1 and #2, appears to sample a higher level of diversity compared to the "all or nothing" SHM pattern of the LC Motifs, especially the LCDR1. These data suggest a highly stringent selection pressure on adapt to the V5 loop, loop D, and associated glycans, and a rather fine-tuned affinity maturation to the CD4bs loop. While our data confirms previous findings on the critical SHM needed on the LC to accommodate the N276-glycan, we also observed dependence on the N276-glycan by earlier PCIN63 intermediates (LCDR1-Motif #4 GGGD (SEQ ID NO: 341)). This dependence on the N276-glycan was more pronounced when interactions with the CDabs-loop and loop D are suboptimal, suggesting that immunization strategies should not focus on glycan-deleted immunogens alone to drive affinity maturation of this lineage.

Altogether, these data suggest that PCIN63 Abs maturation pathway required a fine balance between glycan avoidance to better access the CD4bs and Loop D contact residues, and direct glycan binding to counter lower affinity of early intermediates as Env evolved to escape autologous Ab responses. While acquiring a deletion in LCDR1 to avoid the N276-glycan, as seen in the majority of VRC01-like Abs, might be more difficult to reproduce by vaccination, our data support a vaccine strategy selecting intermediates with N276 glycan dependence to begin followed by affinity maturation to eventually accommodate this key glycan. While follow-up studies will be critical to fully understand the complex evolution of Ab/Env interaction in the PCIN63 lineage, this detailed maturation pathway of a natural minimally mutated VRC01-like bnAb already provide valuable information for immunogen and vaccine design.

Experimental Model and Subject Details

Ethics Statement, Study Participant and Samples Donor PC064 was part of the IAVI sponsored Protocol C cohort in sub-Saharan Africa that involved rapid screening of 613 individuals with a recent history of HIV exposure for HIV antibodies in sub-Saharan Africa (Landais et al., 2016). Samples were collected with written, informed consent, and the study was reviewed and approved by the relevant Ethics and Research Committees.

Donor PC063 was enrolled in the Protocol C longitudinal primary infection cohort approximately 19 weeks (4 months) after infection by a subtype C HIV-1 virus, and was identified as one of the top 20% neutralizers, neutralizing up to 85% of viruses on a 37-virus panel (Landais et al., 2016). The neutralizing activity was first detected in the plasma after 5 year of infection (61 months, 80 weeks) and steadily increased to reach a plateau at 2 years (24 months, 266 weeks), neutralizing 79% of viruses from a large panel (Seaman et al., 2010, Landais et al., 2016). The plasma broadly neutralizing activity was mapped to the CD4 binding site as it was competed by RSC3 and its absorption with rgp120 monomers was competed by b6 and sensitive to the D168R mutation (Landais et al., 2016).

Cell lines. Human embryonic kidney (HEK)-derived 293T, HEK293S N-acetylglucosaminyltransferase I-negative (GnTI−/−), and HeLa-derived TZM-bl cells were maintained in complete Dulbecco's Modified Eagle Medium (herein referred to as cDMEM) containing high-glucose Dulbecco's Modified Eagle Medium (DMEM, Thermo Fisher), 1× Penicillin-Streptomycin (Pen Strep, Thermo Fisher) and 10% fetal bovine serum (FBS, Gemini Bio Products) at 37° C. and 5% CO2. FreeStyle® 293F cells (Thermo Fisher) were maintained in Freestyle 293 Expression Medium at 37° C. and 10% $CO_2$ with shaking at 120 RPM.

Methods Details

Single memory B-cell sorting and isolation of PCIN63 monoclonal antibodies. Sorting of antigen- and epitope-specific memory B cells was performed as previously described (Choi et al., 2016; Sok et al., 2014; Tiller et al., 2008; Wu et al., 2010).

Fluorescent-labeled antibodies recognizing cell surface markers were purchased from BD Biosciences. AVI-tagged WT and D368R YU2-gp140-Foldon proteins (plasmid generously provided by Y. Li) were produced, purified, labeled with biotin (Avidity), and coupled to streptavidin-PE, streptavidin-APC (Life Technologies), and streptavidin-BV421 (BD Biosciences), as previously described (Sok et al., 2014). Cells were stained with the Live/Dead Fixable Near-IR Dead Cell Stain Kit (Life Technologies) for 30 minutes on ice according to the manufacturer's instructions. Cells were then labeled with antibodies for surface markers together with probes for 1 hour in Brilliant Stain buffer (BD Biosciences) on ice. Cells were sorted into individual wells of a 96 well plate containing First Strand buffer containing DTT and RNAseOUT® (Life Technologies) using a BD FACSAria III sorter, and were immediately sealed and stored at −80° C. after sorting each plate.

cDNA was generated from cells sorted into lysis buffer using Superscript® III Reverse Transcriptase (Life Technologies) and random hexamers (Gene Link). Nested PCR amplification of heavy- and light-chain variable regions was performed using Multiplex PCR Kit (Qiagen) and previously described primer sets (Tiller et al., 2008). Amplified heavy- and light-chain variable regions were sequenced and subsequently analyzed using IMGT (the International ImMunoGeneTics Information System, imgt.org) V-quest (Lefranc et al., 2009).

Antibodies of interest were cloned into expression vectors (Tiller et al., 2008) by re-amplification of sequences using the same primers but modified to introduce homology to the cut ends of the vector, and cloning was performed using the Seamless Cloning and Assembly Enzyme mix (Life Technologies) in expression vectors with the appropriate IgG1, Ig kappa or Ig lambda constant domain. Antibodies incorporating targeted amino acid mutations were generated by Quickchange® mutagenesis (Stratagene). Monoclonal antibodies were reconstituted by transient transfection in HEK293 cells followed by purification from serum-free culture supernatants.

PCIN63 antibody expression and purification. Antibodies HC and LC constructs were transiently expressed with the FreeStyle® 293 Expression System (Invitrogen). Supernatant was collected after 4-5 days of culture and whole IgGs were purified with Protein A sepharose (GE Healthcare). Purified proteins purity and integrity checked by SDS-PAGE.

B-cell repertoire next generation sequencing and computational analysis. RNA was prepared (RNEasy® kit, Qiagen) from total PBMCs and was subjected to reverse transcription using barcoding primers that contain unique Ab identifiers as previously described (Briney et al., 2016a). The cDNA was then amplified using a mix of gene specific primers containing unique identifiers. Illumina sequencing adapters and sample-specific indexes were added during a second round of PCR. Samples were quantified using fluorometry (Qubit; Life Technologies), pooled at approximately equimolar concentrations, and the sample pool was re-quantified before loading onto an Illumina MiSeq. Paired-end MiSeq reads were merged with PANDAseq (Masella et al., 2012). GL assignment, junction identification, and other basic Ab information was determined using AbStar (github.com/briney/abstar). Sequences were assigned to clonal lineages using Clonify (Briney et al., 2016a). PCIN63 lineage sequences were clustered at 97.5% identity with USEARCH (Edgar, et al., 2010), and the size of each cluster was recorded. Cluster centroids were used to generate a multiple sequence alignment with MAFFT (Katoh et al., 2005), and a tree file was calculated with FastTree using default settings (Price et al., 2010). The phylogenetic tree was drawn in Python using the ETE Toolkit (Huerta-Cepas et al., 2010).

Single genome amplification (SGA), sequencing and cloning. HIV-1 RNA was isolated from plasma using the Qiagen QIAamp® Viral RNA kit, and reverse transcribed to cDNA using SuperScript® III Reverse Transcriptase (Invitrogen, CA). The envelope genes were amplified from single genome templates (Salazar-Gonzalez et al., 2008) and amplicons were directly sequenced using the ABI PRISM Big Dye Terminator Cycle Sequencing Ready Reaction kit (Applied Biosystems, Foster City, CA) and resolved on an ABI 3100 automated genetic analyser. The full-length env sequences were assembled and edited using Sequencher v.4.5 software (Genecodes, Ann Arbor, MI). Multiple sequence alignments were performed using Clustal X (ver. 1.83) and edited with BioEdit (ver. 7.0.9). Sequence alignments were visualized using Highlighter for Amino Acid Sequences v1.1.0 (beta). The phylogeny was reconstructed using FastTree (Price et al., 2010) with a GTR1CAT model, and rooted on the PI/SU. Signals of selective pressure were detected with MEME (episodic diversifying selection) (Murrell et al., 2012) and DEPS (directional selection) (Kosakovsky-Pond et al., 2008) using the FastTree-generated trees, implemented in Hyphy (Pond et al., 2005).

Selected envelope amplicons were cloned into the expression vector pcDNA 3.1 (directional) (Invitrogen) by re-amplification of SGA first-round products using Pfu Ultra II enzyme (Stratagene) with the EnvM primer, 59-TAGCCCTTCCAGT CCCCCCTTTTCTTTTA-39 (SEQ ID NO: 342) (Gao et al., 1996) and directional primer, EnvAstop, 59-CAC CGGCTTAGGCATCTCC-TATGGCAGGAAGAA-39 (SEQ ID NO: 343) (Kraus et al., 2010). Cloned env genes were sequenced to confirm that they exactly matched the sequenced amplicon. Autologous clones were mutated at key residues within the C-strand using the Stratagene QuickChange II kit (Stratagene) as described by the manufacturer. Mutations were confirmed by sequencing. Envelope clones were used to generate single round of replication Env-pseudoviruses as described below.

Full-length env amplification sequencing and computational analysis. HIV-1 envelope genes were amplified and sequenced as described in Laird-Smith et. al. (2016) (Laird Smith et al., 2016). Briefly, virions were purified from plasma using a sucrose cushion and ultracentrifugation. Viral RNA was extracted (Viral RNA Mini Kit, Qiagen) and subjected to RT-PCR (SuperScript III First Strand, Thermo Fisher). The cDNA was used as template to generate HIV-1 env amplificons, which were then purified (QIAquick, Qiagen). Replicate PCR reactions for each sample were visualized, quantitated (2100 Bioanalyzer System, Agilent Biosciences) and pooled by sample. Preparation and sequencing of SMRTbell template libraries of ~2.6-kb insert size were performed according to the manufacturer's instructions (Pacific Biosciences). Additional details are provided in Supplemental Information.

CCS sequences were constructed using the PacBio SMRTportal software (version 2.3). The Full-Length Envelope Analysis (FLEA) pipeline was used to error correct these CCS reads, and cluster them into near-identical clusters, inferring High Quality Consensus Sequences (HQCSs) for each cluster. Envelope phylogenies, as well as the dynamics of amino acid frequency evolution, were inferred from these HQCSs. MAFFT (v7.164b (Katoh and Standley, 2013), with manual curation, was used to create a multiple sequence alignment. Gappy regions were manually removed when reconstructing phylogenies, since their alignment is uncertain. Phylogenies were reconstructed with FastTree v2.1 (Price et al., 2010), and visualized with FigTree (//tree-.bio.ed.ac.uk/software/figtree/). Frequency kinetic plots and similar analyses were created with custom Mathematica scripts.

Selected full-length autologous env gene sequences were synthesized for representative clones of each time point using GeneArt® gene synthesis services (Life Technologies), then cloned into pcDNA3.1 vector (Life Technologies) for pseudovirus production. Mutagenesis was performed using Quickchange site-directed mutagenesis kit (Agilent Technologies).

Neutralization assay. Plasma and monoclonal antibodies neutralizing activity was assessed using single round of replication in TZM-bl target cells, as described previously (Landais et al., 2016) and in absence of DEAE-dextran. Briefly, wild-type (WT) and mutant pseudoviruses were generated by co-transfection of 293T cells with an Env-expressing plasmid and an Env-deficient genomic backbone plasmid (pSG3ΔEnv). Pseudoviruses were harvested 72 h post transfection for use in neutralization assays. Pseudoviruses incorporating single amino acid mutations were generated by Quickchange mutagenesis (Stratagene). Plasma samples were heat-inactivated at 56° C. for 45 min prior to use in neutralization assays.

Serum adsorptions. Serum adsorptions with antigen-coupled beads were performed using tosyl-activated magnetic beads (Life Technologies), as described previously (Li et al., 2008). Beads coupling was performed at a ratio of 1 mg gp140 per 25 mg of beads. Plasma samples were depleted of Abs binding to these proteins through multiple rounds of immunoprecipitation. The depletion of Abs of the desired specificity was confirmed by ELISA prior to using depleted serum in pseudovirus neutralization assays.

Surface plasmon resonance (SPR) SPR experiments were performed on a Proteon XPR36 instrument (Bio-Rad) using GLC sensor chips (Bio-Rad) and 1×HBS buffer (Teknova) supplemented with 1 mg/mL BSA). Chips were prepared using the Human Antibody Capture Kit (GE Healthcare) according to manufacturer's instructions. For kinetic measurements, approximately 100 RUs of the indicated mAbs were captured onto the sensor surface. 4-fold dilution series of the indicated analytes were flowed over the captured mAbs for 120 seconds, followed by buffer injections for 600 seconds. After each cycle, surfaces were regenerated by four injections of 3 M magnesium chloride with 180 second contact times. Data were analyzed using the ProteOn Manager software (Bio-Rad). Following interspot and column double referencing, data were fitted to a Langmuir 1:1 binding model or equilibrium binding model as appropriate.

ELISA assays Half-area 96-well ELISA plates were coated overnight at 4C with 50 μL PBS containing 250 ng of compound per well. The D7324 polyclonal sheep Ab (Aalto Bioreagents) targeting the C5 domain of gp120 was also used to capture autologous gp120 from pseudovirus stocks lysed by adding 1% NP40 for 30 minutes at room temperature. The wells were washed four times with PBS containing 0.05% Tween 20 and blocked with 3% BSA at room temperature for 1 h. Serial dilutions of sera were then added to the wells, and the plates were incubated at room temperature for 1 hour. After washing four times, goat anti-human IgG F(ab')2 conjugated to alkaline phosphatase (Pierce), diluted 1:1000 in PBS containing 1% BSA and 0.025% Tween 20, was added to the wells. The plates were incubated at room temperature for 1 h, washed four times, and the plates were developed by adding alkaline phosphatase substrate (Sigma) diluted in alkaline phosphatase staining buffer (pH 9.8), according to the manufacturer's instructions. The optical density at 405 nm was read on a microplate reader (Molecular Devices). EC50 values were calculated using Prism6 (GraphPad).

Quantification and Statistical Analysis For all mAb/serum pseudovirus neutralization and ELISA assays (FIGS. 1C, 3A, 3B, 4A, 6A, 8, 9, 11C, 11D, 12) the IC50, or concentration of mAb/dilution of serum needed to obtain 50% neutralization against a given pseudovirus, was calculated from the non-linear regression of the neutralization curve. For neutralization assays in which a fold-change in $IC_{50}$ imparted by a particular virus mutant or virus treatment was reported (FIGS. 4A, 12), the IC50 obtained for one virus/assay condition was divided by the $IC_{50}$ obtained for the other virus/assay condition, as indicated in the figure legends. All neutralization and ELISA assays were repeated at least twice, and data shown are from representative experiments.

SPR measurements (FIG. 10E) were taken over two independent experiments, and data shown are from representative experiments.

SELECTED REFERENCES

Bonsignori, M., et al., 2016. Maturation Pathway from Germline to Broad HIV-1 Neutralizer of a CD4-Mimic Antibody. Cell 165, 449-463.

Briney, B., et al., 2016a. Clonify: unseeded antibody lineage assignment from next-generation sequencing data. Sci. Rep. 6, 23901.

Briney, B., et al., 2016b. Tailored Immunogens Direct Affinity Maturation toward HIV Neutralizing Antibodies. Cell 166, 1459-1470.e11.

Dosenovic, P., et al., 2015. Immunization for HIV-1 Broadly Neutralizing Antibodies in Human Ig Knockin Mice. Cell 161, 1505-1515.

Edgar, R. C., 2010. Search and clustering orders of magnitude faster than BLAST. Bioinformatics 26, 2460-2461. doi: 10.1093/bioinformatics/btq461

Falkowska, E., et al., 2012. PGV04, an HIV-1 gp120 CD4 Binding Site Antibody, Is Broad and Potent in Neutralization but Does Not Induce Conformational Changes Characteristic of CD4. J. Virol. 86, 4394-4403.

Fauci, A. S., 2017. An HIV Vaccine Is Essential for Ending the HIV/AIDS Pandemic. JAMA 318, 1535-1536.

Gao, F., et al., 1996. The heterosexual human immunodeficiency virus type 1 epidemic in Thailand is caused by an intersubtype (A/E) recombinant of African origin. J. Virol. 70, 7013-7029.

Havenar-Daughton, C., et al., 2018. The human naive B cell repertoire contains distinct subclasses for a germline-targeting HIV-1 vaccine immunogen. Sci. Transl. Med. 10, eaat0381.

Huang, J., et al., 2016. Identification of a CD4-Binding-Site Antibody to HIV that Evolved Near-Pan Neutralization Breadth. Immunity 45, 1108-1121.

Huerta-Cepas, J., et al., 2010. ETE: a python Environment for Tree Exploration. BMC Bioinformatics 11, 24.

Jardine, J., et al., 2013. Rational HIV immunogen design to target specific germline B cell receptors. Science 340, 711-716.

Jardine, J. G., et al., 2016a. HIV-1 broadly neutralizing antibody precursor B cells revealed by germline-targeting immunogen. Science 351, 1458-1463.

Jardine, J. G., et al., 2015. HIV-1 VACCINES. Priming a broadly neutralizing antibody response to HIV-1 using a germline-targeting immunogen. Science 349, 156-161.

Jardine, J. G., et al., 2016b. Minimally Mutated HIV-1 Broadly Neutralizing Antibodies to Guide Reductionist Vaccine Design. PLOS Pathog 12, e1005815.

Katoh, K., et al., 2005. MAFFT version 5: improvement in accuracy of multiple sequence alignment. Nucleic Acids Res. 33, 511-518. doi: 10.1093/nar/gki198

Klein, F., et al., 2013. Somatic mutations of the immunoglobulin framework are generally required for broad and potent HIV-1 neutralization. Cell 153, 126-138.

Kong, L., et al., 2016. Key gp120 Glycans Pose Roadblocks to the Rapid Development of VRC01-Class Antibodies in an HIV-1-Infected Chinese Donor. Immunity 44, 939-950.

Kosakovsky Pond, S. L., et al., 2008. A Maximum Likelihood Method for Detecting Directional Evolution in Protein Sequences and Its Application to Influenza A Virus. Mol. Biol. Evol. 25, 1809-1824.

Kraus, M. H., et al., 2010. A rev1-vpu polymorphism unique to HIV-1 subtype A and C strains impairs envelope glycoprotein expression from rev-vpu-env cassettes and reduces virion infectivity in pseudotyping assays. Virology 397, 346-357.

Laird Smith, M., et al., 2016. Rapid sequencing of complete env genes from primary HIV-1 samples. Virus Evol. 2, vew018.

Landais, E., et al., 2017. HIV Envelope Glycoform Heterogeneity and Localized Diversity Govern the Initiation and Maturation of a V2 Apex Broadly Neutralizing Antibody Lineage. Immunity 47, 990-1003.e9.

Landais, E., et al., 2016. Broadly Neutralizing Antibody Responses in a Large Longitudinal Sub-Saharan HIV Primary Infection Cohort. PLOS Pathog. 12, e1005369.

Li, Y., et al., 2012. HIV-1 Neutralizing Antibodies Display Dual Recognition of the Primary and Coreceptor Binding Sites and Preferential Binding to Fully Cleaved Envelope Glycoproteins. J. Virol. 86, 11231-11241.

Li, Y., et al., 2008. Analysis of Neutralization Specificities in Polyclonal Sera Derived from Human Immunodeficiency Virus Type 1-Infected Individuals. J. Virol. 83, 1045-1059.

Lynch, R. M., et al., 2012. The development of CD4 binding site antibodies during HIV-1 infection. J. Virol. 86, 7588-7595.

MacLeod, D. T et al., 2016. Early Antibody Lineage Diversification and Independent Limb Maturation Lead to Broad HIV-1 Neutralization Targeting the Env High-Mannose Patch. Immunity 44, 1215-1226.

Masella, A. P., et al., 2012. PANDAseq: paired-end assembler for illumina sequences. BMC Bioinformatics 13, 31.

McGuire, A. T., et al., 2016. Specifically modified Env immunogens activate B-cell precursors of broadly neutralizing HIV-1 antibodies in transgenic mice. Nat Commun 7, 10618.

McGuire, A. T., et al., 2013. Engineering HIV envelope protein to activate germline B cell receptors of broadly neutralizing anti-CD4 binding site antibodies. Journal of Experimental Medicine.

Murrell, B., et al., 2012. Detecting individual sites subject to episodic diversifying selection. PLOS Genet. 8, e1002764.

Pond, S. L. K., et al., 2005. HyPhy: hypothesis testing using phylogenies. Bioinformatics 21, 676-679.

Price, M. N., et al., 2010. FastTree 2—approximately maximum-likelihood trees for large alignments. PLOS ONE 5, e9490.

Sajadi, M. M., et al., 2018. Identification of Near-Pan-neutralizing Antibodies against HIV-1 by Deconvolution of Plasma Humoral Responses. Cell. 73, 1783-1795.e14.

Salazar-Gonzalez, J. F., et al., 2008. Deciphering Human Immunodeficiency Virus Type 1 Transmission and Early Envelope Diversification by Single-Genome Amplification and Sequencing. J. Virol. 82, 3952-3970.

Scheid, J. F., et al., 2011. Sequence and structural convergence of broad and potent HIV antibodies that mimic CD4 binding. Science 333, 1633-1637.

Seaman, M. S., et al., 2010. Tiered categorization of a diverse panel of HIV-1 Env pseudoviruses for assessment of neutralizing antibodies. J. Virol. 84, 1439-1452.

Sok, D., et al., 2016. Priming HIV-1 broadly neutralizing antibody precursors in human Ig loci transgenic mice. Science. 53, 1557-1560

Sok, D., et al., 2014. Promiscuous Glycan Site Recognition by Antibodies to the High-Mannose Patch of gp120 Broadens Neutralization of HIV. Sci. Transl. Med. 6, 236ra63-236ra63.

Tian, M., et al., 2016. Induction of HIV Neutralizing Antibody Lineages in Mice with Diverse Precursor Repertoires. Cell 166, 1471-1484.e18.

Tiller, T., et al., 2008. Efficient generation of monoclonal antibodies from single human B cells by single cell RT-PCR and expression vector cloning. J. Immunol. Methods 329, 112-124.

Wu, X., et al., 2010. Rational Design of Envelope Identifies Broadly Neutralizing Human Monoclonal Antibodies to HIV-1. Science 329, 856-861.

Wu, X., et al., 2015. Maturation and Diversity of the VRC01-Antibody Lineage over 15 Years of Chronic HIV-1 Infection. Cell 1-17.

Zhang, P., et al., 2018. Interdomain Stabilization Impairs CD4 Binding and Improves Immunogenicity of the HIV-1 Envelope Trimer. Cell Host Microbe. 23, 832-844.e6.

Zhou, T., et al., 2015. Structural Repertoire of HIV-1-Neutralizing Antibodies Targeting the CD4 Supersite in 14 Donors. Cell 1-14.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

Sequences

SEQUENCES

PCIN63-66B; VH CDR1 SEQ ID NO: 1
GYTFTACY;

PCIN63-71B; VH CDR1 SEQ ID NO: 2
GYTFTAYF;

PCIN63-71C; VH CDR1 SEQ ID NO: 3
GYTFTSCY;

PCIN63-71D2b; VH CDR1 SEQ ID NO: 4
GYTFTACY;

PCIN63-71F; VH CDR1 SEQ ID NO: 5
GYSFTDYF;

PCIN63-71G; VH CDR1 SEQ ID NO: 6
GYTFNSCL;

PCIN63-71H; VH CDR1 SEQ ID NO: 7
GYTFTSCY;

PCIN63-71I1a; VH CDR1 SEQ ID NO: 8
GYTFNSCL;

PCIN63-71J2a; VH CDR1 SEQ ID NO: 9
GYTFNSCL;

PCIN63-71K; VH CDR1 SEQ ID NO: 10
GYTFTSCY;

PCIN63-71L; VH CDR1 SEQ ID NO: 11
GYTFTSCY;

PCIN63-71M1a; VH CDR1 SEQ ID NO: 12
GYTFTSCY;

PCIN63-71N1a; VH CDR1 SEQ ID NO: 13
GYTFNTCL;

PCIN63-71O; VH CDR1 SEQ ID NO: 14
GYTFNTCL;

PCIN63-71P; VH CDR1 SEQ ID NO: 15
GYTFNTCL;

PCIN63-77B1b; VH CDR1 SEQ ID NO: 16
GYTFSSCY;

PCIN63-77C; VH CDR1 SEQ ID NO: 17
GYTFTACY;

-continued

PCIN63-77D; VH CDR1 SEQ ID NO: 18
GYTFTSCY;

PCIN63-66B; VH CDR2 SEQ ID NO: 19
INPINGAR;

PCIN63-71B; VH CDR2 SEQ ID NO: 20
INPLHGAV;

PCIN63-71C; VH CDR2 SEQ ID NO: 21
LNPINGAR;

PCIN63-71D2b; VH CDR2 SEQ ID NO: 22
LNPINGAR;

PCIN63-71F; VH CDR2 SEQ ID NO: 23
INPINGAP;

PCIN63-71G; VH CDR2 SEQ ID NO: 24
INPLHGAV;

PCIN63-71H; VH CDR2 SEQ ID NO: 25
LNPINGAR;

PCIN63-71I1a; VH CDR2 SEQ ID NO: 26
INPLHGAV;

PCIN63-71J2a VH CDR2 SEQ ID NO: 27
INPLHGAV;

PCIN63-71K; VH CDR2 SEQ ID NO: 28
LNPINGAR;

PCIN63-71L; VH CDR2 SEQ ID NO: 29
LNPINGAR;

PCIN63-71M1a; VH CDR2 SEQ ID NO: 30
LNPINGAR;

PCIN63-71N1a; VH CDR2 SEQ ID NO: 31
INPLHGAV;

PCIN63-71O; VH CDR2 SEQ ID NO: 32
INPLHGAV;

PCIN63-71P; VH CDR2 SEQ ID NO: 33
INPLHGAV;

PCIN63-77B1b; VH CDR2 SEQ ID NO: 34
LNPINGAR;

PCIN63-77C; VH CDR2 SEQ ID NO: 35
INPINGAR;

PCIN63-77D; VH CDR2 SEQ ID NO: 36
LNPINGAR;

PCIN63-66B; VH CDR3 SEQ ID NO: 37
TRDSSRRDTNWWLDP;

-continued

```
PCIN63-71B; VH CDR3
                                          SEQ ID NO: 38
TTHSSSRDFQWSLDP;

PCIN63-71C; VH CDR3
                                          SEQ ID NO: 39
TRDSSRRDINWWLDP;

PCIN63-71D2b; VH CDR3
                                          SEQ ID NO: 40
TRDSSRRDINWWLDP;

PCIN63-71F; VH CDR3
                                          SEQ ID NO: 41
TRDSSRQQRDWWLDP;

PCIN63-71G; VH CDR3
                                          SEQ ID NO: 42
TRDASRDDRAWRLDP;

PCIN63-71H; VH CDR3
                                          SEQ ID NO: 43
ARDSSREETNWWLDP;

PCIN63-71I1a; VH CDR3
                                          SEQ ID NO: 44
TRDASRDDRAWRLDP;

PCIN63-71J2a; VH CDR3
                                          SEQ ID NO: 45
TRDASRDDRAWRLDP;

PCIN63-71K; VH CDR3
                                          SEQ ID NO: 46
TRDSSRDETNWWLDP;

PCIN63-71L; VH CDR3
                                          SEQ ID NO: 47
TRDSSRDETNWWLDP;

PCIN63-71M1a; VH CDR3
                                          SEQ ID NO: 48
ARDSSRDETNWWLDP;

PCIN63-71N1a; VH CDR3
                                          SEQ ID NO: 49
TRDSSRGNTEWRLDP;

PCIN63-71O; VH CDR3
                                          SEQ ID NO: 50
TRDSSRDNLEWRLDP;

PCIN63-71P; VH CDR3
                                          SEQ ID NO: 51
TRDSSRGDTEWRLDP;

PCIN63-77B1b; VH CDR3
                                          SEQ ID NO: 52
TRDSSRDETNWWLDP;

PCIN63-77C; VH CDR3
                                          SEQ ID NO: 53
TRDSSRRDLEWRLDP;

PCIN63-77D; VH CDR3
                                          SEQ ID NO: 54
ARDSSRDETNWWLDP;

PCIN63-66B; VL CDR1
                                          SEQ ID NO: 55
QGIGSD;

PCIN63-71B; VL CDR1
                                          SEQ ID NO: 56
QGIGNK;

PCIN63-71C; VL CDR1
                                          SEQ ID NO: 57
QGIGSD;
```

-continued

```
PCIN63-71D2b; VL CDR1
                                          SEQ ID NO: 58
QGIGSD;

PCIN63-71F; VL CDR1
                                          SEQ ID NO: 59
QHIGND;

PCIN63-71G; VL CDR1
                                          SEQ ID NO: 60
QGIGSD;

PCIN63-71H; VL CDR1
                                          SEQ ID NO: 61
QGIGSD;

PCIN63-71I1a; VL CDR1
                                          SEQ ID NO: 62
QGIGSD;

PCIN63-71J2a; VL CDR1
                                          SEQ ID NO: 63
QGIGSD;

PCIN63-71K; VL CDR1
                                          SEQ ID NO: 64
QGIGSD;

PCIN63-71L; VL CDR1
                                          SEQ ID NO: 65
QGIGSD;

PCIN63-71M1a; VL CDR1
                                          SEQ ID NO: 66
QGIGSD;

PCIN63-71N1a; VL CDR1
                                          SEQ ID NO: 67
QGIGNN;

PCIN63-71O; VL CDR1
                                          SEQ ID NO: 68
QGIGSD;

PCIN63-71P; VL CDR1
                                          SEQ ID NO: 69
QGIGSD;

PCIN63-77B1b; VL CDR1
                                          SEQ ID NO: 70
QGIGSD;

PCIN63-77C; VL CDR1
                                          SEQ ID NO: 71
QGIGSD;

PCIN63-77D; VL CDR1
                                          SEQ ID NO: 72
QGIGDD;

PCIN63-66B; VL CDR2
                                          SEQ ID NO: 73
KAS;

PCIN63-71B; VL CDR2
                                          SEQ ID NO: 74
KAS;

PCIN63-71C; VL CDR2
                                          SEQ ID NO: 75
KAS;

PCIN63-71D2b; VL CDR2
                                          SEQ ID NO: 76
KAS;

PCIN63-71F; VL CDR2
                                          SEQ ID NO: 77
QAS;
```

-continued

PCIN63-71G; VL CDR2 SEQ ID NO: 78

KAS;

PCIN63-71H; VL CDR2 SEQ ID NO: 79

KAS;

PCIN63-71I1a; VL CDR2 SEQ ID NO: 80

KAS;

PCIN63-71J2a; VL CDR2 SEQ ID NO: 81

KAS;

PCIN63-71K; VL CDR2 SEQ ID NO: 82

KAS;

PCIN63-71L; VL CDR2 SEQ ID NO: 83

KAS;

PCIN63-71M1a; VL CDR2 SEQ ID NO: 84

KAS;

PCIN63-71N1a; VL CDR2 SEQ ID NO: 85

KAS;

PCIN63-71O; VL CDR2 SEQ ID NO: 86

KAS;

PCIN63-71P; VL CDR2 SEQ ID NO: 87

KAS;

PCIN63-77B1b; VL CDR2 SEQ ID NO: 88

KAP;

PCIN63-77C; VL CDR2 SEQ ID NO: 89

KAS;

PCIN63-77D; VL CDR2 SEQ ID NO: 90

KAS;

PCIN63-66B; VL CDR3 SEQ ID NO: 91

QVLET;

PCIN63-71B; VL CDR3 SEQ ID NO: 92

QVYES;

PCIN63-71C; VL CDR3 SEQ ID NO: 93

QVLET;

PCIN63-71D2b; VL CDR3 SEQ ID NO: 94

QVLET;

PCIN63-71F; VL CDR3 SEQ ID NO: 95

QVYES;

PCIN63-71G; VL CDR3 SEQ ID NO: 96

QVVEW;

PCIN63-71H; VL CDR3 SEQ ID NO: 97

QVLET;

-continued

PCIN63-71I1a; VL CDR3 SEQ ID NO: 98

QVFEW;

PCIN63-71J2a; VL CDR3 SEQ ID NO: 99

QVLET;

PCIN63-71K; VL CDR3 SEQ ID NO: 100

QVLET;

PCIN63-71L; VL CDR3 SEQ ID NO: 101

QVLET;

PCIN63-71M1a; VL CDR3 SEQ ID NO: 102

QVLET;

PCIN63-71N1a; VL CDR3 SEQ ID NO: 103

QVYQT;

PCIN63-71O; VL CDR3 SEQ ID NO: 104

QVFEW;

PCIN63-71P; VL CDR3 SEQ ID NO: 105

QVFEW;

PCIN63-77B1b; VL CDR3 SEQ ID NO: 106

QVLET;

PCIN63-77C; VL CDR3 SEQ ID NO: 107

QVLET;

PCIN63-77D; VL CDR3 SEQ ID NO: 108

QAYES;

PCIN63-66B; Motif #1 SEQ ID NO: 109

ACYIHWF;

PCIN63-71B; Motif #1 SEQ ID NO: 110

AYFIHWV;

PCIN63-71C; Motif #1 SEQ ID NO: 111

SCYIHWF;

PCIN63-71D2b; Motif #1 SEQ ID NO: 112

ACYIHWF;

PCIN63-71F; Motif #1 SEQ ID NO: 113

DYFVHWV;

PCIN63-71G; Motif #1 SEQ ID NO: 114

SCLIHWW;

PCIN63-71H; Motif #1 SEQ ID NO: 115

SCYIHWF;

PCIN63-71I1a; Motif #1 SEQ ID NO: 116

SCLIHWW;

PCIN63-71J2a; Motif #1 SEQ ID NO: 117

SCLIHWW;

-continued

PCIN63-71K; Motif #1 SEQ ID NO: 118
SCYIHWF;

PCIN63-71L; Motif #1 SEQ ID NO: 119
SCYIHWF;

PCIN63-71M1a; Motif #1 SEQ ID NO: 120
SCYIHWF;

PCIN63-71N1a; Motif #1 SEQ ID NO: 121
TCLIHWW;

PCIN63-71O; Motif #1 SEQ ID NO: 122
TCLIHWW;

PCIN63-71P; Motif #1 SEQ ID NO: 123
TCLIHWW;

PCIN63-77B1b; Motif #1 SEQ ID NO: 124
SCYIHWF;

PCIN63-77C; Motif #1 SEQ ID NO: 125
ACYIQWF;

PCIN63-77D; Motif #1 SEQ ID NO: 126
SCYIHWF;

PCIN63-66B; Motif #2 SEQ ID NO: 127
NINARNN;

PCIN63-71B; Motif #2 SEQ ID NO: 128
NLHAVNY;

PCIN63-71C; Motif #2 SEQ ID NO: 129
NINARNN;

PCIN63-71D2b; Motif #2 SEQ ID NO: 130
NINARNN;

PCIN63-71F; Motif #2 SEQ ID NO: 131
NINAPNY;

PCIN63-71G; Motif #2 SEQ ID NO: 132
NLHAVNY;

PCIN63-71H; Motif #2 SEQ ID NO: 133
NINARNN;

PCIN63-71I1a; Motif #2 SEQ ID NO: 134
NLHAVNY;

PCIN63-71J2a; Motif #2 SEQ ID NO: 135
NLHAVNY;

PCIN63-71K; Motif #2 SEQ ID NO: 136
NINARNN;

PCIN63-71L; Motif #2 SEQ ID NO: 137
NINARNN;

-continued

PCIN63-71M1a; Motif #2 SEQ ID NO: 138
NINARNQ;

PCIN63-71N1a; Motif #2 SEQ ID NO: 139
NLHAVNY;

PCIN63-71O; Motif #2 SEQ ID NO: 140
NLHAVNY;

PCIN63-71P; Motif #2 SEQ ID NO: 141
NLHAVNY;

PCIN63-77B1b; Motif #2 SEQ ID NO: 142
NINARNQ;

PCIN63-77C; Motif #2 SEQ ID NO: 143
NINARNN;

PCIN63-77D; Motif #2 SEQ ID NO: 144
NINARNH;

PCIN63-66B; Motif #3 SEQ ID NO: 145
PRK;

PCIN63-71B; Motif #3 SEQ ID NO: 146
AHK;

PCIN63-71C; Motif #3 SEQ ID NO: 147
PHK;

PCIN63-71D2b; Motif #3 SEQ ID NO: 148
PHK;

PCIN63-71F; Motif #3 SEQ ID NO: 149
APN;

PCIN63-71G; Motif #3 SEQ ID NO: 150
AHQ;

PCIN63-71H; Motif #3 SEQ ID NO: 151
PYQ;

PCIN63-71I1a; Motif #3 SEQ ID NO: 152
AHQ;

PCIN63-71J2a; Motif #3 SEQ ID NO: 153
AHQ;

PCIN63-71K; Motif #3 SEQ ID NO: 154
PYQ;

PCIN63-71L; Motif #3 SEQ ID NO: 155
PYQ;

PCIN63-71M1a; Motif #3 SEQ ID NO: 156
AYQ;

PCIN63-71N1a; Motif #3 SEQ ID NO: 157
AHN;

PCIN63-71O; Motif #3
SEQ ID NO: 158
AHQ;

PCIN63-71P; Motif #3
SEQ ID NO: 159
AHQ;

PCIN63-77B1b; Motif #3
SEQ ID NO: 160
AYQ;

PCIN63-77C; Motif #3
SEQ ID NO: 161
PQT;

PCIN63-77D; Motif #3
SEQ ID NO: 162
AYQ;

PCIN63-66B; Motif #4
SEQ ID NO: 163
SGGDG;

PCIN63-71B; Motif #4
SEQ ID NO: 164
SGGKG;

PCIN63-71C; Motif #4
SEQ ID NO: 165
GGGDA;

PCIN63-71D2b; Motif #4
SEQ ID NO: 166
GGGDA;

PCIN63-71F; Motif #4
SEQ ID NO: 167
GHGDA;

PCIN63-71G; Motif #4
SEQ ID NO: 168
GGGDG;

PCIN63-71H; Motif #4
SEQ ID NO: 169
GGGDA;

PCIN63-71I1a; Motif #4
SEQ ID NO: 170
GGGDG;

PCIN63-71J2a; Motif #4
SEQ ID NO: 171
GGGDA;

PCIN63-71K; Motif #4
SEQ ID NO: 172
GGGDA;

PCIN63-71L; Motif #4
SEQ ID NO: 173
GGGDA;

PCIN63-71M1a; Motif #4
SEQ ID NO: 174
GGGDA;

PCIN63-71N1a; Motif #4
SEQ ID NO: 175
SGGNG;

PCIN63-71O; Motif #4
SEQ ID NO: 176
GGGDG;

PCIN63-71P; Motif #4
SEQ ID NO: 177
GGGDG;

PCIN63-77B1b; Motif #4
SEQ ID NO: 178
GGGDA;

PCIN63-77C; Motif #4
SEQ ID NO: 179
GGGDA;

PCIN63-77D; Motif #4
SEQ ID NO: 180
SGGDG;

PCIN63-66B; Motif #5
SEQ ID NO: 181
FNKD;

PCIN63-71B; Motif #5
SEQ ID NO: 182
FTKD;

PCIN63-71C; Motif #5
SEQ ID NO: 183
FNKN;

PCIN63-71D2b; Motif #5
SEQ ID NO: 184
FNKN;

PCIN63-71F; Motif #5
SEQ ID NO: 185
YNKS;

PCIN63-71G; Motif #5
SEQ ID NO: 186
HNIN;

PCIN63-71H; Motif #5
SEQ ID NO: 187
FNKN;

PCIN63-71I1a; Motif #5
SEQ ID NO: 188
HNIN;

PCIN63-71J2a; Motif #5
SEQ ID NO: 189
FNKN;

PCIN63-71K; Motif #5
SEQ ID NO: 190
FRKN;

PCIN63-71L; Motif #5
SEQ ID NO: 191
FRKN;

PCIN63-71M1a; Motif #5
SEQ ID NO: 192
FNKN;

PCIN63-71N1a; Motif #5
SEQ ID NO: 193
FSKD;

PCIN63-71O; Motif #5
SEQ ID NO: 194
HNLN;

PCIN63-71P; Motif #5
SEQ ID NO: 195
HNAN;

PCIN63-77B1b; Motif #5
SEQ ID NO: 196
FNKN;

PCIN63-77C; Motif #5
SEQ ID NO: 197
FNKK;

-continued

PCIN63-77D; Motif #5
SEQ ID NO: 198
FNKD;

PCIN63-66B; Motif #6
SEQ ID NO: 199
FHE;

PCIN63-71B; Motif #6
SEQ ID NO: 200
FGD;

PCIN63-71C; Motif #6
SEQ ID NO: 201
FHD;

PCIN63-71D2b; Motif #6
SEQ ID NO: 202
FHD;

PCIN63-71F; Motif #6
SEQ ID NO: 203
SGE;

PCIN63-71G; Motif #6
SEQ ID NO: 204
FHE;

PCIN63-71H; Motif #6
SEQ ID NO: 205
FHD;

PCIN63-71I1a; Motif #6
SEQ ID NO: 206
FHE;

PCIN63-71J2a; Motif #6
SEQ ID NO: 207
FHD;

PCIN63-71K; Motif #6
SEQ ID NO: 208
FHE;

PCIN63-71L; Motif #6
SEQ ID NO: 209
FHE;

PCIN63-71M1a; Motif #6
SEQ ID NO: 210
FHD;

PCIN63-71N1a; Motif #6
SEQ ID NO: 211
SHE;

PCIN63-71O; Motif #6
SEQ ID NO: 212
FHE;

PCIN63-71P; Motif #6
SEQ ID NO: 213
FHE;

PCIN63-77B1b; Motif #6
SEQ ID NO: 214
FHD;

PCIN63-77C; Motif #6
SEQ ID NO: 215
FHD;

PCIN63-77D; Motif #6
SEQ ID NO: 216
FGD;

PCIN63-66B; Motif #7
SEQ ID NO: 217
QVLET;

-continued

PCIN63-71B; Motif #7
SEQ ID NO: 218
QVYES;

PCIN63-71C; Motif #7
SEQ ID NO: 219
QVLET;

PCIN63-71D2b; Motif #7
SEQ ID NO: 220
QVLET;

PCIN63-71F; Motif #7
SEQ ID NO: 221
QVYES;

PCIN63-71G; Motif #7
SEQ ID NO: 222
QVVEW;

PCIN63-71H; Motif #7
SEQ ID NO: 223
QVLET;

PCIN63-71I1a; Motif #7
SEQ ID NO: 224
QVFEW;

PCIN63-71J2a; Motif #7
SEQ ID NO: 225
QVLET;

PCIN63-71K; Motif #7
SEQ ID NO: 226
QVLET;

PCIN63-71L; Motif #7
SEQ ID NO: 227
QVLET;

PCIN63-71M1a; Motif #7
SEQ ID NO: 228
QVLET;

PCIN63-71N1a; Motif #7
SEQ ID NO: 229
QVYQT;

PCIN63-71O; Motif #7
SEQ ID NO: 230
QVFEW;

PCIN63-71P; Motif #7
SEQ ID NO: 231
QVFEW;

PCIN63-77B1b; Motif #7
SEQ ID NO: 232
QVLET;

PCIN63-77C; Motif #7
SEQ ID NO: 233
QVLET;

PCIN63-77D; Motif #7
SEQ ID NO: 234
QAYES;

PCIN63-66B; VH
SEQ ID NO: 235
QVQLVQSGAEVKKPGASMRVSCKASGYTFTACYIHWFRQAPGQGLEWMGW

INPINGARNNPRKFQGRVTMTRDTSIDTAYLELRNLASDDTAMYYCTRDS

SRRDTNWWLDPWGQGTLVTVSS;

-continued

PCIN63-71B; VH

SEQ ID NO: 236
QVQLVQSGAEVKKPGASVRVSCKASGYTFTAYFIHWVRQAPGQGLEWVGW

INPLHGAVNYAHKFQGRVSMTRDTSISTAYMELRSLKSDDTAIYYCTTHS

SSRDFQWSLDPWGQGTLVTVSS;

PCIN63-71C; VH

SEQ ID NO: 237
QVQLVQSGAEVKKPGASMRVSCKASGYTFTSCYIHWFRQAPGQGLEWMGW

LNPINGARNNPHKFQGRITLTRDTSTDTAYLELRNLRSDDTAVYYCTRDS

SRRDTNWWLDPWGQGTLVTVSS;

PCIN63-71D2b; VH

SEQ ID NO: 238
QVQLVQSGAEVKKPGASMRVSCKASGYTFTACYIHWFRQAPGQGLEWMGW

LNPINGARNNPHKFQGRITLTRDTSTDTAYLELRNLRSDDTAVYYCTRDS

SRRDTNWWLDPWGQGALVTVSS;

PCIN63-71F; VH

SEQ ID NO: 239
QVQLVQSGAEVKKPGASVRVSCKASGYSFTDYFVHWVRQAPGQGLEWVGW

INPINGAPNYAPNFRGRITLTRDTSIDTLYMDLRSLRVDDTAVYFCTRDS

SRQQRDWWLDPWGQGTLVTVSS;

PCIN63-71G; VH

SEQ ID NO: 240
QVQLVQSGAEVKKPGASVRVSCKASGYTFNSCLIHWWRQAPGQGLQWMAW

INPLHGAVNYAHQFQGRITVTRDTSIDTAYMELRGLRSDDTATYYCTRDA

SRDDRAWRLDPWGQGTLVIVSS;

PCIN63-71H; VH

SEQ ID NO: 241
QVQLVQSGVAVKKPGASVWVSCKASGYTFTSCYIHWFRQAPGQGLEWMGW

LNPINGARNNPYQFQGRISLTRDTSSETAYLELRNLRSDDTAVYYCARDS

SREETNWWLDPWGQGTLVTVSS;

PCIN63-71I1a; VH

SEQ ID NO: 242
QVQLVQSGAEVKKPGASVRVSCKASGYTFNSCLIHWWRQAPGQGLQWMAW

INPLHGAVNYAHQFQGRITVTRDTSIDTAYMELRGLRSDDTATYYCTRDA

SRDDRAWRLDPWGQGTLVIVSS;

PCIN63-71J2a; VH

SEQ ID NO: 243
QVQLVQSGAEVKKPGASMRVSCKASGYTFTACYIHWFRQAPGQGLEWMGW

LNPINGARNNPHKFQGRITLTRDTSTDTAYLELRNLRSDDTAVYYCTRDS

SRRDTNWWLDPWGQGTLVTVSS;

PCIN63-71K; VH

SEQ ID NO: 244
QVQLVQSGAAVKKPGASVWVSCKASGYTFTSCYIHWFRQAPGQGLEWMGW

LNPINGARNNPYQFQGRISLTRDTSSETAYLELRNLTPDDTAVYYCTRDS

SRDETNWWLDPWGQGTLVTVSS;

PCIN63-71L; VH

SEQ ID NO: 245
QVQLVQSGAAVKKPGASVWVSCKASGYTFTSCYIHWFRQAPGQGLEWMGW

LNPINGARNNPYQFQGRISLTRDTSSETAYLELRNLTPDDTAVYYCTRDS

SRDETNWWLDPWGQGTLVIVSS;

-continued

PCIN63-71M1a; VH

SEQ ID NO: 246
QVQLVQSGAAVKKPGASVWVSCKASGYTFTSCYIHWFRQAPGQGLEWMGW

LNPINGARNQAYQFQGRISLTRDTPSETAYLELRDLRSDDTAVYYCARDS

SRDETNWWLDPWGQGTLVTVSS;

PCIN63-71N1a; VH

SEQ ID NO: 247
QVQLVQSGAEVKKPGASVRVSCKASGYTFNTCLIHWWRQAPGQGLQWLAW

INPLHGAVNYAHNFQGRITVTRDTSIDTAYMELRGLRSDDTATYYCTRDS

SRGNTEWRLDPWGQGTLVTVSS;

PCIN63-71O; VH

SEQ ID NO: 248
QVQLVQSGAEVKKPGASVRVSCKASGYTFNTCLIHWWRQAPGQGLQWVAW

INPLHGAVNYAHQLQGRITVTRDTSIDTAYMELRGLRADDTATYYCTRDS

SRDNLEWRLDPWGQGTLVTVSS;

PCIN63-71P; VH

SEQ ID NO: 249
QVQLVQSGAEVKKPGASVRVSCKASGYTFNTCLIHWWRQAPGQGLQWVAW

INPLHGAVNYAHQLQGRITVTRDTSIDTAHMELRGLRSDDTATYYCTRDS

SRGDTEWRLDPWGQGTLVTVSS;

PCIN63-77B1b; VH

SEQ ID NO: 250
QVQLVQSGAEVKKPGASARVSCKASGYTFTAYFIHWVRQAPGQGLEWVGW

INPLHGAVNYAHKFQGRVSMTRDTSISTAYMELRSLKSDDTAIYYCTTHL

SSRDFSWSWDPWGQGTLVTVSP;

PCIN63-77C; VH

SEQ ID NO: 251
QVQLVQSGAEVKKPGASVRVSCKASGYTFTACYIQWFRQAPGQGLEWMGW

INPINGARNNNPQTFQGRVTLTRDTSIDTAYLELRNLRDDDTAIYYCTRD

SSRRDLEWRLDPWGQGTLVTVSS;

PCIN63-77D; VH

SEQ ID NO: 252
QVQLVQSGAAVKKPGASVWVSCKASGYTFTSCYIHWFRQAPGQGLEWMGW

LNPINGARNHAYQFQGRISLTRDTSSETAYLELRNLRSDDTAVYYCARDS

SRDETNWWLDPWGQGTLVTVSS;

PCIN63-66B; VL

SEQ ID NO: 253
AIRMTQSPATLSASVGERVTITCRASQGIGSDLGWYQQKPGKSPKLLIFK

ASNLKDGVPPRFSGGGFHTEFTLTISSLQPDDFATYYCQVLETFGQGTKV

EIK;

PCIN63-71B; VL

SEQ ID NO: 254
AIRMTQSPATLSASVGDRVTITCRASQGIGNKLGWFQQKPGKAPKPLIFK

ASTLKDGVPSRFSGSGFGTDFTLTISSLQPDDFATYYCQVYESFGQGTKV

EIK;

PCIN63-71C; VL

SEQ ID NO: 255
AIRMTQSPATLSASVGDRVTITCRAGQGIGSDLAWYQQKSGQAPKLLIFK

ASNLKNGVPPRFSGSGFHTDFTLTISGLQPDDFATYYCQVLETFGQGTKV

EIK;

-continued

PCIN63-71D2b; VL

SEQ ID NO: 256
AIRMTQSPATLSASVGDRVTITCRAGQGIGSDLAWYQQKSGQAPKLLIFK

ASNLKNGVPPRFSGSGFHTDFTLTISGLQSDDFATYYCQVLETFGQGTKV

EIK;

PCIN63-71F; VL

SEQ ID NO: 257
AIRMTQSPPTVSASAGDRVTITCRAGQHIGNDLAWYQTKVGMAPKLLIYQ

ASNLKSGVPSRFSGSGSGTEFTLSITSLQPDDFATYYCQVYESFGQGTKV

EIK;

PCIN63-71G; VL

SEQ ID NO: 258
AIRMTQSPATLSASVGDRVTLTCRAGQGIGSDLGWYQQKPGKAPKLLIHK

ASNLINGVPSRFSGSGFHTEFTLTISSLQPDDFATYYCQVVEWFGQGTKV

EIK;

PCIN63-71H; VL

SEQ ID NO: 259
AIRMTQSPATLSASVGDRVTITCRAGQGIGSDLAWYQQKPGQAPKLLIFK

ASNLKNGVPTRFTGSGFHTDFTLTINGLQSDDFATYYCQVLETFGQGTKV

EIK;

PCIN63-71I1a; VL

SEQ ID NO: 260
AIRMTQSPATLSASVGDRVTLTCRAGQGIGSDLGWYQQKPGKAPKLLIHK

ASNLINGVPSRFSGSGFHTEFTLTINSLQPDDFATYYCQVFEWFGPGTKV

EIK;

PCIN63-71J2a; VL

SEQ ID NO: 261
AIRMTQSPATLSASVGDRVTITCRAGQGIGSDLAWYQQKSGQAPKLLIFK

ASNLKNGVPPRFSGSGFHTDFTLTISGLQPDDFATYYCQVLETFGQGTKV

EIK;

PCIN63-71K; VL

SEQ ID NO: 262
AIRMTQSPATLSASVGDRVTITCRAGQGIGSDLAWYQQKPGQAPKLLIFK

ASRLKNGVPTRFTGSGFHTEFTLTISGLQSDDFATYYCQVLETFGQGTKV

EIK;

PCIN63-71L; VL

SEQ ID NO: 263
AIRMTQSPATLSASVGDRVTITCRAGQGIGSDLAWYQQKPGQAPKLLIFK

ASRLKNGVPTRFTGSGFHTEFTLTISGLQSDDFATYYCQVLETFGQGTKV

EIK;

PCIN63-71M1a; VL

SEQ ID NO: 264
AIRMTQSPATLSASVGDRVTITCRAGQGIGSDLAWYQQKSGQAPKLLIFK

ASNLKNGVPPRFSGSGFHTDFTLTISGLQPDDFATYYCQVLETFGQGTKV

EIK;

PCIN63-71N1a; VL

SEQ ID NO: 265
AIRMTQSPATLSASVGDKVTITCRASQGIGNNLGWYQQKPGQAPKLLIFK

ASNSKDGVPPRFSGSGSHTEFTLTINSLQPDDFATYYCQVYQTFGQGTKV

EIK;

PCIN63-71O; VL

SEQ ID NO: 266
AIRMTQSPATLSASVGDRVTLTCRAGQGIGSDLGWYQQKPGKAPKLLIHK

ASNLLNGVPSRFSGSGFHTEFTLTISSLQPDDFATYYCQVFEWFGQGTKV

EIK;

PCIN63-71P; VL

SEQ ID NO: 267
AIRMTQSPATLSASVGDRVTLTCRAGQGIGSDLGWYQQKPGKAPKLLIHK

ASNLANGVPSRFSGRGFHTEFTLTISSLQPDDFATYYCQVFEWFGQGTKV

EIK;

PCIN63-77B1b; VL

SEQ ID NO: 268
AIRMTQSPATLSASVGDRVTITCRAGQGIGSDLAWYQQKPGQAPKLLIFK

ASNLKNGVPTRFTGSGFHTDFTLTISGLQSDDFATYYCQVLETFGQGTKV

EIK;

PCIN63-77C; VL

SEQ ID NO: 269
AIRMTQSPATLSASVGDRVTITCRAGQGIGSDLAWYQQKPGQAPKLLIFK

ASNLKKGVPTRFTGSGFHTDFTLTISGLQSDDFATYYCQVLETFGQGTKV

EIK;

PCIN63-77D; VL

SEQ ID NO: 270
AIRMTQSPATLSAFVGDRVTITCRASQGIGDDLGWYQQKPGKVPKPLIFK

ASNLKDGVPSRFSGSGFGTDFTLTINNLQPDDFATYYCQAYESFGQGTKV

EIK;

PCIN63-66B; VH

SEQ ID NO: 271
CAGGTGCAGCTGGTGCAGTCTGGGGCTGAGGTGAAGAAGCCTGGGGCCTC

AATGAGGGTCTCCTGCAAGGCCTCTGGATACACCTTCACCGCCTGCTATA

TACACTGGTTTCGACAGGCCCCTGGACAAGGCCTTGAGTGGATGGGATGG

ATCAACCCTATCAATGGTGCCAGAAATAATCCACGCAAGTTTCAGGGCAG

GGTCACCATGACCAGGGACACGTCCATTGATACAGCGTACTTGGAACTGC

GCAACCTGGCATCTGACGACACGGCCATGTATTACTGTACGAGAGATTCA

TCGAGGCGTGATACGAATTGGTGGTTGGACCCCTGGGGCCAGGGAACCCT

GGTCACCGTCTCCTCA;

PCIN63-71B; VH

SEQ ID NO: 272
CAGGTGCAGCTGGTGCAGTCTGGGGCTGAGGTGAAGAAGCCTGGGGCCTC

AGTGAGGGTCTCCTGCAAGGCTTCTGGATACACCTTCACCGCCTATTTTA

TACACTGGGTGCGACAGGCCCCTGGACAGGGGCTTGAGTGGGTGGGTTGG

ATCAACCCTCTCCATGGCGCCGTAAACTATGCACACAAATTTCAAGGCAG

GGTCTCCATGACCAGGGACACCTCCATCAGCACAGCCTACATGGAACTTC

GCAGCCTGAAATCTGACGACACGGCCATTTATTACTGTACCACACATTCA

TCGAGCCGTGATTTTCAGTGGTCGTTGGACCCCTGGGGCCAGGGAACCCT

GGTCACCGTCTCCTCA;

-continued

PCIN63-71C; VH

SEQ ID NO: 273

CAGGTGCAGCTGGTGCAGTCTGGGGCTGAGGTGAAGAAGCCTGGGGCCTC
AATGAGGGTCTCCTGCAAGGCCTCTGGATACACCTTCACCTCTTGTTATA
TACACTGGTTTCGACAGGCCCCTGGACAAGGGCTTGAGTGGATGGGATGG
CTCAACCCTATCAATGGTGCCAGAAATAATCCACACAAGTTTCAGGGCAG
GATCACCCTGACCAGGGACACGTCCACTGATACAGCCTACTTGGAACTGC
GCAACCTGAGATCTGACGACACGGCCGTATATTATTGTACGAGAGATTCA
TCGAGGCGTGATACGAATTGGTGGTTGGACCCTTGGGGCCAGGGAACCCT
GGTCACCGTCTCCTCA;

PCIN63-71D2b; VH

SEQ ID NO: 274

CAGGTGCAGCTGGTGCAGTCTGGGGCTGAGGTGAAGAAGCCTGGGGCCTC
AATGAGGGTCTCCTGCAAGGCCTCTGGATACACTTTCACCGCTTGTTATA
TACACTGGTTTCGACAGGCCCCTGGACAAGGGCTTGAGTGGATGGGATGG
CTCAACCCTATCAATGGTGCCAGAAATAATCCACACAAGTTTCAGGGCAG
GATCACCCTGACCAGGGACACGTCCACTGATACAGCCTACTTGGAACTGC
GCAACCTGAGATCTGACGACACGGCCGTGTATTATTGTACGAGAGATTCA
TCGAGGCGTGATACGAATTGGTGGTTGGACCCTTGGGGCCAGGGAGCCCT
GGTCACCGTCTCCTCA;

PCIN63-71F; VH

SEQ ID NO: 275

CAGGTGCAGCTGGTGCAGTCTGGGGCTGAAGTGAAGAAGCCTGGGGCCTC
AGTGAGGGTCTCCTGCAAGGCCTCTGGATACAGCTTCACCGACTACTTTG
TGCACTGGGTGCGACAGGCCCCTGGACAGGGCCTTGAGTGGGTGGGGTGG
ATAAACCCTATTAATGGAGCCCCTAATTATGCACCGAACTTTCGGGGCAG
GATCACCTTGACTAGGGACACATCCATCGACACACTCTATATGGACTTGA
GAAGCCTGAGAGTTGACGACACGGCCGTTTACTTCTGTACGAGAGATTCA
TCGAGGCAACAACGGGACTGGTGGTTAGACCCCTGGGGCCAGGGAACCCT
GGTCACCGTCTCCTCA;

PCIN63-71G; VH

SEQ ID NO: 276

CAGGTGCAGCTGGTGCAGTCTGGGGCTGAGGTGAAGAAGCCTGGGGCCTC
AGTGAGGGTCTCCTGCAAGGCCTCCGGATACACCTTCAACTCCTGCTTAA
TTCATTGGTGGCGACAGGCCCCTGGACAAGGCCTTCAGTGGATGGCTTGG
ATCAACCCTCTCCATGGTGCCGTAAATTATGCACACCAGTTTCAGGGGAG
GATCACCGTGACCAGGGACACGTCCATCGACACTGCCTACATGGAACTGC
GCGGCCTGAGATCTGACGACACGGCCACATATTACTGTACGAGAGATGCA
TCCAGAGATGATCGCGCGTGGCGCTTGGACCCCTGGGGCCAGGGAACACT
GGTCACCGTCTCCTCA;

PCIN63-71H; VH

SEQ ID NO: 277

CAGGTGCAGCTGGTGCAGTCTGGGGTAGCGGTGAAGAAGCCTGGGGCCTC
AGTGTGGGTCTCCTGCAAGGCCTCTGGATACACCTTCACCAGTTGCTATA
TACATTGGTTTCGACAGGCCCCTGGACAAGGGCTTGAGTGGATGGGATGG
CTCAACCCTATCAATGGTGCCAGAAATAATCCATACCAGTTTCAGGGCAG
GATCAGCCTGACCAGGGACACGTCCAGTGAAACAGCCTACTTGGAACTGC
GTAACCTCAGATCTGACGACACGGCCGTCTATTATTGCGCGAGAGATTCT
TCGAGGGAAGAGACGAATTGGTGGCTGGACCCTTGGGGCCAGGGAACCCT
GGTCACCGTCTCCTCA;

PCIN63-71I1a; VH

SEQ ID NO: 278

CAGGTGCAGCTGGTGCAGTCTGGGGCTGAGGTGAAGAAGCCTGGGGCCTC
AGTGAGGGTCTCCTGCAAGGCCTCCGGATACACCTTCAATTCCTGCTTAA
TTCATTGGTGGCGACAGGCCCCTGGACAAGGCCTTCAGTGGATGGCTTGG
ATCAACCCTCTCCATGGTGCCGTAAATTATGCACACCAGTTCCAGGGGAG
GATCACCGTGACCAGGGACACGTCCATCGACACTGCCTACATGGAACTGC
GCGGCCTGAGATCTGACGACACGGCCACATATTACTGTACGAGAGATGCA
TCCAGAGATGATCGCGCGTGGCGCTTGGACCCCTGGGGCCAGGGAACACT
GGTCACCGTCTCCTCA;

PCIN63-71J2a; VH

SEQ ID NO: 279

CAGGTGCAGCTGGTGCAGTCTGGGGCTGAGGTGAAGAAGCCTGGGGCCTC
AATGAGGGTCTCTTGCAAGGCCTCTGGATACACTTTCACCGCTTGTTATA
TACACTGGTTTCGACAGGCCCCTGGACAAGGGCTTGAGTGGATGGGATGG
CTCAACCCTATCAATGGTGCCAGAAATAATCCACACAAGTTTCAGGGCAG
GATCACCCTGACCAGGGACACGTCCACTGATACAGCCTACTTGGAACTGC
GCAACCTGAGATCTGACGACACGGCCGTGTATTATTGTACGAGAGATTCA
TCGAGGCGTGATACGAATTGGTGGTTGGACCCTTGGGGCCAGGGAACCCT
GGTCACCGTCTCCTCA;

PCIN63-71K; VH

SEQ ID NO: 280

CAGGTGCAGCTGGTGCAGTCTGGGGCTGCGGTGAAGAAGCCTGGGGCCTC
AGTGTGGGTCTCCTGCAAGGCCTCTGGATACACCTTCACCAGTTGTTATA
TACATTGGTTTCGACAGGCCCCTGGACAAGGGCTTGAGTGGATGGGATGG
CTCAACCCTATCAATGGTGCCAGAAATAATCCATACCAGTTTCAGGGGAG
GATCAGCCTGACCAGGGACACGTCCAGTGAAACAGCCTACTTGGAACTGC
GTAACCTCACACCAGACGACACGGCCGTCTATTATTGCACGAGAGATTCA
TCGAGGGATGAGACGAATTGGTGGCTGGACCCTTGGGGCCAGGGAACCCT
GGTCACCGTCTCCTCA;

PCIN63-71L; VH

SEQ ID NO: 281

CAGGTGCAGCTGGTGCAGTCTGGGGCTGCGGTGAAGAAGCCTGGGGCCTC
AGTGTGGGTCTCCTGCAAGGCCTCTGGATACACCTTCACCAGTTGTTATA
TACATTGGTTTCGACAGGCCCCTGGACAAGGGCTTGAGTGGATGGGATGG
CTCAACCCTATCAATGGTGCCAGAAATAATCCATACCAGTTTCAGGGGAG
GATCAGCCTGACCAGGGACACGTCCAGTGAAACAGCCTACTTGGAACTGC
GTAACCTCACACCAGACGACACGGCCGTCTATTATTGCACGAGAGATTCA
TCGAGGGATGAGACGAATTGGTGGCTGGACCCTTGGGGCCAGGGAACCCT
GGTCATCGTCTCTTCA;

-continued

PCIN63-71M1a; VH

SEQ ID NO: 282

CAGGTGCAGCTGGTGCAGTCTGGGGCTGCGGTGAAGAAGCCTGGGGCCTC
AGTGTGGGTCTCCTGCAAGGCCTCTGGATACACCTTTACCAGTTGTTATA
TACATTGGTTTCGACAGGCCCCTGGACAAGGGCTTGAGTGGATGGGATGG
CTCAACCCTATCAATGGCGCCAGAAATCAGGCGTACCAGTTTCAGGGCAG
GATTAGCCTGACCAGGGACACGCCCAGTGAAACAGCCTACTTGGAACTGC
GTGACCTCAGATCTGACGACACGGCCGTCTATTATTGCGCGAGAGATTCA
TCGAGGGATGAGACGAATTGGTGGCTGGACCCTTGGGGCCAGGGAACCCT
GGTCACCGTCTCCTCA;

PCIN63-71N1a; VH

SEQ ID NO: 283

CAGGTGCAGCTGGTGCAGTCTGGGGCTGAGGTGAAGAAGCCTGGGGCCTC
AGTGAGGGTCTCCTGCAAGGCTTCCGGATACACTTTCAACACCTGCTTAA
TTCATTGGTGGCGACAGGCCCCTGGACAAGGCCTTCAGTGGCTGGCTTGG
ATCAACCCTCTCCATGGTGCCGTTAACTATGCACACAACTTTCAGGGGAG
GATCACCGTGACCAGGGACACGTCCATCGACACTGCCTACATGGAACTTC
GCGGCCTGAGATCTGACGACACGGCCACATACTACTGCACCAGAGATTCA
TCGAGAGGTAATACGGAGTGGCGCTTGGACCCCTGGGGCCAGGGAACACT
GGTCACCGTCTCCTCA;

PCIN63-71O; VH

SEQ ID NO: 284

CAGGTGCAGCTGGTGCAGTCTGGGGCTGAGGTGAAAAAGCCTGGGGCCTC
AGTGAGGGTCTCCTGCAAGGCTTCCGGATACACGTTCAACACCTGCTTGA
TTCATTGGTGGCGACAGGCCCCTGGACAGGGCCTTCAGTGGGTGGCTTGG
ATCAACCCTCTCCATGGTGCCGTTAATTATGCACACCAATTACAGGGGAG
GATCACCGTGACCAGGGACACGTCTATCGACACTGCCTACATGGAACTGC
GCGGCCTCAGAGCTGACGACACGGCCACCTACTACTGTACGAGAGATTCA
TCGAGAGATAATCTGGAGTGGCGCTTGGACCCCTGGGGCCAGGGAACACT
GGTCACCGTCTCCTCA;

PCIN63-71P; VH

SEQ ID NO: 285

CAGGTGCAGCTGGTGCAGTCTGGGGCTGAGGTGAAAAAGCCTGGGGCCTC
AGTGAGGGTCTCCTGCAAGGCTTCCGGATACACCTTCAACACCTGCTTAA
TTCATTGGTGGCGACAGGCCCCTGGACAGGGCCTTCAGTGGGTGGCTTGG
ATCAACCCTCTCCATGGTGCCGTTAACTATGCACACCAGTTACAGGGGAG
GATCACGGTGACCAGGGACACGTCTATCGACACTGCCCACATGGAACTGC
GCGGCCTCAGATCTGACGACACGGCCACATACTATTGTACCAGAGATTCA
TCGAGAGGTGATACGGAGTGGCGCTTGGACCCCTGGGGCCAGGGAACACT
GGTCACCGTCTCCTCA;

PCIN63-77B1b; VH

SEQ ID NO: 286

CAGGTGCAGCTGGTGCAGTCTGGGGCTGAGGTGAAGAAGCCTGGGGCCTC
AGCGAGGGTCTCCTGCAAGGCTTCTGGATACACCTTCACCGCCTATTTTA
TACACTGGGTGCGACAAGCCCCTGGACAGGGACTTGAGTGGGTGGGTTGG
ATCAACCCTCTCCATGGCGCCGTAAATTATGCACACAAATTTCAGGGCAG
GGTCTCCATGACCAGAGACACCTCCATCAGCACAGCCTACATGGAACTTC
GCAGCCTGAAATCTGACGACACGGCCATTTATTACTGTACCACACATTTG
TCGAGTCGTGATTTTTCGTGGTCGTGGGACCCCTGGGGCCAGGGAACCCT
GGTCACCGTCTCCCCA;

PCIN63-77C; VH

SEQ ID NO: 287

CAGGTGCAGCTGGTGCAGTCTGGGGCTGAGGTGAAGAAACCCGGGGCCTC
AGTGAGGGTCTCCTGCAAGGCCTCTGGATACACCTTCACCGCCTGTTATA
TACAGTGGTTTCGACAGGCCCCTGGACAAGGGCTTGAGTGGATGGGATGG
ATCAACCCTATCAATGGTGCCAGAAATAATAATCCACAGACGTTTCAGGG
CAGGGTCACCCTGACCAGGGACACGTCCATTGATACCGCCTACTTGGAAC
TGCGCAACCTGAGAGATGACGACACGGCCATATATTATTGTACGAGAGAT
TCATCGAGGCGTGATCTGGAGTGGCGGTTGGACCCCTGGGGCCAGGGAAC
CCTGGTCACCGTCTCCTCA;

PCIN63-77D; VH

SEQ ID NO: 288

CAGGTGCAGCTGGTGCAGTCTGGGGCTGCGGTGAAGAAGCCTGGGGCCTC
AGTGTGGGTCTCCTGCAAGGCCTCTGGATACACCTTCACCAGTTGTTATA
TACATTGGTTTCGACAGGCCCCTGGACAAGGGCTTGAGTGGATGGGATGG
CTCAACCCTATCAATGGCGCCAGAAATCATGCATACCAGTTTCAGGGCAG
GATTAGCCTGACCAGGGACACGTCCAGTGAAACAGCCTACTTGGAACTGC
GTAACCTCAGATCTGACGACACGGCCGTCTATTATTGCGCGAGAGATTCA
TCGAGGGATGAGACGAATTGGTGGCTGGACCCTTGGGGCCAGGGAACCCT
GGTCACCGTCTCCTCA;

PCIN63-66B; VL

SEQ ID NO: 289

GCCATCCGGATGACCCAGTCTCCTGCCACCCTGTCTGCATCTGTGGGAGA
AAGAGTCACCATCACTTGCCGGGCAAGTCAGGGCATTGGAAGTGATTTAG
GTTGGTATCAGCAGAAACCAGGGAAATCCCCTAAACTTCTTATCTTTAAG
GCGTCTAATTTAAAAGATGGCGTCCCGCCGAGGTTCAGCGGCGGTGGATT
TCACACAGAATTTACTCTCACCATCAGCAGCCTGCAGCCTGATGATTTTG
CAACTTATTACTGCCAAGTTTTGGAAACATTCGGCCAAGGGACCAAGGTG
GAGATCAAA;

PCIN63-71B; VL

SEQ ID NO: 290

GCCATCCGGATGACCCAGTCTCCTGCCACCCTGTCTGCATCTGTAGGAGA
CAGAGTCACCATCACTTGCCGGGCTAGTCAGGGCATTGGAAATAAATTAG
GGTGGTTTCAGCAGAAACCAGGGAAAGCCCCTAAGCCCCTGATCTTTAAG
GCGTCTACTTTGAAAGATGGGGTCCCATCAAGGTTCAGCGGCAGTGGATT
TGGGACAGATTTCACTCTCACCATCAGCAGCCTGCAGCCTGATGACTTTG
CAACTTACTATTGTCAAGTCTATGAAAGCTTCGGCCAAGGGACCAAGGTG
GAGATCAAA;

-continued

PCIN63-71C; VL

SEQ ID NO: 291
GCCATCCGGATGACCCAGTCTCCTGCCACCCTGTCTGCATCTGTGGGAGA
CAGAGTCACCATCACTTGCCGGGCAGGTCAGGGCATTGGAAGTGATTTAG
CCTGGTATCAGCAGAAATCAGGGCAAGCCCCTAAACTTCTTATCTTTAAG
GCGTCTAATTTAAAAAATGGAGTCCCGCCAAGATTCAGCGGCAGTGGATT
TCACACAGACTTCACTCTCACCATCAGCGGCCTGCAGCCTGATGATTTTG
CGACTTATTACTGCCAAGTTTTGGAAACATTCGGCCAAGGGACCAAGGTG
GAGATCAAA;

PCIN63-71D2b; VL

SEQ ID NO: 292
GCCATCCGGATGACCCAGTCTCCTGCCACCCTGTCTGCATCTGTGGGAGA
CAGAGTCACCATCACTTGCCGGGCAGGTCAGGGCATTGGAAGTGATTTAG
CCTGGTATCAGCAGAAATCAGGGCAAGCCCCTAAACTTCTTATCTTTAAG
GCGTCTAATTTAAAAAATGGAGTCCCGCCAAGATTCAGCGGCAGTGGATT
TCACACAGACTTCACTCTCACCATCAGCGGCCTGCAGTCTGATGATTTTG
CGACTTATTACTGCCAAGTTTTGGAAACATTCGGCCAAGGGACCAAGGTG
GAGATCAAA;

PCIN63-71F; VL

SEQ ID NO: 293
GCCATCCGGATGACCCAGTCTCCTCCCACCGTGTCTGCATCTGCGGGAGA
CAGAGTCACCATCACTTGCCGGGCCGGTCAGCACATTGGTAACGACTTGG
CCTGGTATCAGACGAAAGTGGGGATGGCCCCTAAACTCCTCATCTATCAG
GCGTCTAATTTAAAAAGTGGGGTCCCATCAAGGTTCAGCGGCAGTGGGTC
TGGGACAGAGTTCACTCTTTCCATCACCAGCCTGCAGCCTGATGATTTTG
CAACTTATTACTGCCAAGTTTATGAGTCGTTCGGCCAAGGGACCAAGGTG
GAGATCAAA;

PCIN63-71G; VL

SEQ ID NO: 294
GCCATCCGGATGACCCAGTCTCCTGCCACCCTGTCTGCATCTGTGGGAGA
CAGAGTCACCTTGACTTGCCGGGCAGGACAGGGCATTGGAAGTGATTTAG
GCTGGTATCAGCAGAAACCAGGGAAAGCCCCTAAACTCCTCATACATAAG
GCGTCCAATTTAATAAATGGAGTGCCATCAAGGTTCAGCGGCAGTGGATT
TCACACAGAATTCACTCTCACCATCAGCAGCCTGCAGCCTGATGATTTTG
CAACTTATTACTGTCAAGTTGTTGAATGGTTCGGCCAAGGGACCAAGGTG
GAGATCAAA;

PCIN63-71H; VL

SEQ ID NO: 295
GCCATCCGGATGACCCAGTCTCCTGCCACCCTGTCTGCATCTGTGGGAGA
CAGAGTCACCATCACTTGCCGGGCAGGTCAGGGCATTGGAAGTGATTTAG
CCTGGTATCAGCAGAAACCAGGGCAAGCCCCTAAACTTCTAATCTTTAAG
GCGTCTAATTTAAAAAATGGAGTCCCGACAAGATTCACCGGCAGTGGATT
TCACACAGACTTCACTCTCACCATCAACGGCCTGCAGTCTGATGATTTTG
CGACTTATTACTGCCAAGTTTTGGAGACATTCGGCCAAGGGACCAAGGTG
GAGATCAAA;

-continued

PCIN63-71I1a; VL

SEQ ID NO: 296
GCCATCCGGATGACCCAGTCTCCTGCCACCCTGTCTGCATCTGTGGGAGA
CAGAGTCACCTTGACTTGCCGGGCAGGGCAGGGCATTGGAAGTGATTTAG
GCTGGTATCAGCAGAAACCAGGGAAAGCCCCTAAACTCCTCATACACAAG
GCGTCTAATTTAATAAATGGGGTGCCATCAAGGTTCAGCGGCAGTGGATT
TCACACAGAATTCACACTCACCATCAACAGCCTGCAGCCTGATGATTTTG
CAACTTATTACTGTCAAGTTTTTGAGTGGTTCGGCCCAGGGACCAAGGTG
GAGATCAAA;

PCIN63-71J2a; VL

SEQ ID NO: 297
GCCATCCGGATGACCCAGTCTCCTGCCACCCTGTCTGCATCTGTGGGAGA
CAGAGTCACCATCACTTGCCGGGCAGGTCAGGGCATTGGAAGTGATTTAG
CCTGGTATCAGCAGAAATCAGGGCAAGCCCCTAAACTTCTAATCTTTAAG
GCGTCTAATTTAAAAAATGGAGTCCCGCCAAGATTTAGCGGCAGTGGATT
TCACACAGACTTCACTCTCACCATCAGCGGCCTGCAGCCTGATGATTTTG
CGACTTATTACTGCCAAGTTTTGGAAACATTCGGCCAAGGGACCAAGGTG
GAGATCAAA;

PCIN63-71K; VL

SEQ ID NO: 298
GCCATCCGGATGACCCAGTCTCCTGCCACCCTGTCTGCATCTGTGGGAGA
CAGAGTCACCATCACTTGCCGGGCAGGTCAGGGCATTGGAAGTGATTTAG
CCTGGTATCAGCAGAAACCTGGGCAAGCCCCTAAACTTCTAATCTTTAAG
GCGTCTCGTTTAAAAAATGGAGTCCCGACAAGATTCACCGGCAGTGGATT
TCACACAGAGTTCACTCTCACCATCAGCGGCCTGCAGTCTGATGATTTTG
CGACTTATTACTGCCAAGTTTTGGAAACATTCGGCCAAGGGACCAAGGTG
GAGATCAAA;

PCIN63-71L; VL

SEQ ID NO: 299
GCCATCCGGATGACCCAGTCTCCTGCCACCCTGTCTGCATCTGTGGGAGA
CAGAGTCACCATCACTTGCCGGGCAGGTCAGGGCATTGGAAGTGATTTAG
CCTGGTATCAGCAGAAACCTGGGCAAGCCCCTAAACTTCTAATCTTTAAG
GCGTCTCGTTTAAAAAATGGAGTCCCGACAAGATTCACCGGCAGTGGATT
TCACACAGAGTTCACTCTCACCATCAGCGGCCTGCAGTCTGATGATTTTG
CGACTTATTACTGCCAAGTTTTGGAAACATTCGGCCAAGGGACCAAGGTG
GAGATCAAA;

PCIN63-71M1a; VL

SEQ ID NO: 300
GCCATCCGGATGACCCAGTCTCCTGCCACCCTGTCTGCATCTGTGGGAGA
CAGAGTCACCATCACTTGCCGGGCAGGTCAGGGCATTGGAAGTGATTTAG
CCTGGTATCAGCAGAAATCAGGGCAAGCCCCTAAACTTCTTATCTTTAAG
GCGTCTAATTTAAAAAATGGAGTCCCGCCAAGATTCAGCGGCAGTGGATT
TCACACAGACTTCACTCTCACCATCAGCGGCCTGCAGCCTGATGATTTTG
CGACTTATTACTGCCAAGTTTTGGAAACATTCGGCCAAGGGACCAAGGTG
GAGATCAAA;

PCIN63-71N1a; VL
SEQ ID NO: 301
GCCATCCGGATGACCCAGTCTCCTGCCACCCTGTCTGCATCTGTAGGAGA
CAAAGTCACCATCACTTGCCGGGCAAGTCAGGGCATTGGAAATAATTTAG
GCTGGTATCAGCAGAAACCAGGGCAGGCCCCTAAACTCCTCATCTTTAAG
GCGTCTAATTCAAAAGATGGAGTCCCACCAAGATTCAGCGGTAGTGGATC
TCATACAGAGTTCACTCTCACCATCAACAGCCTGCAGCCTGATGATTTTG
CAACTTATTACTGCCAGGTTTATCAAACCTTCGGCCAAGGGACCAAGGTG
GAGATCAAA;

PCIN63-71O; VL
SEQ ID NO: 302
GCCATCCGGATGACCCAGTCTCCTGCCACCCTGTCTGCATCTGTGGGAGA
CAGAGTCACCTTGACTTGCCGGGCAGGGCAGGGCATTGGAAGTGATTTAG
GGTGGTATCAGCAGAAACCAGGGAAAGCCCCTAAACTCCTCATACATAAG
GCGTCTAATTTACTAAATGGGGTGCCATCAAGGTTCAGCGGCAGTGGATT
TCACACGGAATTCACTCTCACCATCAGCAGCCTGCAACCTGATGATTTTG
CAACTTATTACTGTCAAGTTTTTGAATGGTTCGGCCAAGGGACCAAGGTG
GAGATCAAA;

PCIN63-71P; VL
SEQ ID NO: 303
GCCATCCGGATGACCCAGTCTCCTGCCACCCTGTCTGCATCTGTGGGAGA
CAGAGTCACCTTGACTTGCCGGGCAGGGCAGGGCATTGGAAGTGATTTAG
GGTGGTATCAGCAGAAGCCAGGAAAAGCCCCTAAACTCCTCATACATAAG
GCGTCTAATTTAGCAAATGGGGTGCCATCAAGGTTCAGCGGCCGTGGATT
TCACACAGAGTTCACTCTCACCATCAGCAGCCTGCAGCCTGATGATTTTG
CAACTTATTACTGTCAAGTTTTTGAATGGTTCGGCCAAGGGACCAAGGTG
GAGATCAAA;

PCIN63-77B1b; VL
SEQ ID NO: 304
GCCATCCGGATGACCCAGTCTCCTGCCACCCTGTCTGCATCTGTGGGAGA
CAGAGTCACCATCACTTGCCGGGCAGGTCAGGGCATTGGAAGTGATTTAG
CCTGGTATCAGCAGAAACCAGGGCAAGCCCCTAAACTTCTAATCTTTAAG
GCGTCTAATTTAAAAAATGGAGTCCCGACAAGATTCACCGGCAGTGGATT
TCACACAGACTTCACTCTCACCATCAGCGGCCTGCAGTCTGATGATTTTG
CGACTTATTACTGCCAAGTTTTGGAAACATTCGGCCAAGGGACCAAGGTG
GAGATCAAA;

PCIN63-77C; VL
SEQ ID NO: 305
GCCATCCGGATGACCCAGTCTCCTGCCACCCTGTCTGCATCTGTGGGAGA
TAGAGTCACCATCACTTGCCGGGCAGGTCAGGGCATTGGAAGTGATTTAG
CCTGGTATCAGCAGAAACCAGGGCAAGCCCCTAAACTTCTAATCTTTAAG
GCGTCCAATTTAAAAAAAGGAGTCCCGACAAGATTCACCGGCAGTGGATT
TCACACAGACTTCACTCTCACCATCAGCGGCCTGCAGTCTGATGATTTTG
CGACTTATTACTGCCAAGTTCTGGAAACATTCGGCCAAGGGACCAAGGTG
GAGATCAAA;

PCIN63-77D; VL
SEQ ID NO: 306
GCCATCCGGATGACCCAGTCTCCTGCCACCCTGTCTGCATTTGTAGGAGA
CAGAGTCACCATCACTTGCCGGGCTAGTCAGGGCATTGGAGATGATTTAG
GCTGGTATCAGCAAAAACCAGGGAAAGTCCCTAAGCCCCTGATCTTTAAG
GCGTCTAATTTAAAAGATGGGGTCCCATCGAGGTTCAGCGGCAGCGGATT
TGGGACAGATTTCACTCTCACCATCAACAACCTGCAGCCTGATGACTTTG
CAACTTACTATTGCCAAGCCTATGAAAGCTTCGGCCAAGGGACCAAGGTG
GAGATCAAA;

PCIN63-UCA-HC; VH
SEQ ID NO: 307
QVQLVQSGAEVKKPGASVKVSCKASGYTFTGYYMHWVRQAPGQGLEWMGW
INPNSGGTNYAQKFQGRVTMTRDTSISTAYMELSRLRSDDTAVYYCARDS
SRQQLEWWFDPWGQGTLVTVSS;

PCIN63-UCA-KC1; VL
SEQ ID NO: 308
DIQMTQSPSTLSASVGDRVTITCRASQSISSWLAWYQQKPGKAPKLLIYK
ASSLESGVPSRFSGSGSGTEFTLTISSLQPDDFATYYCQQSEAFGQGTKV
EIK;

PCIN63-UCA-KC2; VL
SEQ ID NO: 309
DIQMTQSPSTLSASVGDRVTITCRASQSISSWLAWYQQKPGKAPKLLIYK
ASSLESGVPSRFSGSGSGTEFTLTISSLQPDDFATYYCQLYETFGQGTKV
EIK;

Motif #1
SEQ ID NO: 310
AXFIXXV;

Motif #1
SEQ ID NO: 311
AXYIXXF;

Motif #1
SEQ ID NO: 312
DXFVXXV;

Motif #1
SEQ ID NO: 313
SXLIXXW;

Motif #1
SEQ ID NO: 314
SXYIXXF;

Motif #1
SEQ ID NO: 315
TXLIXXW;

Motif #2
SEQ ID NO: 316
NXINXAP;

Motif #2
SEQ ID NO: 317
NXINXAR;

Motif #2
SEQ ID NO: 318
NXLHXAV;

Motif #4
SEQ ID NO: 319
GXGXGXDXA;

-continued

Motif #4
SEQ ID NO: 320
GXGXGXDXG;

Motif #4
SEQ ID NO: 321
GXHXGXDXA;

Motif #4
SEQ ID NO: 322
SXGXGXDXG;

Motif #4
SEQ ID NO: 323
SXGXGXKXG;

Motif #4
SEQ ID NO: 324
SXGXGXNXG;

Motif #5
SEQ ID NO: 325
FXXXNXKD;

Motif #5
SEQ ID NO: 326
FXXXNXKK;

Motif #5
SEQ ID NO: 327
FXXXNXKN;

Motif #5
SEQ ID NO: 328
FXXXRXKN;

Motif #5
SEQ ID NO: 329
FXXXSXKD;

-continued

Motif #5
SEQ ID NO: 330
FXXXTXKD;

Motif #5
SEQ ID NO: 331
HXXXNXAN;

Motif #5
SEQ ID NO: 332
HXXXNXIN;

Motif #5
SEQ ID NO: 333
HXXXNXLN;

Motif #5
SEQ ID NO: 334
YXXXNXKS;

Motif #6
SEQ ID NO: 335
FGXD;

Motif #6
SEQ ID NO: 336
FHXD;

Motif #6
SEQ ID NO: 337
FHXE;

Motif #6
SEQ ID NO: 338
SGXE;

Motif #6
SEQ ID NO: 339
SHXE;

What is claimed is:

1. A method of neutralizing a human immunodeficiency virus (HIV) comprising contacting the virus with a sufficient amount of an isolated monoclonal antibody that specifically binds to HIV envelope glycoprotein (Env) and comprises a heavy chain variable region (VH) comprising a VH complementarity determining region 1 (CDR1), VH CDR2, and VH CDR3 and a light chain variable region (VL) comprising a VL CDR1, VL CDR2, and VL CDR3, wherein (a) the VH CDR1 comprises any one of the amino acid sequences of SEQ ID NOs: 1-18;

(b) the VH CDR2 comprises any one of the amino acid sequences of SEQ ID NOs: 19-36;

(c) the VH CDR3 comprises any one of the amino acid sequences of SEQ ID NOs: 37-54;

(d) the VL CDR1 comprises any one of the amino acid sequences of SEQ ID NOs: 55-72;

(e) the VL CDR2 comprises any one of the amino acid sequences of SEQ ID NOs: 73-90; and (f) the VL CDR3 comprises any one of the amino acid sequences of SEQ ID NOs: 91-108.

2. A method for passively immunizing a subject comprising administering to the subject in need thereof an effective amount of a monoclonal antibody or an isolated polynucleotide encoding the antibody, wherein the antibody specifically binds to human immunodeficiency virus envelope glycoprotein (HIV Env) and comprises a heavy chain variable region (VH) comprising a VH complementarity determining region 1 (CDR1), VH CDR2, and VH CDR3 and a light chain variable region (VL) comprising a VL CDR1, VL CDR2, and VL CDR3, wherein (a) the VH CDR1 comprises any one of the amino acid sequences of SEQ ID NOs: 1-18;

(b) the VH CDR2 comprises any one of the amino acid sequences of SEQ ID NOs: 19-36;

(c) the VH CDR3 comprises any one of the amino acid sequences of SEQ ID NOs: 37-54;

(d) the VL CDR1 comprises any one of the amino acid sequences of SEQ ID NOs: 55-72;

(e) the VL CDR2 comprises any one of the amino acid sequences of SEQ ID NOs: 73-90; and (f) the VL CDR3 comprises any one of the amino acid sequences of SEQ ID NOs: 91-108.

3. A method of treating human immunodeficiency virus/acquired immunodeficiency syndrome comprising administering to a subject in need thereof a therapeutically sufficient amount of a monoclonal antibody or an isolated polynucleotide encoding the antibody, wherein the antibody specifically binds to human immunodeficiency virus envelope glycoprotein (HIV Env) and comprises a heavy chain variable region (VH) comprising a VH complementarity determining region 1 (CDR1), VH CDR2, and VH CDR3 and a light chain variable region (VL) comprising a VL CDR1, VL CDR2, and VL CDR3, wherein (a) the VH CDR1 comprises any one of the amino acid sequences of SEQ ID NOs: 1-18;

(b) the VH CDR2 comprises any one of the amino acid sequences of SEQ ID NOs: 19-36;

(c) the VH CDR3 comprises any one of the amino acid sequences of SEQ ID NOs: 37-54;

(d) the VL CDR1 comprises any one of the amino acid sequences of SEQ ID NOs: 55-72;

(e) the VL CDR2 comprises any one of the amino acid sequences of SEQ ID NOs: 73-90; and (f) the VL CDR3 comprises any one of the amino acid sequences of SEQ ID NOs: 91-108.

4. The method of claim 3, further comprising administering at least one additional therapeutic agent.

5. The method of claim 2, wherein the VH CDR1, VH CDR2, VH CDR3, VL CDR1, VL CDR2, and VL CDR3 comprise the amino acid sequences of (a) SEQ ID NOs: 1, 19, 37, 55, 73, and 91, respectively;

(b) SEQ ID NOs: 2, 20, 38, 56, 74, and 92, respectively;

(c) SEQ ID NOs: 3, 21, 39, 57, 75, and 93, respectively;

(d) SEQ ID NOs: 4, 22, 40, 58, 76, and 94, respectively;

(e) SEQ ID NOs: 5, 23, 41, 59, 77, and 95, respectively;

(f) SEQ ID NOs: 6, 24, 42, 60, 78, and 96, respectively;

(g) SEQ ID NOs: 7, 25, 43, 61, 79, and 97, respectively;

(h) SEQ ID NOs: 8, 26, 44, 62, 80, and 98, respectively;

(i) SEQ ID NOs: 9, 27, 45, 63, 81, and 99, respectively;

(j) SEQ ID NOs: 10, 28, 46, 64, 82, and 100, respectively;

(k) SEQ ID NOs: 11, 29, 47, 65, 83, and 101, respectively;

(l) SEQ ID NOs: 12, 30, 48, 66, 84, and 102, respectively;

(m) SEQ ID NOs: 13, 31, 49, 67, 85, and 103, respectively;

(n) SEQ ID NOs: 14, 32, 50, 68, 86, and 104, respectively;

(o) SEQ ID NOs: 15, 33, 51, 69, 87, and 105, respectively;

(p) SEQ ID NOs: 16, 34, 52, 70, 88, and 106, respectively;

(q) SEQ ID NOs: 17, 35, 53, 71, 89, and 107, respectively; or (r) SEQ ID NOs: 18, 36, 54, 72, 90, and 108, respectively.

6. The method of claim 2, wherein the VH comprises one or more of (a) the amino acid sequences of SEQ ID NOs: 109-126 or 310-315 at Kabat positions H31-H37;

(b) the amino acid sequences of SEQ ID NOs: 127-144 or 316-318 at Kabat positions H52-H56; and (c) the amino acid sequences of SEQ ID NOs: 145-162 at Kabat positions H61-H62; and wherein the VL comprises one or more of (d) the amino acid sequences of SEQ ID NOs: 163-180 or 319-324 at Kabat positions L26-L34;

(e) the amino acid sequences of SEQ ID NOs: 181-198 or 325-334 at Kabat positions L49-L56;

(f) the amino acid sequences of SEQ ID NOs: 199-216 or 335-339 at Kabat positions L67-L70; and (g) the amino acid sequences of SEQ ID NOs: 217-234 at Kabat positions L89-L97.

7. The method of claim 2, wherein (a) the VH comprises an amino acid sequence that is at least 95% 90% identical to any one of SEQ ID NOs: 235-252; and b) the VL comprises an amino acid sequence that is at least 95% 90% identical to any one of SEQ ID NOs: 253-270.

8. The method of claim 2, wherein the VH and VL comprise the amino acid sequences of (a) SEQ ID NOs: 235 and 253, respectively;

(b) SEQ ID NOs: 236 and 254, respectively;

(c) SEQ ID NOs: 237 and 255, respectively;

(d) SEQ ID NOs: 238 and 256, respectively;

(e) SEQ ID NOs: 239 and 257, respectively;

(f) SEQ ID NOs: 240 and 258, respectively;

(g) SEQ ID NOs: 241 and 259, respectively;

(h) SEQ ID NOs: 242 and 260, respectively;

(i) SEQ ID NOs: 243 and 261, respectively;

(j) SEQ ID NOs: 244 and 262, respectively;

(k) SEQ ID NOs: 245 and 263, respectively;

(l) SEQ ID NOs: 246 and 264, respectively;

(m) SEQ ID NOs: 247 and 265, respectively;

(n) SEQ ID NOs: 248 and 266, respectively;

(o) SEQ ID NOs: 249 and 267, respectively;

(p) SEQ ID NOs: 250 and 268, respectively;

(q) SEQ ID NOs: 251 and 269, respectively; or (r) SEQ ID NOs: 252 and 270, respectively.

9. The method of claim 2, wherein the antibody further comprises a heavy and/or light chain constant region.

10. The method of claim 2, wherein the antibody is a chimeric antibody, an antibody fragment, a bispecific antibody, or a trispecific antibody.

11. The method of claim 3, wherein the VH CDR1, VH CDR2, VH CDR3, VL CDR1, VL CDR2, and VL CDR3 comprise the amino acid sequences of (a) SEQ ID NOs: 1, 19, 37, 55, 73, and 91, respectively;

(b) SEQ ID NOs: 2, 20, 38, 56, 74, and 92, respectively;

(c) SEQ ID NOs: 3, 21, 39, 57, 75, and 93, respectively;

(d) SEQ ID NOs: 4, 22, 40, 58, 76, and 94, respectively;

(e) SEQ ID NOs: 5, 23, 41, 59, 77, and 95, respectively;

(f) SEQ ID NOs: 6, 24, 42, 60, 78, and 96, respectively;

(g) SEQ ID NOs: 7, 25, 43, 61, 79, and 97, respectively;

(h) SEQ ID NOs: 8, 26, 44, 62, 80, and 98, respectively;

(i) SEQ ID NOs: 9, 27, 45, 63, 81, and 99, respectively;

(j) SEQ ID NOs: 10, 28, 46, 64, 82, and 100, respectively;

(k) SEQ ID NOs: 11, 29, 47, 65, 83, and 101, respectively;

(l) SEQ ID NOs: 12, 30, 48, 66, 84, and 102, respectively;

(m) SEQ ID NOs: 13, 31, 49, 67, 85, and 103, respectively;

(n) SEQ ID NOs: 14, 32, 50, 68, 86, and 104, respectively;

(o) SEQ ID NOs: 15, 33, 51, 69, 87, and 105, respectively;

(p) SEQ ID NOs: 16, 34, 52, 70, 88, and 106, respectively;

(q) SEQ ID NOs: 17, 35, 53, 71, 89, and 107, respectively; or (r) SEQ ID NOs: 18, 36, 54, 72, 90, and 108, respectively.

12. The method of claim 3, wherein the VH comprises one or more of (a) the amino acid sequences of SEQ ID NOs: 109-126 or 310-315 at Kabat positions H31-H37;

(b) the amino acid sequences of SEQ ID NOs: 127-144 or 316-318 at Kabat positions H52-H56; and (c) the amino acid sequences of SEQ ID NOs: 145-162 at Kabat positions H61-H62; and wherein the VL comprises one or more of (d) the amino acid sequences of SEQ ID NOs: 163-180 or 319-324 at Kabat positions L26-L34;

(e) the amino acid sequences of SEQ ID NOs: 181-198 or 325-334 at Kabat positions L49-L56;

(f) the amino acid sequences of SEQ ID NOs: 199-216 or 335-339 at Kabat positions L67-L70; and (g) the amino acid sequences of SEQ ID NOs: 217-234 at Kabat positions L89-L97.

13. The method of claim 3, wherein (a) the VH comprises an amino acid sequence that is at least 95% 90% identical to any one of SEQ ID NOs: 235-252; and b) the VL comprises an amino acid sequence that is at least 95% 90% identical to any one of SEQ ID NOs: 253-270.

14. The method of claim 3, wherein the VH and VL comprise the amino acid sequences of (a) SEQ ID NOs: 235 and 253, respectively;

(b) SEQ ID NOs: 236 and 254, respectively;

(c) SEQ ID NOs: 237 and 255, respectively;

(d) SEQ ID NOs: 238 and 256, respectively;

(e) SEQ ID NOs: 239 and 257, respectively;

(f) SEQ ID NOs: 240 and 258, respectively;

(g) SEQ ID NOs: 241 and 259, respectively;

(h) SEQ ID NOs: 242 and 260, respectively;

(i) SEQ ID NOs: 243 and 261, respectively;

(j) SEQ ID NOs: 244 and 262, respectively;

(k) SEQ ID NOs: 245 and 263, respectively;

(l) SEQ ID NOs: 246 and 264, respectively;

(m) SEQ ID NOs: 247 and 265, respectively;

(n) SEQ ID NOs: 248 and 266, respectively;

(o) SEQ ID NOs: 249 and 267, respectively;

(p) SEQ ID NOs: 250 and 268, respectively;

(q) SEQ ID NOs: 251 and 269, respectively; or (r) SEQ ID NOs: 252 and 270, respectively.

15. The method of claim 3, wherein the antibody further comprises a heavy and/or light chain constant region.

16. The method of claim 3, wherein the antibody is a chimeric antibody, an antibody fragment, a bispecific antibody, or a trispecific antibody.

* * * * *

SEQUENCE LISTING

<160> NUMBER OF SEQ ID NOS: 555

<210> SEQ ID NO 1
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 1

Gly Tyr Thr Phe Thr Ala Cys Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 2

Gly Tyr Thr Phe Thr Ala Tyr Phe
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 3

Gly Tyr Thr Phe Thr Ser Cys Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 4

Gly Tyr Thr Phe Thr Ala Cys Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 5

Gly Tyr Ser Phe Thr Asp Tyr Phe
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 6

Gly Tyr Thr Phe Asn Ser Cys Leu
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 7

Gly Tyr Thr Phe Thr Ser Cys Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 8

Gly Tyr Thr Phe Asn Ser Cys Leu
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 9

Gly Tyr Thr Phe Asn Ser Cys Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 10

Gly Tyr Thr Phe Thr Ser Cys Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 11

Gly Tyr Thr Phe Thr Ser Cys Tyr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 12

Gly Tyr Thr Phe Thr Ser Cys Tyr
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 13

Gly Tyr Thr Phe Asn Thr Cys Leu
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 14

Gly Tyr Thr Phe Asn Thr Cys Leu
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 15

Gly Tyr Thr Phe Asn Thr Cys Leu
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 16

Gly Tyr Thr Phe Ser Ser Cys Tyr
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 17

Gly Tyr Thr Phe Thr Ala Cys Tyr
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 18

Gly Tyr Thr Phe Thr Ser Cys Tyr
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 19

Ile Asn Pro Ile Asn Gly Ala Arg
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 20

Ile Asn Pro Leu His Gly Ala Val
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 21

Leu Asn Pro Ile Asn Gly Ala Arg
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 22

Leu Asn Pro Ile Asn Gly Ala Arg
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 23

Ile Asn Pro Ile Asn Gly Ala Pro
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 24

Ile Asn Pro Leu His Gly Ala Val
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 25

Leu Asn Pro Ile Asn Gly Ala Arg
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 26

Ile Asn Pro Leu His Gly Ala Val
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 27

Ile Asn Pro Leu His Gly Ala Val 1 5

<210> SEQ ID NO 28
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 28

Leu Asn Pro Ile Asn Gly Ala Arg
1 5

<210> SEQ ID NO 29
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 29

Leu Asn Pro Ile Asn Gly Ala Arg
1 5

<210> SEQ ID NO 30
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 30

Leu Asn Pro Ile Asn Gly Ala Arg
1 5

<210> SEQ ID NO 31
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 31

Ile Asn Pro Leu His Gly Ala Val
1 5

<210> SEQ ID NO 32
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 32

Ile Asn Pro Leu His Gly Ala Val
1 5

<210> SEQ ID NO 33
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 33

Ile Asn Pro Leu His Gly Ala Val
1 5

<210> SEQ ID NO 34
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 34

Leu Asn Pro Ile Asn Gly Ala Arg
1 5

<210> SEQ ID NO 35
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 35

Ile Asn Pro Ile Asn Gly Ala Arg
1 5

<210> SEQ ID NO 36
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 36

Leu Asn Pro Ile Asn Gly Ala Arg
1 5

<210> SEQ ID NO 37
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 37

Thr Arg Asp Ser Ser Arg Arg Asp Thr Asn Trp Trp Leu Asp Pro
1 5 10 15

<210> SEQ ID NO 38
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 38

Thr Thr His Ser Ser Ser Arg Asp Phe Gln Trp Ser Leu Asp Pro
1 5 10 15

<210> SEQ ID NO 39
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 39

Thr Arg Asp Ser Ser Arg Arg Asp Thr Asn Trp Trp Leu Asp Pro
1 5 10 15

<210> SEQ ID NO 40
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 40

Thr Arg Asp Ser Ser Arg Arg Asp Thr Asn Trp Trp Leu Asp Pro
1 5 10 15

<210> SEQ ID NO 41
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 41

Thr Arg Asp Ser Ser Arg Gln Gln Arg Asp Trp Trp Leu Asp Pro
1 5 10 15

<210> SEQ ID NO 42
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 42

Thr Arg Asp Ala Ser Arg Asp Asp Arg Ala Trp Arg Leu Asp Pro
1 5 10 15

<210> SEQ ID NO 43
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 43

Ala Arg Asp Ser Ser Arg Glu Glu Thr Asn Trp Trp Leu Asp Pro
1 5 10 15

<210> SEQ ID NO 44
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 44

Thr Arg Asp Ala Ser Arg Asp Asp Arg Ala Trp Arg Leu Asp Pro
1 5 10 15

<210> SEQ ID NO 45
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 45

Thr Arg Asp Ala Ser Arg Asp Asp Arg Ala Trp Arg Leu Asp Pro
1 5 10 15

<210> SEQ ID NO 46
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 46

Thr Arg Asp Ser Ser Arg Asp Glu Thr Asn Trp Trp Leu Asp Pro
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 47

Thr Arg Asp Ser Ser Arg Asp Glu Thr Asn Trp Trp Leu Asp Pro
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 48

Ala Arg Asp Ser Ser Arg Asp Glu Thr Asn Trp Trp Leu Asp Pro
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 49

Thr Arg Asp Ser Ser Arg Gly Asn Thr Glu Trp Arg Leu Asp Pro
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 50

Thr Arg Asp Ser Ser Arg Asp Asn Leu Glu Trp Arg Leu Asp Pro
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 51

Thr Arg Asp Ser Ser Arg Gly Asp Thr Glu Trp Arg Leu Asp Pro
1               5                   10                  15

<210> SEQ ID NO 52

<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 52

Thr Arg Asp Ser Ser Arg Asp Glu Thr Asn Trp Trp Leu Asp Pro
1 5 10 15

<210> SEQ ID NO 53
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 53

Thr Arg Asp Ser Ser Arg Arg Asp Leu Glu Trp Arg Leu Asp Pro
1 5 10 15

<210> SEQ ID NO 54
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 54

Ala Arg Asp Ser Ser Arg Asp Glu Thr Asn Trp Trp Leu Asp Pro
1 5 10 15

<210> SEQ ID NO 55
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 55

Gln Gly Ile Gly Ser Asp
1 5

<210> SEQ ID NO 56
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 56

Gln Gly Ile Gly Asn Lys
1 5

<210> SEQ ID NO 57
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 57

Gln Gly Ile Gly Ser Asp
1 5

<210> SEQ ID NO 58
<211> LENGTH: 6

<212> TYPE: PRT
<213> ORGANISM: Artificial Sequence
<220> FEATURE:
<223> OTHER INFORMATION: Synthetic polypeptide

<400> SEQUENCE: 58

Gln Gly Ile Gly Ser Asp
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 59

Gln His Ile Gly Asn Asp
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 60

Gln Gly Ile Gly Ser Asp
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 61

Gln Gly Ile Gly Ser Asp
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 62

Gln Gly Ile Gly Ser Asp
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 63

Gln Gly Ile Gly Ser Asp
1               5

<210> SEQ ID NO 64
<211> LENGTH: 6
<212> TYPE: PRT

<213> ORGANISM: Artificial Sequence
<220> FEATURE:
<223> OTHER INFORMATION: Synthetic polypeptide

<400> SEQUENCE: 64

Gln Gly Ile Gly Ser Asp
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 65

Gln Gly Ile Gly Ser Asp
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 66

Gln Gly Ile Gly Ser Asp
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 67

Gln Gly Ile Gly Asn Asn
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 68

Gln Gly Ile Gly Ser Asp
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 69

Gln Gly Ile Gly Ser Asp
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 70

Gln Gly Ile Gly Ser Asp
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 71

Gln Gly Ile Gly Ser Asp
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 72

Gln Gly Ile Gly Asp Asp
1               5

<210> SEQ ID NO 73
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 73

Lys Ala Ser
1

<210> SEQ ID NO 74
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 74

Lys Ala Ser
1

<210> SEQ ID NO 75
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 75

Lys Ala Ser
1

<210> SEQ ID NO 76
<211> LENGTH: 3
<212> TYPE: PRT
<213> ORGANISM: Artificial Sequence
<220> FEATURE:

<223> OTHER INFORMATION: Synthetic polypeptide

<400> SEQUENCE: 76

Lys Ala Ser
1

<210> SEQ ID NO 77
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 77

Gln Ala Ser
1

<210> SEQ ID NO 78
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 78

Lys Ala Ser
1

<210> SEQ ID NO 79
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 79

Lys Ala Ser
1

<210> SEQ ID NO 80
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 80

Lys Ala Ser
1

<210> SEQ ID NO 81
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 81

Lys Ala Ser
1

<210> SEQ ID NO 82
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 82

Lys Ala Ser
1

<210> SEQ ID NO 83
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 83

Lys Ala Ser
1

<210> SEQ ID NO 84
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 84

Lys Ala Ser
1

<210> SEQ ID NO 85
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 85

Lys Ala Ser
1

<210> SEQ ID NO 86
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 86

Lys Ala Ser
1

<210> SEQ ID NO 87
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 87

Lys Ala Ser
1

<210> SEQ ID NO 88
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 88

Lys Ala Pro
1

<210> SEQ ID NO 89
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 89

Lys Ala Ser
1

<210> SEQ ID NO 90
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 90

Lys Ala Ser
1

<210> SEQ ID NO 91
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 91

Gln Val Leu Glu Thr
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 92

Gln Val Tyr Glu Ser
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 93

Gln Val Leu Glu Thr
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 94

Gln Val Leu Glu Thr
1 5

<210> SEQ ID NO 95
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 95

Gln Val Tyr Glu Ser
1 5

<210> SEQ ID NO 96
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 96

Gln Val Val Glu Trp
1 5

<210> SEQ ID NO 97
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 97

Gln Val Leu Glu Thr
1 5

<210> SEQ ID NO 98
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 98

Gln Val Phe Glu Trp
1 5

<210> SEQ ID NO 99
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 99

Gln Val Leu Glu Thr
1 5

<210> SEQ ID NO 100
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 100

Gln Val Leu Glu Thr
1               5

<210> SEQ ID NO 101
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 101

Gln Val Leu Glu Thr
1               5

<210> SEQ ID NO 102
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 102

Gln Val Leu Glu Thr
1               5

<210> SEQ ID NO 103
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 103

Gln Val Tyr Gln Thr
1               5

<210> SEQ ID NO 104
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 104

Gln Val Phe Glu Trp
1               5

<210> SEQ ID NO 105
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 105

Gln Val Phe Glu Trp
1               5

<210> SEQ ID NO 106
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 106

Gln Val Leu Glu Thr 1 5

<210> SEQ ID NO 107
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 107

Gln Val Leu Glu Thr
1 5

<210> SEQ ID NO 108
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 108

Gln Ala Tyr Glu Ser
1 5

<210> SEQ ID NO 109
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 109

Ala Cys Tyr Ile His Trp Phe
1 5

<210> SEQ ID NO 110
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 110

Ala Tyr Phe Ile His Trp Val
1 5

<210> SEQ ID NO 111
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 111

Ser Cys Tyr Ile His Trp Phe
1 5

<210> SEQ ID NO 112
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 112

Ala Cys Tyr Ile His Trp Phe
1 5

<210> SEQ ID NO 113
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 113

Asp Tyr Phe Val His Trp Val
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 114

Ser Cys Leu Ile His Trp Trp
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 115

Ser Cys Tyr Ile His Trp Phe
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 116

Ser Cys Leu Ile His Trp Trp
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 117

Ser Cys Leu Ile His Trp Trp
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 118

Ser Cys Tyr Ile His Trp Phe
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 119

Ser Cys Tyr Ile His Trp Phe
1 5

<210> SEQ ID NO 120
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 120

Ser Cys Tyr Ile His Trp Phe
1 5

<210> SEQ ID NO 121
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 121

Thr Cys Leu Ile His Trp Trp
1 5

<210> SEQ ID NO 122
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 122

Thr Cys Leu Ile His Trp Trp
1 5

<210> SEQ ID NO 123
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 123

Thr Cys Leu Ile His Trp Trp
1 5

<210> SEQ ID NO 124
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 124

Ser Cys Tyr Ile His Trp Phe
1 5

<210> SEQ ID NO 125
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 125

Ala Cys Tyr Ile Gln Trp Phe
1 5

<210> SEQ ID NO 126
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 126

Ser Cys Tyr Ile His Trp Phe
1 5

<210> SEQ ID NO 127
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 127

Asn Ile Asn Ala Arg Asn Asn
1 5

<210> SEQ ID NO 128
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 128

Asn Leu His Ala Val Asn Tyr
1 5

<210> SEQ ID NO 129
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 129

Asn Ile Asn Ala Arg Asn Asn
1 5

<210> SEQ ID NO 130
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 130

Asn Ile Asn Ala Arg Asn Asn
1 5

<210> SEQ ID NO 131

<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 131

Asn Ile Asn Ala Pro Asn Tyr
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 132

Asn Leu His Ala Val Asn Tyr
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 133

Asn Ile Asn Ala Arg Asn Asn
1               5

<210> SEQ ID NO 134
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 134

Asn Leu His Ala Val Asn Tyr
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 135

Asn Leu His Ala Val Asn Tyr
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 136

Asn Ile Asn Ala Arg Asn Asn
1               5

<210> SEQ ID NO 137
<211> LENGTH: 7

<212> TYPE: PRT
<213> ORGANISM: Artificial Sequence
<220> FEATURE:
<223> OTHER INFORMATION: Synthetic polypeptide

<400> SEQUENCE: 137

Asn Ile Asn Ala Arg Asn Asn
1 5

<210> SEQ ID NO 138
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 138

Asn Ile Asn Ala Arg Asn Gln
1 5

<210> SEQ ID NO 139
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 139

Asn Leu His Ala Val Asn Tyr
1 5

<210> SEQ ID NO 140
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 140

Asn Leu His Ala Val Asn Tyr
1 5

<210> SEQ ID NO 141
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 141

Asn Leu His Ala Val Asn Tyr
1 5

<210> SEQ ID NO 142
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 142

Asn Ile Asn Ala Arg Asn Gln
1 5

<210> SEQ ID NO 143
<211> LENGTH: 7
<212> TYPE: PRT

<213> ORGANISM: Artificial Sequence
<220> FEATURE:
<223> OTHER INFORMATION: Synthetic polypeptide

<400> SEQUENCE: 143

Asn Ile Asn Ala Arg Asn Asn
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 144

Asn Ile Asn Ala Arg Asn His
1               5

<210> SEQ ID NO 145
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 145

Pro Arg Lys
1

<210> SEQ ID NO 146
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 146

Ala His Lys
1

<210> SEQ ID NO 147
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 147

Pro His Lys
1

<210> SEQ ID NO 148
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 148

Pro His Lys
1

<210> SEQ ID NO 149
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 149

Ala Pro Asn
1

<210> SEQ ID NO 150
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 150

Ala His Gln
1

<210> SEQ ID NO 151
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 151

Pro Tyr Gln
1

<210> SEQ ID NO 152
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 152

Ala His Gln
1

<210> SEQ ID NO 153
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 153

Ala His Gln
1

<210> SEQ ID NO 154
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 154

Pro Tyr Gln
1

<210> SEQ ID NO 155
<211> LENGTH: 3
<212> TYPE: PRT
<213> ORGANISM: Artificial Sequence
<220> FEATURE:

<223> OTHER INFORMATION: Synthetic polypeptide

<400> SEQUENCE: 155

Pro Tyr Gln
1

<210> SEQ ID NO 156
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 156

Ala Tyr Gln
1

<210> SEQ ID NO 157
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 157

Ala His Asn
1

<210> SEQ ID NO 158
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 158

Ala His Gln
1

<210> SEQ ID NO 159
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 159

Ala His Gln
1

<210> SEQ ID NO 160
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 160

Ala Tyr Gln
1

<210> SEQ ID NO 161
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 161

Pro Gln Thr
1

<210> SEQ ID NO 162
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 162

Ala Tyr Gln
1

<210> SEQ ID NO 163
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 163

Ser Gly Gly Asp Gly
1 5

<210> SEQ ID NO 164
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 164

Ser Gly Gly Lys Gly
1 5

<210> SEQ ID NO 165
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 165

Gly Gly Gly Asp Ala
1 5

<210> SEQ ID NO 166
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 166

Gly Gly Gly Asp Ala
1 5

<210> SEQ ID NO 167
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 167

Gly His Gly Asp Ala
1 5

<210> SEQ ID NO 168
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 168

Gly Gly Gly Asp Gly
1 5

<210> SEQ ID NO 169
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 169

Gly Gly Gly Asp Ala
1 5

<210> SEQ ID NO 170
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 170

Gly Gly Gly Asp Gly
1 5

<210> SEQ ID NO 171
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 171

Gly Gly Gly Asp Ala
1 5

<210> SEQ ID NO 172
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 172

Gly Gly Gly Asp Ala
1 5

<210> SEQ ID NO 173
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 173

Gly Gly Gly Asp Ala
1 5

<210> SEQ ID NO 174
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 174

Gly Gly Gly Asp Ala
1 5

<210> SEQ ID NO 175
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 175

Ser Gly Gly Asn Gly
1 5

<210> SEQ ID NO 176
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 176

Gly Gly Gly Asp Gly
1 5

<210> SEQ ID NO 177
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 177

Gly Gly Gly Asp Gly
1 5

<210> SEQ ID NO 178
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 178

Gly Gly Gly Asp Ala
1 5

<210> SEQ ID NO 179
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 179

Gly Gly Gly Asp Ala
1 5

<210> SEQ ID NO 180
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 180

Ser Gly Gly Asp Gly
1 5

<210> SEQ ID NO 181
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 181

Phe Asn Lys Asp
1

<210> SEQ ID NO 182
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 182

Phe Thr Lys Asp
1

<210> SEQ ID NO 183
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 183

Phe Asn Lys Asn
1

<210> SEQ ID NO 184
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 184

Phe Asn Lys Asn
1

<210> SEQ ID NO 185
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 185

Tyr Asn Lys Ser

1

<210> SEQ ID NO 186
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 186

His Asn Ile Asn
1

<210> SEQ ID NO 187
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 187

Phe Asn Lys Asn
1

<210> SEQ ID NO 188
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 188

His Asn Ile Asn
1

<210> SEQ ID NO 189
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 189

Phe Asn Lys Asn
1

<210> SEQ ID NO 190
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 190

Phe Arg Lys Asn
1

<210> SEQ ID NO 191
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 191

Phe Arg Lys Asn
1

<210> SEQ ID NO 192
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 192

Phe Asn Lys Asn
1

<210> SEQ ID NO 193
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 193

Phe Ser Lys Asp
1

<210> SEQ ID NO 194
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 194

His Asn Leu Asn
1

<210> SEQ ID NO 195
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 195

His Asn Ala Asn
1

<210> SEQ ID NO 196
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 196

Phe Asn Lys Asn
1

<210> SEQ ID NO 197
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 197

Phe Asn Lys Lys
1

<210> SEQ ID NO 198
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 198

Phe Asn Lys Asp
1

<210> SEQ ID NO 199
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 199

Phe His Glu
1

<210> SEQ ID NO 200
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 200

Phe Gly Asp
1

<210> SEQ ID NO 201
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 201

Phe His Asp
1

<210> SEQ ID NO 202
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 202

Phe His Asp
1

<210> SEQ ID NO 203
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 203

Ser Gly Glu
1

<210> SEQ ID NO 204
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 204

Phe His Glu
1

<210> SEQ ID NO 205
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 205

Phe His Asp
1

<210> SEQ ID NO 206
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 206

Phe His Glu
1

<210> SEQ ID NO 207
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 207

Phe His Asp
1

<210> SEQ ID NO 208
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 208

Phe His Glu
1

<210> SEQ ID NO 209
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 209

Phe His Glu
1

<210> SEQ ID NO 210

<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 210

Phe His Asp
1

<210> SEQ ID NO 211
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 211

Ser His Glu
1

<210> SEQ ID NO 212
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 212

Phe His Glu
1

<210> SEQ ID NO 213
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 213

Phe His Glu
1

<210> SEQ ID NO 214
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 214

Phe His Asp
1

<210> SEQ ID NO 215
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 215

Phe His Asp
1

<210> SEQ ID NO 216
<211> LENGTH: 3

<212> TYPE: PRT
<213> ORGANISM: Artificial Sequence
<220> FEATURE:
<223> OTHER INFORMATION: Synthetic polypeptide

<400> SEQUENCE: 216

Phe Gly Asp
1

<210> SEQ ID NO 217
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 217

Gln Val Leu Glu Thr
1 5

<210> SEQ ID NO 218
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 218

Gln Val Tyr Glu Ser
1 5

<210> SEQ ID NO 219
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 219

Gln Val Leu Glu Thr
1 5

<210> SEQ ID NO 220
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 220

Gln Val Leu Glu Thr
1 5

<210> SEQ ID NO 221
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 221

Gln Val Tyr Glu Ser
1 5

<210> SEQ ID NO 222
<211> LENGTH: 5
<212> TYPE: PRT

<213> ORGANISM: Artificial Sequence
<220> FEATURE:
<223> OTHER INFORMATION: Synthetic polypeptide

<400> SEQUENCE: 222

Gln Val Val Glu Trp
1               5

<210> SEQ ID NO 223
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 223

Gln Val Leu Glu Thr
1               5

<210> SEQ ID NO 224
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 224

Gln Val Phe Glu Trp
1               5

<210> SEQ ID NO 225
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 225

Gln Val Leu Glu Thr
1               5

<210> SEQ ID NO 226
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 226

Gln Val Leu Glu Thr
1               5

<210> SEQ ID NO 227
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 227

Gln Val Leu Glu Thr
1               5

<210> SEQ ID NO 228
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 228

Gln Val Leu Glu Thr
1 5

<210> SEQ ID NO 229
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 229

Gln Val Tyr Gln Thr
1 5

<210> SEQ ID NO 230
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 230

Gln Val Phe Glu Trp
1 5

<210> SEQ ID NO 231
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 231

Gln Val Phe Glu Trp
1 5

<210> SEQ ID NO 232
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 232

Gln Val Leu Glu Thr
1 5

<210> SEQ ID NO 233
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 233

Gln Val Leu Glu Thr
1 5

<210> SEQ ID NO 234
<211> LENGTH: 5
<212> TYPE: PRT
<213> ORGANISM: Artificial Sequence
<220> FEATURE:

<223> OTHER INFORMATION: Synthetic polypeptide

<400> SEQUENCE: 234

Gln Ala Tyr Glu Ser
1 5

<210> SEQ ID NO 235
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 235

Gln Val Gln Leu Val Gln Ser Gly Ala Glu Val Lys Lys Pro Gly Ala
1 5 10 15

Ser Met Arg Val Ser Cys Lys Ala Ser Gly Tyr Thr Phe Thr Ala Cys
20 25 30

Tyr Ile His Trp Phe Arg Gln Ala Pro Gly Gln Gly Leu Glu Trp Met
35 40 45

Gly Trp Ile Asn Pro Ile Asn Gly Ala Arg Asn Asn Pro Arg Lys Phe
50 55 60

Gln Gly Arg Val Thr Met Thr Arg Asp Thr Ser Ile Asp Thr Ala Tyr
65 70 75 80

Leu Glu Leu Arg Asn Leu Ala Ser Asp Asp Thr Ala Met Tyr Tyr Cys
85 90 95

Thr Arg Asp Ser Ser Arg Arg Asp Thr Asn Trp Trp Leu Asp Pro Trp
100 105 110

Gly Gln Gly Thr Leu Val Thr Val Ser Ser
115 120

<210> SEQ ID NO 236
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 236

Gln Val Gln Leu Val Gln Ser Gly Ala Glu Val Lys Lys Pro Gly Ala
1 5 10 15

Ser Val Arg Val Ser Cys Lys Ala Ser Gly Tyr Thr Phe Thr Ala Tyr
20 25 30

Phe Ile His Trp Val Arg Gln Ala Pro Gly Gln Gly Leu Glu Trp Val
35 40 45

Gly Trp Ile Asn Pro Leu His Gly Ala Val Asn Tyr Ala His Lys Phe
50 55 60

Gln Gly Arg Val Ser Met Thr Arg Asp Thr Ser Ile Ser Thr Ala Tyr
65 70 75 80

Met Glu Leu Arg Ser Leu Lys Ser Asp Asp Thr Ala Ile Tyr Tyr Cys
85 90 95

Thr Thr His Ser Ser Ser Arg Asp Phe Gln Trp Ser Leu Asp Pro Trp
100 105 110

Gly Gln Gly Thr Leu Val Thr Val Ser Ser
115 120

<210> SEQ ID NO 237
<211> LENGTH: 122
<212> TYPE: PRT

<213> ORGANISM: Artificial Sequence
<220> FEATURE:
<223> OTHER INFORMATION: Synthetic polypeptide

<400> SEQUENCE: 237

```
Gln Val Gln Leu Val Gln Ser Gly Ala Glu Val Lys Lys Pro Gly Ala
1               5                   10                  15

Ser Met Arg Val Ser Cys Lys Ala Ser Gly Tyr Thr Phe Thr Ser Cys
            20                  25                  30

Tyr Ile His Trp Phe Arg Gln Ala Pro Gly Gln Gly Leu Glu Trp Met
        35                  40                  45

Gly Trp Leu Asn Pro Ile Asn Gly Ala Arg Asn Asn Pro His Lys Phe
    50                  55                  60

Gln Gly Arg Ile Thr Leu Thr Arg Asp Thr Ser Thr Asp Thr Ala Tyr
65                  70                  75                  80

Leu Glu Leu Arg Asn Leu Arg Ser Asp Asp Thr Ala Val Tyr Tyr Cys
                85                  90                  95

Thr Arg Asp Ser Ser Arg Arg Asp Thr Asn Trp Trp Leu Asp Pro Trp
            100                 105                 110

Gly Gln Gly Thr Leu Val Thr Val Ser Ser
        115                 120
```

<210> SEQ ID NO 238
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 238

```
Gln Val Gln Leu Val Gln Ser Gly Ala Glu Val Lys Lys Pro Gly Ala
1               5                   10                  15

Ser Met Arg Val Ser Cys Lys Ala Ser Gly Tyr Thr Phe Thr Ala Cys
            20                  25                  30

Tyr Ile His Trp Phe Arg Gln Ala Pro Gly Gln Gly Leu Glu Trp Met
        35                  40                  45

Gly Trp Leu Asn Pro Ile Asn Gly Ala Arg Asn Asn Pro His Lys Phe
    50                  55                  60

Gln Gly Arg Ile Thr Leu Thr Arg Asp Thr Ser Thr Asp Thr Ala Tyr
65                  70                  75                  80

Leu Glu Leu Arg Asn Leu Arg Ser Asp Asp Thr Ala Val Tyr Tyr Cys
                85                  90                  95

Thr Arg Asp Ser Ser Arg Arg Asp Thr Asn Trp Trp Leu Asp Pro Trp
            100                 105                 110

Gly Gln Gly Ala Leu Val Thr Val Ser Ser
        115                 120
```

<210> SEQ ID NO 239
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 239

```
Gln Val Gln Leu Val Gln Ser Gly Ala Glu Val Lys Lys Pro Gly Ala
1               5                   10                  15

Ser Val Arg Val Ser Cys Lys Ala Ser Gly Tyr Ser Phe Thr Asp Tyr
            20                  25                  30
```

Phe Val His Trp Val Arg Gln Ala Pro Gly Gln Gly Leu Glu Trp Val
35 40 45

Gly Trp Ile Asn Pro Ile Asn Gly Ala Pro Asn Tyr Ala Pro Asn Phe
50 55 60

Arg Gly Arg Ile Thr Leu Thr Arg Asp Thr Ser Ile Asp Thr Leu Tyr
65 70 75 80

Met Asp Leu Arg Ser Leu Arg Val Asp Asp Thr Ala Val Tyr Phe Cys
85 90 95

Thr Arg Asp Ser Ser Arg Gln Gln Arg Asp Trp Trp Leu Asp Pro Trp
100 105 110

Gly Gln Gly Thr Leu Val Thr Val Ser Ser
115 120

<210> SEQ ID NO 240
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 240

Gln Val Gln Leu Val Gln Ser Gly Ala Glu Val Lys Lys Pro Gly Ala
1 5 10 15

Ser Val Arg Val Ser Cys Lys Ala Ser Gly Tyr Thr Phe Asn Ser Cys
20 25 30

Leu Ile His Trp Trp Arg Gln Ala Pro Gly Gln Gly Leu Gln Trp Met
35 40 45

Ala Trp Ile Asn Pro Leu His Gly Ala Val Asn Tyr Ala His Gln Phe
50 55 60

Gln Gly Arg Ile Thr Val Thr Arg Asp Thr Ser Ile Asp Thr Ala Tyr
65 70 75 80

Met Glu Leu Arg Gly Leu Arg Ser Asp Asp Thr Ala Thr Tyr Tyr Cys
85 90 95

Thr Arg Asp Ala Ser Arg Asp Asp Arg Ala Trp Arg Leu Asp Pro Trp
100 105 110

Gly Gln Gly Thr Leu Val Thr Val Ser Ser
115 120

<210> SEQ ID NO 241
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 241

Gln Val Gln Leu Val Gln Ser Gly Val Ala Val Lys Lys Pro Gly Ala
1 5 10 15

Ser Val Trp Val Ser Cys Lys Ala Ser Gly Tyr Thr Phe Thr Ser Cys
20 25 30

Tyr Ile His Trp Phe Arg Gln Ala Pro Gly Gln Gly Leu Glu Trp Met
35 40 45

Gly Trp Leu Asn Pro Ile Asn Gly Ala Arg Asn Asn Pro Tyr Gln Phe
50 55 60

Gln Gly Arg Ile Ser Leu Thr Arg Asp Thr Ser Ser Glu Thr Ala Tyr
65 70 75 80

Leu Glu Leu Arg Asn Leu Arg Ser Asp Asp Thr Ala Val Tyr Tyr Cys

```
                85                  90                  95

Ala Arg Asp Ser Ser Arg Glu Glu Thr Asn Trp Trp Leu Asp Pro Trp
            100                 105                 110

Gly Gln Gly Thr Leu Val Thr Val Ser Ser
        115                 120


<210> SEQ ID NO 242
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 242

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Asn Ser Cys
            20                  25                  30

Leu Ile His Trp Trp Arg Gln Ala Pro Gly Gln Gly Leu Gln Trp Met
        35                  40                  45

Ala Trp Ile Asn Pro Leu His Gly Ala Val Asn Tyr Ala His Gln Phe
    50                  55                  60

Gln Gly Arg Ile Thr Val Thr Arg Asp Thr Ser Ile Asp Thr Ala Tyr
65                  70                  75                  80

Met Glu Leu Arg Gly Leu Arg Ser Asp Asp Thr Ala Thr Tyr Tyr Cys
                85                  90                  95

Thr Arg Asp Ala Ser Arg Asp Asp Arg Ala Trp Arg Leu Asp Pro Trp
            100                 105                 110

Gly Gln Gly Thr Leu Val Thr Val Ser Ser
        115                 120


<210> SEQ ID NO 243
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 243

Gln Val Gln Leu Val Gln Ser Gly Ala Glu Val Lys Lys Pro Gly Ala
1               5                   10                  15

Ser Met Arg Val Ser Cys Lys Ala Ser Gly Tyr Thr Phe Thr Ala Cys
            20                  25                  30

Tyr Ile His Trp Phe Arg Gln Ala Pro Gly Gln Gly Leu Glu Trp Met
        35                  40                  45

Gly Trp Leu Asn Pro Ile Asn Gly Ala Arg Asn Asn Pro His Lys Phe
    50                  55                  60

Gln Gly Arg Ile Thr Leu Thr Arg Asp Thr Ser Thr Asp Thr Ala Tyr
65                  70                  75                  80

Leu Glu Leu Arg Asn Leu Arg Ser Asp Asp Thr Ala Val Tyr Tyr Cys
                85                  90                  95

Thr Arg Asp Ser Ser Arg Arg Asp Thr Asn Trp Trp Leu Asp Pro Trp
            100                 105                 110

Gly Gln Gly Thr Leu Val Thr Val Ser Ser
        115                 120


<210> SEQ ID NO 244
<211> LENGTH: 122
```

<212> TYPE: PRT
<213> ORGANISM: Artificial Sequence
<220> FEATURE:
<223> OTHER INFORMATION: Synthetic polypeptide

<400> SEQUENCE: 244

```
Gln Val Gln Leu Val Gln Ser Gly Ala Ala Val Lys Lys Pro Gly Ala
1               5                   10                  15

Ser Val Trp Val Ser Cys Lys Ala Ser Gly Tyr Thr Phe Thr Ser Cys
            20                  25                  30

Tyr Ile His Trp Phe Arg Gln Ala Pro Gly Gln Gly Leu Glu Trp Met
        35                  40                  45

Gly Trp Leu Asn Pro Ile Asn Gly Ala Arg Asn Asn Pro Tyr Gln Phe
    50                  55                  60

Gln Gly Arg Ile Ser Leu Thr Arg Asp Thr Ser Ser Glu Thr Ala Tyr
65                  70                  75                  80

Leu Glu Leu Arg Asn Leu Thr Pro Asp Asp Thr Ala Val Tyr Tyr Cys
                85                  90                  95

Thr Arg Asp Ser Ser Arg Asp Glu Thr Asn Trp Trp Leu Asp Pro Trp
            100                 105                 110

Gly Gln Gly Thr Leu Val Thr Val Ser Ser
        115                 120
```

<210> SEQ ID NO 245
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 245

```
Gln Val Gln Leu Val Gln Ser Gly Ala Ala Val Lys Lys Pro Gly Ala
1               5                   10                  15

Ser Val Trp Val Ser Cys Lys Ala Ser Gly Tyr Thr Phe Thr Ser Cys
            20                  25                  30

Tyr Ile His Trp Phe Arg Gln Ala Pro Gly Gln Gly Leu Glu Trp Met
        35                  40                  45

Gly Trp Leu Asn Pro Ile Asn Gly Ala Arg Asn Asn Pro Tyr Gln Phe
    50                  55                  60

Gln Gly Arg Ile Ser Leu Thr Arg Asp Thr Ser Ser Glu Thr Ala Tyr
65                  70                  75                  80

Leu Glu Leu Arg Asn Leu Thr Pro Asp Asp Thr Ala Val Tyr Tyr Cys
                85                  90                  95

Thr Arg Asp Ser Ser Arg Asp Glu Thr Asn Trp Trp Leu Asp Pro Trp
            100                 105                 110

Gly Gln Gly Thr Leu Val Ile Val Ser Ser
        115                 120
```

<210> SEQ ID NO 246
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 246

```
Gln Val Gln Leu Val Gln Ser Gly Ala Ala Val Lys Lys Pro Gly Ala
1               5                   10                  15

Ser Val Trp Val Ser Cys Lys Ala Ser Gly Tyr Thr Phe Thr Ser Cys
```

```
            20                  25                  30

Tyr Ile His Trp Phe Arg Gln Ala Pro Gly Gln Gly Leu Glu Trp Met
        35                  40                  45

Gly Trp Leu Asn Pro Ile Asn Gly Ala Arg Asn Gln Ala Tyr Gln Phe
    50                  55                  60

Gln Gly Arg Ile Ser Leu Thr Arg Asp Thr Pro Ser Glu Thr Ala Tyr
65                  70                  75                  80

Leu Glu Leu Arg Asp Leu Arg Ser Asp Asp Thr Ala Val Tyr Tyr Cys
                85                  90                  95

Ala Arg Asp Ser Ser Arg Asp Glu Thr Asn Trp Trp Leu Asp Pro Trp
            100                 105                 110

Gly Gln Gly Thr Leu Val Thr Val Ser Ser
        115                 120


<210> SEQ ID NO 247
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 247

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Asn Thr Cys
            20                  25                  30

Leu Ile His Trp Trp Arg Gln Ala Pro Gly Gln Gly Leu Gln Trp Leu
        35                  40                  45

Ala Trp Ile Asn Pro Leu His Gly Ala Val Asn Tyr Ala His Asn Phe
    50                  55                  60

Gln Gly Arg Ile Thr Val Thr Arg Asp Thr Ser Ile Asp Thr Ala Tyr
65                  70                  75                  80

Met Glu Leu Arg Gly Leu Arg Ser Asp Asp Thr Ala Thr Tyr Tyr Cys
                85                  90                  95

Thr Arg Asp Ser Ser Arg Gly Asn Thr Glu Trp Arg Leu Asp Pro Trp
            100                 105                 110

Gly Gln Gly Thr Leu Val Thr Val Ser Ser
        115                 120


<210> SEQ ID NO 248
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 248

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Asn Thr Cys
            20                  25                  30

Leu Ile His Trp Trp Arg Gln Ala Pro Gly Gln Gly Leu Gln Trp Val
        35                  40                  45

Ala Trp Ile Asn Pro Leu His Gly Ala Val Asn Tyr Ala His Gln Leu
    50                  55                  60

Gln Gly Arg Ile Thr Val Thr Arg Asp Thr Ser Ile Asp Thr Ala Tyr
65                  70                  75                  80
```

```
Met Glu Leu Arg Gly Leu Arg Ala Asp Asp Thr Ala Thr Tyr Tyr Cys
                85                  90                  95

Thr Arg Asp Ser Ser Arg Asp Asn Leu Glu Trp Arg Leu Asp Pro Trp
            100                 105                 110

Gly Gln Gly Thr Leu Val Thr Val Ser Ser
        115                 120


<210> SEQ ID NO 249
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 249

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Asn Thr Cys
            20                  25                  30

Leu Ile His Trp Trp Arg Gln Ala Pro Gly Gln Gly Leu Gln Trp Val
        35                  40                  45

Ala Trp Ile Asn Pro Leu His Gly Ala Val Asn Tyr Ala His Gln Leu
    50                  55                  60

Gln Gly Arg Ile Thr Val Thr Arg Asp Thr Ser Ile Asp Thr Ala His
65                  70                  75                  80

Met Glu Leu Arg Gly Leu Arg Ser Asp Asp Thr Ala Thr Tyr Tyr Cys
                85                  90                  95

Thr Arg Asp Ser Ser Arg Gly Asp Thr Glu Trp Arg Leu Asp Pro Trp
            100                 105                 110

Gly Gln Gly Thr Leu Val Thr Val Ser Ser
        115                 120


<210> SEQ ID NO 250
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 250

Gln Val Gln Leu Val Gln Ser Gly Ala Glu Val Lys Lys Pro Gly Ala
1               5                   10                  15

Ser Ala Arg Val Ser Cys Lys Ala Ser Gly Tyr Thr Phe Thr Ala Tyr
            20                  25                  30

Phe Ile His Trp Val Arg Gln Ala Pro Gly Gln Gly Leu Glu Trp Val
        35                  40                  45

Gly Trp Ile Asn Pro Leu His Gly Ala Val Asn Tyr Ala His Lys Phe
    50                  55                  60

Gln Gly Arg Val Ser Met Thr Arg Asp Thr Ser Ile Ser Thr Ala Tyr
65                  70                  75                  80

Met Glu Leu Arg Ser Leu Lys Ser Asp Asp Thr Ala Ile Tyr Tyr Cys
                85                  90                  95

Thr Thr His Leu Ser Ser Arg Asp Phe Ser Trp Ser Trp Asp Pro Trp
            100                 105                 110

Gly Gln Gly Thr Leu Val Thr Val Ser Pro
        115                 120


<210> SEQ ID NO 251
```

<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 251

Gln Val Gln Leu Val Gln Ser Gly Ala Glu Val Lys Lys Pro Gly Ala
1 5 10 15

Ser Val Arg Val Ser Cys Lys Ala Ser Gly Tyr Thr Phe Thr Ala Cys
20 25 30

Tyr Ile Gln Trp Phe Arg Gln Ala Pro Gly Gln Gly Leu Glu Trp Met
35 40 45

Gly Trp Ile Asn Pro Ile Asn Gly Ala Arg Asn Asn Asn Pro Gln Thr
50 55 60

Phe Gln Gly Arg Val Thr Leu Thr Arg Asp Thr Ser Ile Asp Thr Ala
65 70 75 80

Tyr Leu Glu Leu Arg Asn Leu Arg Asp Asp Asp Thr Ala Ile Tyr Tyr
85 90 95

Cys Thr Arg Asp Ser Ser Arg Arg Asp Leu Glu Trp Arg Leu Asp Pro
100 105 110

Trp Gly Gln Gly Thr Leu Val Thr Val Ser Ser
115 120

<210> SEQ ID NO 252
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 252

Gln Val Gln Leu Val Gln Ser Gly Ala Ala Val Lys Lys Pro Gly Ala
1 5 10 15

Ser Val Trp Val Ser Cys Lys Ala Ser Gly Tyr Thr Phe Thr Ser Cys
20 25 30

Tyr Ile His Trp Phe Arg Gln Ala Pro Gly Gln Gly Leu Glu Trp Met
35 40 45

Gly Trp Leu Asn Pro Ile Asn Gly Ala Arg Asn His Ala Tyr Gln Phe
50 55 60

Gln Gly Arg Ile Ser Leu Thr Arg Asp Thr Ser Ser Glu Thr Ala Tyr
65 70 75 80

Leu Glu Leu Arg Asn Leu Arg Ser Asp Asp Thr Ala Val Tyr Tyr Cys
85 90 95

Ala Arg Asp Ser Ser Arg Asp Glu Thr Asn Trp Trp Leu Asp Pro Trp
100 105 110

Gly Gln Gly Thr Leu Val Thr Val Ser Ser
115 120

<210> SEQ ID NO 253
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 253

Ala Ile Arg Met Thr Gln Ser Pro Ala Thr Leu Ser Ala Ser Val Gly
1 5 10 15

```
Glu Arg Val Thr Ile Thr Cys Arg Ala Ser Gln Gly Ile Gly Ser Asp
            20                  25                  30

Leu Gly Trp Tyr Gln Gln Lys Pro Gly Lys Ser Pro Lys Leu Leu Ile
        35                  40                  45

Phe Lys Ala Ser Asn Leu Lys Asp Gly Val Pro Pro Arg Phe Ser Gly
    50                  55                  60

Gly Gly Phe His Thr Glu Phe Thr Leu Thr Ile Ser Ser Leu Gln Pro
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100


<210> SEQ ID NO 254
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 254

Ala Ile Arg Met Thr Gln Ser Pro Ala Thr Leu Ser Ala Ser Val Gly
1               5                   10                  15

Asp Arg Val Thr Ile Thr Cys Arg Ala Ser Gln Gly Ile Gly Asn Lys
            20                  25                  30

Leu Gly Trp Phe Gln Gln Lys Pro Gly Lys Ala Pro Lys Pro Leu Ile
        35                  40                  45

Phe Lys Ala Ser Thr Leu Lys Asp Gly Val Pro Ser Arg Phe Ser Gly
    50                  55                  60

Ser Gly Phe Gly Thr Asp Phe Thr Leu Thr Ile Ser Ser Leu Gln Pro
65                  70                  75                  80

Asp Asp Phe Ala Thr Tyr Tyr Cys Gln Val Tyr Glu Ser Phe Gly Gln
                85                  90                  95

Gly Thr Lys Val Glu Ile Lys
            100


<210> SEQ ID NO 255
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 255

Ala Ile Arg Met Thr Gln Ser Pro Ala Thr Leu Ser Ala Ser Val Gly
1               5                   10                  15

Asp Arg Val Thr Ile Thr Cys Arg Ala Gly Gln Gly Ile Gly Ser Asp
            20                  25                  30

Leu Ala Trp Tyr Gln Gln Lys Ser Gly Gln Ala Pro Lys Leu Leu Ile
        35                  40                  45

Phe Lys Ala Ser Asn Leu Lys Asn Gly Val Pro Pro Arg Phe Ser Gly
    50                  55                  60

Ser Gly Phe His Thr Asp Phe Thr Leu Thr Ile Ser Gly Leu Gln Pro
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100
```

<210> SEQ ID NO 256
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 256

```
Ala Ile Arg Met Thr Gln Ser Pro Ala Thr Leu Ser Ala Ser Val Gly
1               5                   10                  15

Asp Arg Val Thr Ile Thr Cys Arg Ala Gly Gln Gly Ile Gly Ser Asp
            20                  25                  30

Leu Ala Trp Tyr Gln Gln Lys Ser Gly Gln Ala Pro Lys Leu Leu Ile
        35                  40                  45

Phe Lys Ala Ser Asn Leu Lys Asn Gly Val Pro Pro Arg Phe Ser Gly
    50                  55                  60

Ser Gly Phe His Thr Asp Phe Thr Leu Thr Ile Ser Gly Leu Gln Ser
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100
```

<210> SEQ ID NO 257
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 257

```
Ala Ile Arg Met Thr Gln Ser Pro Pro Thr Val Ser Ala Ser Ala Gly
1               5                   10                  15

Asp Arg Val Thr Ile Thr Cys Arg Ala Gly Gln His Ile Gly Asn Asp
            20                  25                  30

Leu Ala Trp Tyr Gln Thr Lys Val Gly Met Ala Pro Lys Leu Leu Ile
        35                  40                  45

Tyr Gln Ala Ser Asn Leu Lys Ser Gly Val Pro Ser Arg Phe Ser Gly
    50                  55                  60

Ser Gly Ser Gly Thr Glu Phe Thr Leu Ser Ile Thr Ser Leu Gln Pro
65                  70                  75                  80

Asp Asp Phe Ala Thr Tyr Tyr Cys Gln Val Tyr Glu Ser Phe Gly Gln
                85                  90                  95

Gly Thr Lys Val Glu Ile Lys
            100
```

<210> SEQ ID NO 258
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 258

```
Ala Ile Arg Met Thr Gln Ser Pro Ala Thr Leu Ser Ala Ser Val Gly
1               5                   10                  15

Asp Arg Val Thr Leu Thr Cys Arg Ala Gly Gln Gly Ile Gly Ser Asp
            20                  25                  30
```

```
Leu Gly Trp Tyr Gln Gln Lys Pro Gly Lys Ala Pro Lys Leu Leu Ile
        35                  40                  45

His Lys Ala Ser Asn Leu Ile Asn Gly Val Pro Ser Arg Phe Ser Gly
    50                  55                  60

Ser Gly Phe His Thr Glu Phe Thr Leu Thr Ile Ser Ser Leu Gln Pro
65                  70                  75                  80

Asp Asp Phe Ala Thr Tyr Tyr Cys Gln Val Val Glu Trp Phe Gly Gln
                85                  90                  95

Gly Thr Lys Val Glu Ile Lys
            100
```

<210> SEQ ID NO 259
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 259

```
Ala Ile Arg Met Thr Gln Ser Pro Ala Thr Leu Ser Ala Ser Val Gly
1               5                   10                  15

Asp Arg Val Thr Ile Thr Cys Arg Ala Gly Gln Gly Ile Gly Ser Asp
            20                  25                  30

Leu Ala Trp Tyr Gln Gln Lys Pro Gly Gln Ala Pro Lys Leu Leu Ile
        35                  40                  45

Phe Lys Ala Ser Asn Leu Lys Asn Gly Val Pro Thr Arg Phe Thr Gly
    50                  55                  60

Ser Gly Phe His Thr Asp Phe Thr Leu Thr Ile Asn Gly Leu Gln Ser
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100
```

<210> SEQ ID NO 260
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 260

```
Ala Ile Arg Met Thr Gln Ser Pro Ala Thr Leu Ser Ala Ser Val Gly
1               5                   10                  15

Asp Arg Val Thr Leu Thr Cys Arg Ala Gly Gln Gly Ile Gly Ser Asp
            20                  25                  30

Leu Gly Trp Tyr Gln Gln Lys Pro Gly Lys Ala Pro Lys Leu Leu Ile
        35                  40                  45

His Lys Ala Ser Asn Leu Ile Asn Gly Val Pro Ser Arg Phe Ser Gly
    50                  55                  60

Ser Gly Phe His Thr Glu Phe Thr Leu Thr Ile Asn Ser Leu Gln Pro
65                  70                  75                  80

Asp Asp Phe Ala Thr Tyr Tyr Cys Gln Val Phe Glu Trp Phe Gly Pro
                85                  90                  95

Gly Thr Lys Val Glu Ile Lys
            100
```

<210> SEQ ID NO 261

<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 261

Ala Ile Arg Met Thr Gln Ser Pro Ala Thr Leu Ser Ala Ser Val Gly
1 5 10 15

Asp Arg Val Thr Ile Thr Cys Arg Ala Gly Gln Gly Ile Gly Ser Asp
20 25 30

Leu Ala Trp Tyr Gln Gln Lys Ser Gly Gln Ala Pro Lys Leu Leu Ile
35 40 45

Phe Lys Ala Ser Asn Leu Lys Asn Gly Val Pro Pro Arg Phe Ser Gly
50 55 60

Ser Gly Phe His Thr Asp Phe Thr Leu Thr Ile Ser Gly Leu Gln Pro
65 70 75 80

Asp Asp Phe Ala Thr Tyr Tyr Cys Gln Val Leu Glu Thr Phe Gly Gln
85 90 95

Gly Thr Lys Val Glu Ile Lys
100

<210> SEQ ID NO 262
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 262

Ala Ile Arg Met Thr Gln Ser Pro Ala Thr Leu Ser Ala Ser Val Gly
1 5 10 15

Asp Arg Val Thr Ile Thr Cys Arg Ala Gly Gln Gly Ile Gly Ser Asp
20 25 30

Leu Ala Trp Tyr Gln Gln Lys Pro Gly Gln Ala Pro Lys Leu Leu Ile
35 40 45

Phe Lys Ala Ser Arg Leu Lys Asn Gly Val Pro Thr Arg Phe Thr Gly
50 55 60

Ser Gly Phe His Thr Glu Phe Thr Leu Thr Ile Ser Gly Leu Gln Ser
65 70 75 80

Asp Asp Phe Ala Thr Tyr Tyr Cys Gln Val Leu Glu Thr Phe Gly Gln
85 90 95

Gly Thr Lys Val Glu Ile Lys
100

<210> SEQ ID NO 263
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 263

Ala Ile Arg Met Thr Gln Ser Pro Ala Thr Leu Ser Ala Ser Val Gly
1 5 10 15

Asp Arg Val Thr Ile Thr Cys Arg Ala Gly Gln Gly Ile Gly Ser Asp
20 25 30

Leu Ala Trp Tyr Gln Gln Lys Pro Gly Gln Ala Pro Lys Leu Leu Ile
35 40 45

Phe Lys Ala Ser Arg Leu Lys Asn Gly Val Pro Thr Arg Phe Thr Gly
    50                  55                  60

Ser Gly Phe His Thr Glu Phe Thr Leu Thr Ile Ser Gly Leu Gln Ser
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100

<210> SEQ ID NO 264
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 264

Ala Ile Arg Met Thr Gln Ser Pro Ala Thr Leu Ser Ala Ser Val Gly
1               5                   10                  15

Asp Arg Val Thr Ile Thr Cys Arg Ala Gly Gln Gly Ile Gly Ser Asp
            20                  25                  30

Leu Ala Trp Tyr Gln Gln Lys Ser Gly Gln Ala Pro Lys Leu Leu Ile
        35                  40                  45

Phe Lys Ala Ser Asn Leu Lys Asn Gly Val Pro Pro Arg Phe Ser Gly
    50                  55                  60

Ser Gly Phe His Thr Asp Phe Thr Leu Thr Ile Ser Gly Leu Gln Pro
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100

<210> SEQ ID NO 265
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 265

Ala Ile Arg Met Thr Gln Ser Pro Ala Thr Leu Ser Ala Ser Val Gly
1               5                   10                  15

Asp Lys Val Thr Ile Thr Cys Arg Ala Ser Gln Gly Ile Gly Asn Asn
            20                  25                  30

Leu Gly Trp Tyr Gln Gln Lys Pro Gly Gln Ala Pro Lys Leu Leu Ile
        35                  40                  45

Phe Lys Ala Ser Asn Ser Lys Asp Gly Val Pro Pro Arg Phe Ser Gly
    50                  55                  60

Ser Gly Ser His Thr Glu Phe Thr Leu Thr Ile Asn Ser Leu Gln Pro
65                  70                  75                  80

Asp Asp Phe Ala Thr Tyr Tyr Cys Gln Val Tyr Gln Thr Phe Gly Gln
                85                  90                  95

Gly Thr Lys Val Glu Ile Lys
            100

<210> SEQ ID NO 266
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 266

```
Ala Ile Arg Met Thr Gln Ser Pro Ala Thr Leu Ser Ala Ser Val Gly
1               5                   10                  15

Asp Arg Val Thr Leu Thr Cys Arg Ala Gly Gln Gly Ile Gly Ser Asp
            20                  25                  30

Leu Gly Trp Tyr Gln Gln Lys Pro Gly Lys Ala Pro Lys Leu Leu Ile
        35                  40                  45

His Lys Ala Ser Asn Leu Leu Asn Gly Val Pro Ser Arg Phe Ser Gly
    50                  55                  60

Ser Gly Phe His Thr Glu Phe Thr Leu Thr Ile Ser Ser Leu Gln Pro
65                  70                  75                  80

Asp Asp Phe Ala Thr Tyr Tyr Cys Gln Val Phe Glu Trp Phe Gly Gln
                85                  90                  95

Gly Thr Lys Val Glu Ile Lys
            100
```

<210> SEQ ID NO 267
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 267

```
Ala Ile Arg Met Thr Gln Ser Pro Ala Thr Leu Ser Ala Ser Val Gly
1               5                   10                  15

Asp Arg Val Thr Leu Thr Cys Arg Ala Gly Gln Gly Ile Gly Ser Asp
            20                  25                  30

Leu Gly Trp Tyr Gln Gln Lys Pro Gly Lys Ala Pro Lys Leu Leu Ile
        35                  40                  45

His Lys Ala Ser Asn Leu Ala Asn Gly Val Pro Ser Arg Phe Ser Gly
    50                  55                  60

Arg Gly Phe His Thr Glu Phe Thr Leu Thr Ile Ser Ser Leu Gln Pro
65                  70                  75                  80

Asp Asp Phe Ala Thr Tyr Tyr Cys Gln Val Phe Glu Trp Phe Gly Gln
                85                  90                  95

Gly Thr Lys Val Glu Ile Lys
            100
```

<210> SEQ ID NO 268
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 268

```
Ala Ile Arg Met Thr Gln Ser Pro Ala Thr Leu Ser Ala Ser Val Gly
1               5                   10                  15

Asp Arg Val Thr Ile Thr Cys Arg Ala Gly Gln Gly Ile Gly Ser Asp
            20                  25                  30

Leu Ala Trp Tyr Gln Gln Lys Pro Gly Gln Ala Pro Lys Leu Leu Ile
        35                  40                  45

Phe Lys Ala Ser Asn Leu Lys Asn Gly Val Pro Thr Arg Phe Thr Gly
    50                  55                  60
```

Ser Gly Phe His Thr Asp Phe Thr Leu Thr Ile Ser Gly Leu Gln Ser
65 70 75 80

Asp Asp Phe Ala Thr Tyr Tyr Cys Gln Val Leu Glu Thr Phe Gly Gln
85 90 95

Gly Thr Lys Val Glu Ile Lys
100

<210> SEQ ID NO 269
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 269

Ala Ile Arg Met Thr Gln Ser Pro Ala Thr Leu Ser Ala Ser Val Gly
1 5 10 15

Asp Arg Val Thr Ile Thr Cys Arg Ala Gly Gln Gly Ile Gly Ser Asp
20 25 30

Leu Ala Trp Tyr Gln Gln Lys Pro Gly Gln Ala Pro Lys Leu Leu Ile
35 40 45

Phe Lys Ala Ser Asn Leu Lys Lys Gly Val Pro Thr Arg Phe Thr Gly
50 55 60

Ser Gly Phe His Thr Asp Phe Thr Leu Thr Ile Ser Gly Leu Gln Ser
65 70 75 80

Asp Asp Phe Ala Thr Tyr Tyr Cys Gln Val Leu Glu Thr Phe Gly Gln
85 90 95

Gly Thr Lys Val Glu Ile Lys
100

<210> SEQ ID NO 270
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 270

Ala Ile Arg Met Thr Gln Ser Pro Ala Thr Leu Ser Ala Phe Val Gly
1 5 10 15

Asp Arg Val Thr Ile Thr Cys Arg Ala Ser Gln Gly Ile Gly Asp Asp
20 25 30

Leu Gly Trp Tyr Gln Gln Lys Pro Gly Lys Val Pro Lys Pro Leu Ile
35 40 45

Phe Lys Ala Ser Asn Leu Lys Asp Gly Val Pro Ser Arg Phe Ser Gly
50 55 60

Ser Gly Phe Gly Thr Asp Phe Thr Leu Thr Ile Asn Asn Leu Gln Pro
65 70 75 80

Asp Asp Phe Ala Thr Tyr Tyr Cys Gln Ala Tyr Glu Ser Phe Gly Gln
85 90 95

Gly Thr Lys Val Glu Ile Lys
100

<210> SEQ ID NO 271
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 271
caggtgcagc tggtgcagtc tggggctgag gtgaagaagc ctggggcctc aatgagggtc 60
tcctgcaagg cctctggata caccttcacc gcctgctata tacactggtt tcgacaggcc 120
cctggacaag gccttgagtg gatgggatgg atcaacccta tcaatggtgc cagaaataat 180
ccacgcaagt ttcagggcag ggtcaccatg accagggaca cgtccattga tacagcgtac 240
ttggaactgc gcaacctggc atctgacgac acggccatgt attactgtac gagagattca 300
tcgaggcgtg atacgaattg gtggttggac ccctggggcc agggaaccct ggtcaccgtc 360
tcctca 366

<210> SEQ ID NO 272
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 272
caggtgcagc tggtgcagtc tggggctgag gtgaagaagc ctggggcctc agtgagggtc 60
tcctgcaagg cttctggata caccttcacc gcctatttta tacactgggt gcgacaggcc 120
cctggacagg ggcttgagtg ggtgggttgg atcaaccctc tccatggcgc cgtaaactat 180
gcacacaaat ttcaaggcag ggtctccatg accagggaca cctccatcag cacagcctac 240
atggaacttc gcagcctgaa atctgacgac acggccattt attactgtac cacacattca 300
tcgagccgtg attttcagtg gtcgttggac ccctggggcc agggaaccct ggtcaccgtc 360
tcctca 366

<210> SEQ ID NO 273
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 273
caggtgcagc tggtgcagtc tggggctgag gtgaagaagc ctggggcctc aatgagggtc 60
tcctgcaagg cctctggata caccttcacc tcttgttata tacactggtt tcgacaggcc 120
cctggacaag ggcttgagtg gatgggatgg ctcaacccta tcaatggtgc cagaaataat 180
ccacacaagt ttcagggcag gatcaccctg accagggaca cgtccactga tacagcctac 240
ttggaactgc gcaacctgag atctgacgac acggccgtat attattgtac gagagattca 300
tcgaggcgtg atacgaattg gtggttggac ccttggggcc agggaaccct ggtcaccgtc 360
tcctca 366

<210> SEQ ID NO 274
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 274
caggtgcagc tggtgcagtc tggggctgag gtgaagaagc ctggggcctc aatgagggtc 60
tcctgcaagg cctctggata cactttcacc gcttgttata tacactggtt tcgacaggcc 120
cctggacaag ggcttgagtg gatgggatgg ctcaacccta tcaatggtgc cagaaataat 180
ccacacaagt ttcagggcag gatcaccctg accagggaca cgtccactga tacagcctac 240
ttggaactgc gcaacctgag atctgacgac acggccgtgt attattgtac gagagattca 300
tcgaggcgtg atacgaattg gtggttggac ccttggggcc agggagccct ggtcaccgtc 360
tcctca 366

<210> SEQ ID NO 275
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 275
caggtgcagc tggtgcagtc tggggctgaa gtgaagaagc ctggggcctc agtgagggtc 60
tcctgcaagg cctctggata cagcttcacc gactactttg tgcactgggt gcgacaggcc 120
cctggacagg gccttgagtg ggtggggtgg ataaacccta ttaatggagc ccctaattat 180
gcaccgaact ttcggggcag gatcaccttg actagggaca catccatcga cacactctat 240
atggacttga gaagcctgag agttgacgac acggccgttt acttctgtac gagagattca 300
tcgaggcaac aacgggactg gtggttagac ccctggggcc agggaaccct ggtcaccgtc 360
tcctca 366

<210> SEQ ID NO 276
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 276
caggtgcagc tggtgcagtc tggggctgag gtgaagaagc ctggggcctc agtgagggtc 60
tcctgcaagg cctccggata caccttcaac tcctgcttaa ttcattggtg gcgacaggcc 120
cctggacaag gccttcagtg gatggcttgg atcaaccctc tccatggtgc cgtaaattat 180
gcacaccagt ttcaggggag gatcaccgtg accagggaca cgtccatcga cactgcctac 240
atggaactgc gcggcctgag atctgacgac acggccacat attactgtac gagagatgca 300
tccagagatg atcgcgcgtg gcgcttggac ccctggggcc agggaacact ggtcaccgtc 360
tcctca 366

<210> SEQ ID NO 277
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 277
caggtgcagc tggtgcagtc tggggtagcg gtgaagaagc ctggggcctc agtgtgggtc 60
tcctgcaagg cctctggata caccttcacc agttgctata tacattggtt tcgacaggcc 120
cctggacaag ggcttgagtg gatgggatgg ctcaacccta tcaatggtgc cagaaataat 180
ccataccagt ttcagggcag gatcagcctg accagggaca cgtccagtga aacagcctac 240
ttggaactgc gtaacctcag atctgacgac acggccgtct attattgcgc gagagattct 300
tcgagggaag agacgaattg gtggctggac ccttggggcc agggaaccct ggtcaccgtc 360
tcctca 366

<210> SEQ ID NO 278
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 278
caggtgcagc tggtgcagtc tggggctgag gtgaagaagc ctggggcctc agtgagggtc 60
tcctgcaagg cctccggata caccttcaat tcctgcttaa ttcattggtg gcgacaggcc 120
cctggacaag gccttcagtg gatggcttgg atcaaccctc tccatggtgc cgtaaattat 180
gcacaccagt tccaggggag gatcaccgtg accagggaca cgtccatcga cactgcctac 240
atggaactgc gcggcctgag atctgacgac acggccacat attactgtac gagagatgca 300
tccagagatg atcgcgcgtg gcgcttggac ccctggggcc agggaacact ggtcaccgtc 360
tcctca 366

<210> SEQ ID NO 279
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 279
caggtgcagc tggtgcagtc tggggctgag gtgaagaagc ctggggcctc aatgagggtc 60
tcttgcaagg cctctggata cactttcacc gcttgttata tacactggtt tcgacaggcc 120
cctggacaag ggcttgagtg gatgggatgg ctcaacccta tcaatggtgc cagaaataat 180
ccacacaagt ttcagggcag gatcaccctg accagggaca cgtccactga tacagcctac 240
ttggaactgc gcaacctgag atctgacgac acggccgtgt attattgtac gagagattca 300
tcgaggcgtg atacgaattg gtggttggac ccttggggcc agggaaccct ggtcaccgtc 360
tcctca 366

<210> SEQ ID NO 280
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 280
caggtgcagc tggtgcagtc tggggctgcg gtgaagaagc ctggggcctc agtgtgggtc 60
tcctgcaagg cctctggata caccttcacc agttgttata tacattggtt tcgacaggcc 120
cctggacaag ggcttgagtg gatgggatgg ctcaacccta tcaatggtgc cagaaataat 180
ccataccagt ttcaggggag gatcagcctg accagggaca cgtccagtga aacagcctac 240
ttggaactgc gtaacctcac accagacgac acggccgtct attattgcac gagagattca 300
tcgagggatg agacgaattg gtggctggac ccttggggcc agggaaccct ggtcaccgtc 360
tcctca 366

<210> SEQ ID NO 281
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 281
caggtgcagc tggtgcagtc tggggctgcg gtgaagaagc ctggggcctc agtgtgggtc 60
tcctgcaagg cctctggata caccttcacc agttgttata tacattggtt tcgacaggcc 120
cctggacaag ggcttgagtg gatgggatgg ctcaacccta tcaatggtgc cagaaataat 180
ccataccagt ttcaggggag gatcagcctg accagggaca cgtccagtga aacagcctac 240
ttggaactgc gtaacctcac accagacgac acggccgtct attattgcac gagagattca 300
tcgagggatg agacgaattg gtggctggac ccttggggcc agggaaccct ggtcatcgtc 360
tcttca 366

<210> SEQ ID NO 282
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 282
caggtgcagc tggtgcagtc tggggctgcg gtgaagaagc ctggggcctc agtgtgggtc 60
tcctgcaagg cctctggata cacctttacc agttgttata tacattggtt tcgacaggcc 120
cctggacaag ggcttgagtg gatgggatgg ctcaacccta tcaatggcgc cagaaatcag 180
gcgtaccagt ttcagggcag gattagcctg accagggaca cgcccagtga aacagcctac 240
ttggaactgc gtgacctcag atctgacgac acggccgtct attattgcgc gagagattca 300
tcgagggatg agacgaattg gtggctggac ccttggggcc agggaaccct ggtcaccgtc 360
tcctca 366

<210> SEQ ID NO 283
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 283
caggtgcagc tggtgcagtc tggggctgag gtgaagaagc ctggggcctc agtgagggtc 60
tcctgcaagg cttccggata cactttcaac acctgcttaa ttcattggtg gcgacaggcc 120
cctggacaag gccttcagtg gctggcttgg atcaaccctc tccatggtgc cgttaactat 180
gcacacaact ttcaggggag gatcaccgtg accagggaca cgtccatcga cactgcctac 240
atggaacttc gcggcctgag atctgacgac acggccacat actactgcac cagagattca 300
tcgagaggta atacggagtg gcgcttggac ccctggggcc agggaacact ggtcaccgtc 360
tcctca 366

<210> SEQ ID NO 284
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 284
caggtgcagc tggtgcagtc tggggctgag gtgaaaaagc ctggggcctc agtgagggtc 60
tcctgcaagg cttccggata cacgttcaac acctgcttga ttcattggtg gcgacaggcc 120
cctggacagg gccttcagtg ggtggcttgg atcaaccctc tccatggtgc cgttaattat 180
gcacaccaat tacaggggag gatcaccgtg accagggaca cgtctatcga cactgcctac 240
atggaactgc gcggcctcag agctgacgac acggccacct actactgtac gagagattca 300
tcgagagata atctggagtg gcgcttggac ccctggggcc agggaacact ggtcaccgtc 360
tcctca 366

<210> SEQ ID NO 285
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 285
caggtgcagc tggtgcagtc tggggctgag gtgaaaaagc ctggggcctc agtgagggtc 60
tcctgcaagg cttccggata caccttcaac acctgcttaa ttcattggtg gcgacaggcc 120
cctggacagg gccttcagtg ggtggcttgg atcaaccctc tccatggtgc cgttaactat 180
gcacaccagt tacaggggag gatcacggtg accagggaca cgtctatcga cactgcccac 240
atggaactgc gcggcctcag atctgacgac acggccacat actattgtac cagagattca 300
tcgagaggtg atacggagtg gcgcttggac ccctggggcc agggaacact ggtcaccgtc 360
tcctca 366

<210> SEQ ID NO 286
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 286
caggtgcagc tggtgcagtc tggggctgag gtgaagaagc ctggggcctc agcgagggtc 60
tcctgcaagg cttctggata caccttcacc gcctatttta tacactgggt gcgacaagcc 120
cctggacagg gacttgagtg ggtgggttgg atcaaccctc tccatggcgc cgtaaattat 180
gcacacaaat ttcagggcag ggtctccatg accagagaca cctccatcag cacagcctac 240
atggaacttc gcagcctgaa atctgacgac acggccattt attactgtac cacacatttg 300
tcgagtcgtg atttttcgtg gtcgtgggac ccctggggcc agggaaccct ggtcaccgtc 360
tcccca 366

<210> SEQ ID NO 287
<211> LENGTH: 369
<212> TYPE: DNA
<213> ORGANISM: Artificial Sequence
<220> FEATURE:
<223> OTHER INFORMATION: Synthetic polypeptide

<400> SEQUENCE: 287
caggtgcagc tggtgcagtc tggggctgag gtgaagaaac ccggggcctc agtgagggtc 60
tcctgcaagg cctctggata caccttcacc gcctgttata tacagtggtt tcgacaggcc 120
cctggacaag ggcttgagtg gatgggatgg atcaacccta tcaatggtgc cagaaataat 180
aatccacaga cgtttcaggg cagggtcacc ctgaccaggg acacgtccat tgataccgcc 240
tacttggaac tgcgcaacct gagagatgac gacacggcca tatattattg tacgagagat 300
tcatcgaggc gtgatctgga gtggcggttg gacccctggg gccagggaac cctggtcacc 360
gtctcctca 369

<210> SEQ ID NO 288
<211> LENGTH: 366
<212> TYPE: DNA
<213> ORGANISM: Artificial Sequence
<220> FEATURE:
<223> OTHER INFORMATION: Synthetic polypeptide

<400> SEQUENCE: 288
caggtgcagc tggtgcagtc tggggctgcg gtgaagaagc ctggggcctc agtgtgggtc 60
tcctgcaagg cctctggata caccttcacc agttgttata tacattggtt tcgacaggcc 120
cctggacaag ggcttgagtg gatgggatgg ctcaacccta tcaatggcgc cagaaatcat 180
gcataccagt ttcagggcag gattagcctg accagggaca cgtccagtga aacagcctac 240
ttggaactgc gtaacctcag atctgacgac acggccgtct attattgcgc gagagattca 300
tcgagggatg agacgaattg gtggctggac ccttggggcc agggaaccct ggtcaccgtc 360
tcctca 366

<210> SEQ ID NO 289
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 289
gccatccgga tgacccagtc tcctgccacc ctgtctgcat ctgtgggaga aagagtcacc 60
atcacttgcc gggcaagtca gggcattgga agtgatttag gttggtatca gcagaaacca 120
gggaaatccc ctaaacttct tatctttaag gcgtctaatt taaaagatgg cgtcccgccg 180
aggttcagcg gcggtggatt tcacacagaa tttactctca ccatcagcag cctgcagcct 240
gatgattttg caacttatta ctgccaagtt ttggaaacat tcggccaagg gaccaaggtg 300
gagatcaaa 309

<210> SEQ ID NO 290
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 290
gccatccgga tgacccagtc tcctgccacc ctgtctgcat ctgtaggaga cagagtcacc 60
atcacttgcc gggctagtca gggcattgga aataaattag ggtggtttca gcagaaacca 120
gggaaagccc ctaagcccct gatctttaag gcgtctactt tgaaagatgg ggtcccatca 180
aggttcagcg gcagtggatt tgggacagat ttcactctca ccatcagcag cctgcagcct 240
gatgactttg caacttacta ttgtcaagtc tatgaaagct tcggccaagg gaccaaggtg 300
gagatcaaa 309

<210> SEQ ID NO 291
<211> LENGTH: 309
<212> TYPE: DNA
<213> ORGANISM: Artificial Sequence
<220> FEATURE:

<223> OTHER INFORMATION: Synthetic polypeptide

<400> SEQUENCE: 291
gccatccgga tgacccagtc tcctgccacc ctgtctgcat ctgtgggaga cagagtcacc 60
atcacttgcc gggcaggtca gggcattgga agtgatttag cctggtatca gcagaaatca 120
gggcaagccc ctaaacttct tatctttaag gcgtctaatt taaaaaatgg agtcccgcca 180
agattcagcg gcagtggatt tcacacagac ttcactctca ccatcagcgg cctgcagcct 240
gatgattttg cgacttatta ctgccaagtt ttggaaacat tcggccaagg gaccaaggtg 300
gagatcaaa 309

<210> SEQ ID NO 292
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 292
gccatccgga tgacccagtc tcctgccacc ctgtctgcat ctgtgggaga cagagtcacc 60
atcacttgcc gggcaggtca gggcattgga agtgatttag cctggtatca gcagaaatca 120
gggcaagccc ctaaacttct tatctttaag gcgtctaatt taaaaaatgg agtcccgcca 180
agattcagcg gcagtggatt tcacacagac ttcactctca ccatcagcgg cctgcagtct 240
gatgattttg cgacttatta ctgccaagtt ttggaaacat tcggccaagg gaccaaggtg 300
gagatcaaa 309

<210> SEQ ID NO 293
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 293
gccatccgga tgacccagtc tcctcccacc gtgtctgcat ctgcgggaga cagagtcacc 60
atcacttgcc gggccggtca gcacattggt aacgacttgg cctggtatca gacgaaagtg 120
gggatggccc ctaaactcct catctatcag gcgtctaatt taaaaagtgg ggtcccatca 180
aggttcagcg gcagtgggtc tgggacagag ttcactcttt ccatcaccag cctgcagcct 240
gatgattttg caacttatta ctgccaagtt tatgagtcgt tcggccaagg gaccaaggtg 300
gagatcaaa 309

<210> SEQ ID NO 294
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 294
gccatccgga tgacccagtc tcctgccacc ctgtctgcat ctgtgggaga cagagtcacc 60
ttgacttgcc gggcaggaca gggcattgga agtgatttag gctggtatca gcagaaacca 120
gggaaagccc ctaaactcct catacataag gcgtccaatt taataaatgg agtgccatca 180
aggttcagcg gcagtggatt tcacacagaa ttcactctca ccatcagcag cctgcagcct 240
gatgattttg caacttatta ctgtcaagtt gttgaatggt tcggccaagg gaccaaggtg 300
gagatcaaa 309

<210> SEQ ID NO 295
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 295
gccatccgga tgacccagtc tcctgccacc ctgtctgcat ctgtgggaga cagagtcacc 60
atcacttgcc gggcaggtca gggcattgga agtgatttag cctggtatca gcagaaacca 120
gggcaagccc ctaaacttct aatctttaag gcgtctaatt taaaaaatgg agtcccgaca 180
agattcaccg gcagtggatt tcacacagac ttcactctca ccatcaacgg cctgcagtct 240
gatgattttg cgacttatta ctgccaagtt ttggagacat tcggccaagg gaccaaggtg 300
gagatcaaa 309

<210> SEQ ID NO 296
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 296
gccatccgga tgacccagtc tcctgccacc ctgtctgcat ctgtgggaga cagagtcacc 60
ttgacttgcc gggcagggca gggcattgga agtgatttag gctggtatca gcagaaacca 120
gggaaagccc ctaaactcct catacacaag gcgtctaatt taataaatgg ggtgccatca 180
aggttcagcg gcagtggatt tcacacagaa ttcacactca ccatcaacag cctgcagcct 240
gatgattttg caacttatta ctgtcaagtt tttgagtggt tcggcccagg gaccaaggtg 300
gagatcaaa 309

<210> SEQ ID NO 297
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 297
gccatccgga tgacccagtc tcctgccacc ctgtctgcat ctgtgggaga cagagtcacc 60
atcacttgcc gggcaggtca gggcattgga agtgatttag cctggtatca gcagaaatca 120
gggcaagccc ctaaacttct aatctttaag gcgtctaatt taaaaaatgg agtcccgcca 180
agatttagcg gcagtggatt tcacacagac ttcactctca ccatcagcgg cctgcagcct 240
gatgattttg cgacttatta ctgccaagtt ttggaaacat tcggccaagg gaccaaggtg 300
gagatcaaa 309

<210> SEQ ID NO 298
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 298
gccatccgga tgacccagtc tcctgccacc ctgtctgcat ctgtgggaga cagagtcacc 60
atcacttgcc gggcaggtca gggcattgga agtgatttag cctggtatca gcagaaacct 120
gggcaagccc ctaaacttct aatctttaag gcgtctcgtt taaaaaatgg agtcccgaca 180
agattcaccg gcagtggatt tcacacagag ttcactctca ccatcagcgg cctgcagtct 240
gatgattttg cgacttatta ctgccaagtt ttggaaacat tcggccaagg gaccaaggtg 300
gagatcaaa 309

<210> SEQ ID NO 299
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 299
gccatccgga tgacccagtc tcctgccacc ctgtctgcat ctgtgggaga cagagtcacc 60
atcacttgcc gggcaggtca gggcattgga agtgatttag cctggtatca gcagaaacct 120
gggcaagccc ctaaacttct aatctttaag gcgtctcgtt taaaaaatgg agtcccgaca 180
agattcaccg gcagtggatt tcacacagag ttcactctca ccatcagcgg cctgcagtct 240
gatgattttg cgacttatta ctgccaagtt ttggaaacat tcggccaagg gaccaaggtg 300
gagatcaaa 309

<210> SEQ ID NO 300
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 300
gccatccgga tgacccagtc tcctgccacc ctgtctgcat ctgtgggaga cagagtcacc 60
atcacttgcc gggcaggtca gggcattgga agtgatttag cctggtatca gcagaaatca 120
gggcaagccc ctaaacttct tatctttaag gcgtctaatt taaaaaatgg agtcccgcca 180
agattcagcg gcagtggatt tcacacagac ttcactctca ccatcagcgg cctgcagcct 240
gatgattttg cgacttatta ctgccaagtt ttggaaacat tcggccaagg gaccaaggtg 300
gagatcaaa 309

<210> SEQ ID NO 301
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 301
gccatccgga tgacccagtc tcctgccacc ctgtctgcat ctgtaggaga caaagtcacc 60
atcacttgcc gggcaagtca gggcattgga aataatttag gctggtatca gcagaaacca 120
gggcaggccc ctaaactcct catctttaag gcgtctaatt caaaagatgg agtcccacca 180
agattcagcg gtagtggatc tcatacagag ttcactctca ccatcaacag cctgcagcct 240
gatgattttg caacttatta ctgccaggtt tatcaaacct tcggccaagg gaccaaggtg 300
gagatcaaa 309

<210> SEQ ID NO 302
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 302
gccatccgga tgacccagtc tcctgccacc ctgtctgcat ctgtgggaga cagagtcacc 60
ttgacttgcc gggcagggca gggcattgga agtgatttag ggtggtatca gcagaaacca 120
gggaaagccc ctaaactcct catacataag gcgtctaatt tactaaatgg ggtgccatca 180
aggttcagcg gcagtggatt tcacacggaa ttcactctca ccatcagcag cctgcaacct 240
gatgattttg caacttatta ctgtcaagtt tttgaatggt tcggccaagg gaccaaggtg 300
gagatcaaa 309

<210> SEQ ID NO 303
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 303
gccatccgga tgacccagtc tcctgccacc ctgtctgcat ctgtgggaga cagagtcacc 60
ttgacttgcc gggcagggca gggcattgga agtgatttag ggtggtatca gcagaagcca 120
ggaaaagccc ctaaactcct catacataag gcgtctaatt tagcaaatgg ggtgccatca 180
aggttcagcg gccgtggatt tcacacagag ttcactctca ccatcagcag cctgcagcct 240
gatgattttg caacttatta ctgtcaagtt tttgaatggt tcggccaagg gaccaaggtg 300
gagatcaaa 309

<210> SEQ ID NO 304
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 304
gccatccgga tgacccagtc tcctgccacc ctgtctgcat ctgtgggaga cagagtcacc 60
atcacttgcc gggcaggtca gggcattgga agtgatttag cctggtatca gcagaaacca 120
gggcaagccc ctaaacttct aatctttaag gcgtctaatt taaaaaatgg agtcccgaca 180
agattcaccg gcagtggatt tcacacagac ttcactctca ccatcagcgg cctgcagtct 240
gatgattttg cgacttatta ctgccaagtt ttggaaacat tcggccaagg gaccaaggtg 300
gagatcaaa 309

<210> SEQ ID NO 305
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 305
gccatccgga tgacccagtc tcctgccacc ctgtctgcat ctgtgggaga tagagtcacc 60
atcacttgcc gggcaggtca gggcattgga agtgatttag cctggtatca gcagaaacca 120
gggcaagccc ctaaacttct aatctttaag gcgtccaatt taaaaaaagg agtcccgaca 180
agattcaccg gcagtggatt tcacacagac ttcactctca ccatcagcgg cctgcagtct 240
gatgattttg cgacttatta ctgccaagtt ctggaaacat tcggccaagg gaccaaggtg 300
gagatcaaa 309

<210> SEQ ID NO 306
<211> LENGTH: 309
<212> TYPE: DNA
<213> ORGANISM: Artificial Sequence
<220> FEATURE:
<223> OTHER INFORMATION: Synthetic polypeptide

<400> SEQUENCE: 306
gccatccgga tgacccagtc tcctgccacc ctgtctgcat ttgtaggaga cagagtcacc 60
atcacttgcc gggctagtca gggcattgga gatgatttag gctggtatca gcaaaaacca 120
gggaaagtcc ctaagcccct gatctttaag gcgtctaatt taaaagatgg ggtcccatcg 180
aggttcagcg gcagcggatt tgggacagat ttcactctca ccatcaacaa cctgcagcct 240
gatgactttg caacttacta ttgccaagcc tatgaaagct tcggccaagg gaccaaggtg 300
gagatcaaa 309

<210> SEQ ID NO 307
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 307

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Asp Ser Ser Arg Gln Gln Leu Glu Trp Trp Phe Asp Pro Trp
100 105 110

Gly Gln Gly Thr Leu Val Thr Val Ser Ser
115 120

<210> SEQ ID NO 308
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 308

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

```
Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Glu Ala Phe Gly Gln
                85                  90                  95

Gly Thr Lys Val Glu Ile Lys
            100


<210> SEQ ID NO 309
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 309

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Leu Tyr Glu Thr Phe Gly Gln
                85                  90                  95

Gly Thr Lys Val Glu Ile Lys
            100


<210> SEQ ID NO 310
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 310

Ala Xaa Phe Ile Xaa Xaa Val
1               5


<210> SEQ ID NO 311
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
```

<220> FEATURE:
<221> NAME/KEY: misc_feature
<222> LOCATION: (5)..(6)
<223> OTHER INFORMATION: Xaa can be any naturally occurring amino acid

<400> SEQUENCE: 311

Ala Xaa Tyr Ile Xaa Xaa Phe
1               5

<210> SEQ ID NO 312
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 312

Asp Xaa Phe Val Xaa Xaa Val
1               5

<210> SEQ ID NO 313
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 313

Ser Xaa Leu Ile Xaa Xaa Trp
1               5

<210> SEQ ID NO 314
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 314

Ser Xaa Tyr Ile Xaa Xaa Phe
1               5

<210> SEQ ID NO 315
<211> LENGTH: 7
<212> TYPE: PRT
<213> ORGANISM: Artificial Sequence
<220> FEATURE:

<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 315

Thr Xaa Leu Ile Xaa Xaa Trp
1               5

<210> SEQ ID NO 316
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 316

Asn Xaa Ile Asn Xaa Ala Pro
1               5

<210> SEQ ID NO 317
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 317

Asn Xaa Ile Asn Xaa Ala Arg
1               5

<210> SEQ ID NO 318
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 318

Asn Xaa Leu His Xaa Ala Val
1               5

<210> SEQ ID NO 319
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 319

Gly Xaa Gly Xaa Gly Xaa Asp Xaa Ala
1               5

<210> SEQ ID NO 320
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 320

Gly Xaa Gly Xaa Gly Xaa Asp Xaa Gly
1               5

<210> SEQ ID NO 321
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)

<223> OTHER INFORMATION: Xaa can be any naturally occurring amino acid

<400> SEQUENCE: 321

Gly Xaa His Xaa Gly Xaa Asp Xaa Ala
1               5

<210> SEQ ID NO 322
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 322

Ser Xaa Gly Xaa Gly Xaa Asp Xaa Gly
1               5

<210> SEQ ID NO 323
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 323

Ser Xaa Gly Xaa Gly Xaa Lys Xaa Gly
1               5

<210> SEQ ID NO 324
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)

<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 324

Ser Xaa Gly Xaa Gly Xaa Asn Xaa Gly
1               5

<210> SEQ ID NO 325
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 325

Phe Xaa Xaa Xaa Asn Xaa Lys Asp
1               5

<210> SEQ ID NO 326
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 326

Phe Xaa Xaa Xaa Asn Xaa Lys Lys
1               5

<210> SEQ ID NO 327
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 327

Phe Xaa Xaa Xaa Asn Xaa Lys Asn
1               5

<210> SEQ ID NO 328
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 328

Phe Xaa Xaa Xaa Arg Xaa Lys Asn
1               5

<210> SEQ ID NO 329
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 329

Phe Xaa Xaa Xaa Ser Xaa Lys Asp
1               5

<210> SEQ ID NO 330
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 330

Phe Xaa Xaa Xaa Thr Xaa Lys Asp
1               5

<210> SEQ ID NO 331
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 331

His Xaa Xaa Xaa Asn Xaa Ala Asn
1 5

<210> SEQ ID NO 332
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 332

His Xaa Xaa Xaa Asn Xaa Ile Asn
1 5

<210> SEQ ID NO 333
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 333

His Xaa Xaa Xaa Asn Xaa Leu Asn
1 5

<210> SEQ ID NO 334
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 334

Tyr Xaa Xaa Xaa Asn Xaa Lys Ser
1 5

<210> SEQ ID NO 335
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 335

Phe Gly Xaa Asp
1

<210> SEQ ID NO 336
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 336

Phe His Xaa Asp
1

<210> SEQ ID NO 337
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 337

Phe His Xaa Glu
1

<210> SEQ ID NO 338
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 338

Ser Gly Xaa Glu
1

<210> SEQ ID NO 339
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 339

Ser His Xaa Glu
1

<210> SEQ ID NO 340
<211> LENGTH: 860
<212> TYPE: PRT
<213> ORGANISM: Artificial Sequence
<220> FEATURE:

<223> OTHER INFORMATION: Synthetic polypeptide

<400> SEQUENCE: 340

```
Met Arg Val Met Gly Ile Gln Arg Asn Cys Gln His Leu Phe Arg Trp
1               5                   10                  15

Gly Thr Met Ile Leu Gly Met Ile Ile Ile Cys Ser Ala Ala Glu Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Gln Cys Thr Asn Val Thr Asn Asn Ile Thr Asp Asp Met Arg Gly Glu
    130                 135                 140

Leu Lys Asn Cys Ser Phe Asn Met Thr Thr Glu Leu Arg Asp Lys Lys
145                 150                 155                 160

Gln Lys Val Tyr Ser Leu Phe Tyr Arg Leu Asp Val Val Gln Ile Asn
                165                 170                 175

Glu Asn Gln Gly Asn Arg Ser Asn Asn Ser Asn Lys Glu Tyr Arg Leu
            180                 185                 190

Ile Asn Cys Asn Thr Ser Ala Ile Thr Gln Ala Cys Pro Lys Val Ser
        195                 200                 205

Phe Glu Pro Ile Pro Ile His Tyr Cys Ala Pro Ala Gly Phe Ala Ile
    210                 215                 220

Leu Lys Cys Lys Asp Lys Lys Phe Asn Gly Thr Gly Pro Cys Pro Ser
225                 230                 235                 240

Val Ser Thr Val Gln Cys Thr His Gly Ile Lys Pro Val Val Ser Thr
                245                 250                 255

Gln Leu Leu Leu Asn Gly Ser Leu Ala Glu Glu Glu Val Met Ile Arg
            260                 265                 270

Ser Glu Asn Ile Thr Asn Asn Ala Lys Asn Ile Leu Val Gln Phe Asn
        275                 280                 285

Thr Pro Val Gln Ile Asn Cys Thr Arg Pro Asn Asn Asn Thr Arg Lys
    290                 295                 300

Ser Ile Arg Ile Gly Pro Gly Gln Ala Phe Tyr Ala Thr Gly Asp Ile
305                 310                 315                 320

Ile Gly Asp Ile Arg Gln Ala His Cys Thr Val Ser Lys Ala Thr Trp
                325                 330                 335

Asn Glu Thr Leu Gly Lys Val Val Lys Gln Leu Arg Lys His Phe Gly
            340                 345                 350

Asn Asn Thr Ile Ile Arg Phe Ala Asn Ser Ser Gly Gly Asp Leu Glu
        355                 360                 365

Val Thr Thr His Ser Phe Asn Cys Gly Gly Glu Phe Phe Tyr Cys Asn
    370                 375                 380

Thr Ser Gly Leu Phe Asn Ser Thr Trp Ile Ser Asn Thr Ser Val Gln
385                 390                 395                 400
```

```
Gly Ser Asn Ser Thr Gly Ser Asn Asp Ser Ile Thr Leu Pro Cys Arg
                405                 410                 415

Ile Lys Gln Ile Ile Asn Met Trp Gln Arg Ile Gly Gln Ala Met Tyr
            420                 425                 430

Ala Pro Pro Ile Gln Gly Val Ile Arg Cys Val Ser Asn Ile Thr Gly
        435                 440                 445

Leu Ile Leu Thr Arg Asp Gly Gly Ser Thr Asn Ser Thr Thr Glu Thr
    450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                485                 490                 495

Arg Ala Lys Arg Arg Val Val Gly Arg Glu Lys Arg Ala Val Gly Ile
            500                 505                 510

Gly Ala Val Phe Leu Gly Phe Leu Gly Ala Ala Gly Ser Thr Met Gly
        515                 520                 525

Ala Ala Ser Met Thr Leu Thr Val Gln Ala Arg Asn Leu Leu Ser Gly
    530                 535                 540

Ile Val Gln Gln Gln Ser Asn Leu Leu Arg Ala Ile Glu Ala Gln Gln
545                 550                 555                 560

His Leu Leu Lys Leu Thr Val Trp Gly Ile Lys Gln Leu Gln Ala Arg
                565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Thr Thr Asn Val Pro Trp Asn
        595                 600                 605

Ser Ser Trp Ser Asn Arg Asn Leu Ser Glu Ile Trp Asp Asn Met Thr
    610                 615                 620

Trp Leu Gln Trp Asp Lys Glu Ile Ser Asn Tyr Thr Gln Ile Ile Tyr
625                 630                 635                 640

Gly Leu Leu Glu Glu Ser Gln Asn Gln Gln Glu Lys Asn Glu Gln Asp
                645                 650                 655

Leu Leu Ala Leu Asp Lys Trp Ala Ser Leu Trp Asn Trp Phe Asp Ile
            660                 665                 670

Ser Asn Trp Leu Trp Tyr Ile Lys Ile Phe Ile Met Ile Val Gly Gly
        675                 680                 685

Leu Ile Gly Leu Arg Ile Val Phe Ala Val Leu Ser Val Ile His Arg
    690                 695                 700

Val Arg Gln Gly Tyr Ser Pro Leu Ser Phe Gln Thr His Thr Pro Asn
705                 710                 715                 720

Pro Arg Gly Leu Asp Arg Pro Glu Arg Ile Glu Glu Glu Asp Gly Glu
                725                 730                 735

Gln Asp Arg Gly Arg Ser Thr Arg Leu Val Ser Gly Phe Leu Ala Leu
            740                 745                 750

Ala Trp Asp Asp Leu Arg Ser Leu Cys Leu Phe Cys Tyr His Arg Leu
        755                 760                 765

Arg Asp Phe Ile Leu Ile Ala Ala Arg Ile Val Glu Leu Leu Gly His
    770                 775                 780

Ser Ser Leu Lys Gly Leu Arg Leu Gly Trp Glu Gly Leu Lys Tyr Leu
785                 790                 795                 800

Trp Asn Leu Leu Ala Tyr Trp Gly Arg Glu Leu Lys Ile Ser Ala Ile
                805                 810                 815

Asn Leu Phe Asp Thr Ile Ala Ile Ala Val Ala Glu Trp Thr Asp Arg
```

```
            820                 825                 830

Val Ile Glu Ile Gly Gln Arg Leu Cys Arg Ala Phe Leu His Ile Pro
        835                 840                 845

Arg Arg Ile Arg Gln Gly Leu Glu Arg Ala Leu Leu
    850                 855                 860


<210> SEQ ID NO 341
<211> LENGTH: 4
<212> TYPE: PRT
<213> ORGANISM: Artificial Sequence
<220> FEATURE:
<223> OTHER INFORMATION: recombinant polypeptide

<400> SEQUENCE: 341

Gly Gly Gly Asp
1


<210> SEQ ID NO 342
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 342

tagcccttcc agtccccct tttctttta                                        29


<210> SEQ ID NO 343
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 343

caccggctta ggcatctcct atggcaggaa gaa                                  33


<210> SEQ ID NO 344
<211> LENGTH: 95
<212> TYPE: PRT
<213> ORGANISM: Artificial Sequence
<220> FEATURE:
<223> OTHER INFORMATION: synthetic polypeptide/polynucleotide

<400> SEQUENCE: 344

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr
                85                  90                  95


<210> SEQ ID NO 345
<211> LENGTH: 95
<212> TYPE: PRT
<213> ORGANISM: Artificial Sequence
<220> FEATURE:
```

<223> OTHER INFORMATION: synthetic polypeptide/polynucleotide

<400> SEQUENCE: 345

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Asn Tyr
            20                  25                  30

Ile Leu His Trp Trp Arg Gln Ala Pro Gly Gln Gly Leu Glu Trp Met
        35                  40                  45

Gly Trp Ile Lys Pro Val Phe Gly Ala Val Asn Tyr Ala Arg Gln Phe
    50                  55                  60

Gln Gly Arg Val Thr Met Thr Arg Asp Ile Tyr Arg Glu Ile Ala Tyr
65                  70                  75                  80

Met Glu Leu Ser Arg Leu Arg Ser Asp Asp Thr Ala Val Tyr Tyr
                85                  90                  95

<210> SEQ ID NO 346
<211> LENGTH: 95
<212> TYPE: PRT
<213> ORGANISM: Artificial Sequence
<220> FEATURE:
<223> OTHER INFORMATION: synthetic polypeptide/polynucleotide

<400> SEQUENCE: 346

Ser Gln His Leu Val Gln Ser Gly Thr Gln Val Lys Lys Pro Gly Ala
1               5                   10                  15

Ser Val Arg Ile Ser Cys Gln Ala Ser Gly Tyr Ser Phe Thr Asp Tyr
            20                  25                  30

Val Leu His Trp Trp Arg Gln Ala Pro Gly Gln Gly Leu Glu Trp Met
        35                  40                  45

Gly Trp Ile Lys Pro Val Tyr Gly Ala Arg Asn Tyr Ala Arg Arg Phe
    50                  55                  60

Gln Gly Arg Ile Asn Phe Asp Arg Asp Ile Tyr Arg Glu Ile Ala Phe
65                  70                  75                  80

Met Asp Leu Ser Gly Leu Arg Ser Asp Asp Thr Ala Leu Tyr Phe
                85                  90                  95

<210> SEQ ID NO 347
<211> LENGTH: 95
<212> TYPE: PRT
<213> ORGANISM: Artificial Sequence
<220> FEATURE:
<223> OTHER INFORMATION: synthetic polypeptide/polynucleotide

<400> SEQUENCE: 347

Ser Gln His Leu Val Gln Ser Gly Thr Gln Val Lys Lys Pro Gly Ala
1               5                   10                  15

Ser Val Arg Val Ser Cys Gln Ala Ser Gly Tyr Thr Phe Thr Asn Tyr
            20                  25                  30

Ile Leu His Trp Trp Arg Gln Ala Pro Gly Gln Gly Leu Glu Trp Met
        35                  40                  45

Gly Leu Ile Lys Pro Val Phe Gly Ala Val Asn Tyr Ala Arg Gln Phe
    50                  55                  60

Gln Gly Arg Ile Gln Leu Thr Arg Asp Ile Tyr Arg Glu Ile Ala Phe
65                  70                  75                  80

Leu Asp Leu Ser Gly Leu Arg Ser Asp Asp Thr Ala Val Tyr Tyr
                85                  90                  95

<210> SEQ ID NO 348
<211> LENGTH: 95
<212> TYPE: PRT
<213> ORGANISM: Artificial Sequence
<220> FEATURE:
<223> OTHER INFORMATION: synthetic polypeptide/polynucleotide

<400> SEQUENCE: 348

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Cys
            20                  25                  30

Thr Leu Asn Trp Val Arg Gln Ala Pro Gly Gln Gly Leu Glu Trp Met
        35                  40                  45

Gly Trp Ile Lys Pro Arg Gly Gly Ala Val Asn Tyr Ala Arg Lys Phe
    50                  55                  60

Gln Gly Arg Val Thr Met Thr Arg Asp Val Tyr Ser Asp Thr Ala Tyr
65                  70                  75                  80

Met Glu Leu Ser Arg Leu Arg Ser Asp Asp Thr Ala Val Tyr Tyr
                85                  90                  95
```

<210> SEQ ID NO 349
<211> LENGTH: 95
<212> TYPE: PRT
<213> ORGANISM: Artificial Sequence
<220> FEATURE:
<223> OTHER INFORMATION: synthetic polypeptide/polynucleotide

<400> SEQUENCE: 349

```
Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe
                85                  90                  95
```

<210> SEQ ID NO 350
<211> LENGTH: 93
<212> TYPE: PRT
<213> ORGANISM: Artificial Sequence
<220> FEATURE:
<223> OTHER INFORMATION: synthetic polypeptide/polynucleotide

<400> SEQUENCE: 350

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

Glu Asp Ile Ala Thr Tyr Tyr Cys Gln Gln Tyr Asp Asn
85 90

<210> SEQ ID NO 351
<211> LENGTH: 93
<212> TYPE: PRT
<213> ORGANISM: Artificial Sequence
<220> FEATURE:
<223> OTHER INFORMATION: synthetic polypeptide/polynucleotide

<400> SEQUENCE: 351

Asp Ile Gln Met Thr Gln Ser Pro Ser Thr Leu Ser Ala Ser Val Gly
1 5 10 15

Asp Arg Val Thr Ile Thr Cys Arg Ala Gly Gln Gly Ile Gly Ser Ser
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Phe His Thr Thr Phe Thr Leu Thr Ile Ser Ser Leu Gln Pro
65 70 75 80

Asp Asp Phe Ala Thr Tyr Tyr Cys Ala Val Phe Gln Trp
85 90

<210> SEQ ID NO 352
<211> LENGTH: 93
<212> TYPE: PRT
<213> ORGANISM: Artificial Sequence
<220> FEATURE:
<223> OTHER INFORMATION: synthetic polypeptide/polynucleotide

<400> SEQUENCE: 352

Asp Ile Gln Met Thr Gln Ser Pro Ser Ser Leu Ser Ala Ser Val Gly
1 5 10 15

Asp Arg Val Thr Ile Asn Cys Gln Ala Gly Gln Gly Ile Gly Ser Ser
20 25 30

Leu Asn Trp Tyr Gln Lys Lys Pro Gly Arg Ala Pro Lys Leu Leu Val
35 40 45

His Gly Ala Ser Asn Leu Gln Arg Gly Val Pro Ser Arg Phe Ser Gly
50 55 60

Ser Gly Phe His Thr Thr Phe Thr Leu Thr Ile Ser Ser Leu Gln Pro
65 70 75 80

Asp Asp Val Ala Thr Tyr Phe Cys Ala Val Phe Gln Trp
85 90

<210> SEQ ID NO 353
<211> LENGTH: 93
<212> TYPE: PRT
<213> ORGANISM: Artificial Sequence
<220> FEATURE:
<223> OTHER INFORMATION: synthetic polypeptide/polynucleotide

<400> SEQUENCE: 353

Asp Ile Gln Met Thr Gln Ser Pro Ser Ser Leu Ser Ala Ser Val Gly
1 5 10 15

Asp Arg Val Thr Ile Asn Cys Gln Ala Gly Gln Gly Ile Gly Ser Ser
20 25 30

Leu Asn Trp Tyr Gln Lys Lys Pro Gly Arg Ala Pro Lys Leu Leu Val
35 40 45

```
His Gly Ala Ser Asn Leu Gln Arg Gly Val Pro Ser Arg Phe Ser Gly
    50                  55                  60

Ser Gly Phe His Thr Thr Phe Thr Leu Thr Ile Ser Ser Leu Gln Pro
65                  70                  75                  80

Asp Asp Val Ala Thr Tyr Phe Cys Ala Val Phe Gln Trp
                85                  90


<210> SEQ ID NO 354
<211> LENGTH: 93
<212> TYPE: PRT
<213> ORGANISM: Artificial Sequence
<220> FEATURE:
<223> OTHER INFORMATION: synthetic polypeptide/polynucleotide

<400> SEQUENCE: 354

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn
                85                  90


<210> SEQ ID NO 355
<211> LENGTH: 91
<212> TYPE: PRT
<213> ORGANISM: Artificial Sequence
<220> FEATURE:
<223> OTHER INFORMATION: synthetic polypeptide/polynucleotide

<400> SEQUENCE: 355

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Tyr Gly Ser Leu Ala
            20                  25                  30

Trp Tyr Gln Gln Lys Pro Gly Gln Ala Pro Arg Leu Leu Ile Tyr Asp
        35                  40                  45

Gly Ser Asn Arg Ala Thr Gly Ile Pro Ala Arg Phe Ser Gly Ser Arg
    50                  55                  60

Trp Gly Pro Asp Phe Thr Leu Thr Ile Ser Ser Leu Glu Pro Glu Asp
65                  70                  75                  80

Phe Ala Val Tyr Tyr Cys Gln Gln Tyr Glu Phe
                85                  90


<210> SEQ ID NO 356
<211> LENGTH: 91
<212> TYPE: PRT
<213> ORGANISM: Artificial Sequence
<220> FEATURE:
<223> OTHER INFORMATION: synthetic polypeptide/polynucleotide

<400> SEQUENCE: 356

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
```

```
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Leu Tyr Glu Phe
                85                  90


<210> SEQ ID NO 357
<211> LENGTH: 6
<212> TYPE: PRT
<213> ORGANISM: Artificial Sequence
<220> FEATURE:
<223> OTHER INFORMATION: synthetic polypeptide/polynucleotide

<400> SEQUENCE: 357

Thr Asn Tyr Ile Leu Trp
1               5


<210> SEQ ID NO 358
<211> LENGTH: 4
<212> TYPE: PRT
<213> ORGANISM: Artificial Sequence
<220> FEATURE:
<223> OTHER INFORMATION: synthetic polypeptide/polynucleotide

<400> SEQUENCE: 358

Val Phe Ala Val
1


<210> SEQ ID NO 359
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 359

Gly Gly Gly Ser Asn
1               5


<210> SEQ ID NO 360
<211> LENGTH: 4
<212> TYPE: PRT
<213> ORGANISM: Artificial Sequence
<220> FEATURE:
<223> OTHER INFORMATION: synthetic polypeptide/polynucleotide

<400> SEQUENCE: 360

His Asn Gln Arg
1


<210> SEQ ID NO 361
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 361

Ala Val Phe Gln Trp
1               5
```

<210> SEQ ID NO 362
<211> LENGTH: 6
<212> TYPE: PRT
<213> ORGANISM: Artificial Sequence
<220> FEATURE:
<223> OTHER INFORMATION: synthetic polypeptide/polynucleotide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 362

Xaa Xaa Cys Tyr Ile Phe
1               5

<210> SEQ ID NO 363
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 363

Gln Val Leu Glu Thr
1               5

<210> SEQ ID NO 364
<211> LENGTH: 15
<212> TYPE: PRT
<213> ORGANISM: Artificial Sequence
<220> FEATURE:
<223> OTHER INFORMATION: synthetic polypeptide/polynucleotide

<400> SEQUENCE: 364

Ala Arg Asp Ser Ser Arg Asp Glu Thr Asn Trp Trp Leu Asp Pro
1               5                   10                  15

<210> SEQ ID NO 365
<211> LENGTH: 15
<212> TYPE: PRT
<213> ORGANISM: Artificial Sequence
<220> FEATURE:
<223> OTHER INFORMATION: synthetic polypeptide/polynucleotide

<400> SEQUENCE: 365

Ala Arg Asp Ser Ser Arg Glu Glu Thr Asn Trp Trp Leu Asp Pro
1               5                   10                  15

<210> SEQ ID NO 366
<211> LENGTH: 15
<212> TYPE: PRT
<213> ORGANISM: Artificial Sequence
<220> FEATURE:
<223> OTHER INFORMATION: synthetic polypeptide/polynucleotide

<400> SEQUENCE: 366

Thr Arg Asp Ala Ser Arg Asp Asp Arg Ala Trp Arg Leu Asp Pro
1               5                   10                  15

<210> SEQ ID NO 367
<211> LENGTH: 15
<212> TYPE: PRT
<213> ORGANISM: Artificial Sequence
<220> FEATURE:
<223> OTHER INFORMATION: synthetic polypeptide/polynucleotide

<400> SEQUENCE: 367

Thr Arg Asp Ser Ser Arg Asp Glu Thr Asn Trp Trp Leu Asp Pro
1 5 10 15

<210> SEQ ID NO 368
<211> LENGTH: 15
<212> TYPE: PRT
<213> ORGANISM: Artificial Sequence
<220> FEATURE:
<223> OTHER INFORMATION: synthetic polypeptide/polynucleotide

<400> SEQUENCE: 368

Thr Arg Asp Ser Ser Arg Asp Asn Leu Glu Trp Arg Leu Asp Pro
1 5 10 15

<210> SEQ ID NO 369
<211> LENGTH: 15
<212> TYPE: PRT
<213> ORGANISM: Artificial Sequence
<220> FEATURE:
<223> OTHER INFORMATION: synthetic polypeptide/polynucleotide

<400> SEQUENCE: 369

Thr Arg Asp Ser Ser Arg Gly Asp Thr Glu Trp Arg Leu Asp Pro
1 5 10 15

<210> SEQ ID NO 370
<211> LENGTH: 15
<212> TYPE: PRT
<213> ORGANISM: Artificial Sequence
<220> FEATURE:
<223> OTHER INFORMATION: synthetic polypeptide/polynucleotide

<400> SEQUENCE: 370

Thr Arg Asp Ser Ser Arg Gly Asn Thr Glu Trp Arg Leu Asp Pro
1 5 10 15

<210> SEQ ID NO 371
<211> LENGTH: 15
<212> TYPE: PRT
<213> ORGANISM: Artificial Sequence
<220> FEATURE:
<223> OTHER INFORMATION: synthetic polypeptide/polynucleotide

<400> SEQUENCE: 371

Thr Arg Asp Ser Ser Arg Gln Gln Arg Asp Trp Trp Leu Asp Pro
1 5 10 15

<210> SEQ ID NO 372
<211> LENGTH: 15
<212> TYPE: PRT
<213> ORGANISM: Artificial Sequence
<220> FEATURE:
<223> OTHER INFORMATION: synthetic polypeptide/polynucleotide

<400> SEQUENCE: 372

Thr Arg Asp Ser Ser Arg Arg Asp Leu Glu Trp Arg Leu Asp Pro
1 5 10 15

<210> SEQ ID NO 373
<211> LENGTH: 15
<212> TYPE: PRT
<213> ORGANISM: Artificial Sequence
<220> FEATURE:
<223> OTHER INFORMATION: synthetic polypeptide/polynucleotide

<400> SEQUENCE: 373

Thr Arg Asp Ser Ser Arg Arg Asp Thr Asn Trp Trp Leu Asp Pro 1 5 10 15

<210> SEQ ID NO 374
<211> LENGTH: 15
<212> TYPE: PRT
<213> ORGANISM: Artificial Sequence
<220> FEATURE:
<223> OTHER INFORMATION: synthetic polypeptide/polynucleotide

<400> SEQUENCE: 374

Thr Thr His Ser Ser Arg Arg Asp Phe Gln Trp Ser Leu Asp Pro
1 5 10 15

<210> SEQ ID NO 375
<211> LENGTH: 15
<212> TYPE: PRT
<213> ORGANISM: Artificial Sequence
<220> FEATURE:
<223> OTHER INFORMATION: synthetic polypeptide/polynucleotide

<400> SEQUENCE: 375

Thr Thr His Ser Ser Ser Arg Asp Phe Gln Trp Ser Leu Asp Pro
1 5 10 15

<210> SEQ ID NO 376
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 376

Gln Ala Tyr Glu Ser
1 5

<210> SEQ ID NO 377
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 377

Gln Val Phe Glu Trp
1 5

<210> SEQ ID NO 378
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 378

Gln Val Leu Glu Thr
1 5

<210> SEQ ID NO 379
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 379

Gln Val Val Glu Trp
1 5

<210> SEQ ID NO 380
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 380

Gln Val Tyr Glu Ser
1 5

<210> SEQ ID NO 381
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 381

Gln Val Tyr Gln Thr
1 5

<210> SEQ ID NO 382
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 382

Gln Val Val Gln Trp
1 5

<210> SEQ ID NO 383
<211> LENGTH: 15
<212> TYPE: PRT
<213> ORGANISM: Artificial Sequence
<220> FEATURE:
<223> OTHER INFORMATION: synthetic polypeptide/polynucleotide
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 383

Xaa Xaa Xaa Xaa Ser Xaa Xaa Xaa Xaa Xaa Trp Xaa Xaa Asp Pro
1 5 10 15

<210> SEQ ID NO 384
<211> LENGTH: 98
<212> TYPE: PRT
<213> ORGANISM: Artificial Sequence
<220> FEATURE:
<223> OTHER INFORMATION: synthetic polypeptide/polynucleotide

<400> SEQUENCE: 384

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr 20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg

<210> SEQ ID NO 385
<211> LENGTH: 7
<212> TYPE: PRT
<213> ORGANISM: Artificial Sequence
<220> FEATURE:
<223> OTHER INFORMATION: synthetic polypeptide/polynucleotide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 385

Xaa Val Gln Gln Leu Val Xaa
1 5

<210> SEQ ID NO 386
<211> LENGTH: 16
<212> TYPE: PRT
<213> ORGANISM: Artificial Sequence
<220> FEATURE:
<223> OTHER INFORMATION: synthetic polypeptide/polynucleotide

<400> SEQUENCE: 386

Asn Trp Phe Asp Pro Trp Gly Gln Gly Thr Leu Val Thr Val Ser Ser
1 5 10 15

<210> SEQ ID NO 387
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 387

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Asp Ser Ser Arg Gln Gln Leu Glu Trp Trp Phe Asp Pro Trp 100 105 110

Gly Gln Gly Thr Leu Val Thr Val Ser Ser
115 120

<210> SEQ ID NO 388
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 388

Gln Val Gln Leu Val Gln Ser Gly Ala Glu Val Lys Lys Pro Gly Ala
1 5 10 15

Ser Met Arg Val Ser Cys Lys Ala Ser Gly Tyr Thr Phe Thr Ala Cys
20 25 30

Tyr Ile His Trp Phe Arg Gln Ala Pro Gly Gln Gly Leu Glu Trp Met
35 40 45

Gly Trp Ile Asn Pro Ile Asn Gly Ala Arg Asn Asn Pro Arg Lys Phe
50 55 60

Gln Gly Arg Val Thr Met Thr Arg Asp Thr Ser Ile Asp Thr Ala Tyr
65 70 75 80

Leu Glu Leu Arg Asn Leu Ala Ser Asp Asp Thr Ala Met Tyr Tyr Cys
85 90 95

Thr Arg Asp Ser Ser Arg Arg Asp Thr Asn Trp Trp Leu Asp Pro Trp
100 105 110

Gly Gln Gly Thr Leu Val Thr Val Ser Ser
115 120

<210> SEQ ID NO 389
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 389

Gln Val Gln Leu Val Gln Ser Gly Ala Glu Val Lys Lys Pro Gly Ala
1 5 10 15

Ser Val Arg Val Ser Cys Lys Ala Ser Gly Tyr Thr Phe Thr Ala Tyr
20 25 30

Phe Ile His Trp Val Arg Gln Ala Pro Gly Gln Gly Leu Glu Trp Val
35 40 45

Gly Trp Ile Asn Pro Leu His Gly Ala Val Asn Tyr Ala His Lys Phe
50 55 60

Gln Gly Arg Val Ser Met Thr Arg Asp Thr Ser Ile Ser Thr Ala Tyr
65 70 75 80

Met Glu Leu Arg Ser Leu Lys Ser Asp Asp Thr Ala Ile Tyr Tyr Cys
85 90 95

Thr Thr His Ser Ser Ser Arg Asp Phe Gln Trp Ser Leu Asp Pro Trp
100 105 110

Gly Gln Gly Thr Leu Val Thr Val Ser Ser
115 120

<210> SEQ ID NO 390
<211> LENGTH: 122
<212> TYPE: PRT
<213> ORGANISM: Artificial Sequence
<220> FEATURE:

<223> OTHER INFORMATION: synthetic polypeptide/polynucleotide

<400> SEQUENCE: 390

Gln Val Gln Leu Val Gln Ser Gly Ala Glu Val Lys Lys Pro Gly Ala
1 5 10 15

Ser Met Arg Val Ser Cys Lys Ala Ser Gly Tyr Thr Phe Thr Ser Cys
20 25 30

Tyr Ile His Trp Phe Arg Gln Ala Pro Gly Gln Gly Leu Glu Trp Met
35 40 45

Gly Trp Leu Asn Pro Ile Asn Gly Ala Arg Asn Asn Pro His Lys Phe
50 55 60

Gln Gly Arg Ile Thr Leu Thr Arg Asp Thr Ser Thr Asp Thr Ala Tyr
65 70 75 80

Leu Glu Leu Arg Asn Leu Arg Ser Asp Asp Thr Ala Val Tyr Tyr Cys
85 90 95

Thr Arg Asp Ser Ser Arg Arg Asp Thr Asn Trp Trp Leu Asp Pro Trp
100 105 110

Gly Gln Gly Thr Leu Val Thr Val Ser Ser
115 120

<210> SEQ ID NO 391
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 391

Gln Val Gln Leu Val Gln Ser Gly Ala Glu Val Lys Lys Pro Gly Ala
1 5 10 15

Ser Met Arg Val Ser Cys Lys Ala Ser Gly Tyr Thr Phe Thr Ala Cys
20 25 30

Tyr Ile His Trp Phe Arg Gln Ala Pro Gly Gln Gly Leu Glu Trp Met
35 40 45

Gly Trp Leu Asn Pro Ile Asn Gly Ala Arg Asn Asn Pro His Lys Phe
50 55 60

Gln Gly Arg Ile Thr Leu Thr Arg Asp Thr Ser Thr Asp Thr Ala Tyr
65 70 75 80

Leu Glu Leu Arg Asn Leu Arg Ser Asp Asp Thr Ala Val Tyr Tyr Cys
85 90 95

Thr Arg Asp Ser Ser Arg Arg Asp Thr Asn Trp Trp Leu Asp Pro Trp
100 105 110

Gly Gln Gly Ala Leu Val Thr Val Ser Ser
115 120

<210> SEQ ID NO 392
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 392

Gln Val Gln Leu Val Gln Ser Gly Ala Glu Val Lys Lys Pro Gly Ala
1 5 10 15

Ser Met Arg Val Ser Cys Lys Ala Ser Gly Tyr Thr Phe Thr Ser Cys
20 25 30

Tyr Ile His Trp Phe Arg Gln Ala Pro Gly Gln Gly Leu Glu Trp Met

```
        35                  40                  45

Gly Trp Leu Asn Pro Ile Asn Gly Ala Arg Asn Asn Pro His Lys Phe
    50                  55                  60

Gln Gly Arg Ile Thr Leu Thr Arg Asp Thr Ser Thr Asp Thr Ala Tyr
65                  70                  75                  80

Leu Glu Leu Arg Asn Leu Arg Ser Asp Asp Thr Ala Val Tyr Tyr Cys
                85                  90                  95

Thr Arg Asp Ser Ser Arg Arg Asp Thr Asn Trp Trp Leu Asp Pro Trp
            100                 105                 110

Gly Gln Gly Thr Leu Val Thr Val Ser Ser
        115                 120


<210> SEQ ID NO 393
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 393

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Ser Phe Thr Asp Tyr
            20                  25                  30

Phe Val His Trp Val Arg Gln Ala Pro Gly Gln Gly Leu Glu Trp Val
        35                  40                  45

Gly Trp Ile Asn Pro Ile Asn Gly Ala Pro Asn Tyr Ala Pro Asn Phe
    50                  55                  60

Arg Gly Arg Ile Thr Leu Thr Arg Asp Thr Ser Ile Asp Thr Leu Tyr
65                  70                  75                  80

Met Asp Leu Arg Ser Leu Arg Val Asp Asp Thr Ala Val Tyr Phe Cys
                85                  90                  95

Thr Arg Asp Ser Ser Arg Gln Gln Arg Asp Trp Trp Leu Asp Pro Trp
            100                 105                 110

Gly Gln Gly Thr Leu Val Thr Val Ser Ser
        115                 120


<210> SEQ ID NO 394
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 394

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Asn Ser Cys
            20                  25                  30

Leu Ile His Trp Trp Arg Gln Ala Pro Gly Gln Gly Leu Gln Trp Met
        35                  40                  45

Ala Trp Ile Asn Pro Leu His Gly Ala Val Asn Tyr Ala His Gln Phe
    50                  55                  60

Gln Gly Arg Ile Thr Val Thr Arg Asp Thr Ser Ile Asp Thr Ala Tyr
65                  70                  75                  80

Met Glu Leu Arg Gly Leu Arg Ser Asp Asp Thr Ala Thr Tyr Tyr Cys
                85                  90                  95
```

Thr Arg Asp Ala Ser Arg Asp Asp Arg Ala Trp Arg Leu Asp Pro Trp
100 105 110

Gly Gln Gly Thr Leu Val Thr Val Ser Ser
115 120

<210> SEQ ID NO 395
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 395

Gln Val Gln Leu Val Gln Ser Gly Val Ala Val Lys Lys Pro Gly Ala
1 5 10 15

Ser Val Trp Val Ser Cys Lys Ala Ser Gly Tyr Thr Phe Thr Ser Cys
20 25 30

Tyr Ile His Trp Phe Arg Gln Ala Pro Gly Gln Gly Leu Glu Trp Met
35 40 45

Gly Trp Leu Asn Pro Ile Asn Gly Ala Arg Asn Asn Pro Tyr Gln Phe
50 55 60

Gln Gly Arg Ile Ser Leu Thr Arg Asp Thr Ser Ser Glu Thr Ala Tyr
65 70 75 80

Leu Glu Leu Arg Asn Leu Arg Ser Asp Asp Thr Ala Val Tyr Tyr Cys
85 90 95

Ala Arg Asp Ser Ser Arg Glu Glu Thr Asn Trp Trp Leu Asp Pro Trp
100 105 110

Gly Gln Gly Thr Leu Val Thr Val Ser Ser
115 120

<210> SEQ ID NO 396
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 396

Gln Val Gln Leu Val Gln Ser Gly Ala Glu Val Lys Lys Pro Gly Ala
1 5 10 15

Ser Val Arg Val Ser Cys Lys Ala Ser Gly Tyr Thr Phe Asn Ser Cys
20 25 30

Leu Ile His Trp Trp Arg Gln Ala Pro Gly Gln Gly Leu Gln Trp Met
35 40 45

Ala Trp Ile Asn Pro Leu His Gly Ala Val Asn Tyr Ala His Gln Phe
50 55 60

Gln Gly Arg Ile Thr Val Thr Arg Asp Thr Ser Ile Asp Thr Ala Tyr
65 70 75 80

Met Glu Leu Arg Gly Leu Arg Ser Asp Asp Thr Ala Thr Tyr Tyr Cys
85 90 95

Thr Arg Asp Ala Ser Arg Asp Asp Arg Ala Trp Arg Leu Asp Pro Trp
100 105 110

Gly Gln Gly Thr Leu Val Thr Val Ser Ser
115 120

<210> SEQ ID NO 397
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 397

Gln Val Gln Leu Val Gln Ser Gly Ala Glu Val Lys Lys Pro Gly Ala
1 5 10 15

Ser Met Arg Val Ser Cys Lys Ala Ser Gly Tyr Thr Phe Thr Ala Cys
20 25 30

Tyr Ile His Trp Phe Arg Gln Ala Pro Gly Gln Gly Leu Glu Trp Met
35 40 45

Gly Trp Leu Asn Pro Ile Asn Gly Ala Arg Asn Asn Pro His Lys Phe
50 55 60

Gln Gly Arg Ile Thr Leu Thr Arg Asp Thr Ser Thr Asp Thr Ala Tyr
65 70 75 80

Leu Glu Leu Arg Asn Leu Arg Ser Asp Asp Thr Ala Val Tyr Tyr Cys
85 90 95

Thr Arg Asp Ser Ser Arg Arg Asp Thr Asn Trp Trp Leu Asp Pro Trp
100 105 110

Gly Gln Gly Thr Leu Val Thr Val Ser Ser
115 120

<210> SEQ ID NO 398
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 398

Gln Val Gln Leu Val Gln Ser Gly Ala Ala Val Lys Lys Pro Gly Ala
1 5 10 15

Ser Val Trp Val Ser Cys Lys Ala Ser Gly Tyr Thr Phe Thr Ser Cys
20 25 30

Tyr Ile His Trp Phe Arg Gln Ala Pro Gly Gln Gly Leu Glu Trp Met
35 40 45

Gly Trp Leu Asn Pro Ile Asn Gly Ala Arg Asn Asn Pro Tyr Gln Phe
50 55 60

Gln Gly Arg Ile Ser Leu Thr Arg Asp Thr Ser Ser Glu Thr Ala Tyr
65 70 75 80

Leu Glu Leu Arg Asn Leu Thr Pro Asp Asp Thr Ala Val Tyr Tyr Cys
85 90 95

Thr Arg Asp Ser Ser Arg Asp Glu Thr Asn Trp Trp Leu Asp Pro Trp
100 105 110

Gly Gln Gly Thr Leu Val Thr Val Ser Ser
115 120

<210> SEQ ID NO 399
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 399

Gln Val Gln Leu Val Gln Ser Gly Ala Ala Val Lys Lys Pro Gly Ala
1 5 10 15

Ser Val Trp Val Ser Cys Lys Ala Ser Gly Tyr Thr Phe Thr Ser Cys
20 25 30

Tyr Ile His Trp Phe Arg Gln Ala Pro Gly Gln Gly Leu Glu Trp Met
35 40 45

Gly Trp Leu Asn Pro Ile Asn Gly Ala Arg Asn Asn Pro Tyr Gln Phe
50 55 60

Gln Gly Arg Ile Ser Leu Thr Arg Asp Thr Ser Ser Glu Thr Ala Tyr
65 70 75 80

Leu Glu Leu Arg Asn Leu Thr Pro Asp Asp Thr Ala Val Tyr Tyr Cys
85 90 95

Thr Arg Asp Ser Ser Arg Asp Glu Thr Asn Trp Trp Leu Asp Pro Trp
100 105 110

Gly Gln Gly Thr Leu Val Ile Val Ser Ser
115 120

<210> SEQ ID NO 400
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 400

Gln Val Gln Leu Val Gln Ser Gly Ala Ala Val Lys Lys Pro Gly Ala
1 5 10 15

Ser Val Trp Val Ser Cys Lys Ala Ser Gly Tyr Thr Phe Thr Ser Cys
20 25 30

Tyr Ile His Trp Phe Arg Gln Ala Pro Gly Gln Gly Leu Glu Trp Met
35 40 45

Gly Trp Leu Asn Pro Ile Asn Gly Ala Arg Asn Gln Ala Tyr Gln Phe
50 55 60

Gln Gly Arg Ile Ser Leu Thr Arg Asp Thr Pro Ser Glu Thr Ala Tyr
65 70 75 80

Leu Glu Leu Arg Asp Leu Arg Ser Asp Asp Thr Ala Val Tyr Tyr Cys
85 90 95

Ala Arg Asp Ser Ser Arg Asp Glu Thr Asn Trp Trp Leu Asp Pro Trp
100 105 110

Gly Gln Gly Thr Leu Val Thr Val Ser Ser
115 120

<210> SEQ ID NO 401
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 401

Gln Val Gln Leu Val Gln Ser Gly Ala Glu Val Lys Lys Pro Gly Ala
1 5 10 15

Ser Val Arg Val Ser Cys Lys Ala Ser Gly Tyr Thr Phe Asn Thr Cys
20 25 30

Leu Ile His Trp Trp Arg Gln Ala Pro Gly Gln Gly Leu Gln Trp Leu
35 40 45

Ala Trp Ile Asn Pro Leu His Gly Ala Val Asn Tyr Ala His Asn Phe
50 55 60

Gln Gly Arg Ile Thr Val Thr Arg Asp Thr Ser Ile Asp Thr Ala Tyr
65 70 75 80

Met Glu Leu Arg Gly Leu Arg Ser Asp Asp Thr Ala Thr Tyr Tyr Cys
85 90 95

Thr Arg Asp Ser Ser Arg Gly Asn Thr Glu Trp Arg Leu Asp Pro Trp
100 105 110

Gly Gln Gly Thr Leu Val Thr Val Ser Ser
115 120

<210> SEQ ID NO 402
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 402

Gln Val Gln Leu Val Gln Ser Gly Ala Glu Val Lys Lys Pro Gly Ala
1 5 10 15

Ser Val Arg Val Ser Cys Lys Ala Ser Gly Tyr Thr Phe Asn Thr Cys
20 25 30

Leu Ile His Trp Trp Arg Gln Ala Pro Gly Gln Gly Leu Gln Trp Val
35 40 45

Ala Trp Ile Asn Pro Leu His Gly Ala Val Asn Tyr Ala His Gln Leu
50 55 60

Gln Gly Arg Ile Thr Val Thr Arg Asp Thr Ser Ile Asp Thr Ala Tyr
65 70 75 80

Met Glu Leu Arg Gly Leu Arg Ala Asp Asp Thr Ala Thr Tyr Tyr Cys
85 90 95

Thr Arg Asp Ser Ser Arg Asp Asn Leu Glu Trp Arg Leu Asp Pro Trp
100 105 110

Gly Gln Gly Thr Leu Val Thr Val Ser Ser
115 120

<210> SEQ ID NO 403
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 403

Gln Val Gln Leu Val Gln Ser Gly Ala Glu Val Lys Lys Pro Gly Ala
1 5 10 15

Ser Val Arg Val Ser Cys Lys Ala Ser Gly Tyr Thr Phe Asn Thr Cys
20 25 30

Leu Ile His Trp Trp Arg Gln Ala Pro Gly Gln Gly Leu Gln Trp Val
35 40 45

Ala Trp Ile Asn Pro Leu His Gly Ala Val Asn Tyr Ala His Gln Leu
50 55 60

Gln Gly Arg Ile Thr Val Thr Arg Asp Thr Ser Ile Asp Thr Ala His
65 70 75 80

Met Glu Leu Arg Gly Leu Arg Ser Asp Asp Thr Ala Thr Tyr Tyr Cys
85 90 95

Thr Arg Asp Ser Ser Arg Gly Asp Thr Glu Trp Arg Leu Asp Pro Trp
100 105 110

Gly Gln Gly Thr Leu Val Thr Val Ser Ser
115 120

<210> SEQ ID NO 404
<211> LENGTH: 122
<212> TYPE: PRT

<213> ORGANISM: Artificial Sequence
<220> FEATURE:
<223> OTHER INFORMATION: synthetic polypeptide/polynucleotide

<400> SEQUENCE: 404

Gln Val Gln Leu Val Gln Ser Gly Ala Glu Val Lys Lys Pro Gly Ala
1 5 10 15

Ser Val Arg Val Ser Cys Lys Ala Ser Gly Tyr Thr Phe Thr Ala Tyr
20 25 30

Phe Ile His Trp Ile Arg Gln Ala Pro Gly Gln Gly Leu Glu Trp Val
35 40 45

Gly Trp Ile Asn Pro Leu His Gly Ala Val Asn Tyr Ala His Lys Phe
50 55 60

Gln Gly Arg Val Ser Met Thr Arg Asp Thr Ser Ile Ser Thr Ala Tyr
65 70 75 80

Met Glu Leu Arg Ser Leu Lys Ser Asp Asp Thr Ala Ile Tyr Tyr Cys
85 90 95

Thr Thr His Ser Ser Arg Arg Asp Phe Gln Trp Ser Leu Asp Pro Trp
100 105 110

Gly Gln Gly Thr Leu Val Thr Val Ser Ser
115 120

<210> SEQ ID NO 405
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 405

Gln Val Gln Leu Val Gln Ser Gly Ala Ala Val Lys Lys Pro Gly Ala
1 5 10 15

Ser Val Trp Val Ser Cys Lys Ala Ser Gly Tyr Thr Phe Ser Ser Cys
20 25 30

Tyr Ile His Trp Phe Arg Gln Ala Pro Gly Gln Gly Leu Glu Trp Met
35 40 45

Gly Trp Leu Asn Pro Ile Asn Gly Ala Arg Asn Gln Ala Tyr Gln Phe
50 55 60

Gln Gly Arg Ile Ser Leu Thr Arg Asp Thr Ser Ser Glu Thr Ala Tyr
65 70 75 80

Leu Glu Leu Arg Lys Leu Thr Pro Asp Asp Thr Ala Val Tyr Tyr Cys
85 90 95

Thr Arg Asp Ser Ser Arg Asp Glu Thr Asn Trp Trp Leu Asp Pro Trp
100 105 110

Gly Gln Gly Thr Leu Val Thr Val Ser Ser
115 120

<210> SEQ ID NO 406
<211> LENGTH: 123
<212> TYPE: PRT
<213> ORGANISM: Artificial Sequence
<220> FEATURE:
<223> OTHER INFORMATION: synthetic polypeptide/polynucleotide

<400> SEQUENCE: 406

Gln Val Gln Leu Val Gln Ser Gly Ala Glu Val Lys Lys Pro Gly Ala
1 5 10 15

Ser Val Arg Val Ser Cys Lys Ala Ser Gly Tyr Thr Phe Thr Ala Cys
20 25 30

Tyr Ile Gln Trp Phe Arg Gln Ala Pro Gly Gln Gly Leu Glu Trp Met
35 40 45

Gly Trp Ile Asn Pro Ile Asn Gly Ala Arg Asn Asn Asn Pro Gln Thr
50 55 60

Phe Gln Gly Arg Val Thr Leu Thr Arg Asp Thr Ser Ile Asp Thr Ala
65 70 75 80

Tyr Leu Glu Leu Arg Asn Leu Arg Asp Asp Asp Thr Ala Ile Tyr Tyr
85 90 95

Cys Thr Arg Asp Ser Ser Arg Arg Asp Leu Glu Trp Arg Leu Asp Pro
100 105 110

Trp Gly Gln Gly Thr Leu Val Thr Val Ser Ser
115 120

<210> SEQ ID NO 407
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 407

Gln Val Gln Leu Val Gln Ser Gly Ala Ala Val Lys Lys Pro Gly Ala
1 5 10 15

Ser Val Trp Val Ser Cys Lys Ala Ser Gly Tyr Thr Phe Thr Ser Cys
20 25 30

Tyr Ile His Trp Phe Arg Gln Ala Pro Gly Gln Gly Leu Glu Trp Met
35 40 45

Gly Trp Leu Asn Pro Ile Asn Gly Ala Arg Asn His Ala Tyr Gln Phe
50 55 60

Gln Gly Arg Ile Ser Leu Thr Arg Asp Thr Ser Ser Glu Thr Ala Tyr
65 70 75 80

Leu Glu Leu Arg Asn Leu Arg Ser Asp Asp Thr Ala Val Tyr Tyr Cys
85 90 95

Ala Arg Asp Ser Ser Arg Asp Glu Thr Asn Trp Trp Leu Asp Pro Trp
100 105 110

Gly Gln Gly Thr Leu Val Thr Val Ser Ser
115 120

<210> SEQ ID NO 408
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 408

Gln Val Gln Leu Val Gln Ser Gly Ala Ala Val Lys Lys Pro Gly Ala
1 5 10 15

Ser Val Trp Val Ser Cys Lys Ala Ser Gly Tyr Thr Phe Thr Ser Cys
20 25 30

Tyr Ile His Trp Phe Arg Leu Ala Pro Gly Gln Gly Leu Glu Trp Met
35 40 45

Gly Trp Leu Asn Pro Ile Asn Gly Ala Arg Asn His Ala Tyr Gln Phe
50 55 60

Gln Gly Arg Ile Ser Leu Thr Arg Asp Thr Ser Ser Glu Thr Ala Tyr
65 70 75 80

Leu Glu Leu Arg Asn Leu Thr Pro Asp Asp Thr Ala Val Tyr Tyr Cys

```
                85                  90                  95

Thr Arg Asp Ser Ser Arg Asp Glu Thr Asn Trp Trp Leu Asp Pro Trp
            100                 105                 110

Gly Gln Gly Thr Leu Val Thr Val Ser Ser
        115                 120


<210> SEQ ID NO 409
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 409

Gln Val Gln Leu Val Gln Ser Gly Ala Ala Val Lys Lys Pro Gly Ala
1               5                   10                  15

Ser Val Trp Val Ser Cys Lys Ala Ser Gly Tyr Thr Phe Ser Ser Cys
            20                  25                  30

Tyr Ile His Trp Phe Arg Gln Ala Pro Gly Gln Gly Leu Glu Trp Met
        35                  40                  45

Gly Trp Leu Asn Pro Ile Asn Gly Ala Arg Asn Gln Ala Tyr Gln Phe
    50                  55                  60

Gln Gly Arg Ile Ser Leu Thr Arg Asp Thr Ser Ser Glu Thr Ala Tyr
65                  70                  75                  80

Leu Glu Leu Arg Lys Leu Thr Pro Asp Asp Thr Ala Val Tyr Tyr Cys
                85                  90                  95

Thr Arg Asp Ser Ser Arg Asp Glu Thr Asn Trp Trp Leu Asp Pro Trp
            100                 105                 110

Gly Gln Gly Thr Leu Val Thr Val Ser Ser
        115                 120


<210> SEQ ID NO 410
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 410

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Ala Arg Gly Ser Lys Asn Cys Asp Tyr Asn Trp Asp Phe Glu Pro Trp
            100                 105                 110

Gly Arg Gly Thr Pro Val Ile Val Ser Ser
        115                 120


<210> SEQ ID NO 411
<211> LENGTH: 122
```

<212> TYPE: PRT
<213> ORGANISM: Artificial Sequence
<220> FEATURE:
<223> OTHER INFORMATION: synthetic polypeptide/polynucleotide

<400> SEQUENCE: 411

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Cys
            20                  25                  30

Thr Leu Asn Trp Val Arg Gln Ala Pro Gly Gln Gly Leu Glu Trp Met
        35                  40                  45

Gly Trp Ile Lys Pro Arg Gly Gly Ala Val Asn Tyr Ala Arg Lys Phe
    50                  55                  60

Gln Gly Arg Val Thr Met Thr Arg Asp Val Tyr Ser Asp Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ser Lys Asn Cys Asp Tyr Asn Trp Asp Phe Glu Pro Trp
            100                 105                 110

Gly Gln Gly Thr Leu Val Thr Val Ser Ser
        115                 120

<210> SEQ ID NO 412
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 412

Ser Gln His Leu Val Gln Ser Gly Thr Gln Val Lys Lys Pro Gly Ala
1               5                   10                  15

Ser Val Arg Val Ser Cys Gln Ala Ser Gly Tyr Thr Phe Thr Asn Tyr
            20                  25                  30

Ile Leu His Trp Trp Arg Gln Ala Pro Gly Gln Gly Leu Glu Trp Met
        35                  40                  45

Gly Leu Ile Lys Pro Val Phe Gly Ala Val Asn Tyr Ala Arg Gln Phe
    50                  55                  60

Gln Gly Arg Ile Gln Leu Thr Arg Asp Ile Tyr Arg Glu Ile Ala Phe
65                  70                  75                  80

Leu Asp Leu Ser Gly Leu Arg Ser Asp Asp Thr Ala Val Tyr Tyr Cys
                85                  90                  95

Ala Arg Asp Glu Ser Gly Asp Asp Leu Lys Trp His Leu His Pro Trp
            100                 105                 110

Gly Gln Gly Thr Gln Val Ile Val Ser Pro
        115                 120

<210> SEQ ID NO 413
<211> LENGTH: 122
<212> TYPE: PRT
<213> ORGANISM: Artificial Sequence
<220> FEATURE:
<223> OTHER INFORMATION: synthetic polypeptide/polynucleotide

<400> SEQUENCE: 413

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Asn Tyr

```
            20                  25                  30

Ile Leu His Trp Trp Arg Gln Ala Pro Gly Gln Gly Leu Glu Trp Met
        35                  40                  45

Gly Trp Ile Lys Pro Val Phe Gly Ala Val Asn Tyr Ala Arg Gln Phe
    50                  55                  60

Gln Gly Arg Val Thr Met Thr Arg Asp Ile Tyr Arg Glu Ile Ala Tyr
65                  70                  75                  80

Met Glu Leu Ser Arg Leu Arg Ser Asp Asp Thr Ala Val Tyr Tyr Cys
                85                  90                  95

Ala Arg Asp Glu Ser Gly Asp Asp Leu Lys Trp His Leu His Pro Trp
            100                 105                 110

Gly Gln Gly Thr Leu Val Thr Val Ser Ser
        115                 120


<210> SEQ ID NO 414
<211> LENGTH: 96
<212> TYPE: PRT
<213> ORGANISM: Artificial Sequence
<220> FEATURE:
<223> OTHER INFORMATION: synthetic polypeptide/polynucleotide

<400> SEQUENCE: 414

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Pro
                85                  90                  95


<210> SEQ ID NO 415
<211> LENGTH: 12
<212> TYPE: PRT
<213> ORGANISM: Artificial Sequence
<220> FEATURE:
<223> OTHER INFORMATION: synthetic polypeptide/polynucleotide

<400> SEQUENCE: 415

Trp Thr Phe Gly Gln Gly Thr Lys Val Glu Ile Lys
1               5                   10


<210> SEQ ID NO 416
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 416

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45
```

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Leu Tyr Glu Thr Phe Gly Gln
85 90 95

Gly Thr Lys Val Glu Ile Lys
100

<210> SEQ ID NO 417
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 417

Ala Ile Arg Met Thr Gln Ser Pro Ala Thr Leu Ser Ala Ser Val Gly
1 5 10 15

Asp Arg Val Thr Leu Thr Cys Arg Ala Gly Gln Gly Ile Gly Ser Asp
20 25 30

Leu Gly Trp Tyr Gln Gln Lys Pro Gly Lys Ala Pro Lys Leu Leu Ile
35 40 45

His Lys Ala Ser Asn Leu Ile Asn Gly Val Pro Ser Arg Phe Ser Gly
50 55 60

Ser Gly Phe His Thr Glu Phe Thr Leu Thr Ile Ser Ser Leu Gln Pro
65 70 75 80

Asp Asp Phe Ala Thr Tyr Tyr Cys Gln Val Val Gln Trp Phe Gly Gln
85 90 95

Gly Thr Lys Val Glu Ile Lys
100

<210> SEQ ID NO 418
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 418

Ala Ile Arg Met Thr Gln Ser Pro Ala Thr Leu Ser Ala Ser Val Gly
1 5 10 15

Glu Arg Val Thr Ile Thr Cys Arg Ala Ser Gln Gly Ile Gly Ser Asp
20 25 30

Leu Gly Trp Tyr Gln Gln Lys Pro Gly Lys Ser Pro Lys Leu Leu Ile
35 40 45

Phe Lys Ala Ser Asn Leu Lys Asp Gly Val Pro Pro Arg Phe Ser Gly
50 55 60

Gly Gly Phe His Thr Glu Phe Thr Leu Thr Ile Ser Ser Leu Gln Pro
65 70 75 80

Asp Asp Phe Ala Thr Tyr Tyr Cys Gln Val Leu Glu Thr Phe Gly Gln
85 90 95

Gly Thr Lys Val Glu Ile Lys
100

<210> SEQ ID NO 419
<211> LENGTH: 103
<212> TYPE: PRT

<213> ORGANISM: Artificial Sequence
<220> FEATURE:
<223> OTHER INFORMATION: synthetic polypeptide/polynucleotide

<400> SEQUENCE: 419

```
Ala Ile Arg Met Thr Gln Ser Pro Pro Thr Val Ser Ala Ser Ala Gly
1               5                   10                  15

Asp Arg Val Thr Ile Thr Cys Arg Ala Gly Gln His Ile Gly Asn Asp
            20                  25                  30

Leu Ala Trp Tyr Gln Thr Lys Val Gly Met Ala Pro Lys Leu Leu Ile
        35                  40                  45

Tyr Glu Ala Ser Asn Leu Lys Ser Gly Val Pro Ser Arg Phe Ser Gly
    50                  55                  60

Ser Gly Phe Gly Thr Glu Phe Thr Leu Ser Ile Thr Ser Leu Gln Pro
65                  70                  75                  80

Asp Asp Phe Ala Thr Tyr Tyr Cys Gln Val Tyr Glu Ser Phe Gly Gln
                85                  90                  95

Gly Thr Lys Val Glu Ile Lys
            100
```

<210> SEQ ID NO 420
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 420

```
Ala Ile Arg Met Thr Gln Ser Pro Ala Thr Leu Ser Ala Ser Val Gly
1               5                   10                  15

Asp Arg Val Thr Ile Thr Cys Arg Ala Ser Gln Gly Ile Gly Asn Lys
            20                  25                  30

Leu Gly Trp Phe Gln Gln Lys Pro Gly Lys Ala Pro Lys Pro Leu Ile
        35                  40                  45

Phe Lys Ala Ser Thr Leu Lys Asp Gly Val Pro Ser Arg Phe Ser Gly
    50                  55                  60

Ser Gly Phe Gly Thr Asp Phe Thr Leu Thr Ile Ser Ser Leu Gln Pro
65                  70                  75                  80

Asp Asp Phe Ala Thr Tyr Tyr Cys Gln Val Tyr Glu Ser Phe Gly Gln
                85                  90                  95

Gly Thr Lys Val Glu Ile Lys
            100
```

<210> SEQ ID NO 421
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 421

```
Ala Ile Arg Met Thr Gln Ser Pro Ala Thr Leu Ser Ala Ser Val Gly
1               5                   10                  15

Asp Arg Val Thr Ile Thr Cys Arg Ala Gly Gln Gly Ile Gly Ser Asp
            20                  25                  30

Leu Ala Trp Tyr Gln Gln Lys Ser Gly Gln Ala Pro Lys Leu Leu Ile
        35                  40                  45

Phe Lys Ala Ser Asn Leu Lys Asn Gly Val Pro Pro Arg Phe Ser Gly
    50                  55                  60
```

Ser Gly Phe His Thr Asp Phe Thr Leu Thr Ile Ser Gly Leu Gln Pro
65 70 75 80

Asp Asp Phe Ala Thr Tyr Tyr Cys Gln Val Leu Glu Thr Phe Gly Gln
85 90 95

Gly Thr Lys Val Glu Ile Lys
100

<210> SEQ ID NO 422
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 422

Ala Ile Arg Met Thr Gln Ser Pro Ala Thr Leu Ser Ala Ser Val Gly
1 5 10 15

Asp Arg Val Thr Ile Thr Cys Arg Ala Gly Gln Gly Ile Gly Ser Asp
20 25 30

Leu Ala Trp Tyr Gln Gln Lys Ser Gly Gln Ala Pro Lys Leu Leu Ile
35 40 45

Phe Lys Ala Ser Asn Leu Lys Asn Gly Val Pro Pro Arg Phe Ser Gly
50 55 60

Ser Gly Phe His Thr Asp Phe Thr Leu Thr Ile Ser Gly Leu Gln Ser
65 70 75 80

Asp Asp Phe Ala Thr Tyr Tyr Cys Gln Val Leu Glu Thr Phe Gly Gln
85 90 95

Gly Thr Lys Val Glu Ile Lys
100

<210> SEQ ID NO 423
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 423

Ala Ile Arg Met Thr Gln Ser Pro Pro Thr Val Ser Ala Ser Ala Gly
1 5 10 15

Asp Arg Val Thr Ile Thr Cys Arg Ala Gly Gln His Ile Gly Asn Asp
20 25 30

Leu Ala Trp Tyr Gln Thr Lys Val Gly Met Ala Pro Lys Leu Leu Ile
35 40 45

Tyr Gln Ala Ser Asn Leu Lys Ser Gly Val Pro Ser Arg Phe Ser Gly
50 55 60

Ser Gly Ser Gly Thr Glu Phe Thr Leu Ser Ile Thr Ser Leu Gln Pro
65 70 75 80

Asp Asp Phe Ala Thr Tyr Tyr Cys Gln Val Tyr Glu Ser Phe Gly Gln
85 90 95

Gly Thr Lys Val Glu Ile Lys
100

<210> SEQ ID NO 424
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 424

Ala Ile Arg Met Thr Gln Ser Pro Ala Thr Leu Ser Ala Ser Val Gly
1               5                   10                  15

Asp Arg Val Thr Leu Thr Cys Arg Ala Gly Gln Gly Ile Gly Ser Asp
            20                  25                  30

Leu Gly Trp Tyr Gln Gln Lys Pro Gly Lys Ala Pro Lys Leu Leu Ile
        35                  40                  45

His Lys Ala Ser Asn Leu Ile Asn Gly Val Pro Ser Arg Phe Ser Gly
    50                  55                  60

Ser Gly Phe His Thr Glu Phe Thr Leu Thr Ile Ser Ser Leu Gln Pro
65                  70                  75                  80

Asp Asp Phe Ala Thr Tyr Tyr Cys Gln Val Val Glu Trp Phe Gly Gln
                85                  90                  95

Gly Thr Lys Val Glu Ile Lys
            100

<210> SEQ ID NO 425
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 425

Ala Ile Arg Met Thr Gln Ser Pro Ala Thr Leu Ser Ala Ser Val Gly
1               5                   10                  15

Asp Arg Val Thr Ile Thr Cys Arg Ala Gly Gln Gly Ile Gly Ser Asp
            20                  25                  30

Leu Ala Trp Tyr Gln Gln Lys Pro Gly Gln Ala Pro Lys Leu Leu Ile
        35                  40                  45

Phe Lys Ala Ser Asn Leu Lys Asn Gly Val Pro Thr Arg Phe Thr Gly
    50                  55                  60

Ser Gly Phe His Thr Asp Phe Thr Leu Thr Ile Asn Gly Leu Gln Ser
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100

<210> SEQ ID NO 426
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 426

Ala Ile Arg Met Thr Gln Ser Pro Ala Thr Leu Ser Ala Ser Val Gly
1               5                   10                  15

Asp Arg Val Thr Leu Thr Cys Arg Ala Gly Gln Gly Ile Gly Ser Asp
            20                  25                  30

Leu Gly Trp Tyr Gln Gln Lys Pro Gly Lys Ala Pro Lys Leu Leu Ile
        35                  40                  45

His Lys Ala Ser Asn Leu Ile Asn Gly Val Pro Ser Arg Phe Ser Gly
    50                  55                  60

Ser Gly Phe His Thr Glu Phe Thr Leu Thr Ile Asn Ser Leu Gln Pro
65                  70                  75                  80

```
Asp Asp Phe Ala Thr Tyr Tyr Cys Gln Val Phe Glu Trp Phe Gly Pro
                85                  90                  95

Gly Thr Lys Val Glu Ile Lys
            100


<210> SEQ ID NO 427
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 427

Ala Ile Arg Met Thr Gln Ser Pro Ala Thr Leu Ser Ala Ser Val Gly
1               5                   10                  15

Asp Arg Val Thr Ile Thr Cys Arg Ala Gly Gln Gly Ile Gly Ser Asp
            20                  25                  30

Leu Ala Trp Tyr Gln Gln Lys Ser Gly Gln Ala Pro Lys Leu Leu Ile
        35                  40                  45

Phe Lys Ala Ser Asn Leu Lys Asn Gly Val Pro Pro Arg Phe Ser Gly
    50                  55                  60

Ser Gly Phe His Thr Asp Phe Thr Leu Thr Ile Ser Gly Leu Gln Pro
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100


<210> SEQ ID NO 428
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 428

Ala Ile Arg Met Thr Gln Ser Pro Ala Thr Leu Ser Ala Ser Val Gly
1               5                   10                  15

Asp Arg Val Thr Ile Thr Cys Arg Ala Gly Gln Gly Ile Gly Ser Asp
            20                  25                  30

Leu Ala Trp Tyr Gln Gln Lys Pro Gly Gln Ala Pro Lys Leu Leu Ile
        35                  40                  45

Phe Lys Ala Ser Arg Leu Lys Asn Gly Val Pro Thr Arg Phe Thr Gly
    50                  55                  60

Ser Gly Phe His Thr Glu Phe Thr Leu Thr Ile Ser Gly Leu Gln Ser
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100


<210> SEQ ID NO 429
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 429
```

```
Ala Ile Arg Met Thr Gln Ser Pro Ala Thr Leu Ser Ala Ser Val Gly
1               5                   10                  15

Asp Arg Val Thr Ile Thr Cys Arg Ala Gly Gln Gly Ile Gly Ser Asp
            20                  25                  30

Leu Ala Trp Tyr Gln Gln Lys Pro Gly Gln Ala Pro Lys Leu Leu Ile
        35                  40                  45

Phe Lys Ala Ser Arg Leu Lys Asn Gly Val Pro Thr Arg Phe Thr Gly
    50                  55                  60

Ser Gly Phe His Thr Glu Phe Thr Leu Thr Ile Ser Gly Leu Gln Ser
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100


<210> SEQ ID NO 430
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 430

Ala Ile Arg Met Thr Gln Ser Pro Ala Thr Leu Ser Ala Ser Val Gly
1               5                   10                  15

Asp Arg Val Thr Ile Thr Cys Arg Ala Gly Gln Gly Ile Gly Ser Asp
            20                  25                  30

Leu Ala Trp Tyr Gln Gln Lys Ser Gly Gln Ala Pro Lys Leu Leu Ile
        35                  40                  45

Phe Lys Ala Ser Asn Leu Lys Asn Gly Val Pro Pro Arg Phe Ser Gly
    50                  55                  60

Ser Gly Phe His Thr Asp Phe Thr Leu Thr Ile Ser Gly Leu Gln Pro
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100


<210> SEQ ID NO 431
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 431

Ala Ile Arg Met Thr Gln Ser Pro Ala Thr Leu Ser Ala Ser Val Gly
1               5                   10                  15

Asp Lys Val Thr Ile Thr Cys Arg Ala Ser Gln Gly Ile Gly Asn Asn
            20                  25                  30

Leu Gly Trp Tyr Gln Gln Lys Pro Gly Gln Ala Pro Lys Leu Leu Ile
        35                  40                  45

Phe Lys Ala Ser Asn Ser Lys Asp Gly Val Pro Pro Arg Phe Ser Gly
    50                  55                  60

Ser Gly Ser His Thr Glu Phe Thr Leu Thr Ile Asn Ser Leu Gln Pro
65                  70                  75                  80

Asp Asp Phe Ala Thr Tyr Tyr Cys Gln Val Tyr Gln Thr Phe Gly Gln
                85                  90                  95
```

Gly Thr Lys Val Glu Ile Lys
100

<210> SEQ ID NO 432
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 432

Ala Ile Arg Met Thr Gln Ser Pro Ala Thr Leu Ser Ala Ser Val Gly
1 5 10 15

Asp Arg Val Thr Leu Thr Cys Arg Ala Gly Gln Gly Ile Gly Ser Asp
20 25 30

Leu Gly Trp Tyr Gln Gln Lys Pro Gly Lys Ala Pro Lys Leu Leu Ile
35 40 45

His Lys Ala Ser Asn Leu Leu Asn Gly Val Pro Ser Arg Phe Ser Gly
50 55 60

Ser Gly Phe His Thr Glu Phe Thr Leu Thr Ile Ser Ser Leu Gln Pro
65 70 75 80

Asp Asp Phe Ala Thr Tyr Tyr Cys Gln Val Phe Glu Trp Phe Gly Gln
85 90 95

Gly Thr Lys Val Glu Ile Lys
100

<210> SEQ ID NO 433
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 433

Ala Ile Arg Met Thr Gln Ser Pro Ala Thr Leu Ser Ala Ser Val Gly
1 5 10 15

Asp Arg Val Thr Leu Thr Cys Arg Ala Gly Gln Gly Ile Gly Ser Asp
20 25 30

Leu Gly Trp Tyr Gln Gln Lys Pro Gly Lys Ala Pro Lys Leu Leu Ile
35 40 45

His Lys Ala Ser Asn Leu Ala Asn Gly Val Pro Ser Arg Phe Ser Gly
50 55 60

Arg Gly Phe His Thr Glu Phe Thr Leu Thr Ile Ser Ser Leu Gln Pro
65 70 75 80

Asp Asp Phe Ala Thr Tyr Tyr Cys Gln Val Phe Glu Trp Phe Gly Gln
85 90 95

Gly Thr Lys Val Glu Ile Lys
100

<210> SEQ ID NO 434
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 434

Ala Ile Arg Met Thr Gln Ser Pro Ala Thr Leu Ser Ala Ser Val Gly
1 5 10 15

```
Asp Arg Val Thr Ile Thr Cys Arg Ala Gly Gln Gly Ile Gly Ser Asp
            20                  25                  30

Leu Ala Trp Tyr Gln Gln Lys Pro Gly Gln Ala Pro Lys Leu Leu Ile
        35                  40                  45

Phe Lys Ala Ser Asn Leu Lys Asn Gly Val Pro Thr Arg Phe Thr Gly
    50                  55                  60

Ser Gly Phe His Thr Asp Phe Thr Leu Thr Ile Ser Gly Leu Gln Ser
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100


<210> SEQ ID NO 435
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 435

Ala Ile Arg Met Thr Gln Ser Pro Ala Thr Leu Ser Ala Ser Val Gly
1               5                   10                  15

Asp Arg Val Thr Ile Thr Cys Arg Ala Gly Gln Gly Ile Gly Ser Asp
            20                  25                  30

Leu Ala Trp Tyr Gln Gln Lys Pro Gly Gln Ala Pro Lys Leu Leu Ile
        35                  40                  45

Phe Lys Ala Ser Asn Leu Lys Lys Gly Val Pro Thr Arg Phe Thr Gly
    50                  55                  60

Ser Gly Phe His Thr Asp Phe Thr Leu Thr Ile Ser Gly Leu Gln Ser
65                  70                  75                  80

Asp Asp Phe Ala Thr Tyr Tyr Cys Gln Val Leu Glu Thr Phe Gly Gln
                85                  90                  95

Gly Thr Lys Val Glu Ile Lys
            100


<210> SEQ ID NO 436
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 436

Ala Ile Arg Met Thr Gln Ser Pro Ala Thr Leu Ser Ala Phe Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Val Pro Lys Pro Leu Ile
        35                  40                  45

Phe Lys Ala Ser Asn Leu Lys Asp Gly Val Pro Ser Arg Phe Ser Gly
    50                  55                  60

Ser Gly Phe Gly Thr Asp Phe Thr Leu Thr Ile Asn Asn Leu Gln Pro
65                  70                  75                  80

Asp Asp Phe Ala Thr Tyr Tyr Cys Gln Ala Tyr Glu Ser Phe Gly Gln
                85                  90                  95

Gly Thr Lys Val Glu Ile Lys
            100
```

<210> SEQ ID NO 437
<211> LENGTH: 101
<212> TYPE: PRT
<213> ORGANISM: Artificial Sequence
<220> FEATURE:
<223> OTHER INFORMATION: synthetic polypeptide/polynucleotide

<400> SEQUENCE: 437

```
Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Leu Tyr Glu Phe Phe Gly Gln Gly Thr
                85                  90                  95

Lys Val Asp Ile Lys
            100
```

<210> SEQ ID NO 438
<211> LENGTH: 101
<212> TYPE: PRT
<213> ORGANISM: Artificial Sequence
<220> FEATURE:
<223> OTHER INFORMATION: synthetic polypeptide/polynucleotide

<400> SEQUENCE: 438

```
Asp Ile Gln Met Thr Gln Ser Pro Ser Thr Leu Ser Ala Ser Val Gly
1               5                   10                  15

Asp Arg Val Thr Ile Thr Cys Arg Thr Ser Gln Tyr Gly Ser Leu Ala
            20                  25                  30

Trp Tyr Gln Gln Lys Pro Gly Lys Ala Pro Lys Leu Leu Ile Tyr Lys
        35                  40                  45

Gly Ser Ser Leu Glu Ser Gly Val Pro Asp Arg Phe Ser Gly Ser Arg
    50                  55                  60

Trp Gly Pro Glu Phe Thr Leu Thr Ile Ser Ser Leu Gln Pro Asp Asp
65                  70                  75                  80

Phe Ala Thr Tyr Tyr Cys Gln Leu Tyr Glu Phe Phe Gly Gln Gly Thr
                85                  90                  95

Lys Val Glu Ile Lys
            100
```

<210> SEQ ID NO 439
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 439

```
Asp Ile Gln Met Thr Gln Ser Pro Ser Ser Leu Ser Ala Ser Val Gly
1               5                   10                  15

Asp Arg Val Thr Ile Asn Cys Gln Ala Gly Gln Gly Ile Gly Ser Ser
            20                  25                  30
```

```
Leu Asn Trp Tyr Gln Lys Lys Pro Gly Arg Ala Pro Lys Leu Leu Val
        35                  40                  45

His Gly Ala Ser Asn Leu Gln Arg Gly Val Pro Ser Arg Phe Ser Gly
    50                  55                  60

Ser Gly Phe His Thr Thr Phe Thr Leu Thr Ile Ser Ser Leu Gln Pro
65                  70                  75                  80

Asp Asp Val Ala Thr Tyr Phe Cys Ala Val Phe Gln Trp Phe Gly Pro
                85                  90                  95

Gly Thr Lys Val Asp Ile Lys
            100
```

<210> SEQ ID NO 440
<211> LENGTH: 103
<212> TYPE: PRT
<213> ORGANISM: Artificial Sequence
<220> FEATURE:
<223> OTHER INFORMATION: synthetic polypeptide/polynucleotide

<400> SEQUENCE: 440

```
Asp Ile Gln Met Thr Gln Ser Pro Ser Thr Leu Ser Ala Ser Val Gly
1               5                   10                  15

Asp Arg Val Thr Ile Thr Cys Arg Ala Gly Gln Gly Ile Gly Ser Ser
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Phe His Thr Thr Phe Thr Leu Thr Ile Ser Ser Leu Gln Pro
65                  70                  75                  80

Asp Asp Phe Ala Thr Tyr Tyr Cys Ala Val Phe Gln Trp Phe Gly Gln
                85                  90                  95

Gly Thr Lys Val Glu Ile Lys
            100
```

<210> SEQ ID NO 441
<211> LENGTH: 8
<212> TYPE: DNA
<213> ORGANISM: Artificial Sequence
<220> FEATURE:
<223> OTHER INFORMATION: synthetic polypeptide/polynucleotide

<400> SEQUENCE: 441 gcgagaga 8

<210> SEQ ID NO 442
<211> LENGTH: 21
<212> TYPE: DNA
<213> ORGANISM: Artificial Sequence
<220> FEATURE:
<223> OTHER INFORMATION: synthetic polypeptide/polynucleotide

<400> SEQUENCE: 442
gggtatagca gcagctggta c 21

<210> SEQ ID NO 443
<211> LENGTH: 17
<212> TYPE: DNA
<213> ORGANISM: Artificial Sequence
<220> FEATURE:
<223> OTHER INFORMATION: synthetic polypeptide/polynucleotide

<400> SEQUENCE: 443
acaactggtt cgacccc 17

<210> SEQ ID NO 444
<211> LENGTH: 45
<212> TYPE: DNA
<213> ORGANISM: Artificial Sequence
<220> FEATURE:
<223> OTHER INFORMATION: synthetic polypeptide/polynucleotide

<400> SEQUENCE: 444
gcgagagatt cctcgaggca gcagctggag tggtggttcg acccc 45

<210> SEQ ID NO 445
<211> LENGTH: 26
<212> TYPE: DNA
<213> ORGANISM: Artificial Sequence
<220> FEATURE:
<223> OTHER INFORMATION: synthetic polypeptide/polynucleotide

<400> SEQUENCE: 445
tgccaacagt ataatagtta ttctcc 26

<210> SEQ ID NO 446
<211> LENGTH: 22
<212> TYPE: DNA
<213> ORGANISM: Artificial Sequence
<220> FEATURE:
<223> OTHER INFORMATION: synthetic polypeptide/polynucleotide

<400> SEQUENCE: 446
gtggacgttc ggccaaggga cc 22

<210> SEQ ID NO 447
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 447
caacagtcgg aggcg 15

<210> SEQ ID NO 448
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 448
caactttatg agacg 15

<210> SEQ ID NO 449
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 449
caacagtcga ggacg 15

<210> SEQ ID NO 450
<211> LENGTH: 15
<212> TYPE: DNA

<213> ORGANISM: Artificial Sequence
<220> FEATURE:
<223> OTHER INFORMATION: synthetic polypeptide/polynucleotide

<400> SEQUENCE: 450
caacagcagg agacg 15

<210> SEQ ID NO 451
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 451
catcatcgga gggcg 15

<210> SEQ ID NO 452
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 452
caacagtata ggacg 15

<210> SEQ ID NO 453
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 453
cgacagtcgg aggcg 15

<210> SEQ ID NO 454
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 454
caacagtcgg gggcg 15

<210> SEQ ID NO 455
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 455
caacagtata attcg 15

<210> SEQ ID NO 456
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 456
caacattata ggacg 15

<210> SEQ ID NO 457
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 457
caacatgggt ggacg 15

<210> SEQ ID NO 458
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 458
caacagtata agacg 15

<210> SEQ ID NO 459
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 459
caacattcgg gggcg 15

<210> SEQ ID NO 460
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 460
caacattttg gggcg 15

<210> SEQ ID NO 461
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 461
caacagtata atagg 15

<210> SEQ ID NO 462
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 462
caacagacgg ggacg 15

<210> SEQ ID NO 463
<211> LENGTH: 15
<212> TYPE: DNA
<213> ORGANISM: Artificial Sequence
<220> FEATURE:

<223> OTHER INFORMATION: synthetic polypeptide/polynucleotide

<400> SEQUENCE: 463
caacagtatg agacg 15

<210> SEQ ID NO 464
<211> LENGTH: 15
<212> TYPE: DNA
<213> ORGANISM: Artificial Sequence
<220> FEATURE:
<223> OTHER INFORMATION: synthetic polypeptide/polynucleotide

<400> SEQUENCE: 464
caacagcagg ggacg 15

<210> SEQ ID NO 465
<211> LENGTH: 14
<212> TYPE: PRT
<213> ORGANISM: Artificial Sequence
<220> FEATURE:
<223> OTHER INFORMATION: synthetic polypeptide/polynucleotide

<400> SEQUENCE: 465

Cys Ala Arg Asp Ser Ser Arg Gln Gln Glu Leu Trp Trp Phe
1 5 10

<210> SEQ ID NO 466
<211> LENGTH: 6
<212> TYPE: PRT
<213> ORGANISM: Artificial Sequence
<220> FEATURE:
<223> OTHER INFORMATION: synthetic polypeptide/polynucleotide

<400> SEQUENCE: 466

Thr Phe Gly Gln Gly Thr
1 5

<210> SEQ ID NO 467
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 467

Gln Gln Ser Glu Ala
1 5

<210> SEQ ID NO 468
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 468

Gln Leu Tyr Glu Thr
1 5

<210> SEQ ID NO 469
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 469

Gln Gln Ser Arg Thr
1 5

<210> SEQ ID NO 470
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 470

Gln Gln Gln Glu Thr
1 5

<210> SEQ ID NO 471
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 471

His His Arg Arg Leu
1 5

<210> SEQ ID NO 472
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 472

Gln Gln Tyr Arg Thr
1 5

<210> SEQ ID NO 473
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 473

Arg Gln Ser Glu Ala
1 5

<210> SEQ ID NO 474
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 474

Gln Gln Ser Gly Ala
1 5

<210> SEQ ID NO 475
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 475

Gln Gln Tyr Asn Ser
1 5

<210> SEQ ID NO 476
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 476

Gln His Tyr Arg Thr
1 5

<210> SEQ ID NO 477
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 477

Gln His Gly Trp Thr
1 5

<210> SEQ ID NO 478
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 478

Gln Gln Tyr Lys Thr
1 5

<210> SEQ ID NO 479
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 479

Gln His Ser Gly Ala
1 5

<210> SEQ ID NO 480
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 480

Gln His Phe Gly Ala
1 5

<210> SEQ ID NO 481
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 481

Gln Gln Tyr Asn Arg 1 5

<210> SEQ ID NO 482
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 482

Gln Gln Thr Gly Thr
1 5

<210> SEQ ID NO 483
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 483

Gln Gln Tyr Glu Thr
1 5

<210> SEQ ID NO 484
<211> LENGTH: 5
<212> TYPE: PRT
<213> ORGANISM: Artificial Sequence
<220> FEATURE:
<223> OTHER INFORMATION: synthetic polypeptide/polynucleotide

<400> SEQUENCE: 484

Gln Gln Gln Gly Thr
1 5

<210> SEQ ID NO 485
<211> LENGTH: 4
<212> TYPE: PRT
<213> ORGANISM: Artificial Sequence
<220> FEATURE:
<223> OTHER INFORMATION: synthetic polypeptide/polynucleotide

<400> SEQUENCE: 485

Gly Gly Gly Gly
1

<210> SEQ ID NO 486
<211> LENGTH: 4
<212> TYPE: PRT
<213> ORGANISM: Artificial Sequence
<220> FEATURE:
<223> OTHER INFORMATION: synthetic polypeptide/polynucleotide

<400> SEQUENCE: 486

Ser Ser Ser Ala
1

<210> SEQ ID NO 487
<211> LENGTH: 96
<212> TYPE: PRT
<213> ORGANISM: Artificial Sequence
<220> FEATURE:
<223> OTHER INFORMATION: synthetic polypeptide/polynucleotide

<400> SEQUENCE: 487

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

<210> SEQ ID NO 488
<211> LENGTH: 110
<212> TYPE: PRT
<213> ORGANISM: Artificial Sequence
<220> FEATURE:
<223> OTHER INFORMATION: synthetic polypeptide/polynucleotide

<400> SEQUENCE: 488

Gln Val Gln Leu Val Gln Ser Gly Gly Gln Met Lys Lys Pro Gly Glu
1 5 10 15

Ser Met Arg Ile Ser Cys Arg Ala Ser Gly Tyr Glu Phe Ile Asp Cys
20 25 30

Thr Leu Asn Trp Ile Arg Leu Ala Pro Gly Lys Arg Pro Glu Trp Met
35 40 45

Gly Trp Leu Lys Pro Arg Gly Gly Ala Val Asn Tyr Ala Arg Pro Leu
50 55 60

Gln Gly Arg Val Thr Met Thr Arg Asp Val Tyr Ser Asp Thr Ala Phe
65 70 75 80

Leu Glu Leu Arg Ser Leu Thr Val Asp Asp Thr Ala Val Tyr Phe Cys
85 90 95

Thr Arg Gly Lys Asn Cys Asp Tyr Asn Trp Asp Phe Glu His
100 105 110

<210> SEQ ID NO 489
<211> LENGTH: 114
<212> TYPE: PRT
<213> ORGANISM: Artificial Sequence
<220> FEATURE:
<223> OTHER INFORMATION: synthetic polypeptide/polynucleotide

<400> SEQUENCE: 489

Gln Val Arg Leu Ser Gln Ser Gly Gly Gln Met Lys Lys Pro Gly Glu
1 5 10 15

Ser Met Arg Leu Ser Cys Arg Ala Ser Gly Tyr Glu Phe Leu Asn Cys
20 25 30

Pro Ile Asn Trp Ile Arg Leu Ala Pro Gly Arg Arg Pro Glu Trp Met
35 40 45

Gly Trp Leu Lys Pro Arg Gly Gly Ala Val Asn Tyr Ala Arg Lys Phe
50 55 60

Gln Gly Arg Val Thr Met Thr Arg Asp Val Tyr Ser Asp Thr Ala Phe
65 70 75 80

Leu Glu Leu Arg Ser Leu Thr Ser Asp Asp Thr Ala Val Tyr Phe Cys
85 90 95

Thr Arg Gly Lys Tyr Cys Thr Ala Arg Asp Tyr Tyr Asn Trp Asp Phe
100 105 110

Glu His

<210> SEQ ID NO 490
<211> LENGTH: 110
<212> TYPE: PRT
<213> ORGANISM: Artificial Sequence
<220> FEATURE:
<223> OTHER INFORMATION: synthetic polypeptide/polynucleotide

<400> SEQUENCE: 490

Gln Val Gln Leu Val Gln Ser Gly Gly Gln Met Lys Lys Pro Gly Glu
1 5 10 15

Ser Met Arg Ile Ser Cys Gln Ala Ser Gly Tyr Glu Phe Ile Asp Cys
20 25 30

Thr Leu Asn Trp Val Arg Leu Ala Pro Gly Arg Arg Pro Glu Trp Met
35 40 45

Gly Trp Leu Lys Pro Arg Gly Gly Ala Val Asn Tyr Ala Arg Pro Leu
50 55 60

Gln Gly Arg Val Thr Met Thr Arg Asp Val Tyr Ser Asp Thr Ala Phe
65 70 75 80

Leu Glu Leu Arg Ser Leu Thr Ala Asp Asp Thr Ala Val Tyr Tyr Cys
85 90 95

Thr Arg Gly Lys Asn Cys Asp Tyr Asn Trp Asp Phe Glu His
100 105 110

<210> SEQ ID NO 491
<211> LENGTH: 119
<212> TYPE: PRT
<213> ORGANISM: Artificial Sequence
<220> FEATURE:
<223> OTHER INFORMATION: synthetic polypeptide/polynucleotide

<400> SEQUENCE: 491

Gln Val Gln Leu Val Gln Ser Gly Ala Val Ile Lys Thr Pro Gly Ser
1 5 10 15

Ser Val Lys Ile Ser Cys Arg Ala Ser Gly Tyr Asn Phe Arg Asp Tyr
20 25 30

Ser Ile His Trp Val Arg Leu Ile Pro Asp Lys Gly Phe Glu Trp Ile
35 40 45

Gly Trp Ile Lys Pro Leu Trp Gly Ala Val Ser Tyr Ala Arg Gln Leu
50 55 60

Gln Gly Arg Val Ser Met Thr Arg Gln Leu Ser Gln Asp Pro Asp Asp
65 70 75 80

Pro Asp Trp Gly Val Ala Tyr Met Glu Phe Ser Gly Leu Thr Pro Ala
85 90 95

Asp Thr Ala Glu Tyr Phe Cys Val Arg Arg Gly Ser Cys Asp Tyr Cys
100 105 110

Gly Asp Phe Pro Trp Gln Tyr
115

<210> SEQ ID NO 492
<211> LENGTH: 120
<212> TYPE: PRT
<213> ORGANISM: Artificial Sequence
<220> FEATURE:
<223> OTHER INFORMATION: synthetic polypeptide/polynucleotide

<400> SEQUENCE: 492

Glu Val Gln Leu Val Glu Ser Gly Pro Val Met Arg Lys Pro Gly Ser
1 5 10 15

```
Ser Met Lys Ile Ser Cys Ala Thr Ser Gly Tyr Asn Phe Arg Asp Phe
            20                  25                  30

Ser Ile His Trp Val Arg Phe Asn Arg Arg Tyr Gly Phe Glu Trp Ile
        35                  40                  45

Gly Trp Ile Lys Pro Met Trp Gly Ala Val Asn Tyr Ala Arg Gln Leu
    50                  55                  60

Gln Gly Arg Val Ser Met Ser Arg Leu Phe Ser Gln Asp Leu Tyr Tyr
65                  70                  75                  80

Pro Asp Arg Gly Thr Ala Tyr Leu Glu Phe Ser Gly Leu Thr Ser Ala
                85                  90                  95

Asp Thr Ala Asp Tyr Phe Cys Val Arg Arg Gly Ser Ser Cys Pro His
            100                 105                 110

Cys Gly Asp Phe His Phe Glu His
        115                 120


<210> SEQ ID NO 493
<211> LENGTH: 114
<212> TYPE: PRT
<213> ORGANISM: Artificial Sequence
<220> FEATURE:
<223> OTHER INFORMATION: synthetic polypeptide/polynucleotide

<400> SEQUENCE: 493

Gln Val Arg Leu Ser Gln Ser Gly Gly Gln Met Lys Lys Pro Gly Asp
1               5                   10                  15

Ser Met Arg Ile Ser Cys Arg Ala Ser Gly Tyr Glu Phe Ile Asn Cys
            20                  25                  30

Pro Ile Asn Trp Ile Arg Leu Ala Pro Gly Lys Arg Pro Glu Trp Met
        35                  40                  45

Gly Trp Met Lys Pro Arg Gly Gly Ala Val Ser Tyr Ala Arg Gln Leu
    50                  55                  60

Gln Gly Arg Val Thr Met Thr Arg Asp Met Tyr Ser Glu Thr Ala Phe
65                  70                  75                  80

Leu Glu Leu Arg Ser Leu Thr Ser Asp Asp Thr Ala Val Tyr Phe Cys
                85                  90                  95

Thr Arg Gly Lys Tyr Cys Thr Ala Arg Asp Tyr Tyr Asn Trp Asp Phe
            100                 105                 110

Glu His


<210> SEQ ID NO 494
<211> LENGTH: 121
<212> TYPE: PRT
<213> ORGANISM: Artificial Sequence
<220> FEATURE:
<223> OTHER INFORMATION: synthetic polypeptide/polynucleotide

<400> SEQUENCE: 494

Gln Val Gln Leu Val Gln Ser Gly Thr Gln Met Lys Glu Pro Gly Ala
1               5                   10                  15

Ser Val Thr Ile Ser Cys Val Thr Ser Gly Tyr Glu Phe Val Glu Ile
            20                  25                  30

Leu Ile Asn Trp Val Arg Gln Val Pro Gly Arg Gly Leu Glu Trp Met
        35                  40                  45

Gly Trp Met Asn Pro Arg Gly Gly Gly Val Asn Tyr Ala Arg Gln Phe
    50                  55                  60

Gln Gly Lys Val Thr Met Thr Arg Asp Val Tyr Arg Asp Thr Ala Tyr
65                  70                  75                  80
```

```
Leu Thr Leu Ser Gly Leu Thr Ser Gly Asp Thr Ala Lys Tyr Phe Cys
                85                  90                  95

Val Arg Gly Arg Ser Cys Cys Gly Gly Arg Arg His Cys Asn Gly Ala
            100                 105                 110

Asp Cys Phe Asn Trp Asp Phe Gln His
        115                 120


<210> SEQ ID NO 495
<211> LENGTH: 111
<212> TYPE: PRT
<213> ORGANISM: Artificial Sequence
<220> FEATURE:
<223> OTHER INFORMATION: synthetic polypeptide/polynucleotide

<400> SEQUENCE: 495

Gln Val Arg Leu Val Gln Ser Gly Asn Gln Val Arg Lys Pro Gly Ala
1               5                   10                  15

Ser Val Arg Ile Ser Cys Glu Ala Ser Gly Tyr Lys Phe Ile Asp His
            20                  25                  30

Phe Ile His Trp Val Arg Gln Val Pro Gly His Gly Leu Glu Trp Leu
        35                  40                  45

Gly Trp Ile Asn Pro Arg Gly Gly Gly Val Asn Tyr Ser Arg Thr Ser
    50                  55                  60

Phe Gln Gly Lys Leu Ser Met Thr Met Thr Arg Asp Asn Phe Glu Glu
65                  70                  75                  80

Thr Ala Tyr Leu Asp Leu Ser Lys Leu Asn Pro Gly Asp Thr Ala Val
                85                  90                  95

Tyr Phe Cys Ala Arg Gly Phe Ala Gly Tyr Glu Trp Ser Phe Ile
            100                 105                 110


<210> SEQ ID NO 496
<211> LENGTH: 110
<212> TYPE: PRT
<213> ORGANISM: Artificial Sequence
<220> FEATURE:
<223> OTHER INFORMATION: synthetic polypeptide/polynucleotide

<400> SEQUENCE: 496

Gln Val Gln Phe Val Gln Ser Gly Ala Glu Val Lys Lys Pro Gly Ala
1               5                   10                  15

Ser Val Arg Val Ser Cys Glu Ala Ser Gly Tyr Ser Phe Thr Asp Tyr
            20                  25                  30

Val Leu Gln Trp Ile Arg Gln Ala Pro Gly Gln Arg Pro Glu Trp Met
        35                  40                  45

Gly Trp Ile Lys Pro Glu Arg Gly Ala Val Ser Tyr Ala Pro Gln Phe
    50                  55                  60

Gln Gly Arg Leu Thr Leu Thr Arg Asp Leu Tyr Thr Glu Thr Ala Tyr
65                  70                  75                  80

Met His Phe Lys Asn Leu Arg Ser Asp Asp Thr Ala Ile Tyr Tyr Cys
                85                  90                  95

Ala Arg Gly Val Arg Arg Asp Ala Ser Trp Trp Leu Gln Phe
            100                 105                 110


<210> SEQ ID NO 497
<211> LENGTH: 111
<212> TYPE: PRT
<213> ORGANISM: Artificial Sequence
<220> FEATURE:
<223> OTHER INFORMATION: synthetic polypeptide/polynucleotide
```

<400> SEQUENCE: 497

Ser Gln Arg Leu Val Gln Ser Gly Pro Gln Val Arg Lys Pro Gly Ser
1               5                   10                  15

Ser Val Arg Ile Ser Cys Glu Thr Ser Gly Tyr Thr Phe Asn Ala Tyr
            20                  25                  30

Ile Leu His Trp Phe Arg Gln Ala Pro Gly Arg Ser Phe Glu Trp Met
        35                  40                  45

Gly Trp Ile Lys Pro Lys Phe Gly Ala Val Asn Tyr Ala His Ser Phe
    50                  55                  60

Gln Gly Arg Ile Thr Leu Thr Arg Asp Ile Tyr Arg Glu Thr Ala Phe
65                  70                  75                  80

Leu Asp Leu Thr Gly Leu Arg Phe Asp Asp Thr Ala Val Tyr Tyr Cys
                85                  90                  95

Ala Arg Asp Arg Leu Tyr Asp Gly Ser Ser Trp Arg Leu Asp Pro
            100                 105                 110

<210> SEQ ID NO 498
<211> LENGTH: 120
<212> TYPE: PRT
<213> ORGANISM: Artificial Sequence
<220> FEATURE:
<223> OTHER INFORMATION: synthetic polypeptide/polynucleotide

<400> SEQUENCE: 498

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Asp Tyr Ser Pro
            20                  25                  30

Tyr Trp Val Asn Pro Ala Pro Glu His Phe Ile His Phe Leu Arg Gln
        35                  40                  45

Ala Pro Gly Gln Gln Leu Glu Trp Leu Ala Trp Met Asn Pro Thr Asn
    50                  55                  60

Gly Ala Val Asn Tyr Ala Trp Tyr Leu Asn Gly Arg Val Thr Ala Thr
65                  70                  75                  80

Arg Asp Arg Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His
        115                 120

<210> SEQ ID NO 499
<211> LENGTH: 114
<212> TYPE: PRT
<213> ORGANISM: Artificial Sequence
<220> FEATURE:
<223> OTHER INFORMATION: synthetic polypeptide/polynucleotide

<400> SEQUENCE: 499

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Pro
    50                  55                  60

Asp Phe Arg Gln Arg Val Ser Leu Thr Arg Asp Arg Asp Leu Phe Thr
65 70 75 80

Ala His Met Asp Ile Arg Gly Leu Thr Gln Gly Asp Thr Ala Thr Tyr
85 90 95

Phe Cys Ala Arg Gln Lys Phe Tyr Thr Gly Gly Gln Gly Trp Tyr Phe
100 105 110

Asp Leu

<210> SEQ ID NO 500
<211> LENGTH: 109
<212> TYPE: PRT
<213> ORGANISM: Artificial Sequence
<220> FEATURE:
<223> OTHER INFORMATION: synthetic polypeptide/polynucleotide

<400> SEQUENCE: 500

Glu Val Arg Leu Val Gln Ser Gly Ala Glu Val Lys Lys Pro Gly Ala
1 5 10 15

Ser Val Arg Val Ser Cys Ala Ala Ser Gly Tyr Thr Phe Thr Asp Phe
20 25 30

Asp Ile His Trp Leu Arg Gln Ala Pro Gly Arg Gly Leu Glu Trp Met
35 40 45

Gly Trp Val Arg Pro Leu Gly Gly Gly Val Ser Tyr Ala Arg Gln Phe
50 55 60

Gln Gly Arg Val Thr Met Thr Arg Asp Phe Tyr Ile Asp Thr Ala Phe
65 70 75 80

Met Asp Phe Arg Asn Leu Lys Met Asp Asp Thr Ala Leu Tyr Phe Cys
85 90 95

Ala Arg Met Gly Ala Ala Arg Glu Trp Asp Phe Gln Tyr
100 105

<210> SEQ ID NO 501
<211> LENGTH: 111
<212> TYPE: PRT
<213> ORGANISM: Artificial Sequence
<220> FEATURE:
<223> OTHER INFORMATION: synthetic polypeptide/polynucleotide

<400> SEQUENCE: 501

Gln Val His Leu Met Gln Ser Gly Thr Glu Met Lys Lys Pro Gly Ala
1 5 10 15

Ser Val Arg Val Thr Cys Gln Thr Ser Gly Tyr Thr Phe Ser Asp Tyr
20 25 30

Phe Ile His Trp Leu Arg Gln Val Pro Gly Arg Gly Phe Glu Trp Met
35 40 45

Gly Trp Met Asn Pro Gln Trp Gly Gln Val Asn Tyr Ala Arg Thr Phe
50 55 60

Gln Gly Arg Val Thr Met Thr Arg Asp Val Tyr Arg Glu Val Ala Tyr
65 70 75 80

Leu Asp Leu Arg Ser Leu Thr Phe Ala Asp Thr Ala Val Tyr Phe Cys
85 90 95

Ala Arg Arg Met Arg Ser Gln Asp Arg Glu Trp Asp Phe Gln His
100 105 110

<210> SEQ ID NO 502
<211> LENGTH: 111
<212> TYPE: PRT
<213> ORGANISM: Artificial Sequence
<220> FEATURE:

<223> OTHER INFORMATION: synthetic polypeptide/polynucleotide

<400> SEQUENCE: 502

Arg Ala His Leu Val Gln Ser Gly Thr Ala Met Lys Lys Pro Gly Ala
1 5 10 15

Ser Val Arg Val Ser Cys Gln Thr Ser Gly Tyr Thr Phe Thr Ala His
20 25 30

Ile Leu Phe Trp Phe Arg Gln Ala Pro Gly Arg Gly Leu Glu Trp Val
35 40 45

Gly Trp Ile Lys Pro Gln Tyr Gly Ala Val Asn Phe Gly Gly Gly Phe
50 55 60

Arg Asp Arg Val Thr Leu Thr Arg Asp Val Tyr Arg Glu Ile Ala Tyr
65 70 75 80

Met Asp Ile Arg Gly Leu Lys Pro Asp Asp Thr Ala Val Tyr Tyr Cys
85 90 95

Ala Arg Asp Arg Ser Tyr Gly Asp Ser Ser Trp Ala Leu Asp Ala
100 105 110

<210> SEQ ID NO 503
<211> LENGTH: 111
<212> TYPE: PRT
<213> ORGANISM: Artificial Sequence
<220> FEATURE:
<223> OTHER INFORMATION: synthetic polypeptide/polynucleotide

<400> SEQUENCE: 503

Ser Gln His Leu Val Gln Ser Gly Thr Gln Val Lys Lys Pro Gly Ala
1 5 10 15

Ser Val Arg Ile Ser Cys Gln Ala Ser Gly Tyr Ser Phe Thr Asp Tyr
20 25 30

Val Leu His Trp Trp Arg Gln Ala Pro Gly Gln Gly Leu Glu Trp Met
35 40 45

Gly Trp Ile Lys Pro Val Tyr Gly Ala Arg Asn Tyr Ala Arg Arg Phe
50 55 60

Gln Gly Arg Ile Asn Phe Asp Arg Asp Ile Tyr Arg Glu Ile Ala Phe
65 70 75 80

Met Asp Leu Ser Gly Leu Arg Ser Asp Asp Thr Ala Leu Tyr Phe Cys
85 90 95

Ala Arg Asp Gly Ser Gly Asp Asp Thr Ser Trp His Leu Asp Pro
100 105 110

<210> SEQ ID NO 504
<211> LENGTH: 111
<212> TYPE: PRT
<213> ORGANISM: Artificial Sequence
<220> FEATURE:
<223> OTHER INFORMATION: synthetic polypeptide/polynucleotide

<400> SEQUENCE: 504

Ser Gln His Leu Val Gln Ser Gly Thr Gln Val Lys Lys Pro Gly Ala
1 5 10 15

Ser Val Arg Val Ser Cys Gln Ala Ser Gly Tyr Thr Phe Thr Asn Tyr
20 25 30

Ile Leu His Trp Trp Arg Gln Ala Pro Gly Gln Gly Leu Glu Trp Met
35 40 45

Gly Leu Ile Lys Pro Val Phe Gly Ala Val Asn Tyr Ala Arg Gln Phe
50 55 60

Gln Gly Arg Ile Gln Leu Thr Arg Asp Ile Tyr Arg Glu Ile Ala Phe

```
65                  70                  75                  80

Leu Asp Leu Ser Gly Leu Arg Ser Asp Asp Thr Ala Val Tyr Tyr Cys
                85                  90                  95

Ala Arg Asp Glu Ser Gly Asp Asp Leu Lys Trp His Leu His Pro
            100                 105                 110


<210> SEQ ID NO 505
<211> LENGTH: 112
<212> TYPE: PRT
<213> ORGANISM: Artificial Sequence
<220> FEATURE:
<223> OTHER INFORMATION: synthetic polypeptide/polynucleotide

<400> SEQUENCE: 505

Gln Val His Leu Ser Gln Ser Gly Ala Ala Val Thr Lys Pro Gly Ala
1               5                   10                  15

Ser Val Arg Val Ser Cys Glu Ala Ser Gly Tyr Lys Ile Ser Asp His
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Gln Phe
    50                  55                  60

Gln Gly Arg Val Ser Leu Thr Arg Gln Ala Ser Trp Asp Phe Asp Thr
65                  70                  75                  80

Tyr Ser Phe Tyr Met Asp Leu Lys Ala Val Arg Ser Asp Asp Thr Ala
                85                  90                  95

Ile Tyr Phe Cys Ala Arg Gln Arg Ser Asp Phe Trp Asp Phe Asp Val
            100                 105                 110


<210> SEQ ID NO 506
<211> LENGTH: 112
<212> TYPE: PRT
<213> ORGANISM: Artificial Sequence
<220> FEATURE:
<223> OTHER INFORMATION: synthetic polypeptide/polynucleotide

<400> SEQUENCE: 506

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Gln Phe
    50                  55                  60

Gln Gly Arg Val Ser Leu Thr Arg His Ala Ser Trp Asp Phe Asp Thr
65                  70                  75                  80

Phe Ser Phe Tyr Met Asp Leu Lys Ala Leu Arg Ser Asp Asp Thr Ala
                85                  90                  95

Val Tyr Phe Cys Ala Arg Gln Arg Ser Asp Tyr Trp Asp Phe Asp Val
            100                 105                 110


<210> SEQ ID NO 507
<211> LENGTH: 110
<212> TYPE: PRT
<213> ORGANISM: Artificial Sequence
<220> FEATURE:
<223> OTHER INFORMATION: synthetic polypeptide/polynucleotide

<400> SEQUENCE: 507
```

Gln Val Gln Leu Val Gln Ser Gly Ala Glu Val Lys Lys Pro Gly Ala
1 5 10 15

Ser Val Arg Val Ser Cys Lys Ala Ser Gly Tyr Thr Phe Asn Ser Cys
20 25 30

Leu Ile His Trp Trp Arg Gln Ala Pro Gly Gln Gly Leu Gln Trp Met
35 40 45

Ala Trp Asn Pro Leu His Gly Ala Val Asn Tyr Ala His Gln Phe Gln
50 55 60

Gly Arg Ile Thr Val Thr Arg Asp Thr Ser Ile Asp Thr Ala Tyr Arg
65 70 75 80

Gly Leu Ser Arg Leu Arg Ser Asp Thr Thr Ala Val Thr Tyr Cys Thr
85 90 95

Arg Asp Ala Ser Arg Asp Asp Arg Ala Trp Arg Leu Asp Pro
100 105 110

<210> SEQ ID NO 508
<211> LENGTH: 89
<212> TYPE: PRT
<213> ORGANISM: Artificial Sequence
<220> FEATURE:
<223> OTHER INFORMATION: synthetic polypeptide/polynucleotide

<400> SEQUENCE: 508

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys
85

<210> SEQ ID NO 509
<211> LENGTH: 91
<212> TYPE: PRT
<213> ORGANISM: Artificial Sequence
<220> FEATURE:
<223> OTHER INFORMATION: synthetic polypeptide/polynucleotide

<400> SEQUENCE: 509

Glu Ile Val Leu Thr Gln Ser Pro Gly Thr Leu Ser Leu Ser Pro Gly
1 5 10 15

Glu Thr Ala Ile Ile Ser Cys Arg Thr Ser Gln Tyr Gly Ser Leu Ala
20 25 30

Trp Tyr Gln Gln Arg Pro Gly Gln Ala Pro Arg Leu Val Ile Tyr Ser
35 40 45

Gly Ser Thr Arg Ala Ala Gly Ile Pro Asp Arg Phe Ser Gly Ser Arg
50 55 60

Trp Gly Pro Asp Tyr Asn Leu Thr Ile Ser Asn Leu Glu Ser Gly Asp
65 70 75 80

Phe Gly Val Tyr Tyr Cys Gln Gln Tyr Glu Phe
85 90

<210> SEQ ID NO 510
<211> LENGTH: 91
<212> TYPE: PRT
<213> ORGANISM: Artificial Sequence
<220> FEATURE:
<223> OTHER INFORMATION: synthetic polypeptide/polynucleotide

<400> SEQUENCE: 510

Glu Ile Val Leu Thr Gln Ser Pro Ala Thr Leu Ser Leu Ser Pro Gly
1 5 10 15

Glu Thr Ala Ile Ile Ser Cys Arg Thr Ser Gln Ser Gly Ser Leu Ala
20 25 30

Trp Tyr Gln Gln Arg Pro Gly Gln Ala Pro Arg Leu Val Ile Tyr Ser
35 40 45

Gly Ser Thr Arg Ala Ala Gly Ile Pro Asp Arg Phe Ser Gly Ser Arg
50 55 60

Trp Gly Ala Asp Tyr Asn Leu Ser Ile Ser Asn Leu Glu Ser Gly Asp
65 70 75 80

Phe Gly Val Tyr Tyr Cys Gln Gln Tyr Glu Phe
85 90

<210> SEQ ID NO 511
<211> LENGTH: 91
<212> TYPE: PRT
<213> ORGANISM: Artificial Sequence
<220> FEATURE:
<223> OTHER INFORMATION: synthetic polypeptide/polynucleotide

<400> SEQUENCE: 511

Glu Ile Val Leu Thr Gln Ser Pro Gly Thr Leu Ser Leu Ser Pro Gly
1 5 10 15

Glu Thr Ala Ile Ile Ser Cys Arg Thr Ser Gln Tyr Gly Ser Leu Ala
20 25 30

Trp Tyr Gln Gln Arg Pro Gly Gln Ala Pro Arg Leu Val Ile Tyr Ser
35 40 45

Gly Ser Thr Arg Ala Ala Gly Ile Pro Asp Arg Phe Ser Gly Ser Arg
50 55 60

Trp Gly Pro Asp Tyr Asn Leu Thr Ile Arg Asn Leu Glu Ser Gly Asp
65 70 75 80

Phe Gly Leu Tyr Tyr Cys Gln Gln Tyr Glu Phe
85 90

<210> SEQ ID NO 512
<211> LENGTH: 92
<212> TYPE: PRT
<213> ORGANISM: Artificial Sequence
<220> FEATURE:
<223> OTHER INFORMATION: synthetic polypeptide/polynucleotide

<400> SEQUENCE: 512

Glu Ile Val Leu Thr Gln Ser Pro Gly Ile Leu Ser Leu Ser Pro Gly
1 5 10 15

Glu Thr Ala Thr Leu Phe Cys Lys Ala Ser Gln Gly Gly Asn Ala Met
20 25 30

Thr Trp Tyr Gln Lys Arg Arg Gly Gln Val Pro Arg Leu Leu Ile Tyr
35 40 45

Asp Thr Ser Arg Arg Ala Ser Gly Val Pro Asp Arg Phe Val Gly Ser
50 55 60

Gly Ser Gly Thr Asp Phe Phe Leu Thr Ile Asn Lys Leu Asp Arg Glu
65 70 75 80

Asp Phe Ala Val Tyr Tyr Cys Gln Gln Phe Glu Phe
85 90

<210> SEQ ID NO 513
<211> LENGTH: 92
<212> TYPE: PRT
<213> ORGANISM: Artificial Sequence
<220> FEATURE:
<223> OTHER INFORMATION: synthetic polypeptide/polynucleotide

<400> SEQUENCE: 513

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Gly Gly Asn Ser Leu
20 25 30

Asn Trp Tyr Gln Lys Arg Arg Gly Gln Thr Pro Arg Leu Leu Ile Tyr
35 40 45

Asp Thr Ser Arg Arg Ala Ser Asp Ile Pro Glu Lys Phe Val Gly Ser
50 55 60

Gly Ser Gly Thr Asp Phe Ser Leu Thr Ile Thr Lys Val Gly Pro Glu
65 70 75 80

Asp Phe Ala Val Tyr Tyr Cys Gln Gln Phe Glu Phe
85 90

<210> SEQ ID NO 514
<211> LENGTH: 91
<212> TYPE: PRT
<213> ORGANISM: Artificial Sequence
<220> FEATURE:
<223> OTHER INFORMATION: synthetic polypeptide/polynucleotide

<400> SEQUENCE: 514

Glu Ile Val Leu Thr Gln Ser Pro Ala Thr Leu Ser Leu Ser Pro Gly
1 5 10 15

Glu Arg Ala Ile Leu Ser Cys Arg Thr Ser Gln Tyr Gly Ser Leu Ala
20 25 30

Trp Tyr Gln Gln Arg Pro Gly Gln Ala Pro Arg Leu Val Ile Tyr Ala
35 40 45

Gly Ser Thr Arg Ala Thr Gly Ile Pro Asp Arg Phe Ser Gly Ser Arg
50 55 60

Trp Gly Ala Glu Tyr Asn Leu Thr Ile Ser Asn Leu Glu Ser Glu Asp
65 70 75 80

Phe Gly Val Tyr Tyr Cys Gln Gln Tyr Glu Phe
85 90

<210> SEQ ID NO 515
<211> LENGTH: 94
<212> TYPE: PRT
<213> ORGANISM: Artificial Sequence
<220> FEATURE:
<223> OTHER INFORMATION: synthetic polypeptide/polynucleotide

<400> SEQUENCE: 515

Tyr Ile Gly Val Thr Gln Ser Pro Ala Ile Leu Ser Val Ser Leu Gly
1 5 10 15

Glu Arg Val Thr Leu Ser Cys Lys Thr Ser Gln Ala Ile Thr Pro Arg
20 25 30

His Leu Val Trp His Arg Gln Lys Gly Gly Gln Ala Pro Ser Leu Val
35 40 45

Met Thr Gly Thr Ser Glu Arg Ala Ser Gly Ile Pro Asp Arg Phe Ile
    50                  55                  60

Gly Ser Gly Ser Gly Thr Asp Phe Thr Leu Thr Ile Thr Arg Leu Glu
65                  70                  75                  80

Ala Glu Asp Phe Ala Val Tyr Tyr Cys Gln Cys Leu Glu Ala
                85                  90

<210> SEQ ID NO 516
<211> LENGTH: 94
<212> TYPE: PRT
<213> ORGANISM: Artificial Sequence
<220> FEATURE:
<223> OTHER INFORMATION: synthetic polypeptide/polynucleotide

<400> SEQUENCE: 516

Glu Ile Val Leu Thr Gln Ser Pro Gly Thr Leu Ser Leu Ser Pro Gly
1               5                   10                  15

Glu Thr Ala Thr Leu Ser Cys Arg Thr Ser Gln Gly Ile Leu Ser Asn
            20                  25                  30

Gln Leu Ala Trp His Gln Gln Arg Arg Gly Gln Pro Pro Arg Leu Leu
        35                  40                  45

Ile Tyr Gly Gly Ser Asn Arg Ala Pro Gly Ile Pro Glu Arg Phe Thr
    50                  55                  60

Gly Ser Gly Ser Gly Thr Asp Phe Val Leu Thr Ile Lys Arg Leu Glu
65                  70                  75                  80

Arg Asp Asp Phe Ala Val Tyr Tyr Cys Gln Ile Leu Glu Phe
                85                  90

<210> SEQ ID NO 517
<211> LENGTH: 91
<212> TYPE: PRT
<213> ORGANISM: Artificial Sequence
<220> FEATURE:
<223> OTHER INFORMATION: synthetic polypeptide/polynucleotide

<400> SEQUENCE: 517

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30

Trp Tyr Gln Lys Lys Pro Gly Gln Pro Pro Lys Leu Leu Ile Phe Ala
        35                  40                  45

Thr Ser Lys Arg Ala Ser Gly Ile Pro Asp Arg Phe Ser Gly Ser Gln
    50                  55                  60

Phe Gly Lys Gln Tyr Thr Leu Thr Ile Thr Arg Met Glu Pro Glu Asp
65                  70                  75                  80

Phe Ala Arg Tyr Tyr Cys Gln Gln Leu Glu Phe
                85                  90

<210> SEQ ID NO 518
<211> LENGTH: 89
<212> TYPE: PRT
<213> ORGANISM: Artificial Sequence
<220> FEATURE:
<223> OTHER INFORMATION: synthetic polypeptide/polynucleotide

<400> SEQUENCE: 518

Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr

```
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ala Arg Phe Ser Gly Arg Arg Trp Gly
    50                  55                  60

Gln Glu Tyr Asn Leu Thr Ile Asn Asn Leu Gln Pro Glu Asp Val Ala
65                  70                  75                  80

Thr Tyr Phe Cys Gln Val Tyr Glu Phe
                85


<210> SEQ ID NO 519
<211> LENGTH: 89
<212> TYPE: PRT
<213> ORGANISM: Artificial Sequence
<220> FEATURE:
<223> OTHER INFORMATION: synthetic polypeptide/polynucleotide

<400> SEQUENCE: 519

Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ser Arg Phe Ser Gly Arg Arg Trp Gly
    50                  55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe
                85


<210> SEQ ID NO 520
<211> LENGTH: 88
<212> TYPE: PRT
<213> ORGANISM: Artificial Sequence
<220> FEATURE:
<223> OTHER INFORMATION: synthetic polypeptide/polynucleotide

<400> SEQUENCE: 520

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys
                85


<210> SEQ ID NO 521
<211> LENGTH: 93
<212> TYPE: PRT
<213> ORGANISM: Artificial Sequence
<220> FEATURE:
<223> OTHER INFORMATION: synthetic polypeptide/polynucleotide

<400> SEQUENCE: 521
```

```
Glu Ile Val Met Thr Gln Ser Pro Val Thr Val Ser Val Ser Arg Gly
1               5                   10                  15

Gly Thr Ala Thr Leu Ser Cys Arg Ala Ser Gln Gly Val Gly Ser Asp
            20                  25                  30

Val Ala Trp Tyr Gln His Lys Pro Gly Gln Thr Pro Arg Leu Leu Ile
        35                  40                  45

Tyr Gly Ala Ser Thr Arg Ala Ser Gly Val Pro Glu Arg Phe Ser Gly
    50                  55                  60

Ser Gly Phe His Val Asp Phe Thr Leu Ser Ile Ser Gly Leu Gln Pro
65                  70                  75                  80

Glu Asp Val Ala Ile Tyr Tyr Cys Gln Gln Tyr Glu Thr
                85                  90


<210> SEQ ID NO 522
<211> LENGTH: 88
<212> TYPE: PRT
<213> ORGANISM: Artificial Sequence
<220> FEATURE:
<223> OTHER INFORMATION: synthetic polypeptide/polynucleotide

<400> SEQUENCE: 522

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys
                85


<210> SEQ ID NO 523
<211> LENGTH: 93
<212> TYPE: PRT
<213> ORGANISM: Artificial Sequence
<220> FEATURE:
<223> OTHER INFORMATION: synthetic polypeptide/polynucleotide

<400> SEQUENCE: 523

Asp Ile Gln Met Thr Gln Ser Pro Ser Ser Leu Ala Val Ser Val Gly
1               5                   10                  15

Gly Arg Val Thr Ile Thr Cys Arg Ala Ser Gln Gly Ile Gly Ser Asp
            20                  25                  30

Leu His Trp Tyr Gln Gln Lys Arg Gly Arg Pro Pro Lys Ile Leu Ile
        35                  40                  45

His His Ala Ser Ala Arg Glu Glu Gly Val Pro Ser Arg Phe Gly Gly
    50                  55                  60

Ser Gly Ser His Thr Pro Phe Ile Phe Thr Ile Asn Asp Leu Gln Leu
65                  70                  75                  80

Asp Asp Val Ala Thr Tyr Tyr Cys Gln Val Ile Glu Ser
                85                  90


<210> SEQ ID NO 524
<211> LENGTH: 93
<212> TYPE: PRT
```

<213> ORGANISM: Artificial Sequence
<220> FEATURE:
<223> OTHER INFORMATION: synthetic polypeptide/polynucleotide

<400> SEQUENCE: 524

```
Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Ala Gly Lys Ala Pro Lys Leu Leu Val
        35                  40                  45

Ser Asp Ala Ser Thr Leu Glu Gly Gly Val Pro Ser Arg Phe Ser Gly
    50                  55                  60

Ser Gly Phe His Gln Asn Phe Ser Leu Thr Ile Ser Ser Leu Gln Ala
65                  70                  75                  80

Glu Asp Val Ala Thr Tyr Phe Cys Gln Gln Tyr Glu Thr
                85                  90
```

<210> SEQ ID NO 525
<211> LENGTH: 93
<212> TYPE: PRT
<213> ORGANISM: Artificial Sequence
<220> FEATURE:
<223> OTHER INFORMATION: synthetic polypeptide/polynucleotide

<400> SEQUENCE: 525

```
Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Thr Ser Ser Val Glu Asp Gly Val Pro Ser Arg Phe Ser Gly
    50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe
                85                  90
```

<210> SEQ ID NO 526
<211> LENGTH: 93
<212> TYPE: PRT
<213> ORGANISM: Artificial Sequence
<220> FEATURE:
<223> OTHER INFORMATION: synthetic polypeptide/polynucleotide

<400> SEQUENCE: 526

```
Asp Ile Gln Met Thr Gln Ser Pro Ser Ser Leu Ser Ala Ser Val Gly
1               5                   10                  15

Asp Arg Val Thr Ile Thr Cys Gln Ala Gly Gln Gly Ile Gly Ser Ser
            20                  25                  30

Leu Gln Trp Tyr Gln Gln Lys Pro Gly Lys Ala Pro Lys Leu Leu Val
        35                  40                  45

His Gly Ala Ser Asn Leu His Arg Gly Val Pro Ser Arg Phe Ser Gly
    50                  55                  60

Ser Gly Phe His Thr Thr Phe Ser Leu Thr Ile Ser Gly Leu Gln Arg
65                  70                  75                  80

Asp Asp Phe Ala Thr Tyr Phe Cys Ala Val Leu Glu Phe
                85                  90
```

<210> SEQ ID NO 527
<211> LENGTH: 93
<212> TYPE: PRT
<213> ORGANISM: Artificial Sequence
<220> FEATURE:
<223> OTHER INFORMATION: synthetic polypeptide/polynucleotide

<400> SEQUENCE: 527

Asp Ile Gln Met Thr Gln Ser Pro Ser Ser Leu Ser Ala Ser Val Gly
1 5 10 15

Asp Arg Val Thr Ile Asn Cys Gln Ala Gly Gln Gly Ile Gly Ser Ser
20 25 30

Leu Asn Trp Tyr Gln Lys Lys Pro Gly Arg Ala Pro Lys Leu Leu Val
35 40 45

His Gly Ala Ser Asn Leu Gln Arg Gly Val Pro Ser Arg Phe Ser Gly
50 55 60

Ser Gly Phe His Thr Thr Phe Thr Leu Thr Ile Ser Ser Leu Gln Pro
65 70 75 80

Asp Asp Val Ala Thr Tyr Phe Cys Ala Val Phe Gln Trp
85 90

<210> SEQ ID NO 528
<211> LENGTH: 90
<212> TYPE: PRT
<213> ORGANISM: Artificial Sequence
<220> FEATURE:
<223> OTHER INFORMATION: synthetic polypeptide/polynucleotide

<400> SEQUENCE: 528

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys
85 90

<210> SEQ ID NO 529
<211> LENGTH: 94
<212> TYPE: PRT
<213> ORGANISM: Artificial Sequence
<220> FEATURE:
<223> OTHER INFORMATION: synthetic polypeptide/polynucleotide

<400> SEQUENCE: 529

Gln Ser Ala Leu Thr Gln Pro Ala Ser Val Ser Gly Ser Pro Gly Gln
1 5 10 15

Ser Ile Thr Ile Ser Cys Thr Ala Ser Ser Asp Phe Arg Gly Phe Ser
20 25 30

Ser Val Ser Trp Tyr Gln Gln Val Pro Gly Arg Ala Pro Lys Leu Leu
35 40 45

Ile Phe Ser Val Asn Arg Arg Pro Ser Gly Ile Ser His Arg Phe Ser
50 55 60

Gly Ser Lys Ser Gly Asn Thr Ala Ser Leu Thr Ile Ser Gly Leu Gln
65 70 75 80

Ile Glu Asp Glu Ala Asp Tyr His Cys Asn Ala Tyr Glu Phe
85 90

<210> SEQ ID NO 530
<211> LENGTH: 89
<212> TYPE: PRT
<213> ORGANISM: Artificial Sequence
<220> FEATURE:
<223> OTHER INFORMATION: synthetic polypeptide/polynucleotide

<400> SEQUENCE: 530

Gln Ser Ala Leu Thr Gln Pro Pro Ser Val Ser Gly Ser Pro Gly Gln
1 5 10 15

Ser Ile Thr Leu Ser Cys Thr Gly Ala Ser Thr Ser Val Ala Trp Tyr
20 25 30

Gln Gln Tyr Ala Asp Lys Ala Pro Arg Leu Ile Val Phe Asp Gly Asn
35 40 45

Lys Arg Pro Ser Asp Ile Ser Ser Arg Phe Ser Gly Ser Gln Ser Gly
50 55 60

Gly Thr Ala Ser Leu Thr Ile Ser Gly Leu Gln Ser Glu Asp Glu Ala
65 70 75 80

Tyr Tyr His Cys Asn Ala Phe Glu Phe
85

<210> SEQ ID NO 531
<211> LENGTH: 88
<212> TYPE: PRT
<213> ORGANISM: Artificial Sequence
<220> FEATURE:
<223> OTHER INFORMATION: synthetic polypeptide/polynucleotide

<400> SEQUENCE: 531

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys
85

<210> SEQ ID NO 532
<211> LENGTH: 93
<212> TYPE: PRT
<213> ORGANISM: Artificial Sequence
<220> FEATURE:
<223> OTHER INFORMATION: synthetic polypeptide/polynucleotide

<400> SEQUENCE: 532

Asp Ile Gln Met Thr Gln Ser Pro Ala Thr Leu Ser Ala Ser Val Gly
1 5 10 15

Asp Arg Val Thr Ile Thr Cys Arg Ala Gly Gln Gly Ile Gly Ser Asp
20 25 30

Leu Ala Trp Tyr Gln Gln Lys Pro Gly Gln Ala Pro Lys Leu Leu Ile 35 40 45

Phe Lys Ala Ser Asn Leu Lys Asn Gly Val Pro Thr Arg Phe Thr Gly
50 55 60

Ser Gly Phe His Thr Asp Phe Thr Leu Thr Ile Asn Gly Leu Gln Ser
65 70 75 80

Asp Asp Phe Ala Thr Tyr Tyr Cys Gln Val Leu Glu Thr
85 90

<210> SEQ ID NO 533
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: Xaa can be Val or Ala
<220> FEATURE:
<221> NAME/KEY: MISC_FEATURE
<222> LOCATION: (3)..(3)
<223> OTHER INFORMATION: Xaa can be Leu or Tyr or Phe or Val
<220> FEATURE:
<221> NAME/KEY: MISC_FEATURE
<222> LOCATION: (4)..(4)
<223> OTHER INFORMATION: Xaa can be Glu or Gln
<220> FEATURE:
<221> NAME/KEY: MISC_FEATURE
<222> LOCATION: (5)..(5)
<223> OTHER INFORMATION: Xaa can be Thr or Ser or Trp
<220> FEATURE:
<221> NAME/KEY: MISC_FEATURE
<222> LOCATION: (6)..(6)
<223> OTHER INFORMATION: Xaa can be Thr or Ser or Trp

<400> SEQUENCE: 533

Gln Xaa Xaa Xaa Xaa Xaa
1 5

<210> SEQ ID NO 534
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Gln or Ala or Asn
<220> FEATURE:
<221> NAME/KEY: MISC_FEATURE
<222> LOCATION: (2)..(2)
<223> OTHER INFORMATION: Xaa can be Gln or Val or Ala or Cys or Ile
<220> FEATURE:
<221> NAME/KEY: MISC_FEATURE
<222> LOCATION: (3)..(3)
<223> OTHER INFORMATION: Xaa can be Tyr or Leu or Phe or Ile
<220> FEATURE:
<221> NAME/KEY: MISC_FEATURE
<222> LOCATION: (4)..(4)
<223> OTHER INFORMATION: Xaa can be Glu or Gln
<220> FEATURE:
<221> NAME/KEY: MISC_FEATURE
<222> LOCATION: (5)..(5)
<223> OTHER INFORMATION: Xaa can be Phe or Thr or Ala or Ser or Trp

<400> SEQUENCE: 534

Xaa Xaa Xaa Xaa Xaa
1 5

<210> SEQ ID NO 535

<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..()
<223> OTHER INFORMATION: Xaa can be Gly or Ser
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa can be Gly or Ser
<220> FEATURE:
<221> NAME/KEY: MISC_FEATURE
<222> LOCATION: (4)..(4)
<223> OTHER INFORMATION: Xaa can be Asp or Asn
<220> FEATURE:
<221> NAME/KEY: MISC_FEATURE
<222> LOCATION: (5)..(5)
<223> OTHER INFORMATION: Xaa can be Ala or Gly

<400> SEQUENCE: 535

Xaa Xaa Gly Xaa Xaa
1               5

<210> SEQ ID NO 536
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Ser or Gly
<220> FEATURE:
<221> NAME/KEY: MISC_FEATURE
<222> LOCATION: (2)..(2)
<223> OTHER INFORMATION: Xaa can be Gly or Ser or His
<220> FEATURE:
<221> NAME/KEY: MISC_FEATURE
<222> LOCATION: (4)..(4)
<223> OTHER INFORMATION: Xaa can be Asp or Trp
<220> FEATURE:
<221> NAME/KEY: MISC_FEATURE
<222> LOCATION: (5)..(5)
<223> OTHER INFORMATION: Xaa can be Gly or Ala

<400> SEQUENCE: 536

Xaa Xaa Gly Xaa Xaa
1               5

<210> SEQ ID NO 537
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be Ser or Asn
<220> FEATURE:
<221> NAME/KEY: MISC_FEATURE
<222> LOCATION: (3)..(3)
<223> OTHER INFORMATION: Xaa can be Ser or Asn

<400> SEQUENCE: 537

Ser Xaa Xaa Trp Ala 1 5

<210> SEQ ID NO 538
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Phe or His or Tyr
<220> FEATURE:
<221> NAME/KEY: MISC_FEATURE
<222> LOCATION: (2)..(2)
<223> OTHER INFORMATION: Xaa can be Asn or Arg or Thr or Ser
<220> FEATURE:
<221> NAME/KEY: MISC_FEATURE
<222> LOCATION: (3)..(3)
<223> OTHER INFORMATION: Xaa can be Lys or Ile or Ala or Leu or Gln
<220> FEATURE:
<221> NAME/KEY: MISC_FEATURE
<222> LOCATION: (4)..(4)
<223> OTHER INFORMATION: Xaa can be Asn or Asp or Ser or Ala or Lys

<400> SEQUENCE: 538

Xaa Xaa Xaa Xaa
1

<210> SEQ ID NO 539
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Phe or His or Tyr
<220> FEATURE:
<221> NAME/KEY: MISC_FEATURE
<222> LOCATION: (2)..(2)
<223> OTHER INFORMATION: Xaa can be Asn or Thr
<220> FEATURE:
<221> NAME/KEY: MISC_FEATURE
<222> LOCATION: (3)..(3)
<223> OTHER INFORMATION: Xaa can be Lys or Ile or Leu
<220> FEATURE:
<221> NAME/KEY: MISC_FEATURE
<222> LOCATION: (4)..(4)
<223> OTHER INFORMATION: Xaa can be Asn or Ser or Asp

<400> SEQUENCE: 539

Xaa Xaa Xaa Xaa
1

<210> SEQ ID NO 540
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Tyr or Ser or His
<220> FEATURE:
<221> NAME/KEY: MISC_FEATURE
<222> LOCATION: (2)..(2)
<223> OTHER INFORMATION: Xaa can be Ser or Thr or Asn or Ile
<220> FEATURE:
<221> NAME/KEY: MISC_FEATURE
<222> LOCATION: (3)..(3)
<223> OTHER INFORMATION: Xaa can be Glu or Gln
<220> FEATURE:
<221> NAME/KEY: MISC_FEATURE
<222> LOCATION: (4)..(4)
<223> OTHER INFORMATION: Xaa can be Ser or Arg or Gly or Asn

<400> SEQUENCE: 540

Xaa Xaa Xaa Xaa
1

<210> SEQ ID NO 541
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be Ile or Leu
<220> FEATURE:
<221> NAME/KEY: MISC_FEATURE
<222> LOCATION: (3)..(3)
<223> OTHER INFORMATION: Xaa can be Asn or His
<220> FEATURE:
<221> NAME/KEY: MISC_FEATURE
<222> LOCATION: (5)..(5)
<223> OTHER INFORMATION: Xaa can be Arg or Val or Pro

<400> SEQUENCE: 541

Asn Xaa Xaa Ala Xaa
1               5

<210> SEQ ID NO 542
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be Leu or Ile or Asn
<220> FEATURE:
<221> NAME/KEY: MISC_FEATURE
<222> LOCATION: (3)..(3)
<223> OTHER INFORMATION: Xaa can be His or Asn
<220> FEATURE:
<221> NAME/KEY: MISC_FEATURE
<222> LOCATION: (4)..(4)
<223> OTHER INFORMATION: Xaa can be Ala or Gly
<220> FEATURE:
<221> NAME/KEY: MISC_FEATURE
<222> LOCATION: (5)..(5)
<223> OTHER INFORMATION: Xaa can be Val or Pro or Thr or Arg

<400> SEQUENCE: 542

Asn Xaa Xaa Xaa Xaa
1               5

<210> SEQ ID NO 543
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be Asn or Lys or Asp or Tyr
<220> FEATURE:
<221> NAME/KEY: MISC_FEATURE
<222> LOCATION: (3)..(3)
<223> OTHER INFORMATION: Xaa can be Ser or Thr or Asn
<220> FEATURE:
<221> NAME/KEY: MISC_FEATURE
<222> LOCATION: (4)..(4)
<223> OTHER INFORMATION: Xaa can be Gly or Asp or Ala or Val

<400> SEQUENCE: 543

Asn Xaa Xaa Xaa Thr
1               5

<210> SEQ ID NO 544
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Ser or Ala or Thr or Asp
<220> FEATURE:
<221> NAME/KEY: MISC_FEATURE
<222> LOCATION: (2)..(2)
<223> OTHER INFORMATION: Xaa can be Tyr or Leu or Phe
<220> FEATURE:
<221> NAME/KEY: MISC_FEATURE
<222> LOCATION: (3)..(3)
<223> OTHER INFORMATION: Xaa can be Ile or Val
<220> FEATURE:
<221> NAME/KEY: MISC_FEATURE
<222> LOCATION: (4)..(4)
<223> OTHER INFORMATION: Xaa can be Phe or Trp or Val or Ile

<400> SEQUENCE: 544

Xaa Xaa Xaa Xaa
1

<210> SEQ ID NO 545
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Thr or Ala or Ser or Gly or Asp
<220> FEATURE:
<221> NAME/KEY: MISC_FEATURE
<222> LOCATION: (2)..(2)
<223> OTHER INFORMATION: Xaa can be Leu or Tyr or Phe
<220> FEATURE:
<221> NAME/KEY: MISC_FEATURE
<222> LOCATION: (3)..(3)
<223> OTHER INFORMATION: Xaa can be Ile or Met or Leu or Val
<220> FEATURE:
<221> NAME/KEY: MISC_FEATURE
<222> LOCATION: (4)..(4)
<223> OTHER INFORMATION: Xaa can be Trp or Val or Phe or Leu

<400> SEQUENCE: 545

Xaa Xaa Xaa Xaa
1

<210> SEQ ID NO 546
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Gly or Asp or Ala or Ser
<220> FEATURE:
<221> NAME/KEY: MISC_FEATURE
<222> LOCATION: (2)..(2)
<223> OTHER INFORMATION: Xaa can be Tyr or Phe
<220> FEATURE:
<221> NAME/KEY: MISC_FEATURE
<222> LOCATION: (3)..(3)
<223> OTHER INFORMATION: Xaa can be Met or Ile or Leu

<400> SEQUENCE: 546

Xaa Xaa Xaa Val
1

<210> SEQ ID NO 547
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Asn or Thr
<220> FEATURE:
<221> NAME/KEY: MISC_FEATURE
<222> LOCATION: (2)..(2)
<223> OTHER INFORMATION: Xaa can be Ser or Thr
<220> FEATURE:
<221> NAME/KEY: MISC_FEATURE
<222> LOCATION: (4)..(4)
<223> OTHER INFORMATION: Xaa can be Leu or Tyr
<220> FEATURE:
<221> NAME/KEY: MISC_FEATURE
<222> LOCATION: (6)..(6)
<223> OTHER INFORMATION: Xaa can be Trp or Phe

<400> SEQUENCE: 547

Xaa Xaa Cys Xaa Ile Xaa
1               5

<210> SEQ ID NO 548
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Leu or Thr
<220> FEATURE:
<221> NAME/KEY: MISC_FEATURE
<222> LOCATION: (2)..(2)
<223> OTHER INFORMATION: Xaa can be His or Asn
<220> FEATURE:
<221> NAME/KEY: MISC_FEATURE
<222> LOCATION: (4)..(4)
<223> OTHER INFORMATION: Xaa can be Tyr or His

<400> SEQUENCE: 548

Xaa Xaa Ala Xaa
1

<210> SEQ ID NO 549
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Gly or Ser

```
<220> FEATURE:
<221> NAME/KEY: MISC_FEATURE
<222> LOCATION: (4)..(4)
<223> OTHER INFORMATION: Xaa can be Asp or Lys

<400> SEQUENCE: 549

Xaa Gly Gly Xaa Gly
1               5


<210> SEQ ID NO 550
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be His or Phe
<220> FEATURE:
<221> NAME/KEY: MISC_FEATURE
<222> LOCATION: (2)..(2)
<223> OTHER INFORMATION: Xaa can be Asn or Thr
<220> FEATURE:
<221> NAME/KEY: MISC_FEATURE
<222> LOCATION: (3)..(3)
<223> OTHER INFORMATION: Xaa can be Ile or Lys or Ala
<220> FEATURE:
<221> NAME/KEY: MISC_FEATURE
<222> LOCATION: (4)..(4)
<223> OTHER INFORMATION: Xaa can be Asn or Asp

<400> SEQUENCE: 550

Xaa Xaa Xaa Xaa
1


<210> SEQ ID NO 551
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be Val or Ala
<220> FEATURE:
<221> NAME/KEY: MISC_FEATURE
<222> LOCATION: (3)..(3)
<223> OTHER INFORMATION: Xaa can be Phe or Val or Tyr
<220> FEATURE:
<221> NAME/KEY: MISC_FEATURE
<222> LOCATION: (5)..(5)
<223> OTHER INFORMATION: Xaa can be Trp or Ser

<400> SEQUENCE: 551

Gln Xaa Xaa Glu Xaa
1               5


<210> SEQ ID NO 552
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Xaa can be Asn or Gln

<400> SEQUENCE: 552

Ile Asn Ala Xaa
```

1

<210> SEQ ID NO 553
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Gly or Ser
<220> FEATURE:
<221> NAME/KEY: MISC_FEATURE
<222> LOCATION: (5)..(5)
<223> OTHER INFORMATION: Xaa can be Ala or Gly

<400> SEQUENCE: 553

Xaa Gly Gly Asp Xaa
1               5

<210> SEQ ID NO 554
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be Asn or Arg
<220> FEATURE:
<221> NAME/KEY: MISC_FEATURE
<222> LOCATION: (4)..(4)
<223> OTHER INFORMATION: Xaa can be Asn or Asp or Lys

<400> SEQUENCE: 554

Phe Xaa Lys Xaa
1

<210> SEQ ID NO 555
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be Ala or Thr or Val
<220> FEATURE:
<221> NAME/KEY: MISC_FEATURE
<222> LOCATION: (3)..(3)
<223> OTHER INFORMATION: Xaa can be Gly or Asp or Gln or Arg or Ala or
      Met
<220> FEATURE:
<221> NAME/KEY: MISC_FEATURE
<222> LOCATION: (5)..(5)
<223> OTHER INFORMATION: Xaa can be Tyr or Gly
<220> FEATURE:
<221> NAME/KEY: MISC_FEATURE
<222> LOCATION: (6)..(6)
<223> OTHER INFORMATION: Xaa can be Cys or Gly or Lys or Ser
<220> FEATURE:
<221> NAME/KEY: MISC_FEATURE
<222> LOCATION: (7)..(7)
<223> OTHER INFORMATION: Xaa can be Arg or Ser or Thr or Glu or Phe or
      Gly or Met or Gln
<220> FEATURE:
<221> NAME/KEY: MISC_FEATURE
<222> LOCATION: (8)..(8)
<223> OTHER INFORMATION: Xaa can be Lys or Ser or Ala or Cys or Leu or
      Arg or Val or Tyr
<220> FEATURE:

```
<221> NAME/KEY: MISC_FEATURE
<222> LOCATION: (9)..(9)
<223> OTHER INFORMATION: Xaa can be Arg or Gly or Asn or Tyr or Asp or
      Pro or Ser or Thr
<220> FEATURE:
<221> NAME/KEY: MISC_FEATURE
<222> LOCATION: (10)..(10)
<223> OTHER INFORMATION: Xaa can be Asp or Gly or Arg or Cys or Ala or
      Phe or His or Gln or Tyr
<220> FEATURE:
<221> NAME/KEY: MISC_FEATURE
<222> LOCATION: (11)..(11)
<223> OTHER INFORMATION: Xaa can be Asp or Ala or Cys or Gly or Ser or
      Tyr or Arg
<220> FEATURE:
<221> NAME/KEY: MISC_FEATURE
<222> LOCATION: (12)..(12)
<223> OTHER INFORMATION: Xaa can be Tyr or Gly or Ser or Asp or Arg or
      Ala or Leu or Gln or Thr
<220> FEATURE:
<221> NAME/KEY: MISC_FEATURE
<222> LOCATION: (13)..(13)
<223> OTHER INFORMATION: Xaa can be Asn or Ser or Glu or Asp or Tyr or
      Phe or Gly or Lys
<220> FEATURE:
<221> NAME/KEY: MISC_FEATURE
<222> LOCATION: (14)..(14)
<223> OTHER INFORMATION: Xaa can be Trp or Phe or Glu
<220> FEATURE:
<221> NAME/KEY: MISC_FEATURE
<222> LOCATION: (15)..(15)
<223> OTHER INFORMATION: Xaa can be Asp or His or Ala or Trp or Pro or
      Arg or Tyr
<220> FEATURE:
<221> NAME/KEY: MISC_FEATURE
<222> LOCATION: (16)..(16)
<223> OTHER INFORMATION: Xaa can be Phe or Leu or Ser or Trp or Tyr
<220> FEATURE:
<221> NAME/KEY: MISC_FEATURE
<222> LOCATION: (17)..(17)
<223> OTHER INFORMATION: Xaa can be Asp or Glu or Gln or Ala or Phe or
      His
<220> FEATURE:
<221> NAME/KEY: MISC_FEATURE
<222> LOCATION: (18)..(18)
<223> OTHER INFORMATION: Xaa can be His or Pro or Val or Tyr or Ala or
      Phe or Ile or Leu

<400> SEQUENCE: 555

Xaa Arg Xaa Lys Xaa Xaa Xaa Xaa Xaa Xaa Xaa Xaa Xaa Xaa Xaa Xaa
1               5                   10                  15

Xaa Xaa
```